United States Patent
Zhang et al.

(10) Patent No.: US 10,981,900 B2
(45) Date of Patent: Apr. 20, 2021

(54) SPIRO COMPOUND AND USE THEREOF

(71) Applicant: MEDSHINE DISCOVERY INC., Jiangsu (CN)

(72) Inventors: Peng Zhang, Shanghai (CN); Lingyun Wu, Shanghai (CN); Jun Yin, Shanghai (CN); Jian Li, Shanghai (CN); Shuhui Chen, Shanghai (CN)

(73) Assignee: MEDSHINE DISCOVERY INC., Shanghai (CN)

(*) Notice: Subject to any disclaimer, the term of this patent is extended or adjusted under 35 U.S.C. 154(b) by 0 days.

(21) Appl. No.: 16/489,476

(22) PCT Filed: Feb. 28, 2018

(86) PCT No.: PCT/CN2018/077512
§ 371 (c)(1),
(2) Date: Aug. 28, 2019

(87) PCT Pub. No.: WO2018/157813
PCT Pub. Date: Sep. 7, 2018

(65) Prior Publication Data
US 2020/0048235 A1  Feb. 13, 2020

(30) Foreign Application Priority Data

Feb. 28, 2017 (CN) .......................... 201710113078.8

(51) Int. Cl.
| | | |
|---|---|---|
| *C07D 413/12* | (2006.01) | |
| *C07D 417/10* | (2006.01) | |
| *C07D 409/10* | (2006.01) | |
| *C07F 7/02* | (2006.01) | |
| *C07D 413/10* | (2006.01) | |
| *C07D 403/10* | (2006.01) | |

(52) U.S. Cl.
CPC ......... *C07D 413/10* (2013.01); *C07D 403/10* (2013.01); *C07D 409/10* (2013.01); *C07D 413/12* (2013.01); *C07D 417/10* (2013.01); *C07F 7/02* (2013.01)

(58) Field of Classification Search
CPC .. C07D 413/12; C07D 417/10; C07D 409/10; C07F 7/02
See application file for complete search history.

(56) References Cited

U.S. PATENT DOCUMENTS

| 8,188,102 B2 | 5/2012 | Lee et al. |
| 9,388,147 B2* | 7/2016 | Martinborough ....... A61P 37/06 |
| 9,725,439 B2 | 8/2017 | Xiao et al. |

FOREIGN PATENT DOCUMENTS

CN            106279128 A       1/2017

* cited by examiner

*Primary Examiner* — Laura L Stockton
(74) *Attorney, Agent, or Firm* — McDermott Will & Emery LLP

(57) ABSTRACT

The present disclosure relates to a series of tricyclic compounds and the use thereof as receptor agonists of sphingosine-1-phosphate subtype 1 (S1P1), and in particular relates to compounds as shown in formula (I) or pharmaceutically acceptable salts thereof.

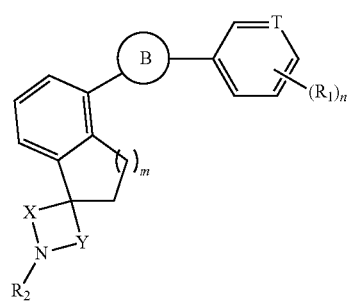

22 Claims, No Drawings

SPIRO COMPOUND AND USE THEREOF

CROSS REFERENCE TO RELATED APPLICATION

The present application is a national stage filing under 35 U.S.C. § 371 of International Application No. PCT/CN2018/077512, filed Feb. 28, 2018, which claims the benefit of the Chinese Patent Application No. 201710113078.8, filed on Feb. 28, 2017 with the National Intellectual Property Administration of the People's Republic of China, the entire contents of each of which are incorporated herein by reference herein in their entireties.

TECHNICAL FIELD

The present disclosure relates to a series of tricyclic compounds and their use as agonists of sphingosine-1-phosphate subtype 1 (S1P1) receptor, in particular to a compound represented by formula (I) or a pharmaceutically acceptable salt thereof.

BACKGROUND OF THE INVENTION

Sphingosine-1-phosphate (S1P) is a pleiotropic lipid mediator with a broad spectrum of physiological activities including cell proliferation, survival, lymphocyte trafficking, cytoskeletal organization and morphogenesis. Sphingosine is catalyzed by enzyme ceramide and released from ceramide. Sphingosine is phosphorylated under the catalysis of sphingosine kinase to produce sphingosine-1-phosphate (S1P) and interacts with the sphingosine-1-phosphate receptor (S1PR) to bring physiological activity.

Sphingosine-1-phosphate receptor 1 (S1PR1), also known as endothelial cell differentiation gene 1 (EDG1), is a G protein-coupled receptor, which belongs to the endothelial cell differentiation gene (EDG) receptor family, and is a protein encoded by the S1PR1 gene. The sphingosine-1-phosphate receptor (S1PR) includes five subtypes (S1PR1-5), in which sphingosine-1-phosphate receptor 1 (S1PR1) is abundantly distributed on the endothelial cell membrane. Like other G-protein coupled receptors, S1PR1 detects its ligand from the outside of a cell and activates intracellular signaling pathways to cause cellular responses.

Sphingosine-1-phosphate (S1P) is very important in humans, which mainly regulates the vascular system and immune system. Small molecular S1P1 agonists and inhibitors mimic the binding mechanism of sphingosine-1-phosphate (S1P) to receptors, and have been shown to have important physiological roles in their signaling systems. Activation of sphingosine-1-phosphate receptor 1 (S1PR1) disrupts lymphocyte trafficking, and isolate lymphocytes in lymph nodes and other secondary lymphoid organs, thereby resulting in rapid and reversible lymphopenia. Clinical studies have shown that lymphocyte isolation reduces inflammation or autoimmune disease responses and is critical for immune regulation.

Currently, published in vivo pharmacodynamic studies of sphingosine-1-phosphate receptor 1 (S1PR1) agonists are used to treat or prevent autoimmune diseases. The discovery and application of novel sphingosine-1-phosphate receptor 1 (S1PR1) agonists has broad prospects.

SUMMARY OF THE INVENTION

Disclosed herein is a compound represented by formula (I) or a pharmaceutically acceptable salt thereof,

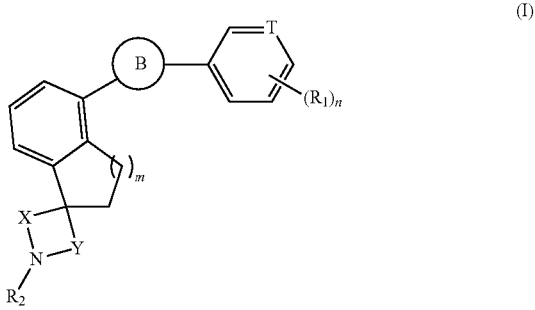

wherein each $R_1$ is independently selected from the group consisting of H, F, Cl, Br, I, OH, $NH_2$ and CN, or is independently selected from the group consisting of $C_{1-6}$ alkyl and $C_{1-6}$ heteroalkyl, each of which is optionally substituted by 1, 2 or 3 R;

$R_2$ is H, or is selected from the group consisting of $C_{1-6}$ alkyl and $C_{1-6}$ heteroalkyl, each of which is optionally substituted by 1, 2 or 3 R;

T is selected from the group consisting of N and CH;

moiety

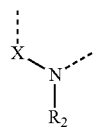

is selected from the group consisting of

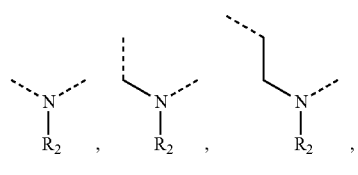

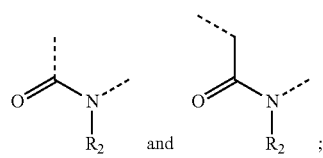

moiety

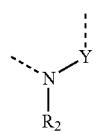

is selected from the group consisting of

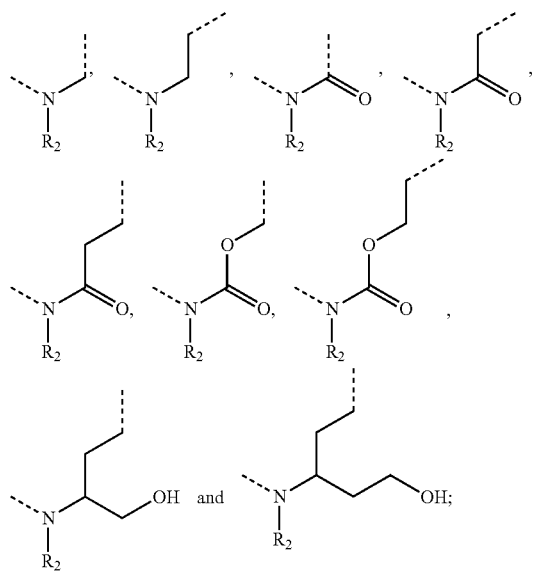

ring B is selected from the group consisting of phenyl and 5- to 6-membered heteroaryl;
m is 1 or 2;
n is 0, 1, 2 or 3;
R is selected from the group consisting of F, Cl, Br, I, OH, $NH_2$, CN and COOH, or is selected from the group consisting of $C_{1-6}$ alkyl, $C_{1-6}$ alkoxy, N,N-di($C_{1-6}$ alkyl)amino, and $C_{3-6}$ cycloalkyl;
the heteroatom or the heteroatom group of the $C_{1-6}$ heteroalkyl and the 5- to 6-membered heteroaryl is each independently selected from the group consisting of N, O, S, NH, —NHC(═O)—, —S(═O)— and —S(═O)$_2$—; and
the number of the heteroatom or the heteroatom group is 1, 2, 3 or 4.
In some embodiments disclosed herein, the above R is F, Cl, Br, I, OH, $NH_2$, CN, COOH, Me, Et, $N(CH_3)_2$,

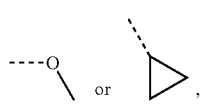

and other variables are as defined above.
In some embodiments disclosed herein, the above $R_1$ is each independently selected from the group consisting of H, F, Cl, Br, I, OH, $NH_2$ and CN, or is independently selected from the group consisting of $C_{1-3}$ alkyl, $C_{1-3}$ alkoxy, $C_{1-3}$ alkylamino and $C_{1-3}$ alkyl-S(═O)$_2$—, each of which is optionally substituted by 1, 2 or 3 R, and other variables are as defined above.
In some embodiments disclosed herein, the above $R_1$ is each independently selected from the group consisting of H, F, Cl, Br, I, OH, $NH_2$ and CN, or is independently selected from the group consisting of Me, Et,

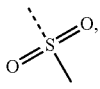

each of which is optionally substituted by 1, 2 or 3 R, and other variables are as defined above.
In some embodiments disclosed herein, the above $R_1$ is each independently selected from the group consisting of H, F, Cl, Br, I, OH, $NH_2$, CN, Me, Et,

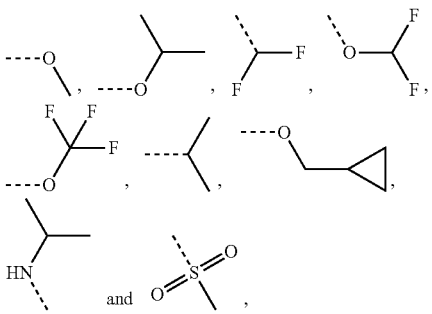

and other variables are as defined above.
In some embodiments disclosed herein, the above $R_2$ is selected from the group consisting of $C_{1-4}$ alkyl, $C_{1-3}$ alkyl-O—$C_{1-3}$ alkyl-, $C_{1-3}$ alkyl-S(═O)$_2$—$C_{1-3}$ alkyl-, $C_{1-3}$ alkyl-NHC$_{1-3}$ alkyl, and $C_{1-3}$ alkyl-NHC(═O)—$C_{1-3}$ alkyl, each of which is optionally substituted by 1, 2 or 3 R, and other variables are as defined above.
In some embodiments disclosed herein, the above $R_2$ is selected from the group consisting of Me, Et,

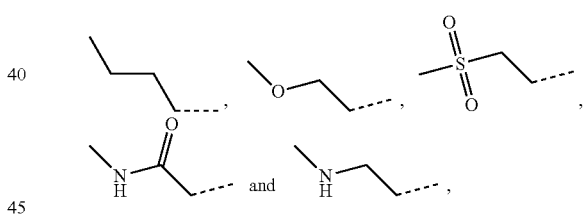

each of which is optionally substituted by 1, 2 or 3 R, and other variables are as defined above.
In some embodiments disclosed herein, the above $R_2$ is selected from the group consisting of

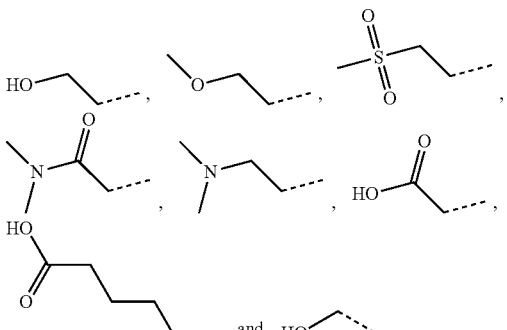

and other variables are as defined above.

In some embodiments disclosed herein, the above moiety ring

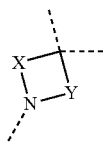

is selected from the group consisting of

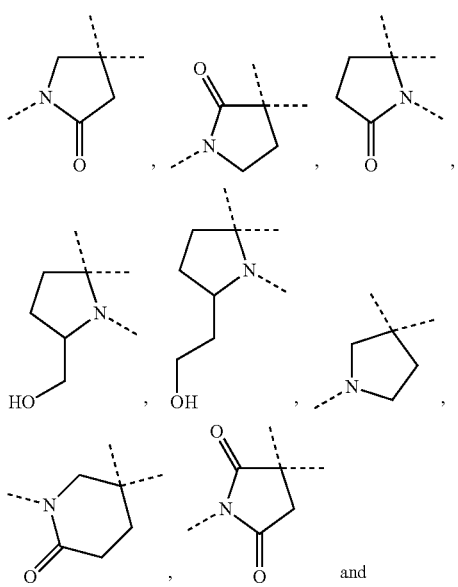

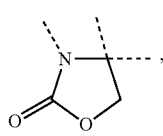

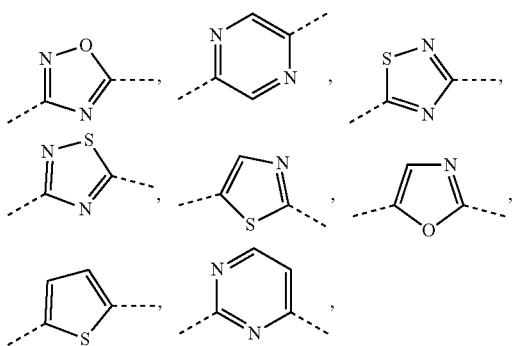

and other variables are as defined above.

In some embodiments disclosed herein, the above ring B is selected from the group consisting of 1,2,4-oxadiazolyl, 1,2,4-thiadiazolyl, pyrazinyl, thiazolyl, oxazolyl and pyrimidinyl, and other variables are as defined above.

In some embodiments disclosed herein, the above ring B is selected from the group consisting of

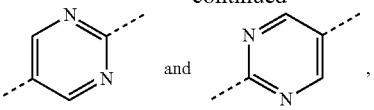

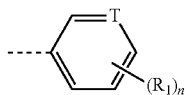 and and other variables are as defined above.

In some embodiments disclosed herein, the above moiety

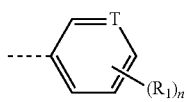

is selected from the group consisting of

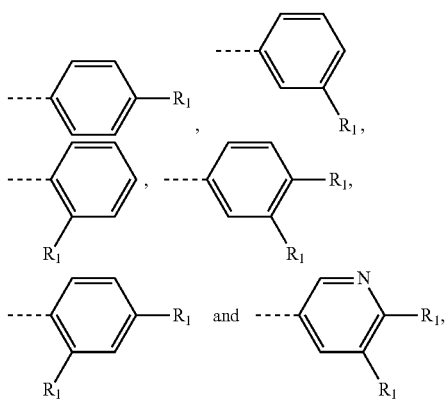

and other variables are as defined above.

In some embodiments disclosed herein, the above moiety

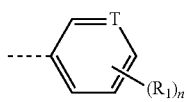

is selected from the group consisting of

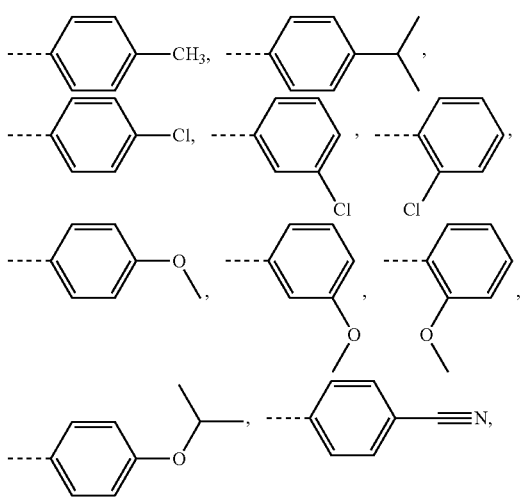

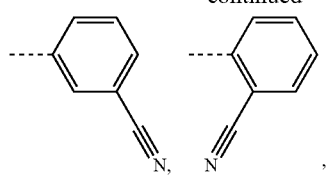
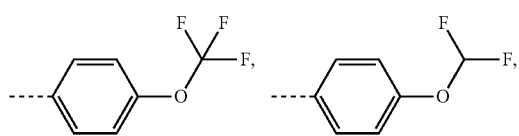
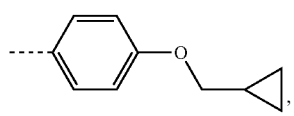
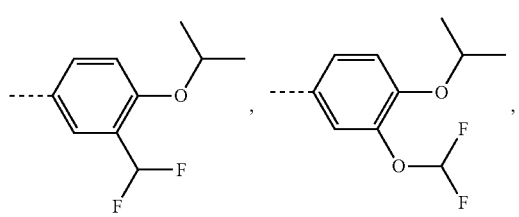
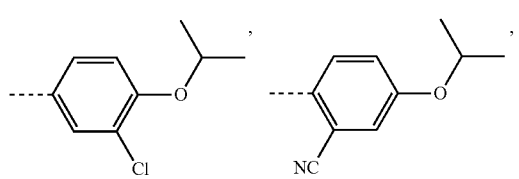
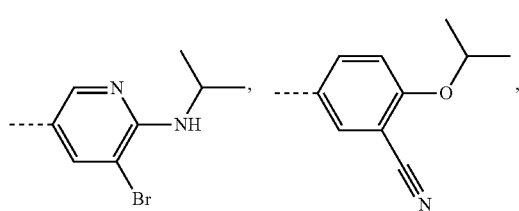
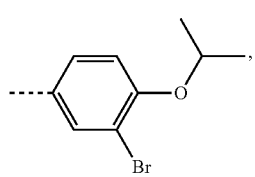
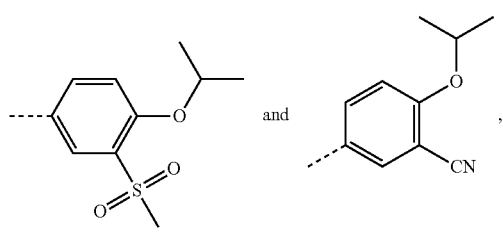
and other variables are as defined above.
In some embodiments disclosed herein, the above moiety
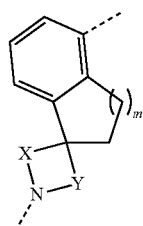
is selected from the group consisting of
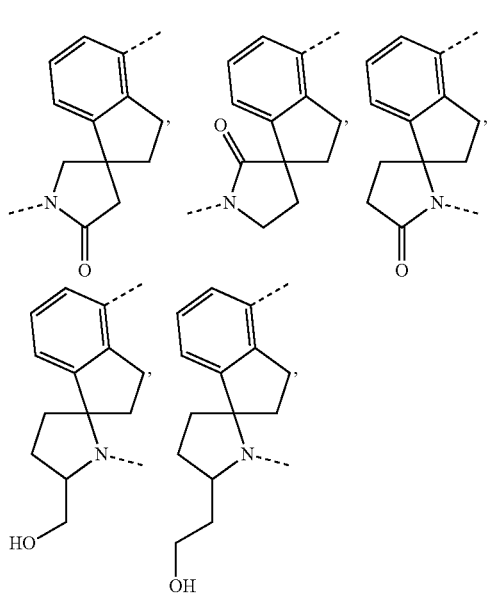
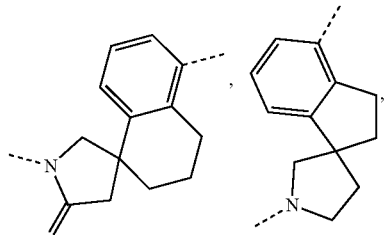
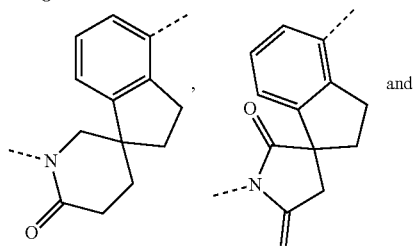
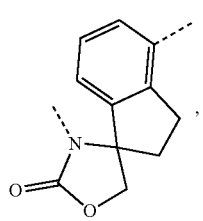
and other variables are as defined above.

In some embodiments disclosed herein, the above moiety

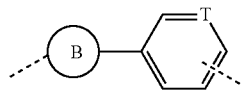

is selected from the group consisting of

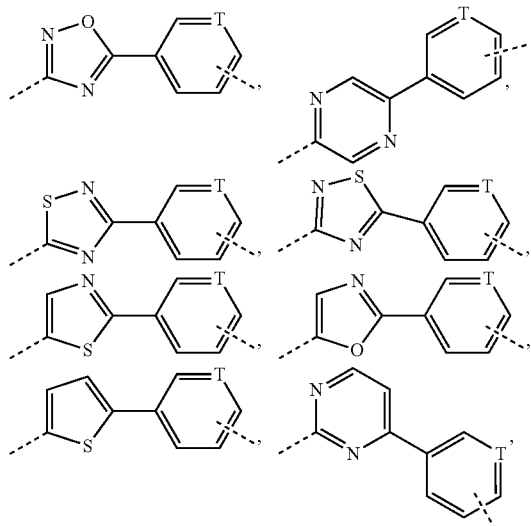

and

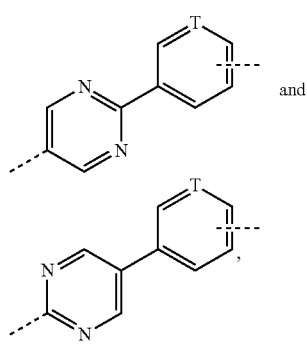

and other variables are as defined above.

In some embodiments disclosed herein, the above R is selected from the group
consisting of F, Cl, Br, I, OH, NH$_2$, CN, COOH, Me, Et, N(CH$_3$)$_2$,

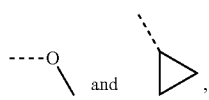

and other variables are as defined above.

In some embodiments disclosed herein, the above R$_1$ is each independently selected from the group consisting of H, F, Cl, Br, I, OH, NH$_2$ and CN, or is independently selected from the group consisting of C$_{1-3}$ alkyl, C$_{1-3}$ alkoxy, C$_{1-3}$ alkylamino and C$_{1-3}$ alkyl-S(=O)$_2$—, each of which is optionally substituted by 1, 2 or 3 R, and other variables are as defined above.

In some embodiments disclosed herein, the above R$_1$ is each independently selected from the group consisting of H, F, Cl, Br, I, OH, NH$_2$ and CN, or is independently selected from the group consisting of Me, Et,

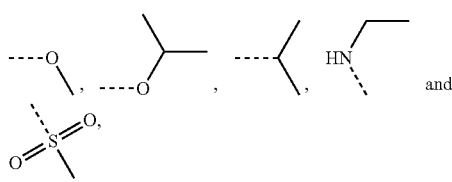

each of which is optionally substituted by 1, 2 or 3 R, and other variables are as defined above.

In some embodiments disclosed herein, the above R$_1$ is each independently selected from the group consisting of H, F, Cl, Br, I, OH, NH$_2$, CN, Me, Et.

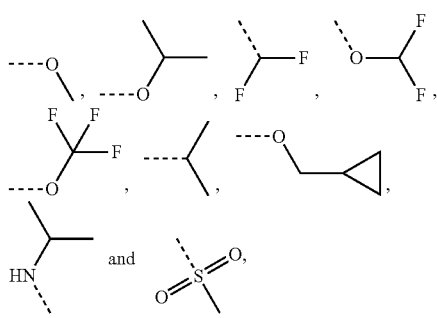

and other variables are as defined above.

In some embodiments disclosed herein, the above R$_2$ is selected from the group consisting of C$_{1-4}$ alkyl, C$_{1-3}$ alkyl-O—C$_{1-3}$ alkyl, C$_{1-3}$ alkyl-S(=O)$_2$—C$_{1-3}$ alkyl- and C$_{1-3}$ alkyl-NHC(=O)—C$_{1-3}$ alkyl, each of which is optionally substituted by 1, 2 or 3 R, and other variables are as defined above.

In some embodiments disclosed herein, the above R$_2$ is selected from the group consisting of Me, Et,

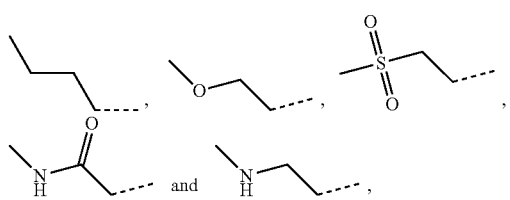

each of which is optionally substituted by 1, 2 or 3 R, and other variables are as defined above.

In some embodiments disclosed herein, the above R$_2$ is selected from the group consisting of

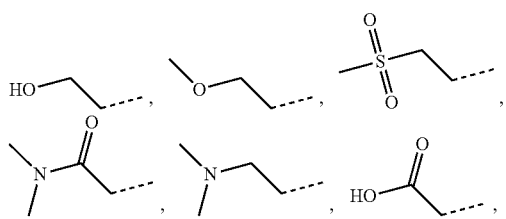

-continued

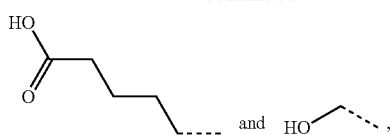

and other variables are as defined above.

In some embodiments disclosed herein, the above moiety ring

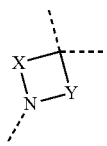

is selected from the group consisting of

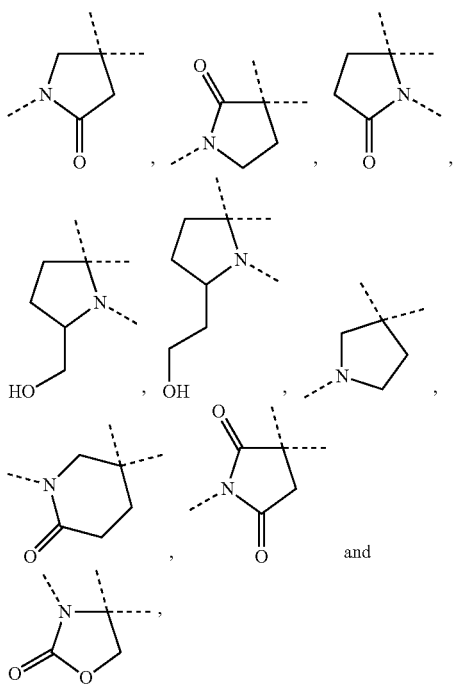

and other variables are as defined above.

In some embodiments disclosed herein, the above ring B is selected from the group consisting of 1,2,4-oxadiazolyl, 1,2,4-thiadiazolyl, pyrazinyl, thiazolyl, oxazolyl and pyrimidinyl, and other variables are as defined above.

In some embodiments disclosed herein, the above ring B is selected from the group consisting of

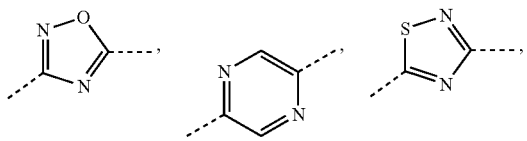

-continued

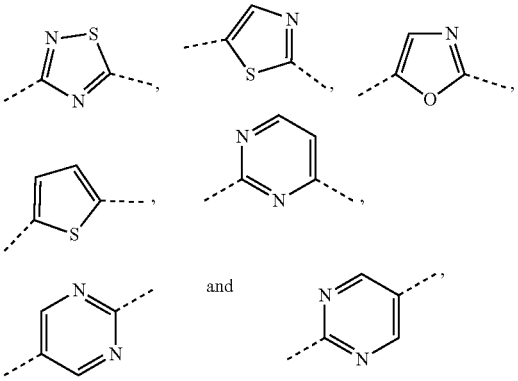

and other variables are as defined above.

In some embodiments disclosed herein, the above moiety

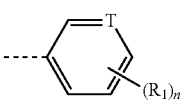

is selected from the group consisting of

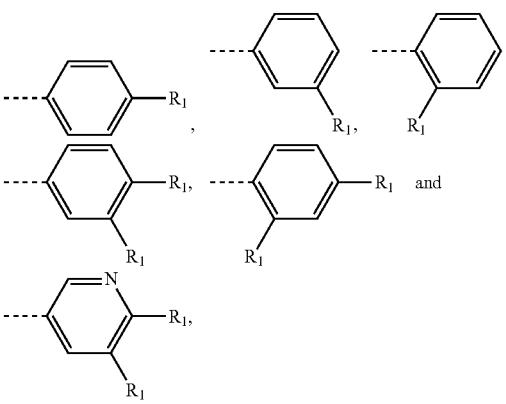

and other variables are as defined above.

In some embodiments disclosed herein, the above moiety

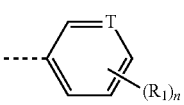

is selected from the group consisting of

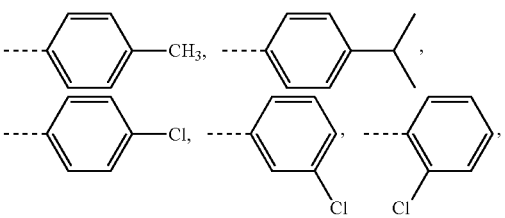

-continued
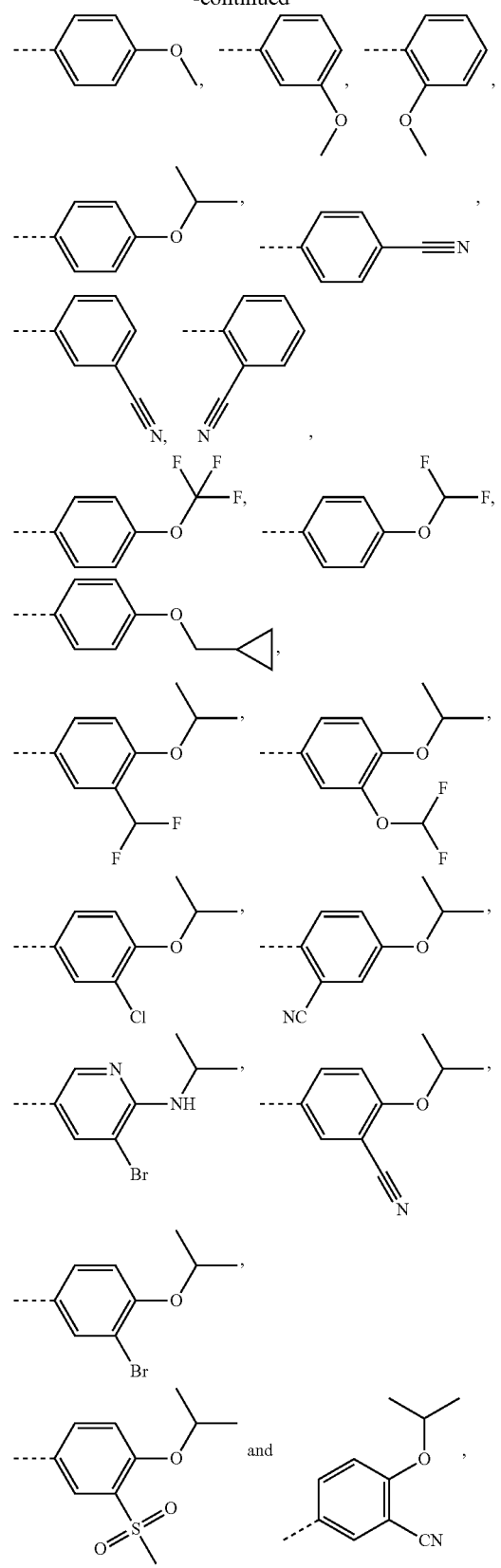
and other variables are as defined above.
In some embodiments disclosed herein, the above moiety
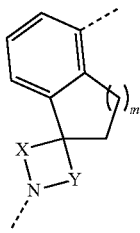
is selected from the group consisting of
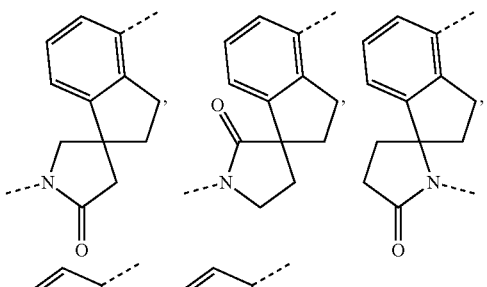
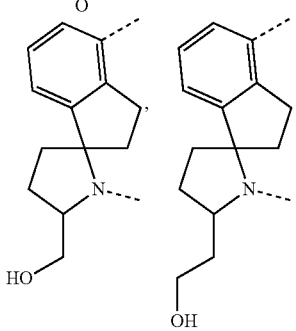
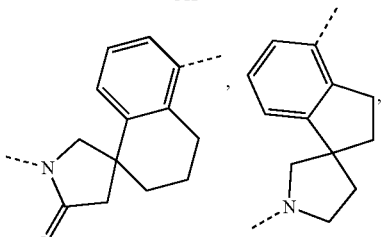
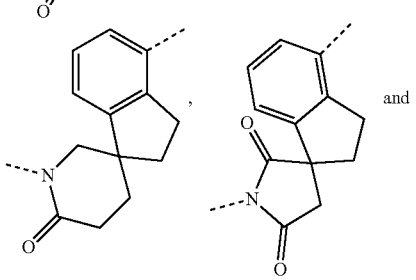
and
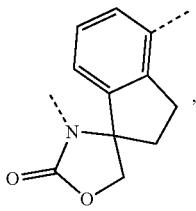
and other variables are as defined above.

In some embodiments disclosed herein, the above moiety

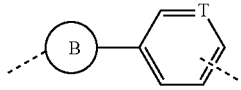

is selected from the group consisting of

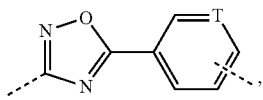,

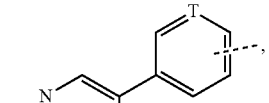,


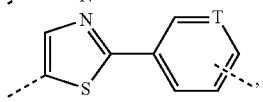

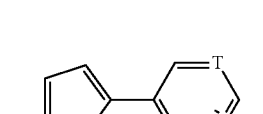

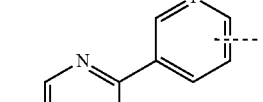

and

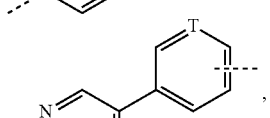, and other variables are as defined above.

In some embodiments disclosed herein, the above compound, or the pharmaceutically acceptable salt thereof, is selected from the group consisting of

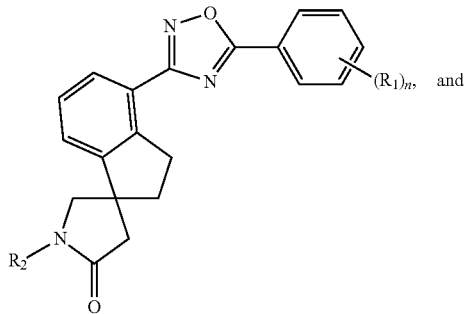

(I-1)

and

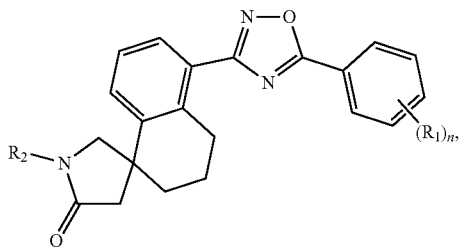

(I-2)

wherein n, $R_1$ and $R_2$ are as defined above.

In some embodiments disclosed herein, the above compound, or the pharmaceutically acceptable salt thereof, selected from the group consisting of

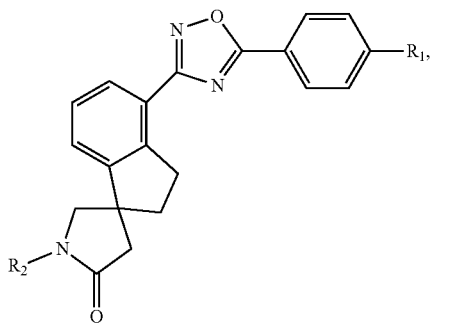

(11-1)

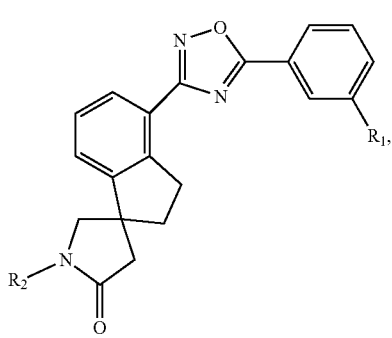

(11-2)

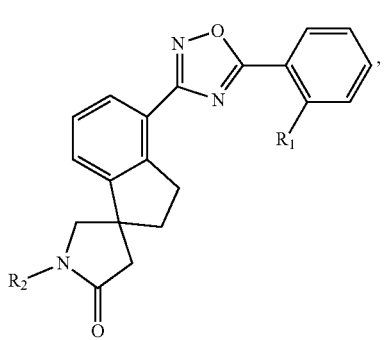

(11-3)

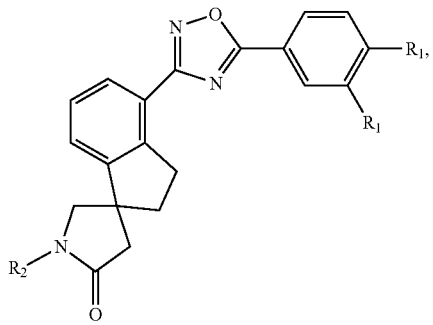
(11-4)

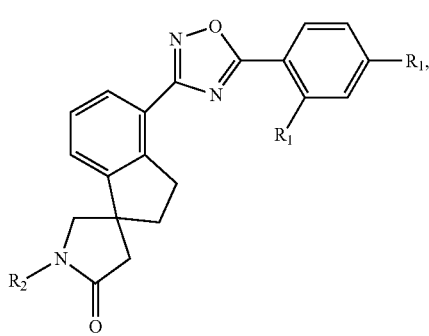
(11-5)

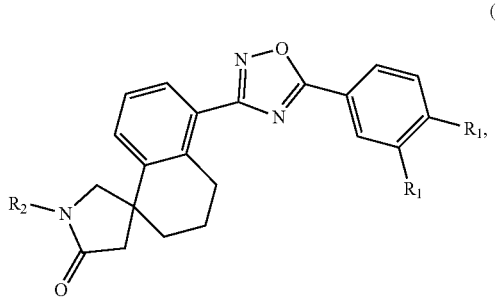
(11-6)

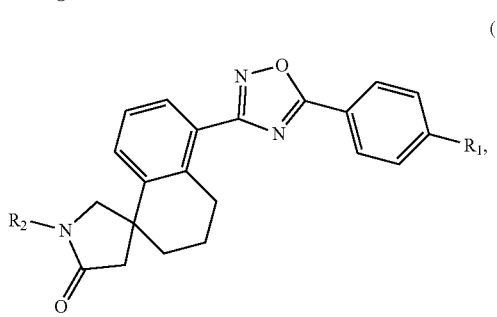
(11-7)

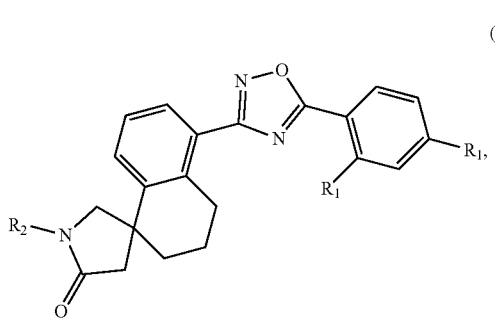
(11-8)

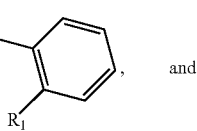
(11-9) and

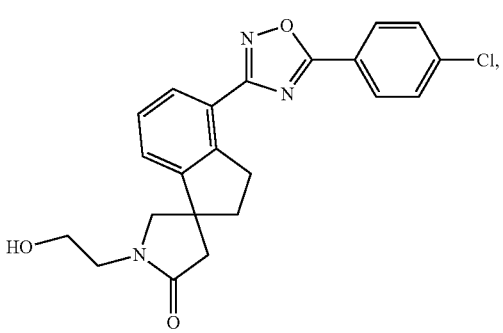
(11-10)

wherein $R_1$ and $R_2$ are as defined above.

The present disclosure also includes some embodiments that are obtained by combining any of the above definitions for the above variables.

The present disclosure also provides a compound represented by the following formula or a pharmaceutically acceptable salt thereof, which is selected from the group consisting of

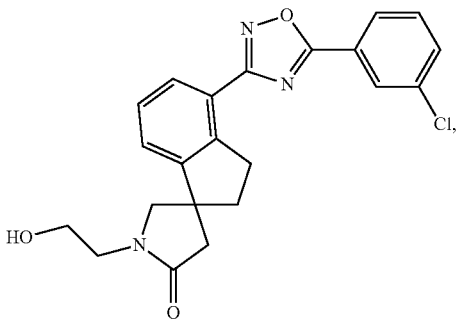

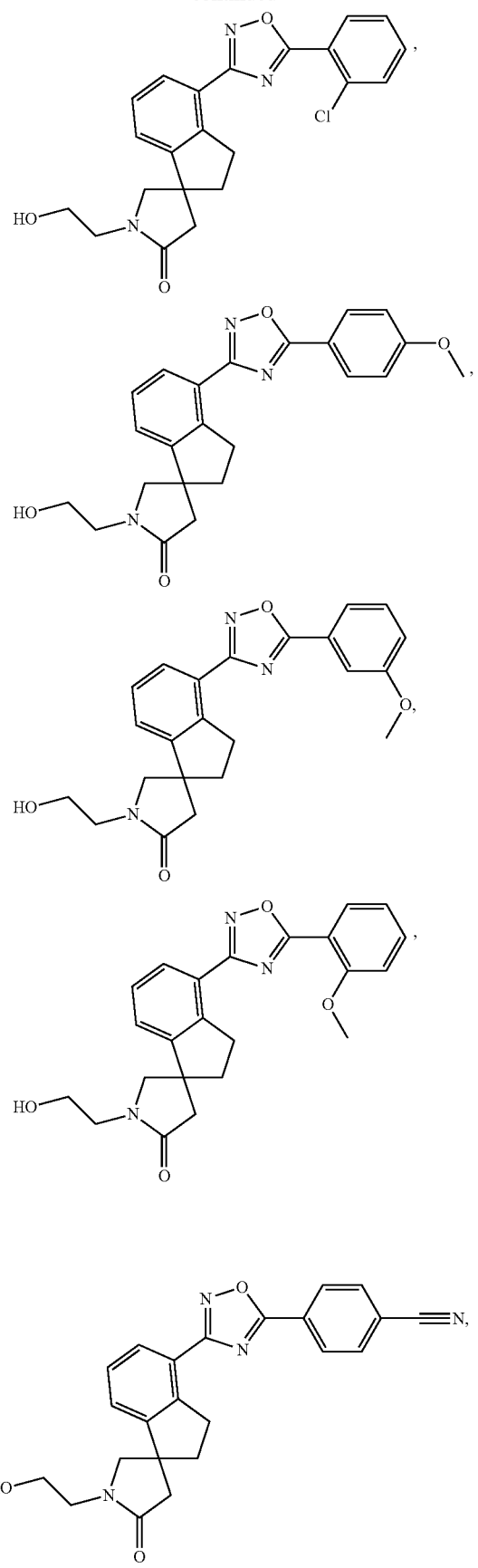
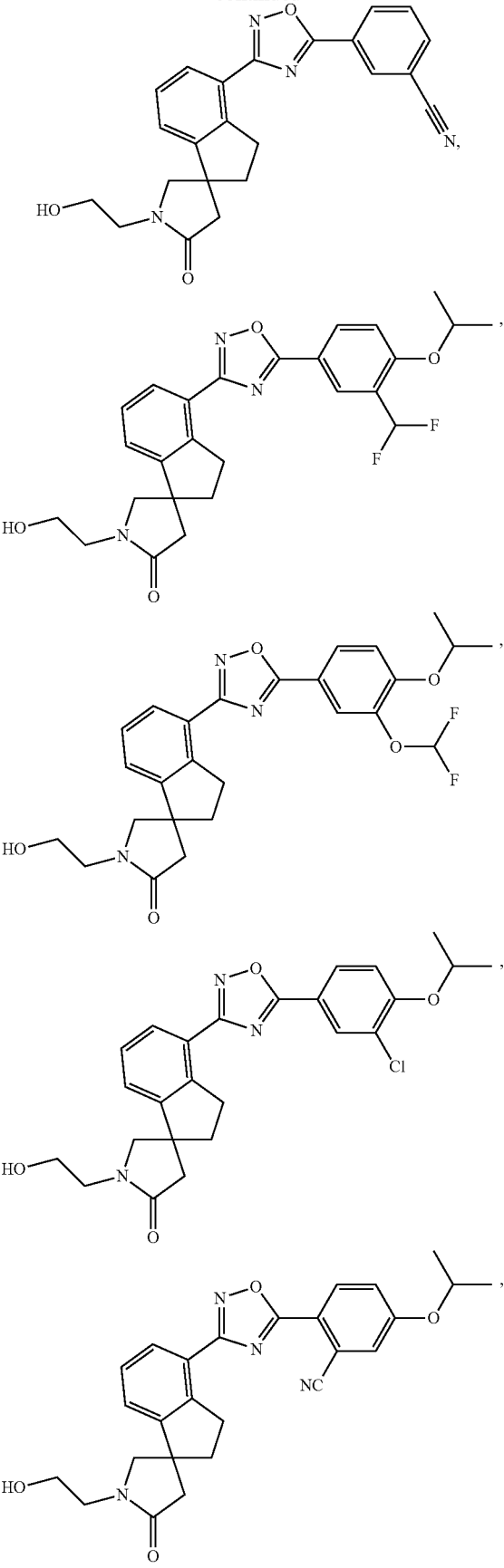

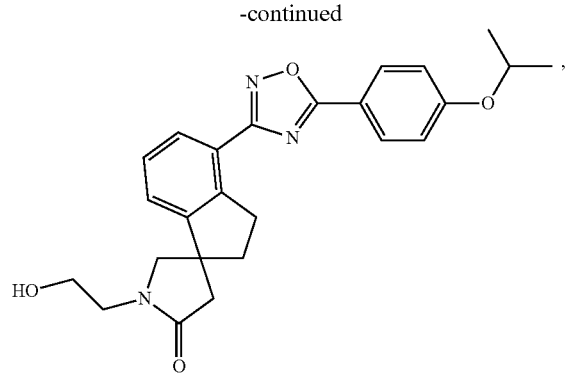
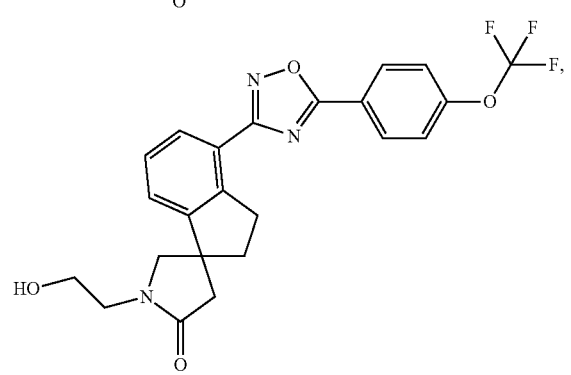
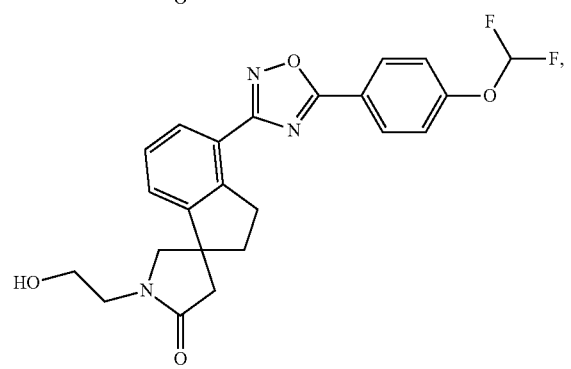
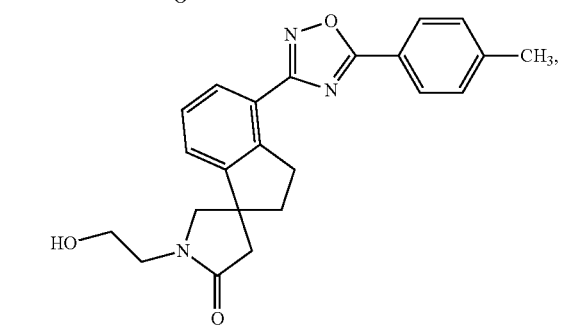
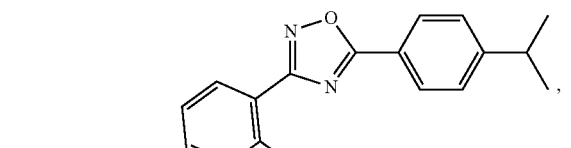
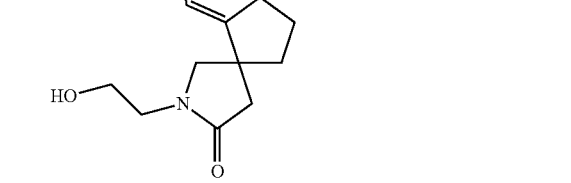
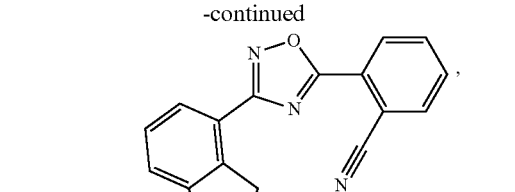
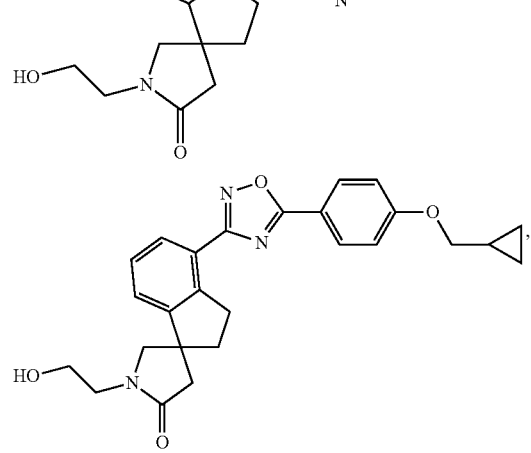

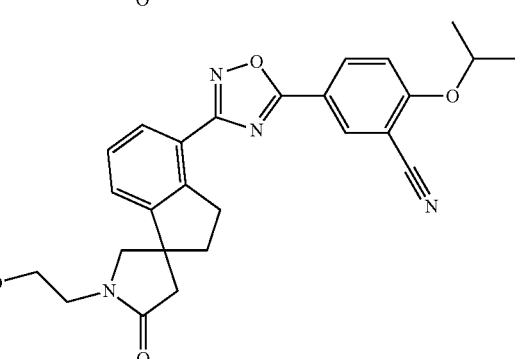
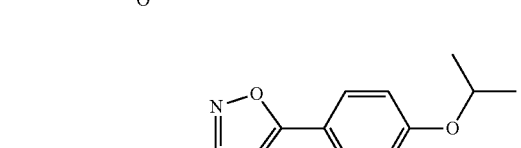
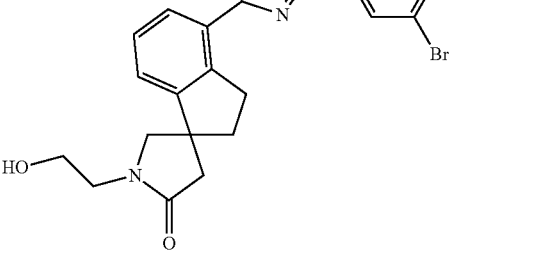

23
-continued
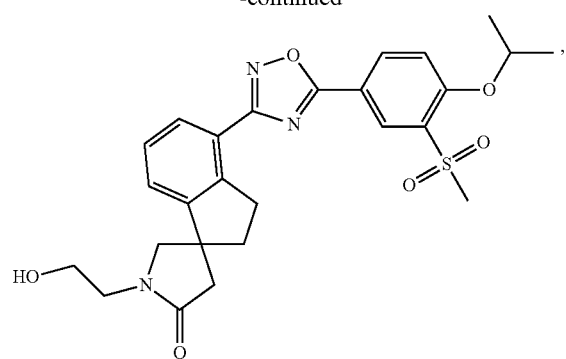
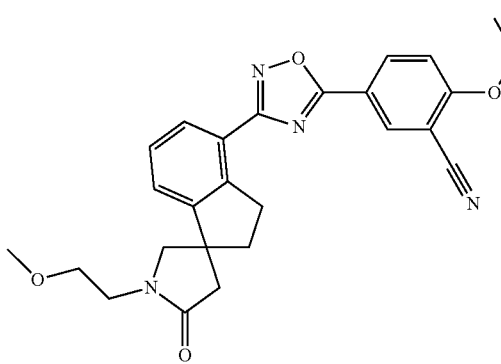
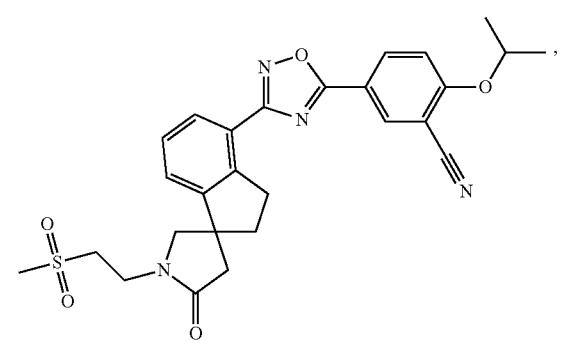
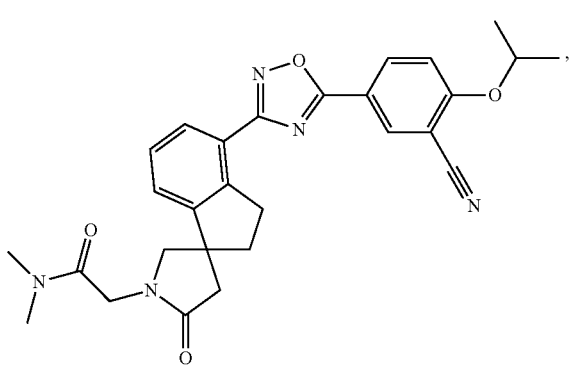
24
-continued
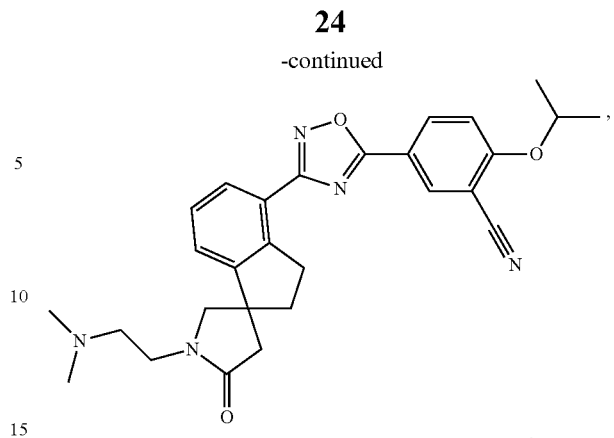
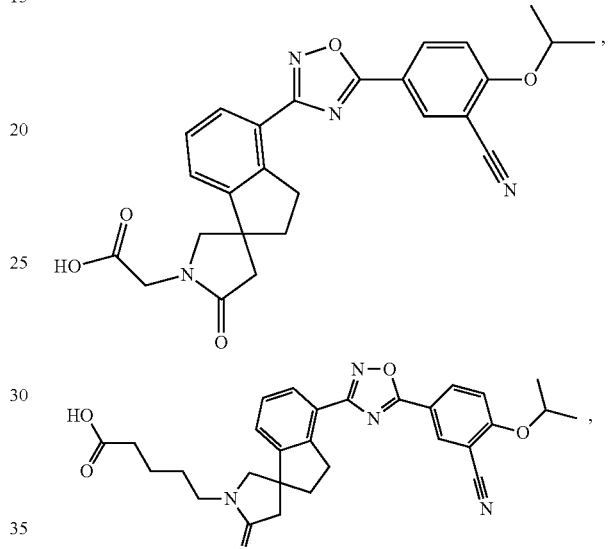
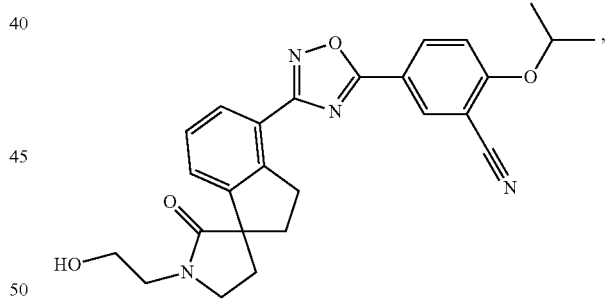
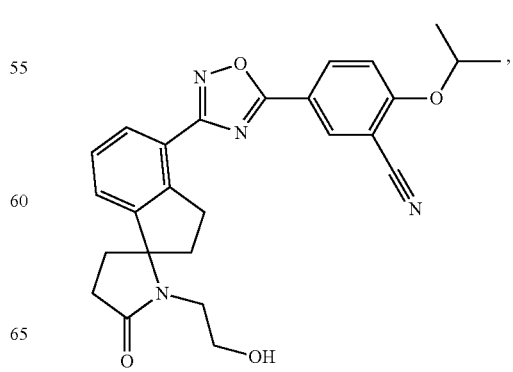

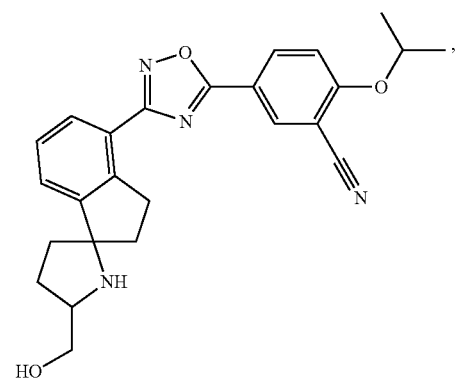
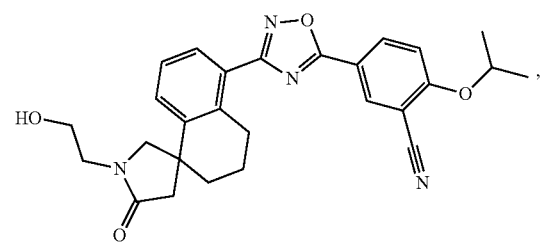
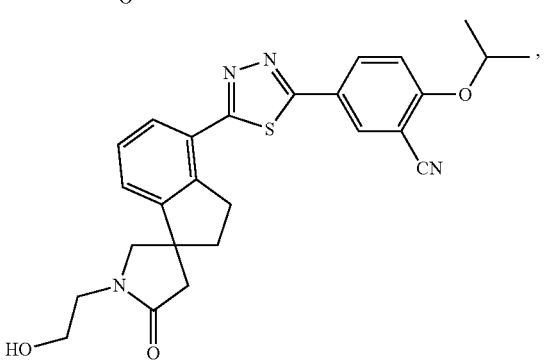
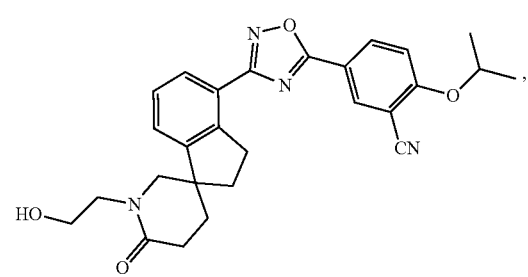
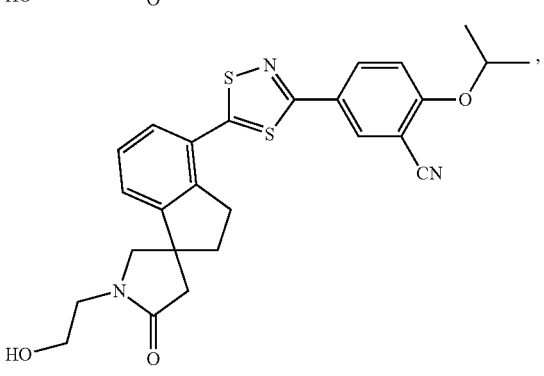
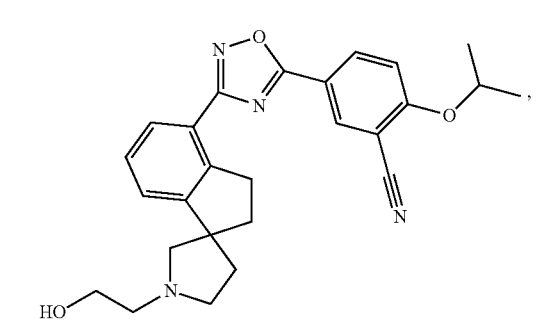
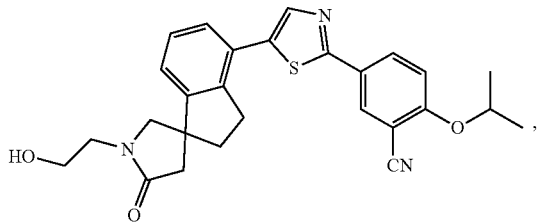
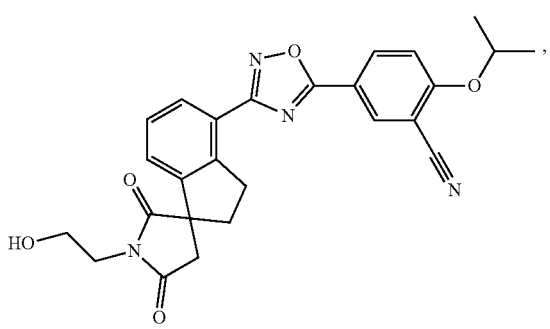
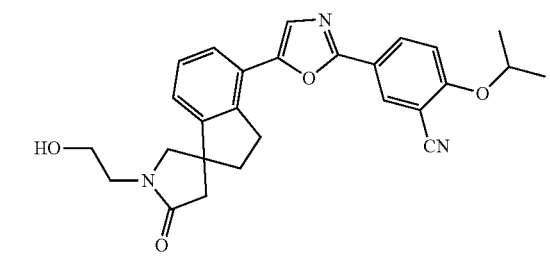

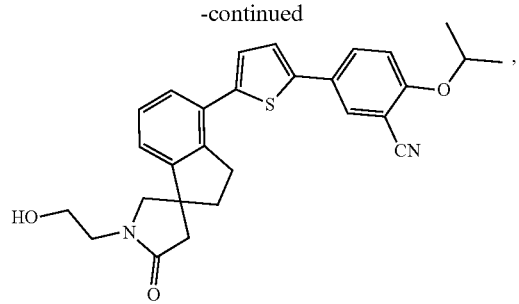
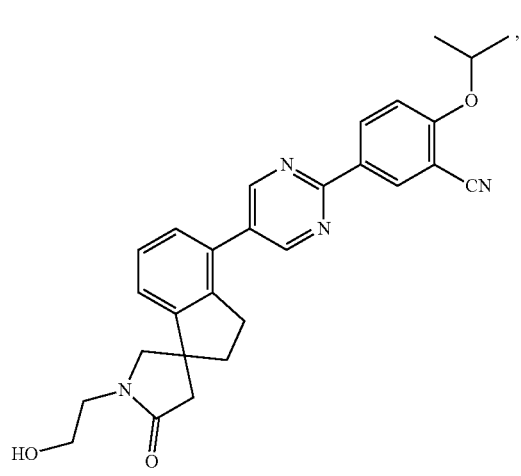
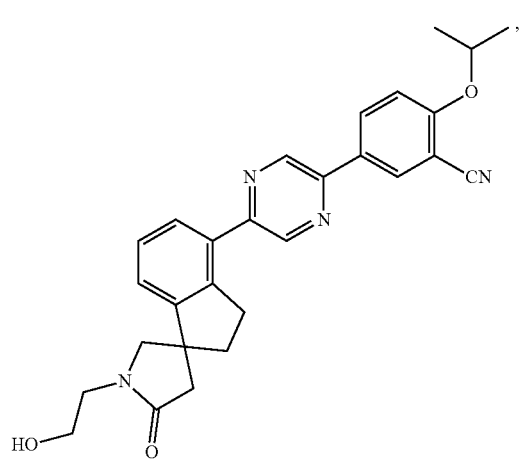
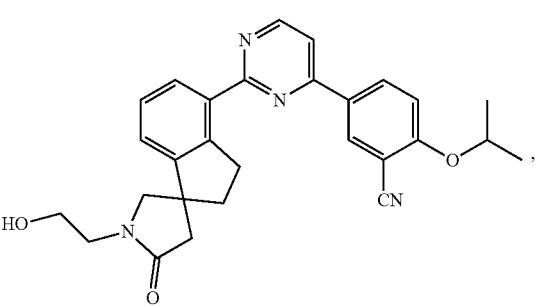
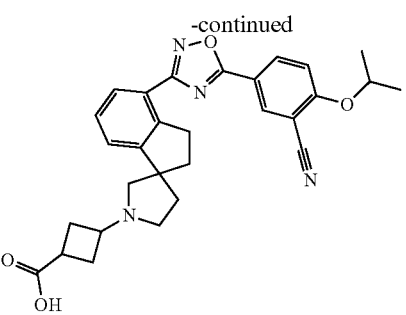
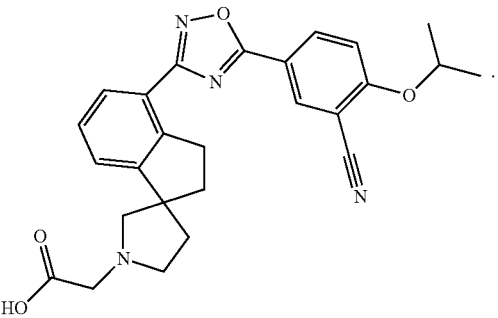 [SMILES: CC(C)Oc1ccc(-c2nc(-c3cccc4c3CCC43CCN(CC(=O)O)C3)no2)cc1C#N]
In some embodiments disclosed herein, the above compound, or the pharmaceutically acceptable salt thereof, is selected from the group consisting of
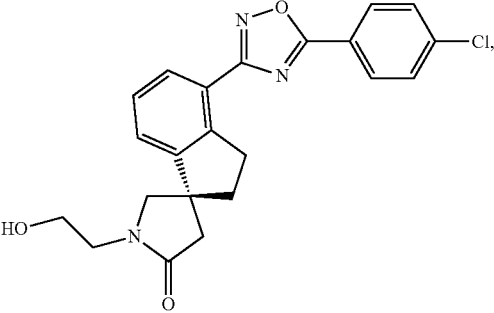
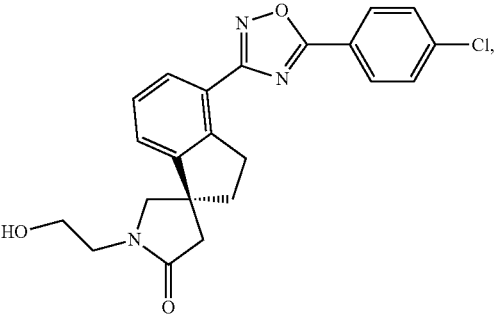
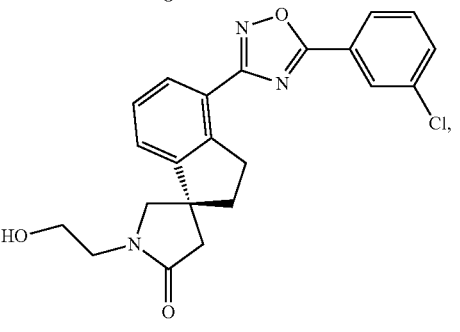

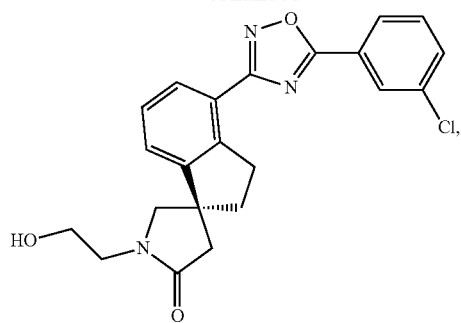
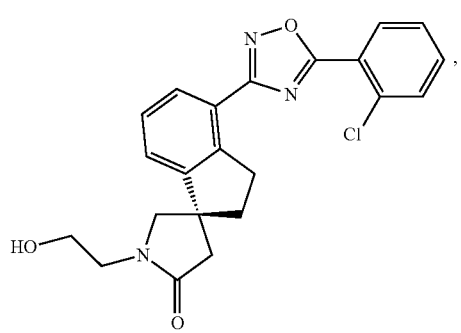
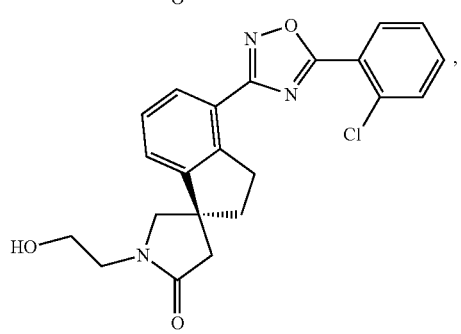

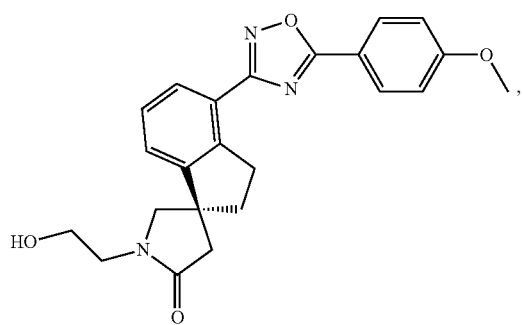
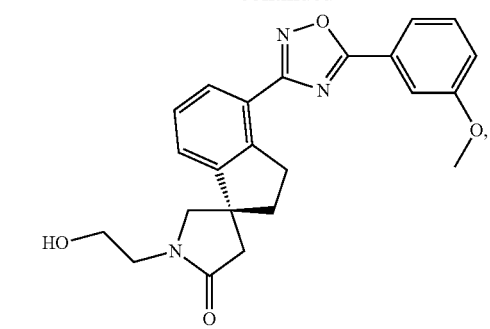
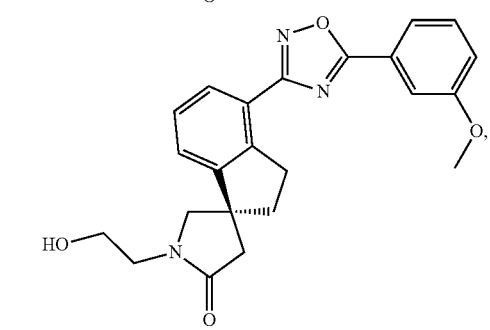
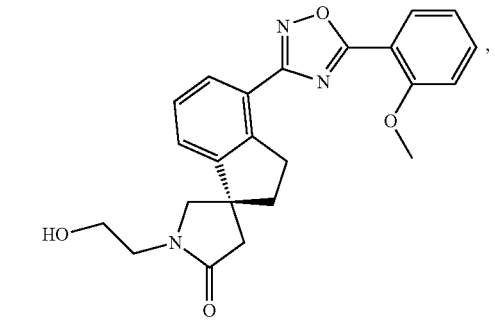
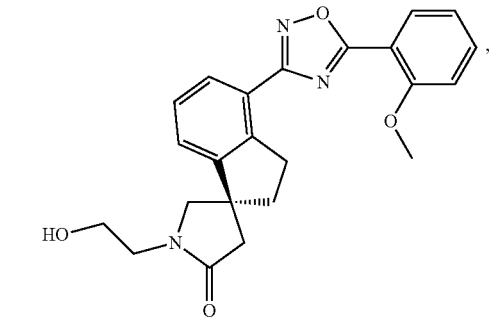
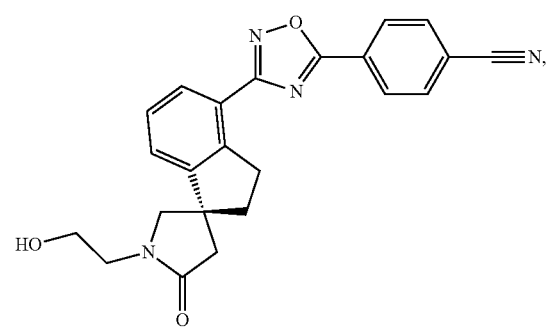

-continued
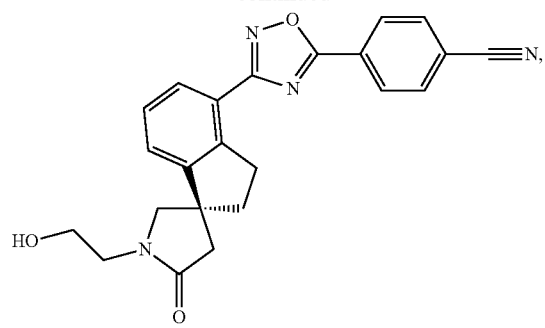

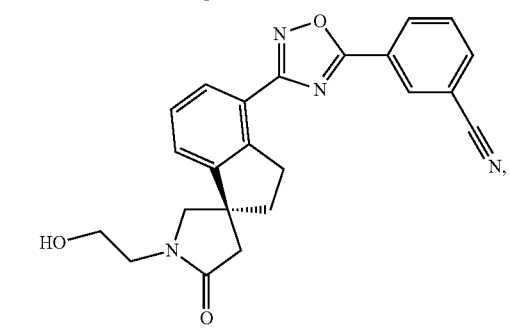
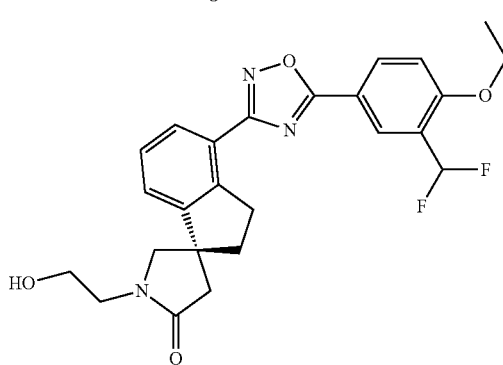
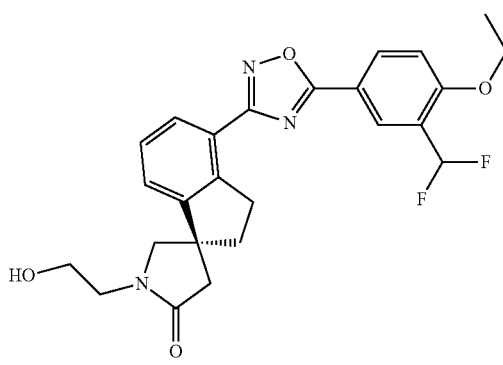
-continued
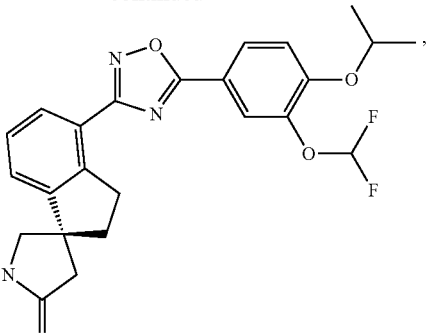
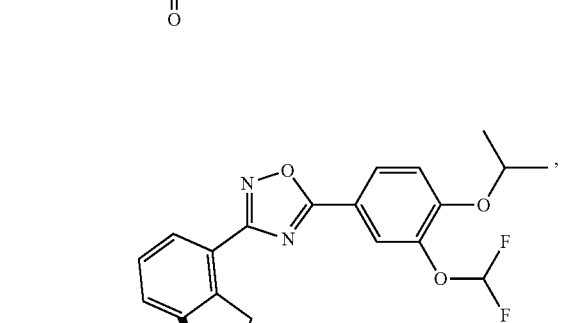
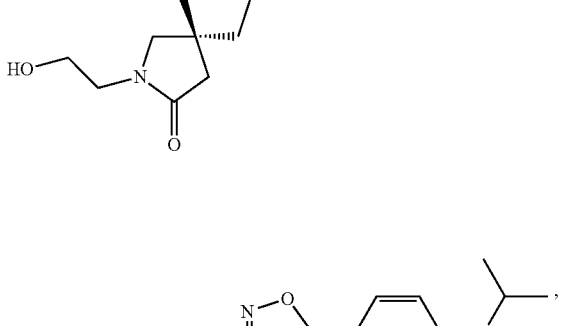
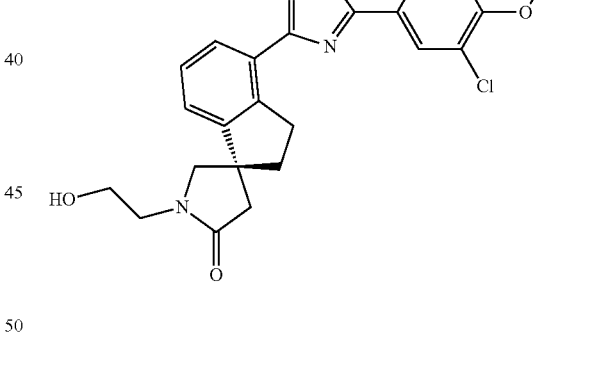
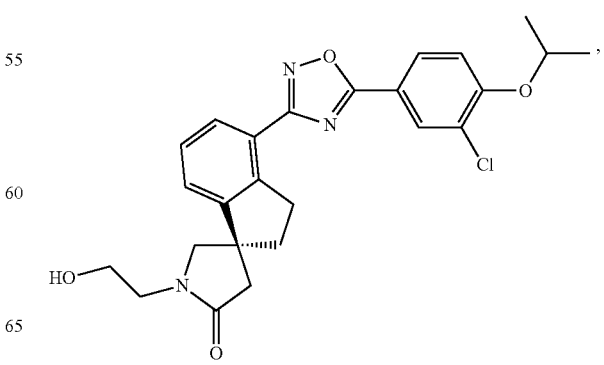

33
-continued
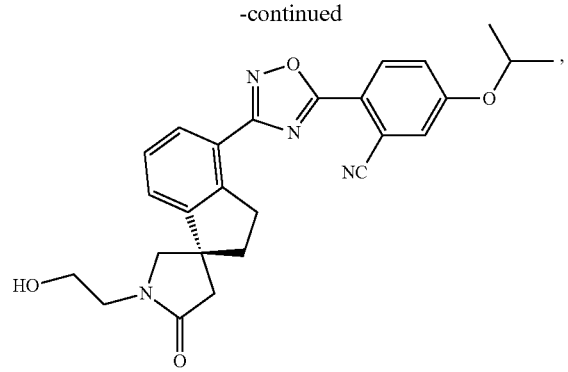
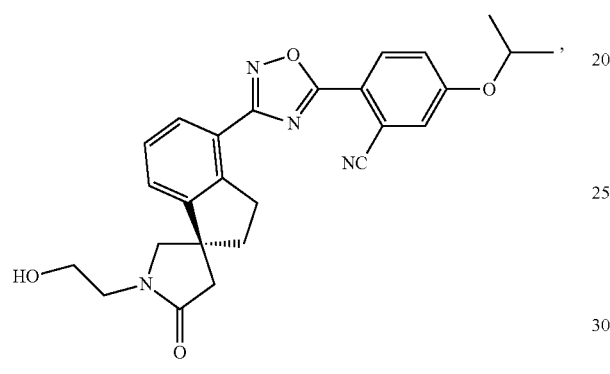
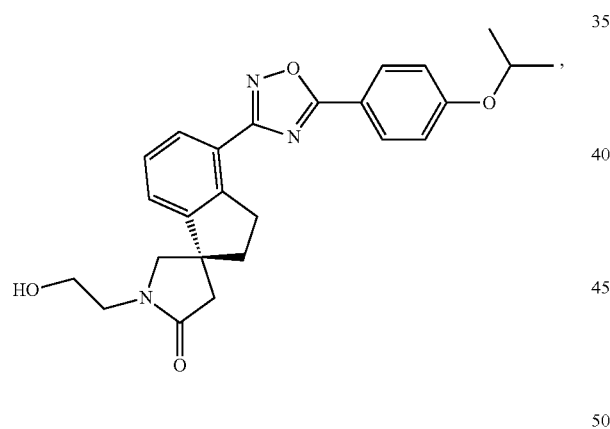
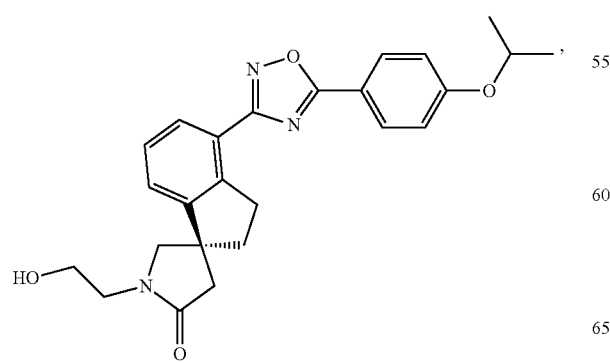
34
-continued
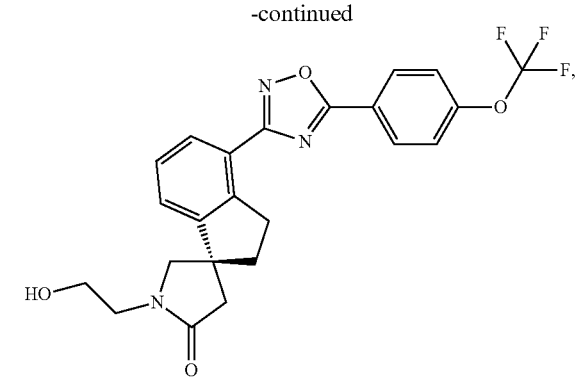
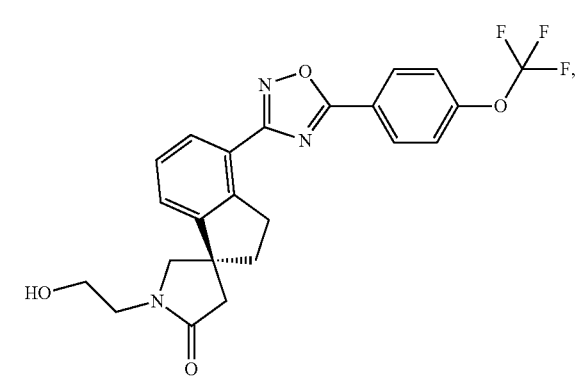
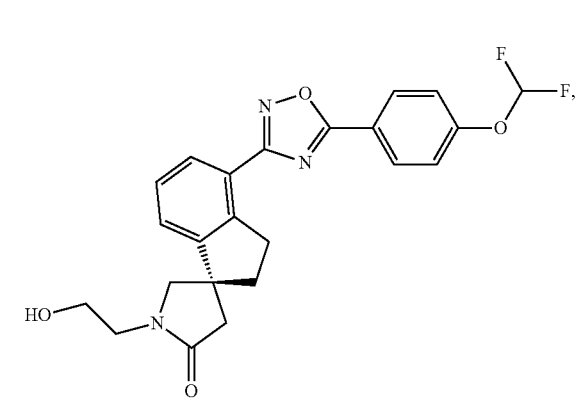
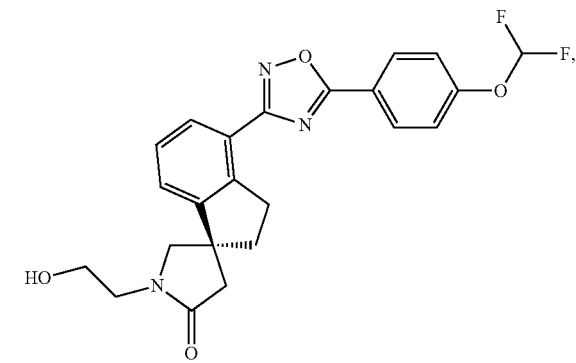

35
-continued

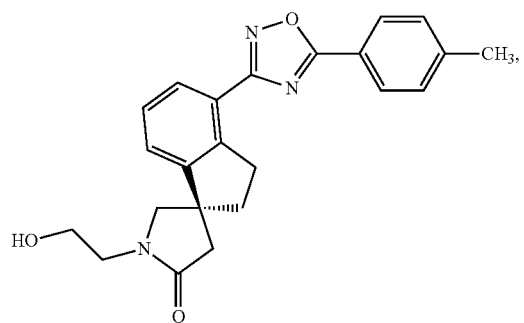
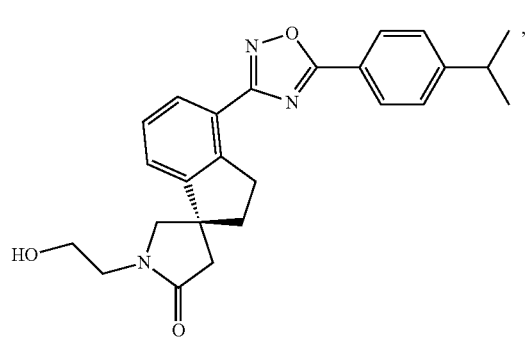
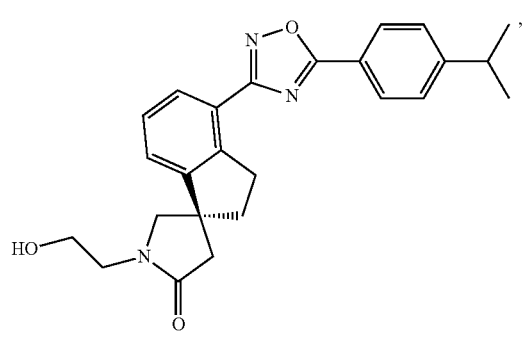
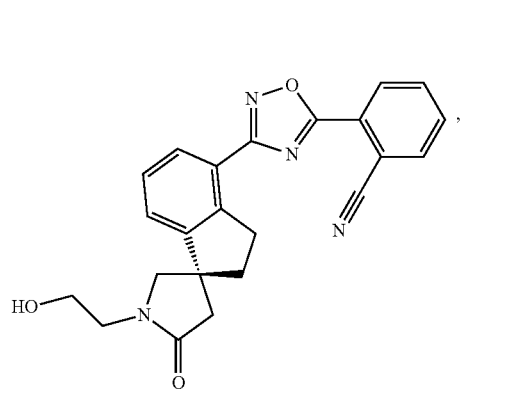
36
-continued
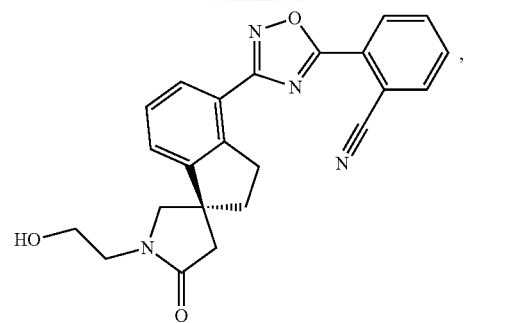
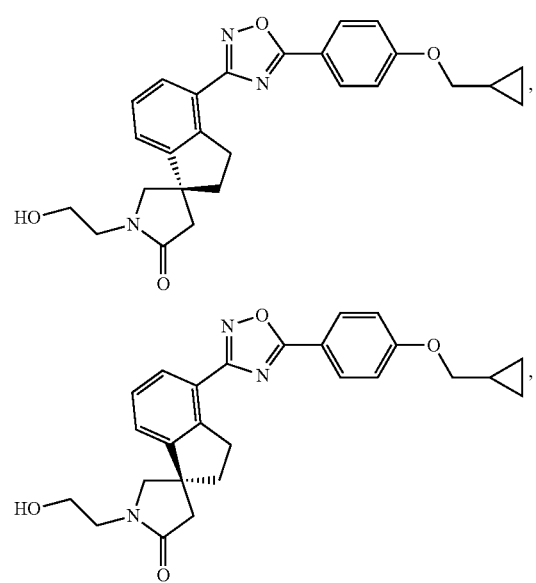
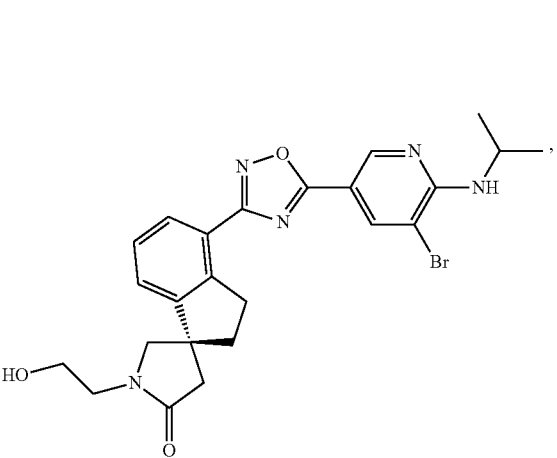

37
-continued
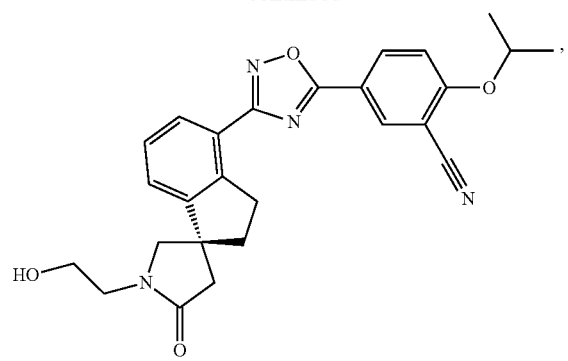
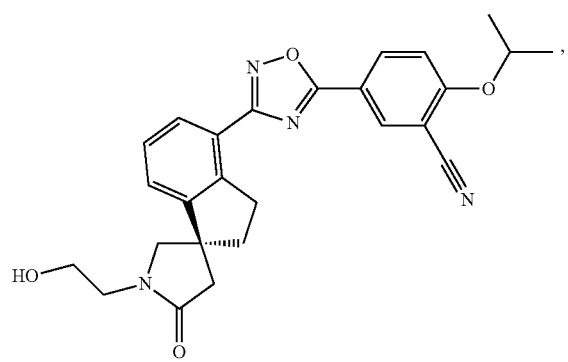
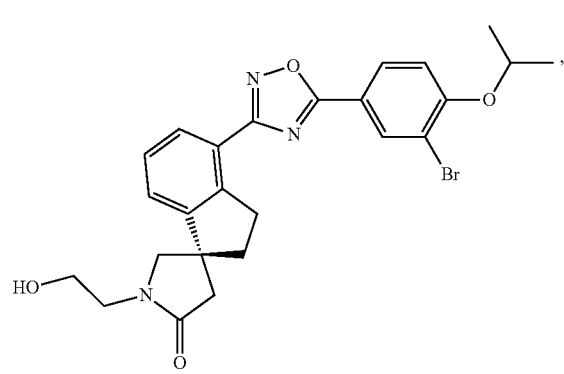
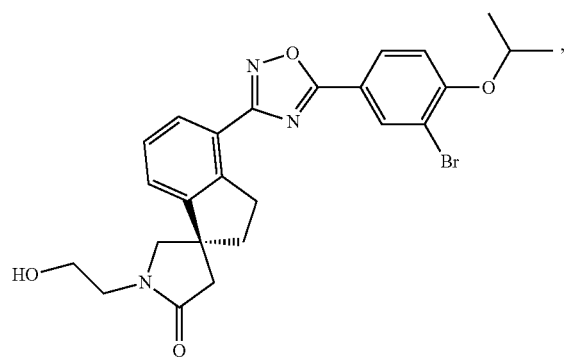
38
-continued
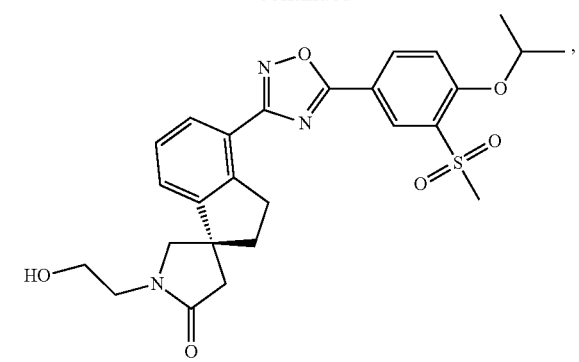
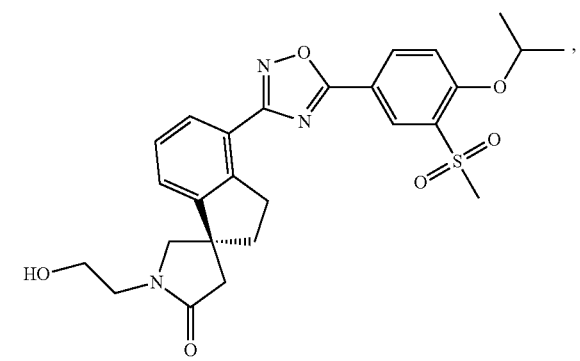
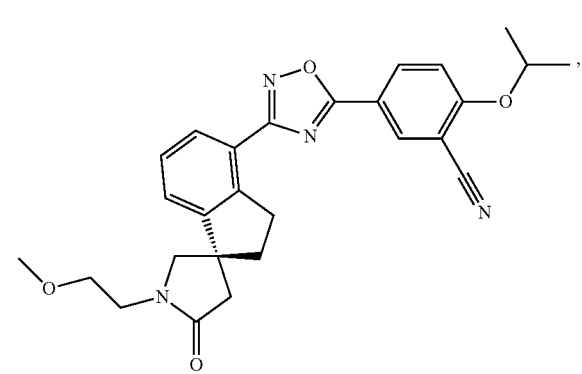
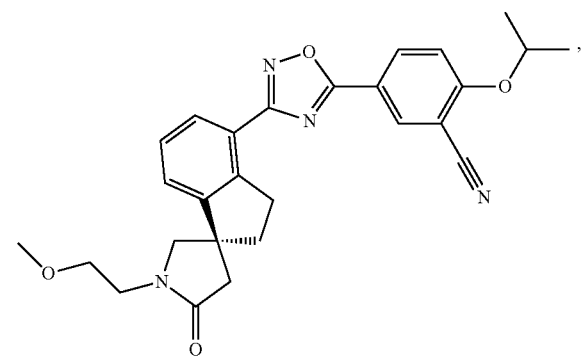

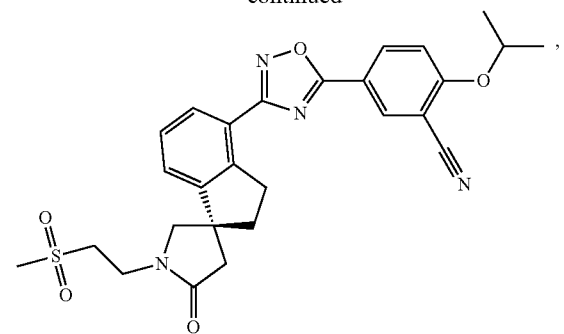
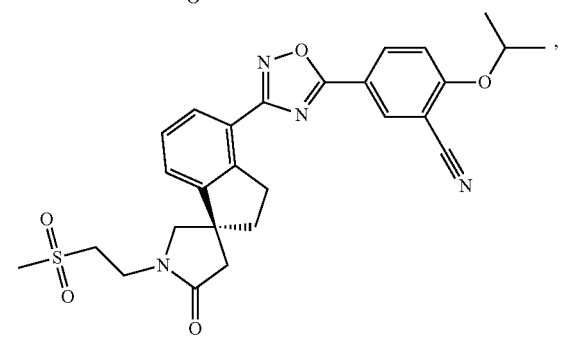
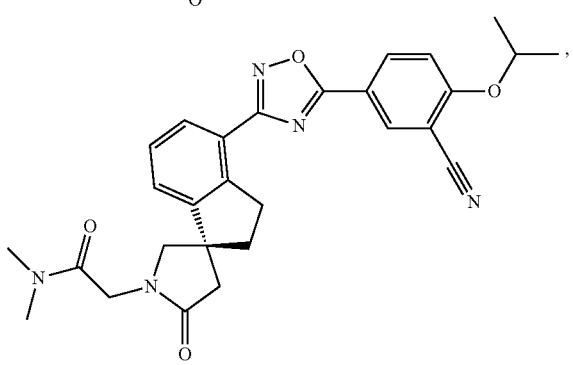
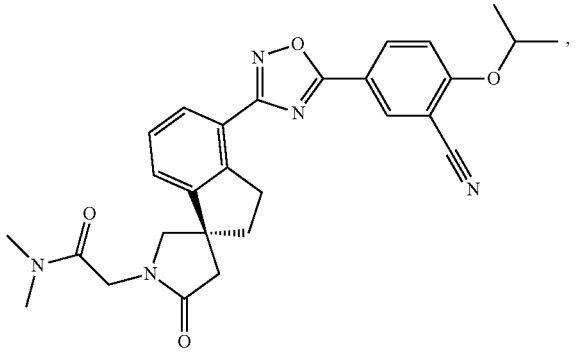
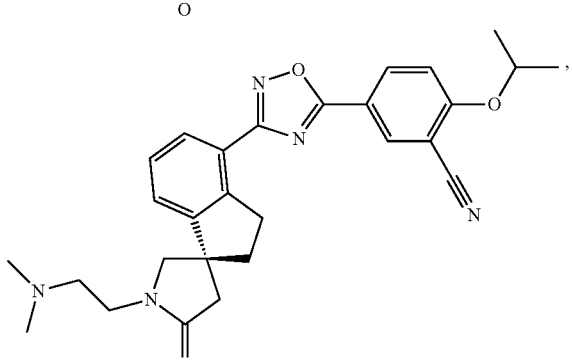

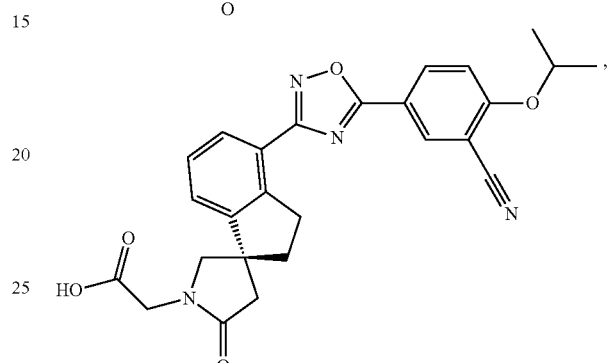
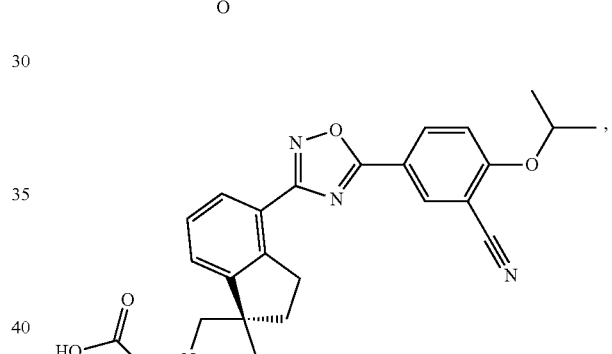
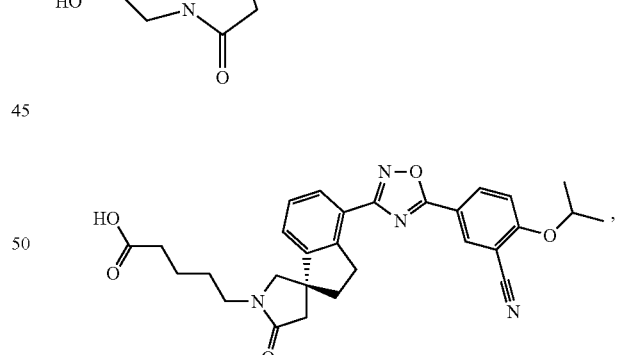
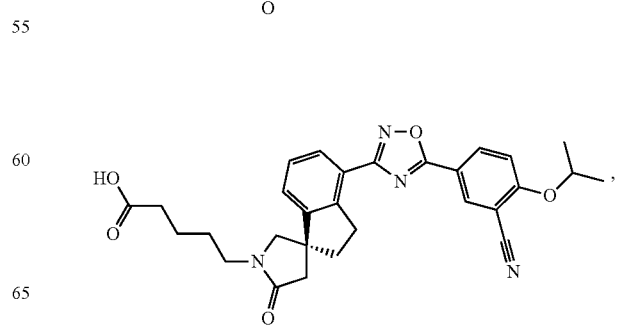

41
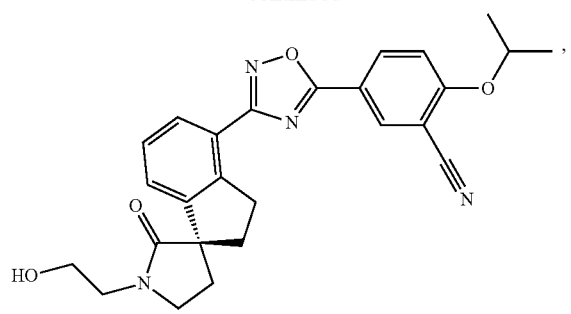,
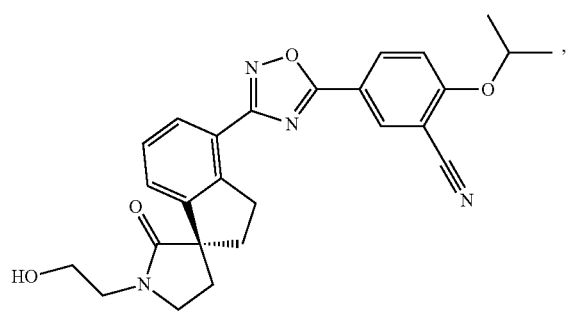,
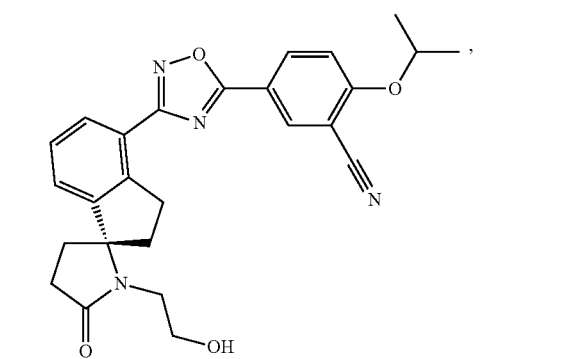,
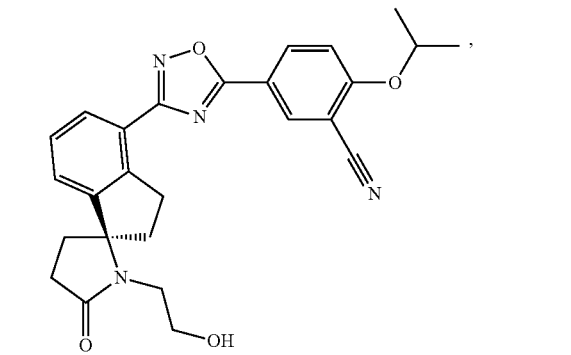,
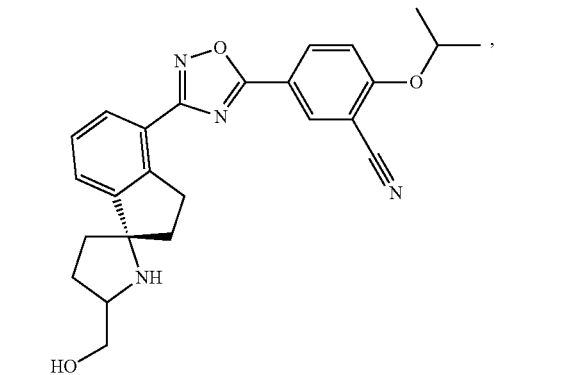,
42
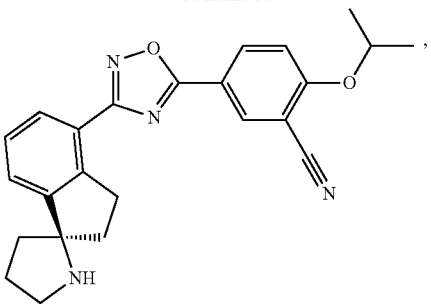,
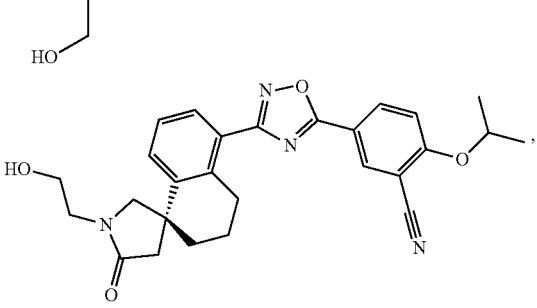,
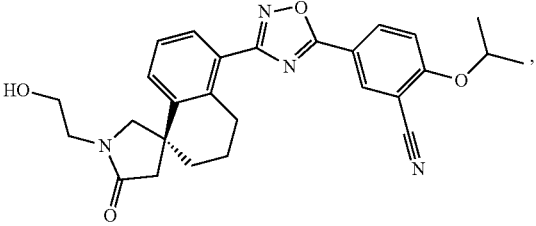,
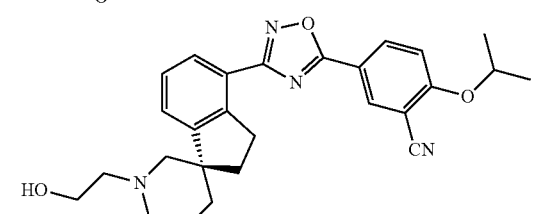,
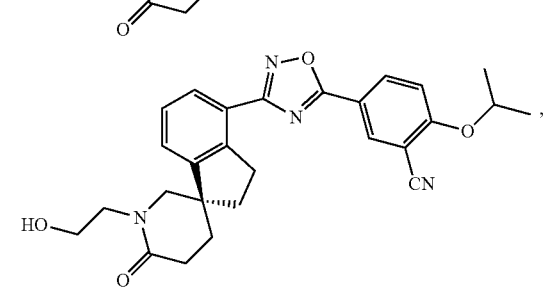,
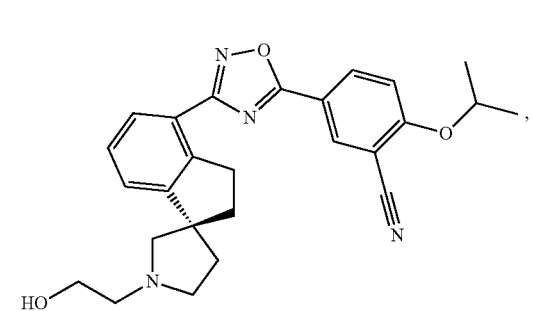, 43
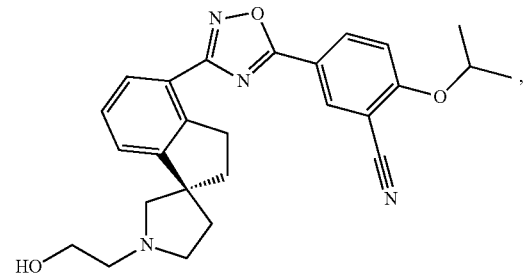
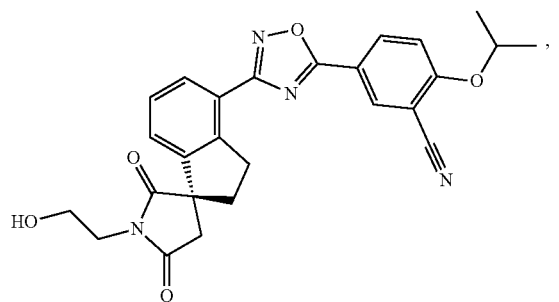
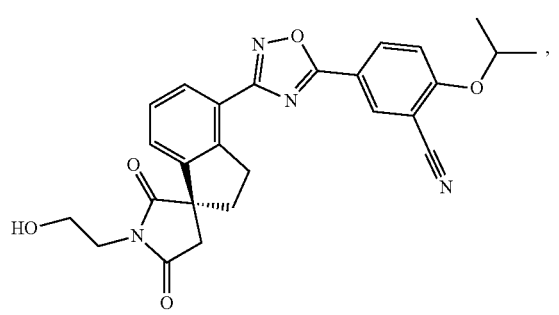
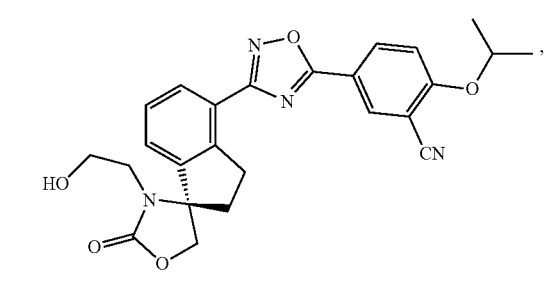
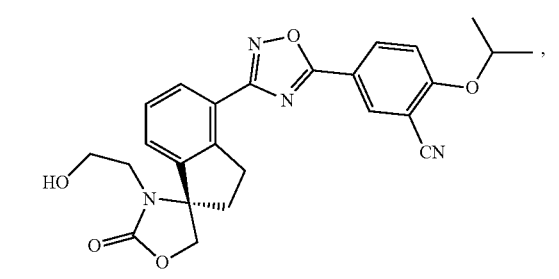
44
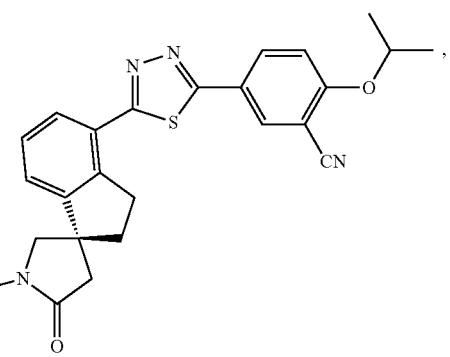
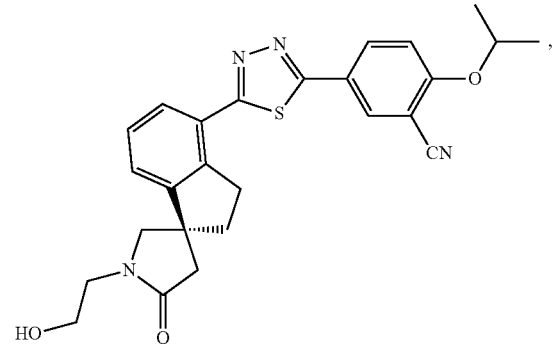
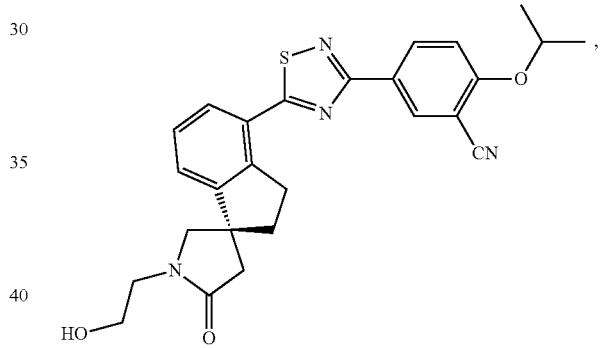
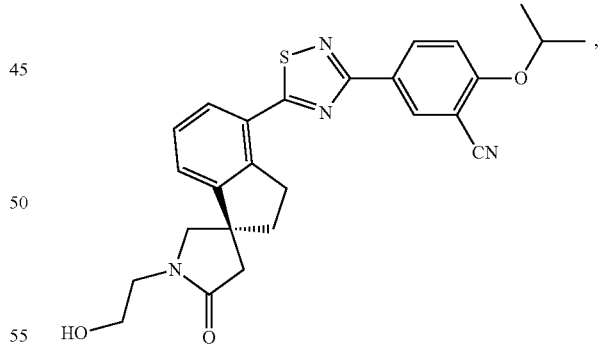
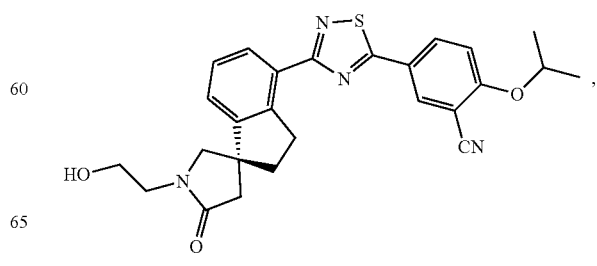

45
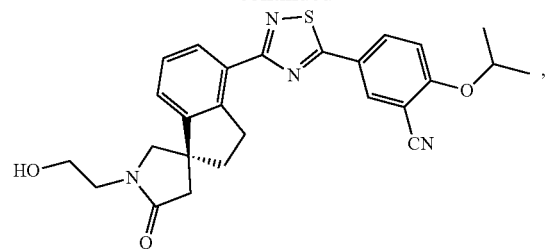
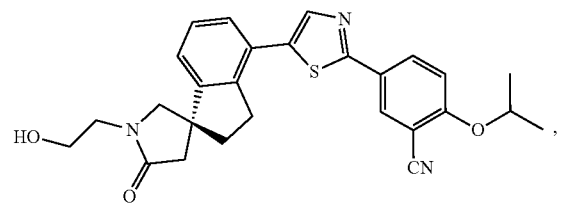
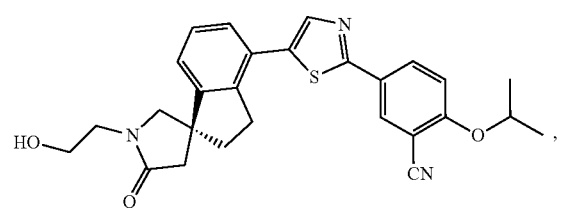
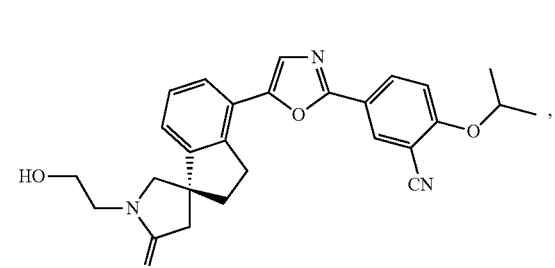
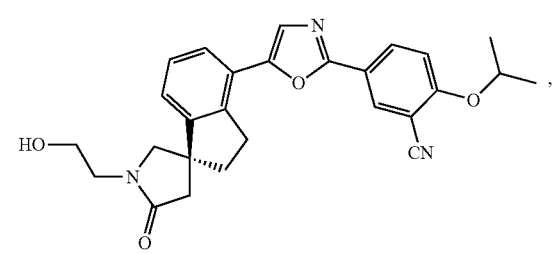
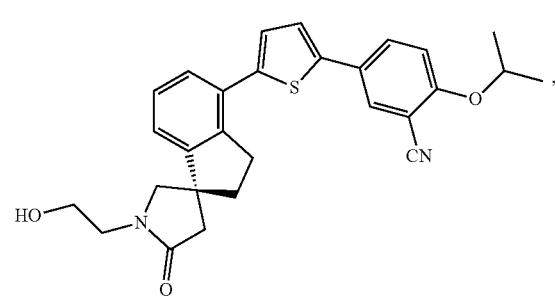
46
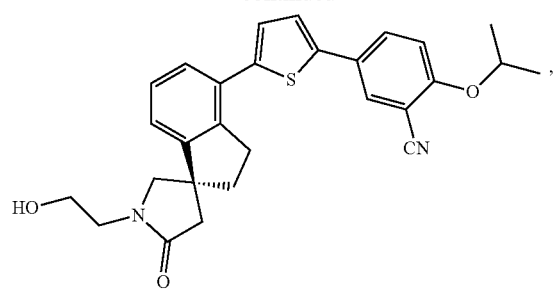
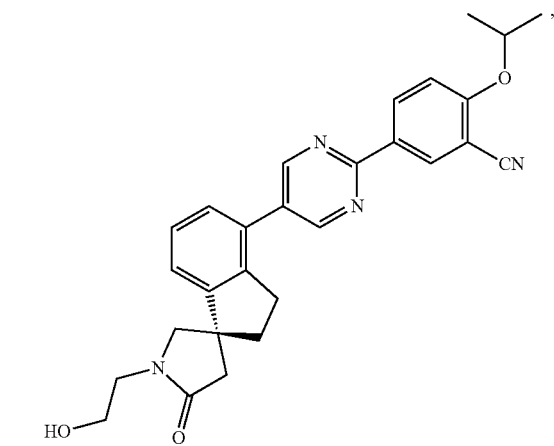
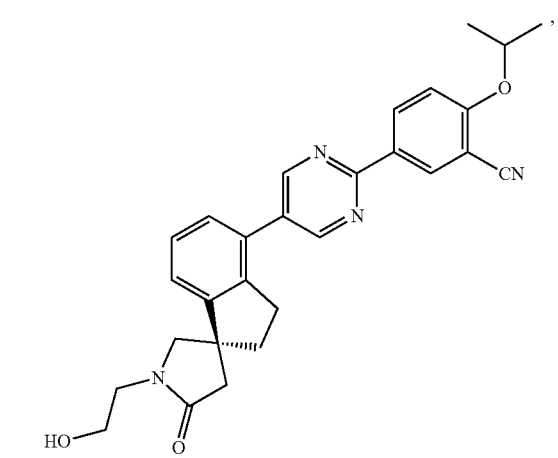
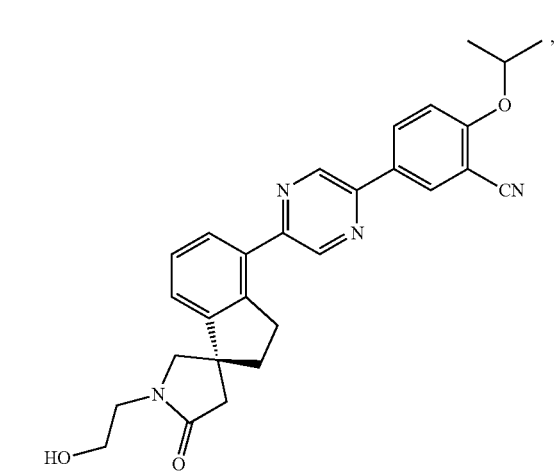

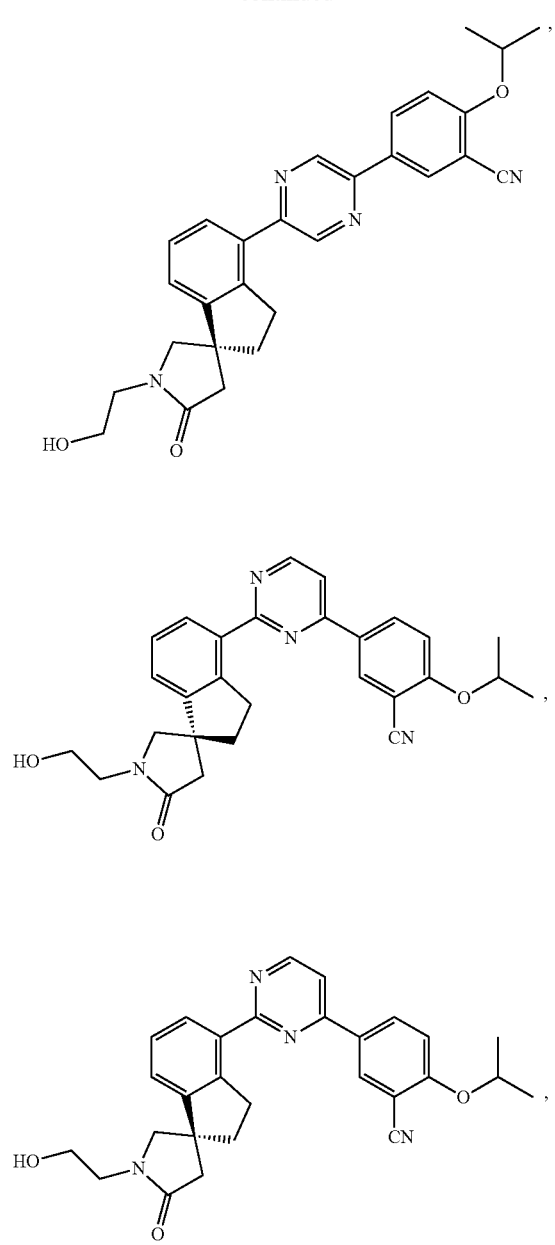

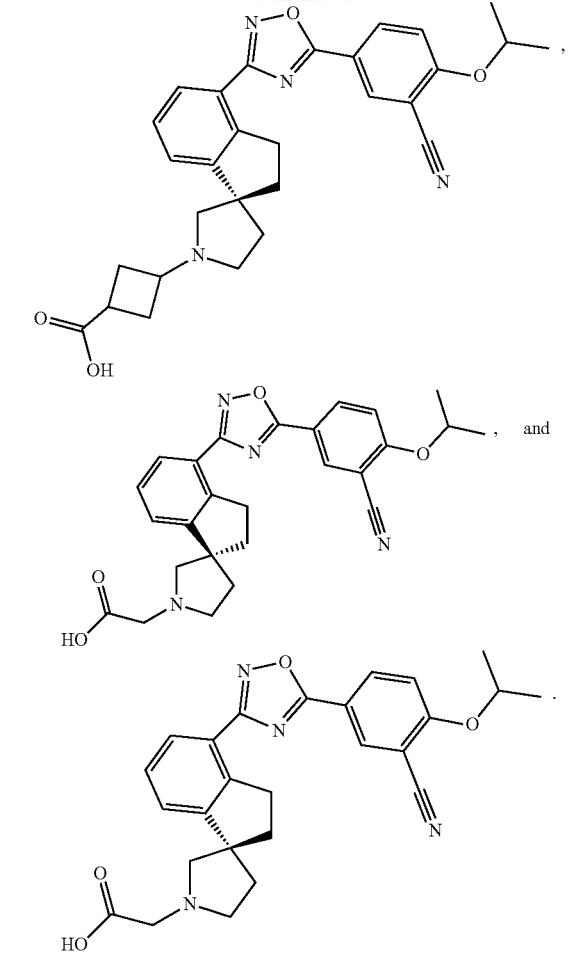

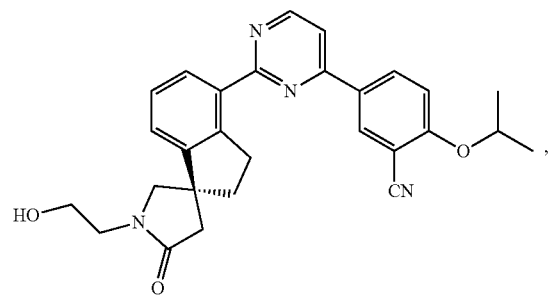

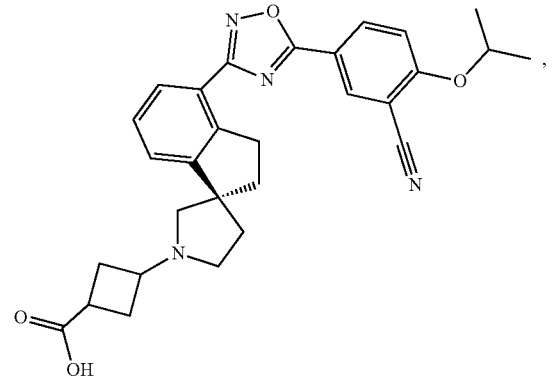

The present disclosure also provides a pharmaceutical composition comprising a therapeutically effective amount of the above compound or the pharmaceutically acceptable salt thereof as an active ingredient and pharmaceutically acceptable carriers.

The present disclosure also provides use of the above compound or the pharmaceutically acceptable salt thereof or the above composition in the manufacture of a medicament for treating a disease associated with S1P1 receptor.

Disclosed herein is a compound represented by formula (I), an optical isomer thereof or a pharmaceutically acceptable salt thereof,

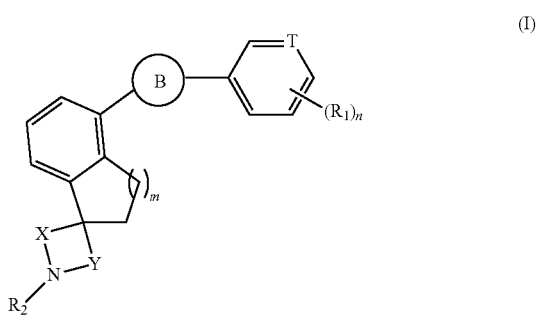

(I)

wherein
each R₁ is independently selected from the group consisting of H, F, Cl, Br, I, OH, NH₂ and CN, or is independently selected from the group consisting of C₁₋₆ alkyl and C₁₋₆ heteroalkyl, each of which is optionally substituted by 1, 2 or 3 R;

R₂ is H, or is selected from the group consisting of C₁₋₆ alkyl, C₁₋₆ heteroalkyl and C₃₋₆ cycloalkyl, each of which is optionally substituted by 1, 2 or 3 R;

T is N or CH;

moiety

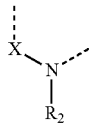

is selected from the group consisting of

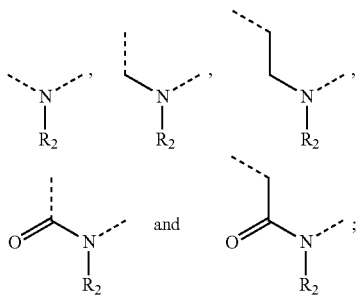

moiety

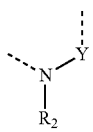

is selected from the group consisting of

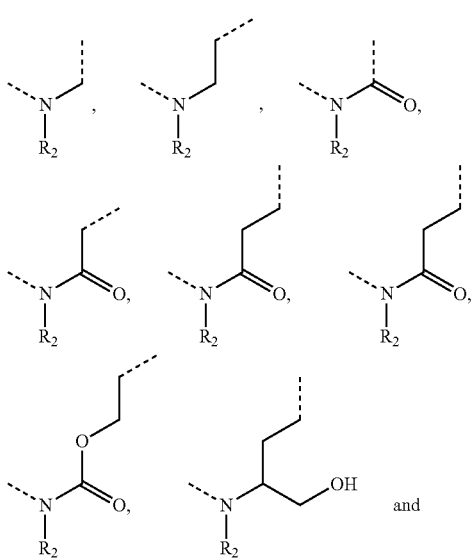

-continued

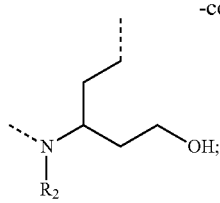

ring B is selected from the group consisting of phenyl and 5- to 6-membered heteroaryl;

m is 1 or 2;

n is 0, 1, 2 or 3;

R is selected from the group consisting of F, Cl, Br, I, OH, NH₂, CN and COOH, or is selected from the group consisting of C₁₋₆ alkyl, C₁₋₆ alkoxy, N,N-di(C₁₋₆ alkyl)amino and C₃₋₆ cycloalkyl;

the heteroatom or the heteroatom group of the C₁₋₆ heteroalkyl and the 5- to 6-membered heteroaryl are each independently selected from the group consisting of N, O, S, NH, —NHC(=O)—, —S(=O)— and —S(=O)₂—; and the number of the heteroatom or the heteroatom group is 1, 2, 3 or 4.

In some embodiments disclosed herein, in the above compound, the optical isomer thereof, or the pharmaceutically acceptable salt thereof, R is selected from the group consisting of F, Cl, Br, I, OH, NH₂, CN, COOH, Me, Et, N(CH₃)₂,

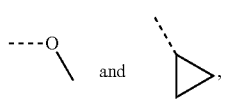

and other variables are as defined above.

In some embodiments disclosed herein, in the above compound, the optical isomer thereof, or the pharmaceutically acceptable salt thereof, R₁ is each independently selected from the group consisting of H, F, Cl, Br, I, OH, NH₂ and CN, or is independently selected from the group consisting of C₁₋₃ alkyl, C₁₋₃ alkoxy, C₁₋₃ alkylamino and C₁₋₃ alkyl-S(=O)₂—, each of which is optionally substituted by 1, 2 or 3 R, and other variables are as defined above.

In some embodiments disclosed herein, in the above compound, the optical isomer thereof, or the pharmaceutically acceptable salt thereof, R₁ is each independently selected from the group consisting of H, F, Cl, Br, I, OH, NH₂ and CN, or is independently selected from the group consisting of Me, Et,

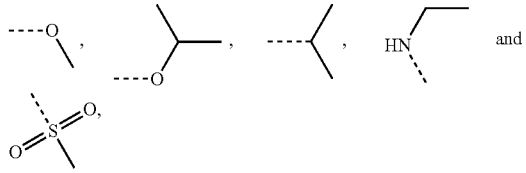

each of which is optionally substituted by 1, 2 or 3 R, and other variables are as defined above.

In some embodiments disclosed herein, in the above compound, the optical isomer thereof, or the pharmaceutically acceptable salt thereof, R₁ is each independently selected from the group consisting of H, F, Cl, Br, I, OH, NH$_2$, CN, Me, Et,

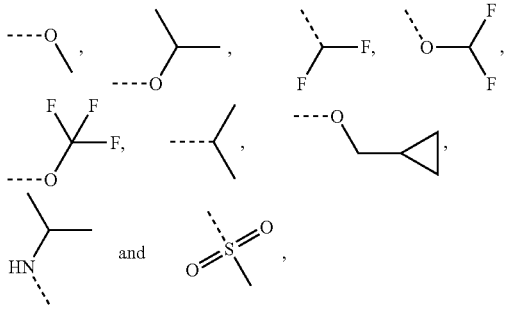

and other variables are as defined above.

In some embodiments disclosed herein, in the above compound, the optical isomer thereof, or the pharmaceutically acceptable salt thereof, R$_2$ is selected from the group consisting of C$_{1-4}$ alkyl, C$_{1-3}$ alkyl-O—C$_{1-3}$ alkyl-, C$_{1-3}$ alkyl-S(=O)$_2$—C$_{1-3}$ alkyl-, C$_{1-3}$ alkyl-NH—C$_{1-3}$ alkyl-, C$_{1-3}$ alkyl-NHC(=O)—C$_{1-3}$ alkyl- and C$_{3-6}$cycloalkyl, each of which is optionally substituted by 1, 2 or 3 R, and other variables are as defined above.

In some embodiments disclosed herein, in the above compound, the optical isomer thereof, or the pharmaceutically acceptable salt thereof, R$_2$ is selected from the group consisting of Me, Et,

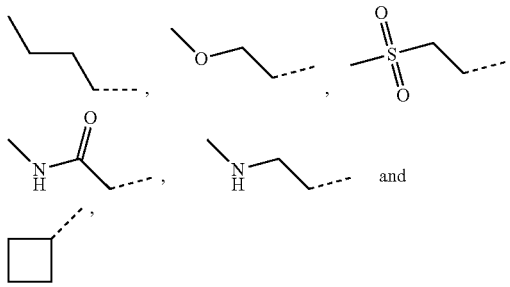

each of which is optionally substituted by 1, 2 or 3 R, and other variables are as defined above.

In some embodiments disclosed herein, in the above compound, the optical isomer thereof, or the pharmaceutically acceptable salt thereof, R$_2$ is selected from the group consisting of

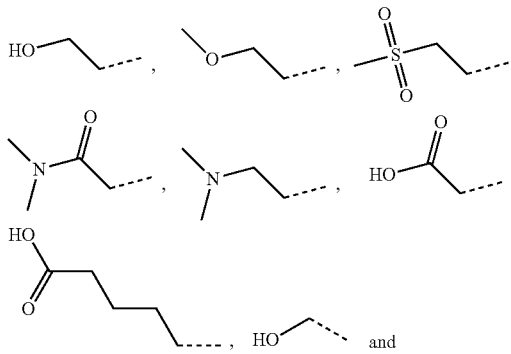

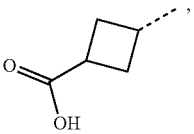

and other variables are as defined above.

In some embodiments disclosed herein, in the above compound, the optical isomer thereof, or the pharmaceutically acceptable salt thereof, the moiety ring

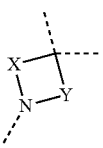

is selected from the group consisting of

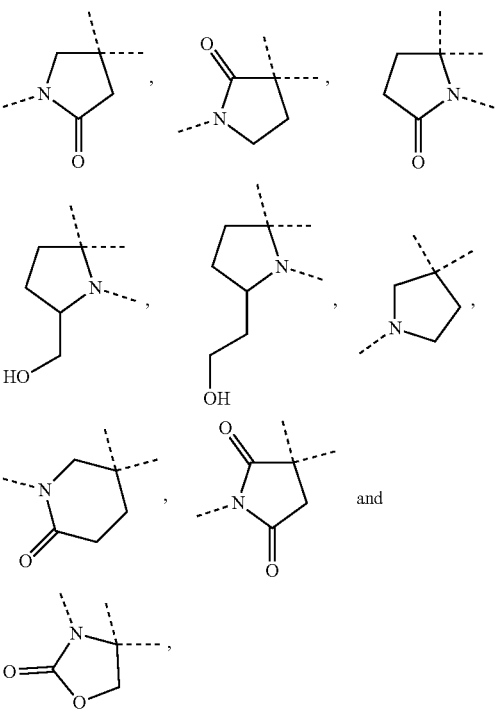

and other variables are as defined above.

In some embodiments disclosed herein, in the above compound, the optical isomer thereof, or the pharmaceutically acceptable salt thereof, the ring B is selected from the group consisting of 1,2,4-oxadiazolyl, 1,2,4-thiadiazolyl, pyrazinyl, thiazolyl, oxazolyl and pyrimidinyl, and other variables are as defined above.

In some embodiments disclosed herein, in the above compound, the optical isomer thereof, or the pharmaceuti cally acceptable salt thereof, the ring B is selected from the group consisting of

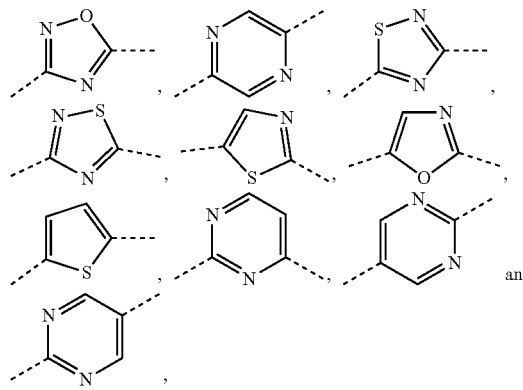

and other variables are as defined above.

In some embodiments disclosed herein, in the above compound, the optical isomer thereof, or the pharmaceutically acceptable salt thereof, the moiety

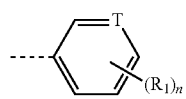

is selected from the group consisting of

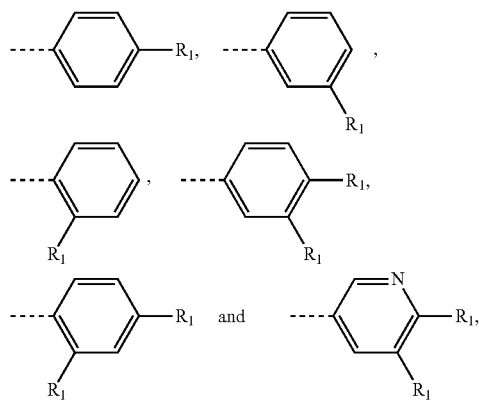

and other variables are as defined above.

In some embodiments disclosed herein, in the above compound, the optical isomer thereof, or the pharmaceutically acceptable salt thereof, the moiety

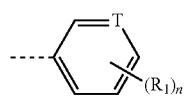

is selected from the group consisting of

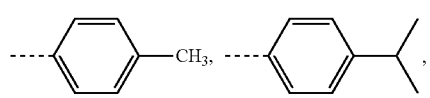

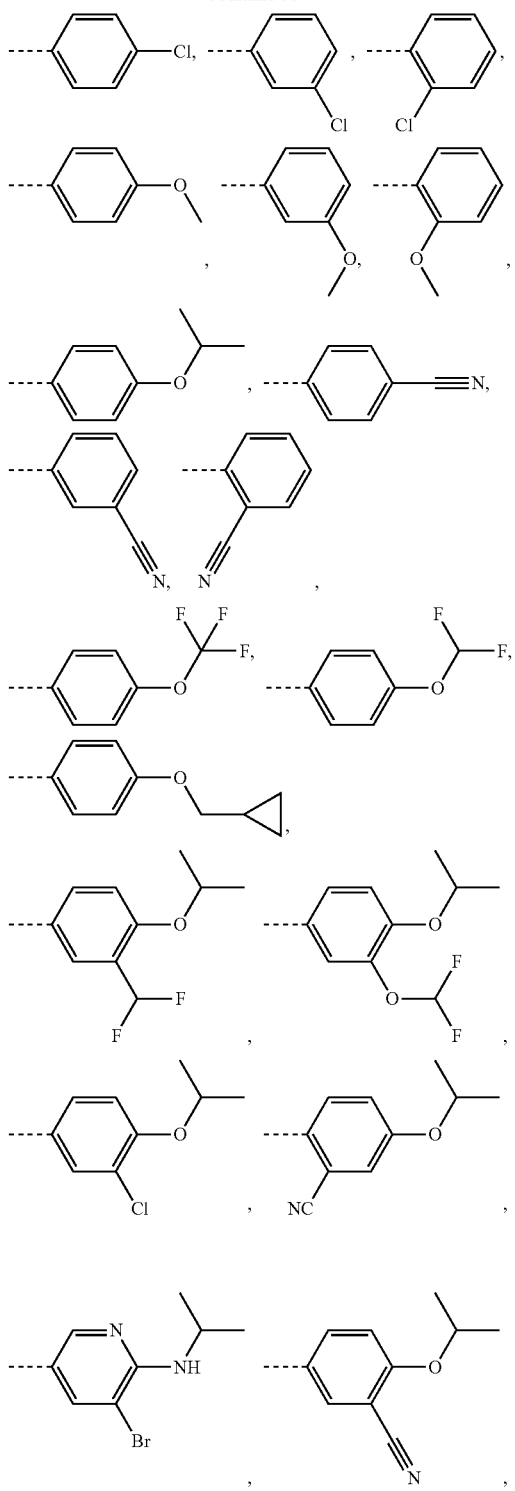

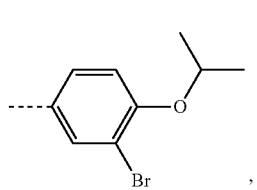

-continued

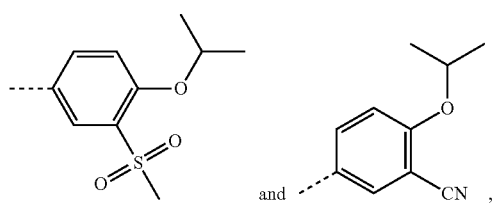

and other variables are as defined above.

In some embodiments disclosed herein, in the above compound, the optical isomer thereof, or the pharmaceutically acceptable salt thereof, the moiety

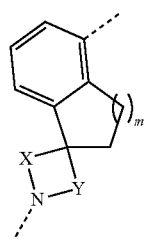

is selected from the group consisting of

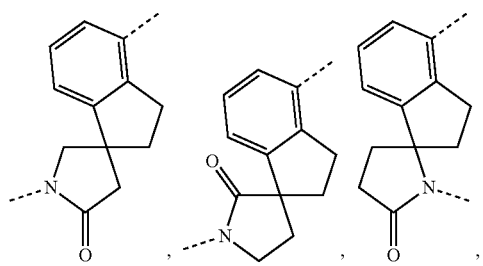

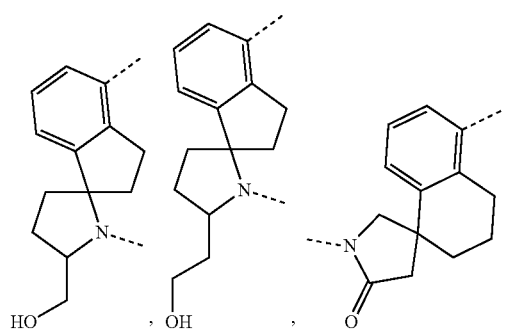

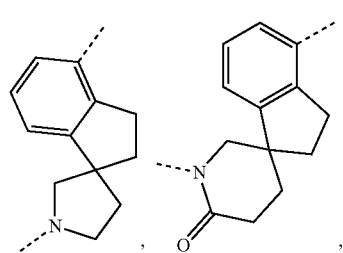

-continued

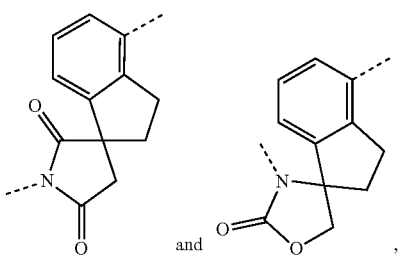

and other variables are as defined above.

In some embodiments disclosed herein, in the above compound, the optical isomer thereof, or the pharmaceutically acceptable salt thereof, the moiety

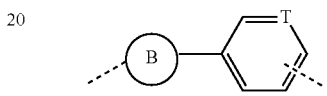

is selected from the group consisting of

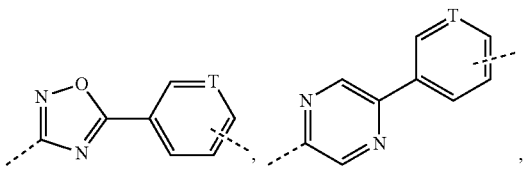

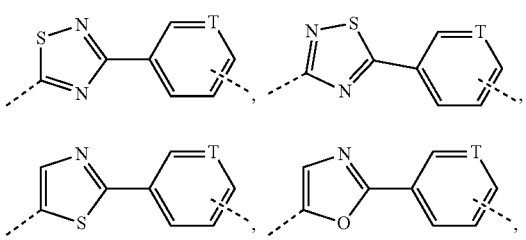

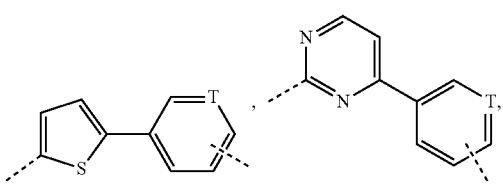

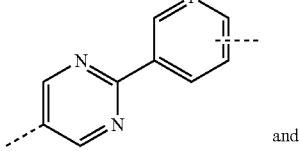

and

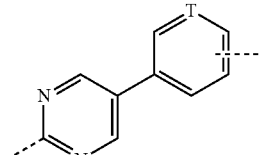

and other variables are as defined above.

In some embodiments disclosed herein, the above compound, the optical isomer thereof, or the pharmaceutically acceptable salt thereof, is selected from the group consisting of

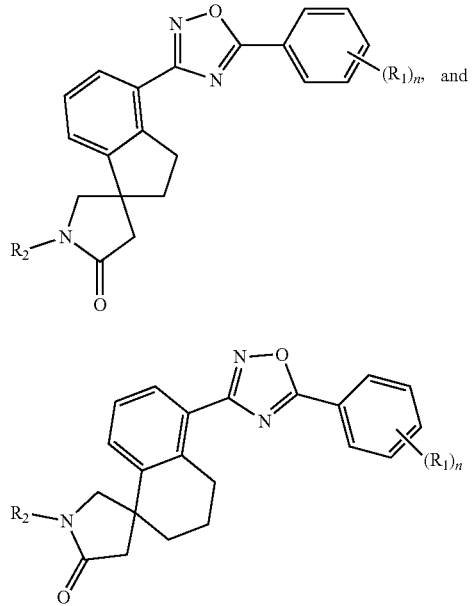

(I-1)

(I-2)

wherein n, $R_1$ and $R_2$ are as defined above.

In some embodiments disclosed herein, the above compound, the optical isomer thereof, or the pharmaceutically acceptable salt thereof, is selected from the group consisting of

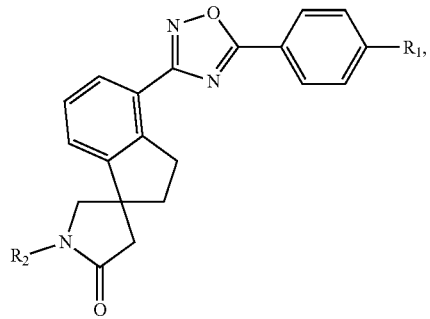

(II-1)

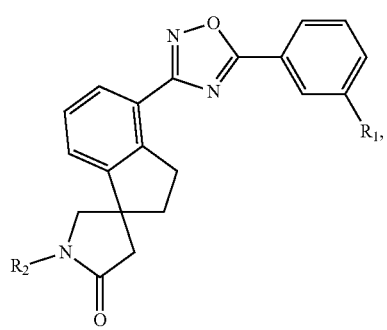

(II-2)

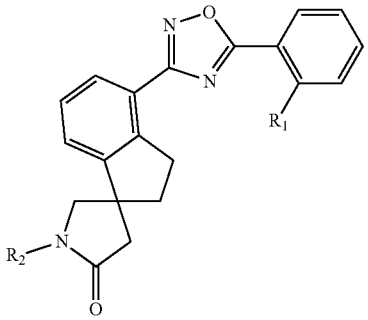

(II-3)

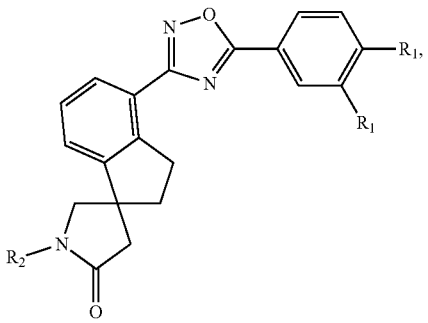

(II-4)

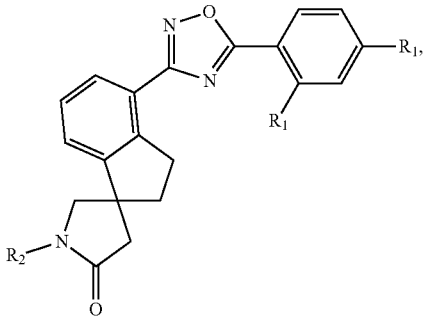

(II-5)

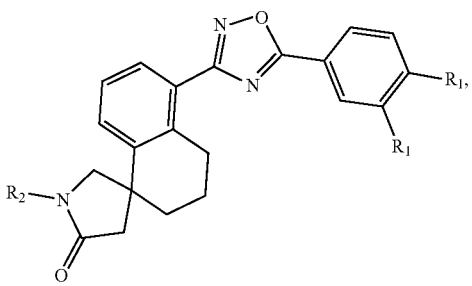

(II-6)

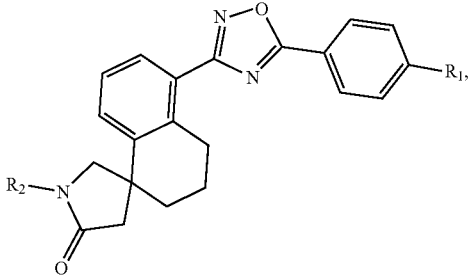

(II-7)

-continued
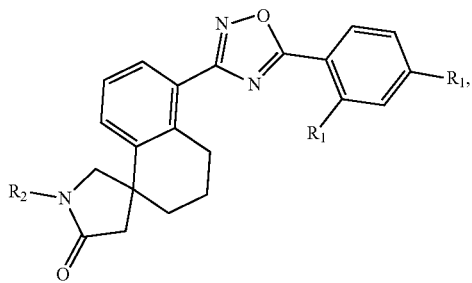
(II-8)
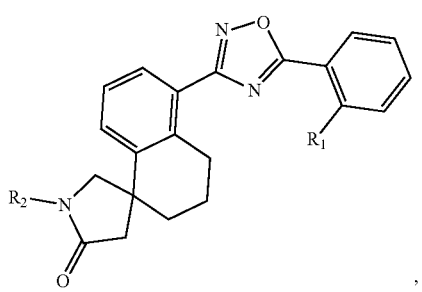
(II-9)
, and
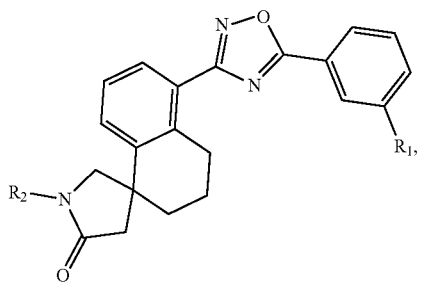
(II-10)
wherein R₁ and R₂ are as defined above.
The present disclosure also provides a compound represented by the following formula, an optical isomer thereof or a pharmaceutically acceptable salt thereof, which is selected from the group consisting of
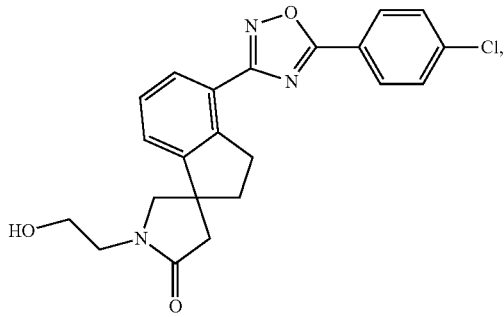
-continued
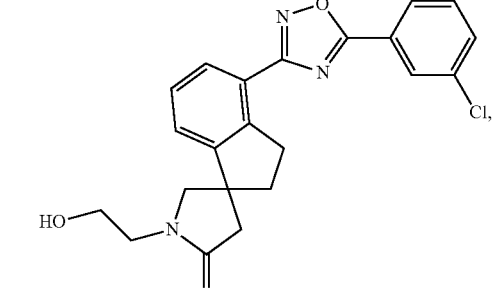
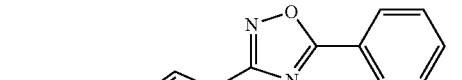
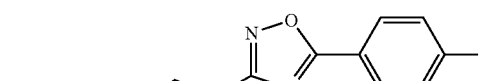
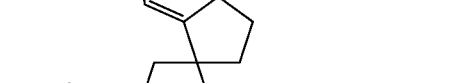
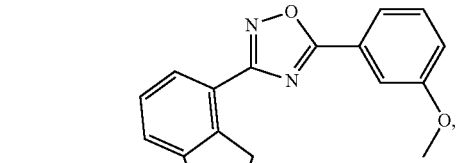
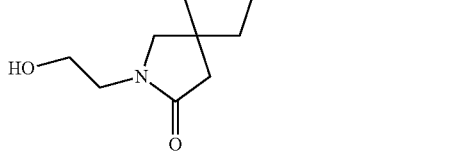
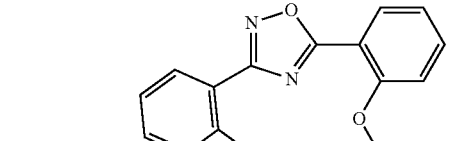
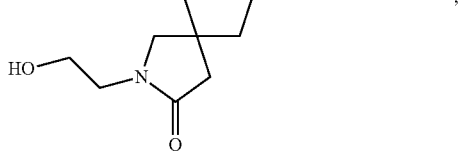

61
-continued
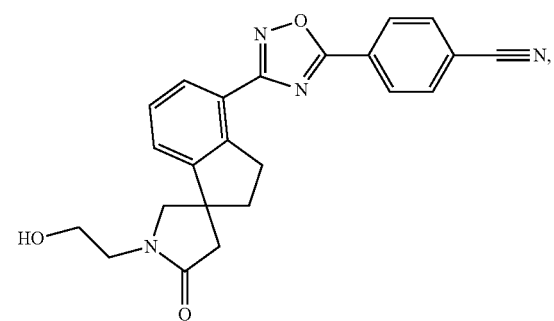
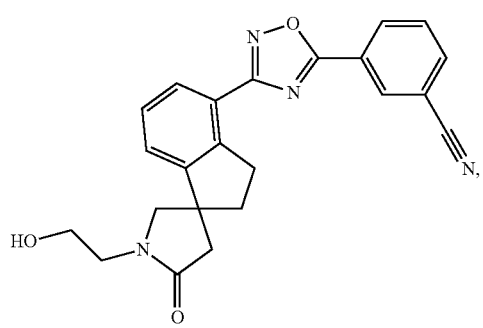
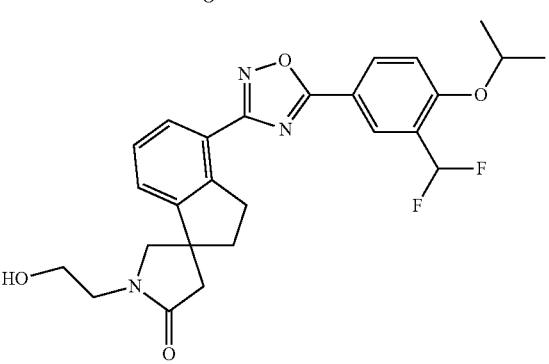
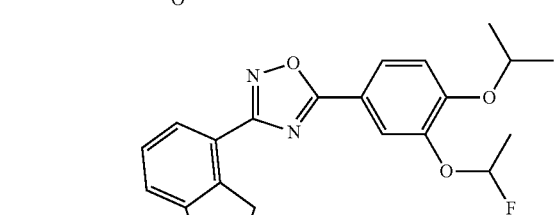
62
-continued
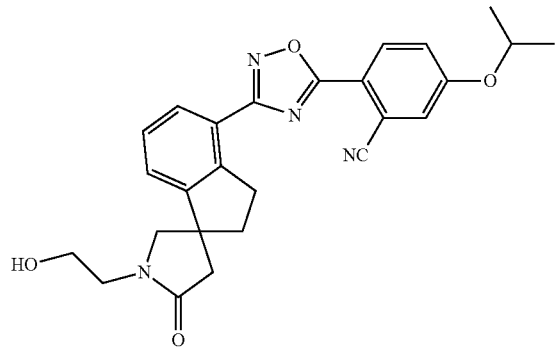
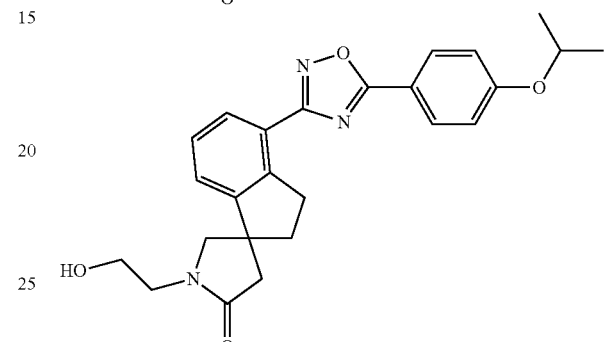
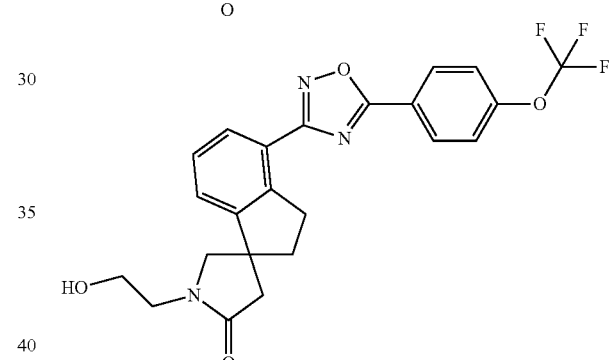
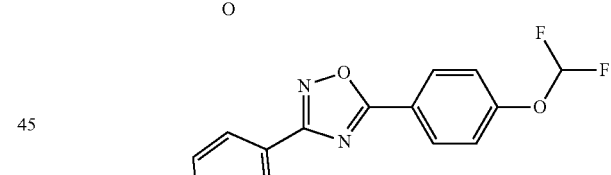
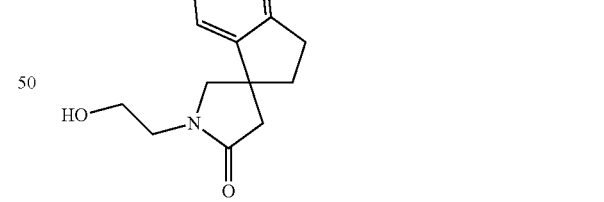
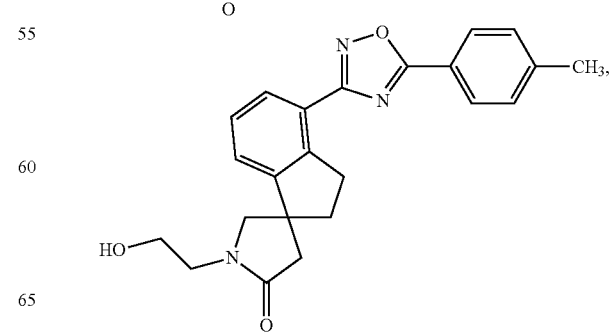

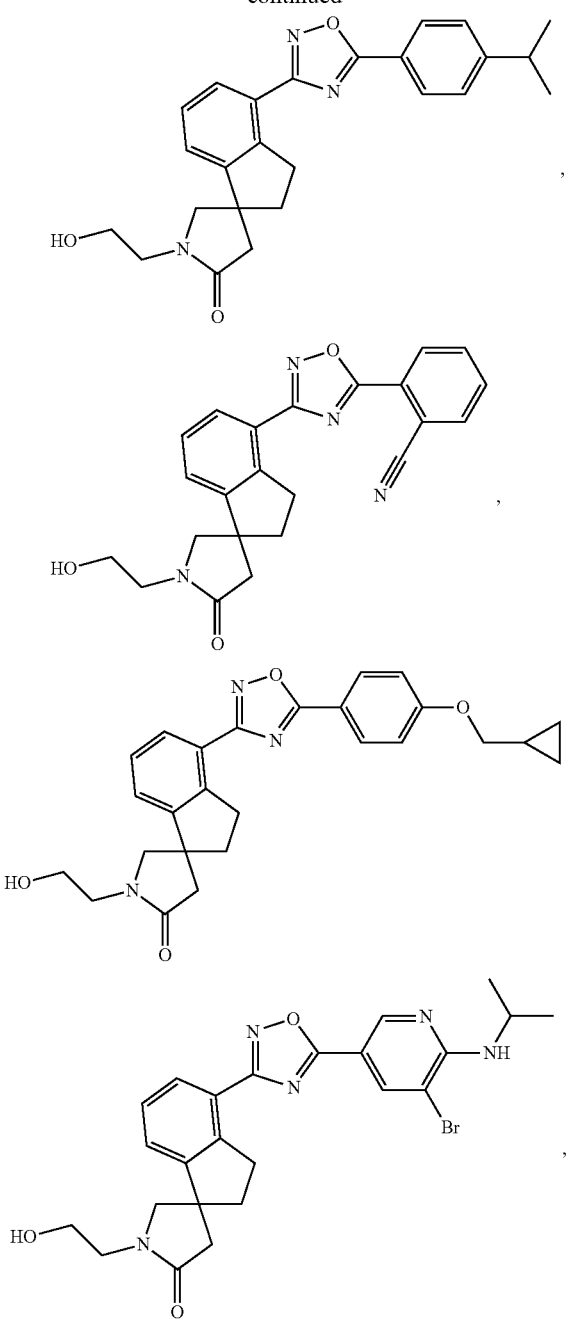
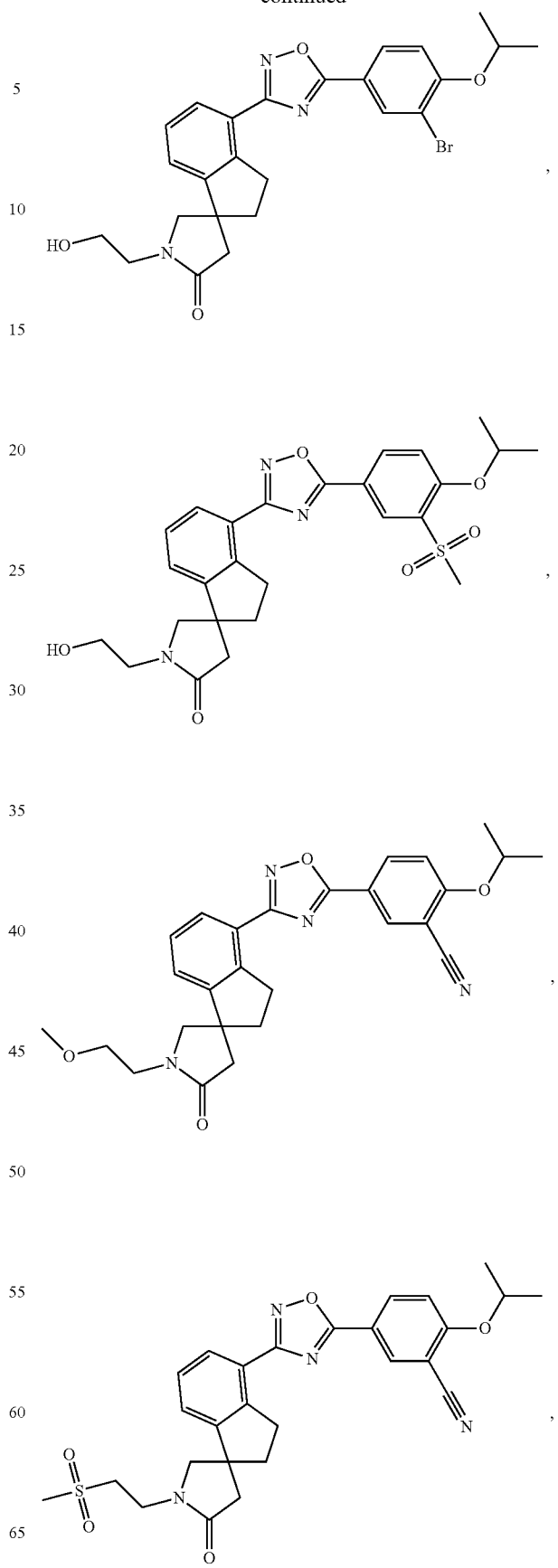

65
-continued
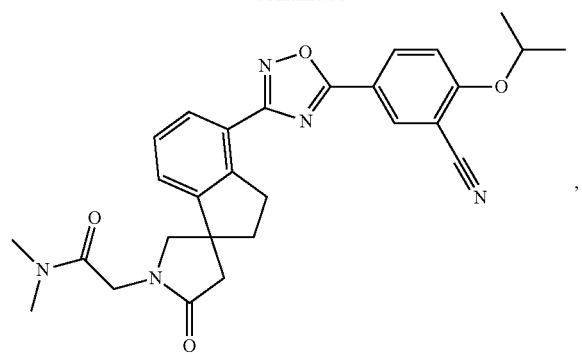
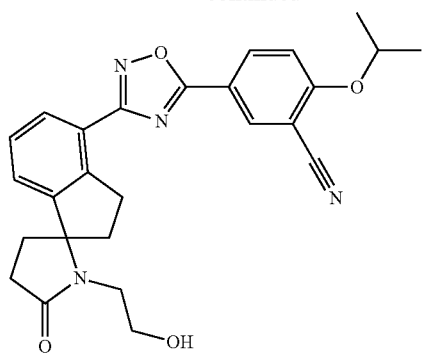
66
-continued
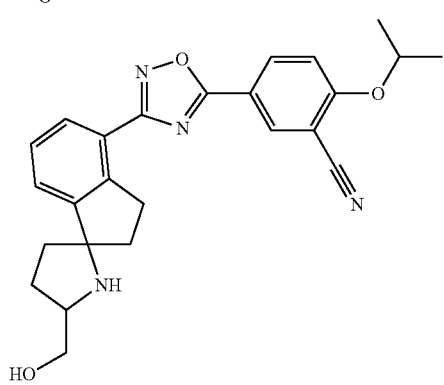
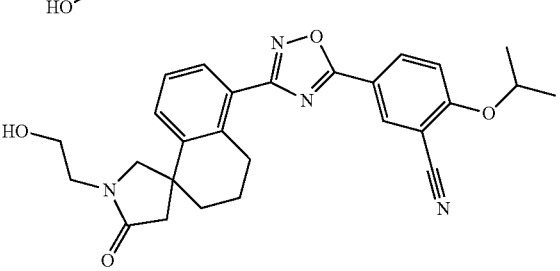
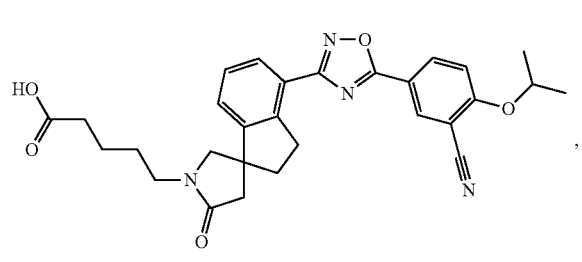
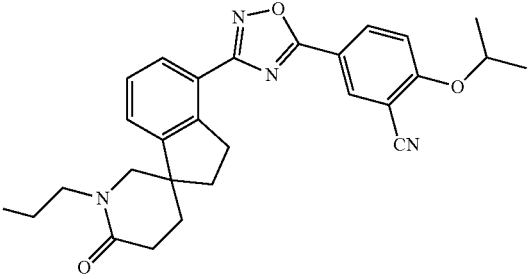
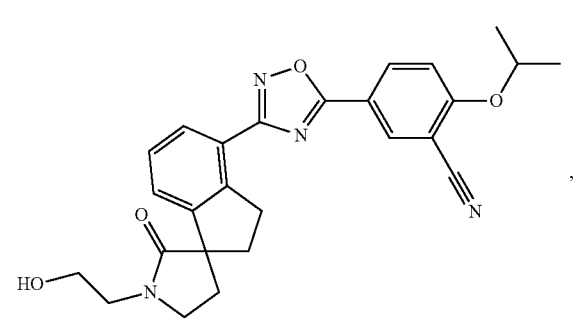
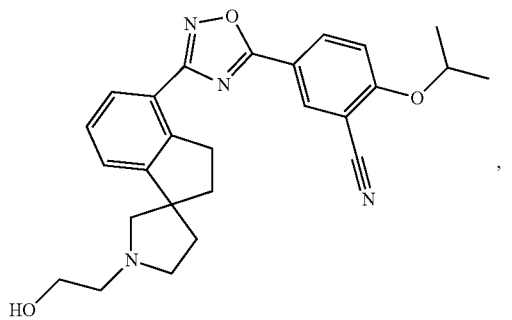

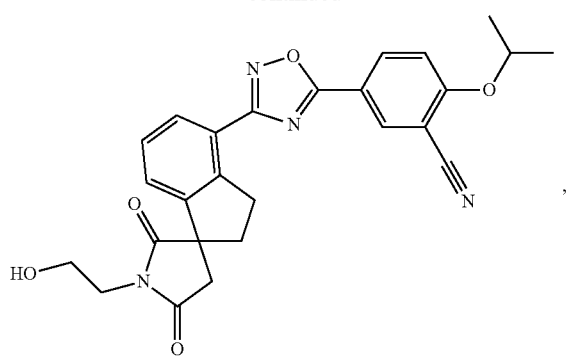,
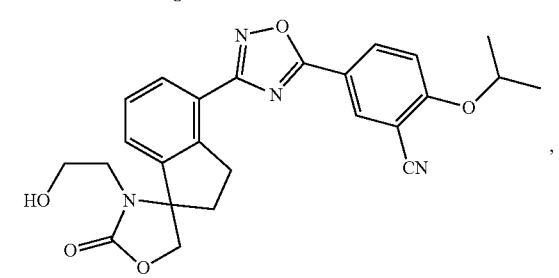,
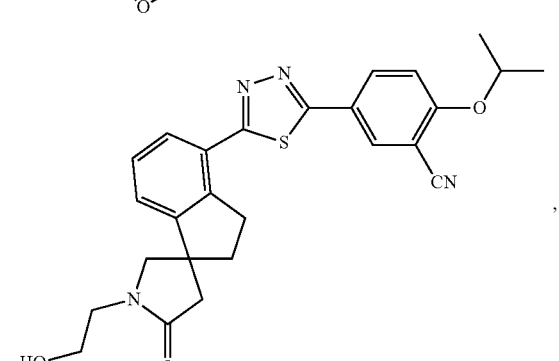,
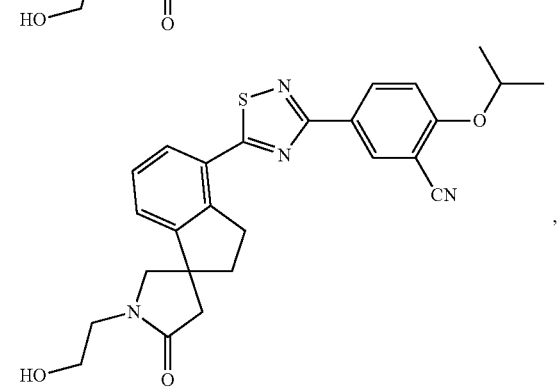,
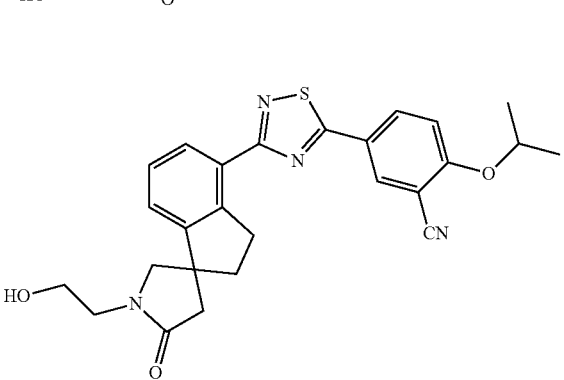,
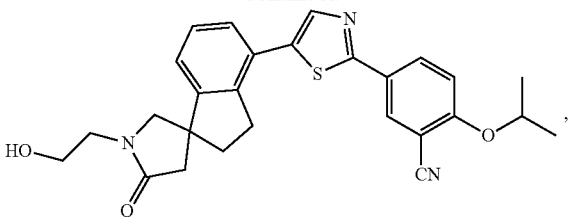,
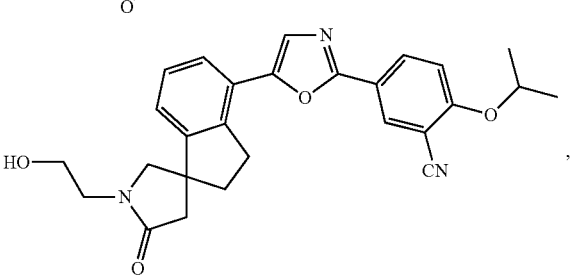,
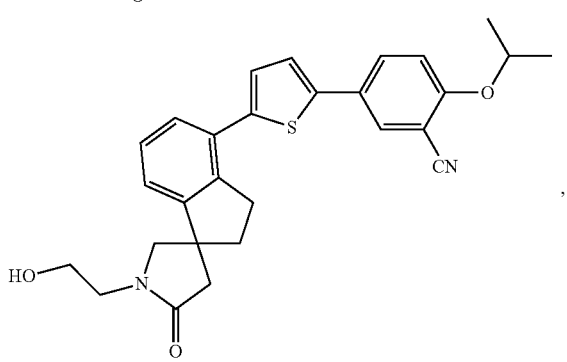,
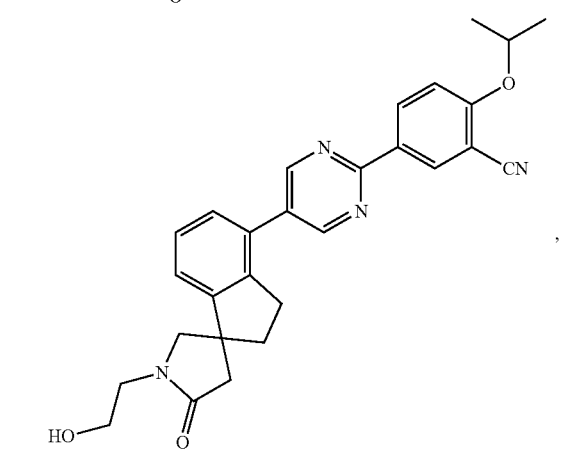,
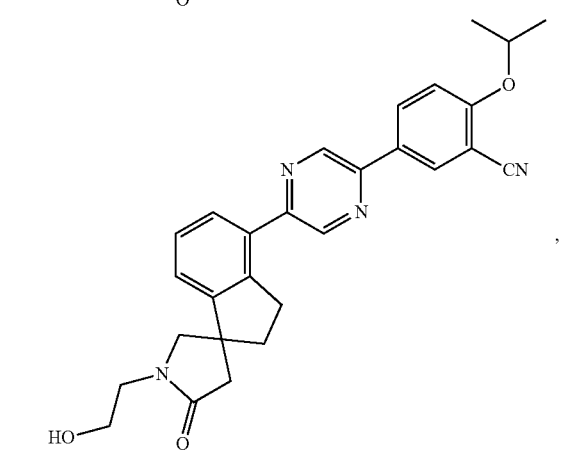,

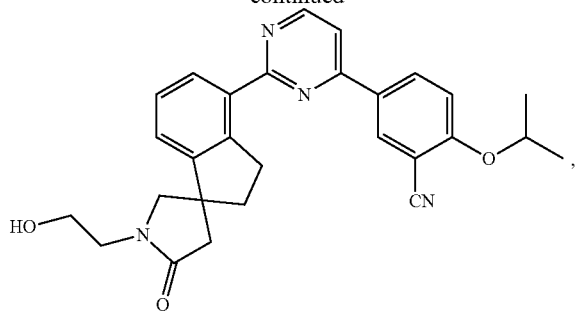
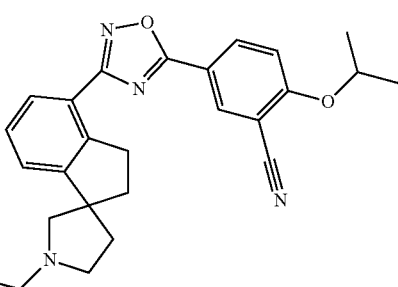
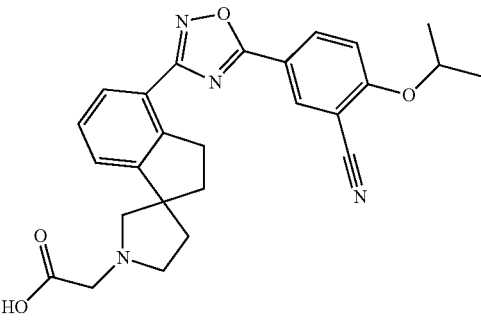
In some embodiments disclosed herein, the above compound, the optical isomer thereof, or the pharmaceutically acceptable salt thereof, is selected from the group consisting of
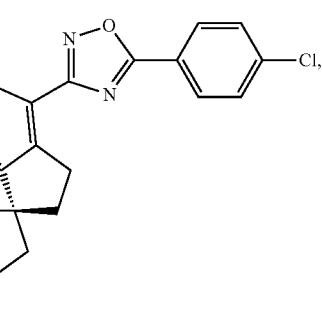
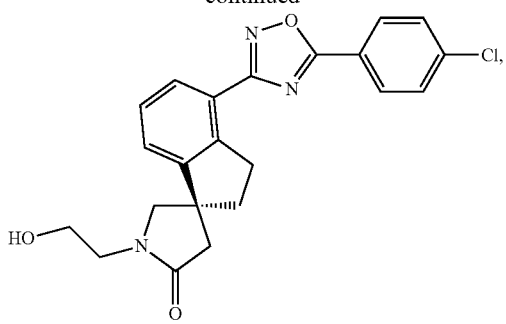
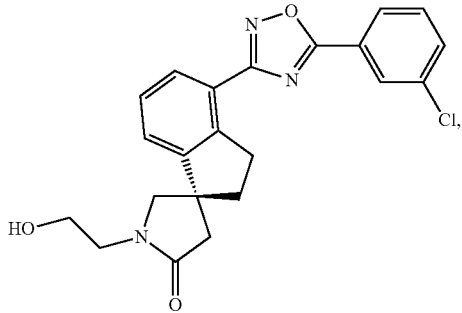
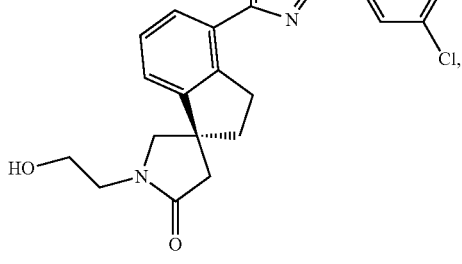
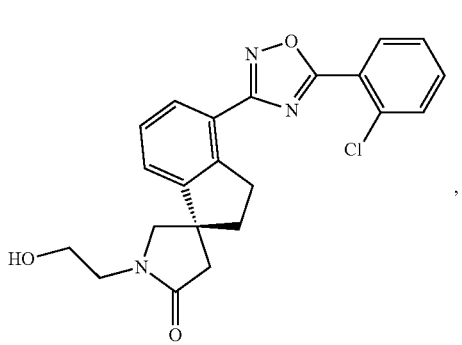
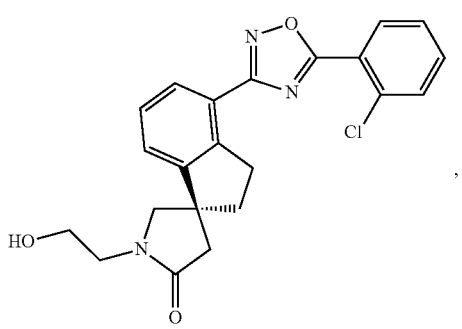

71
-continued
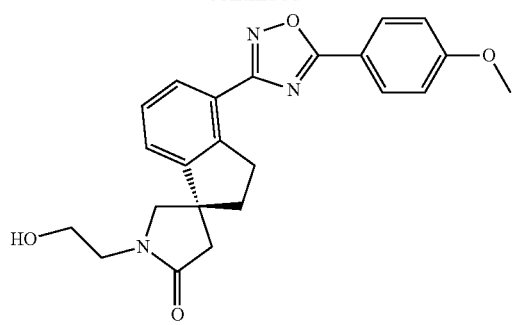,
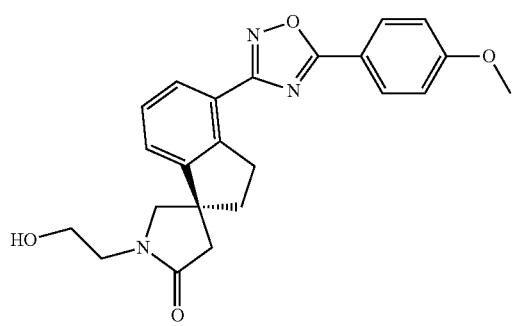,
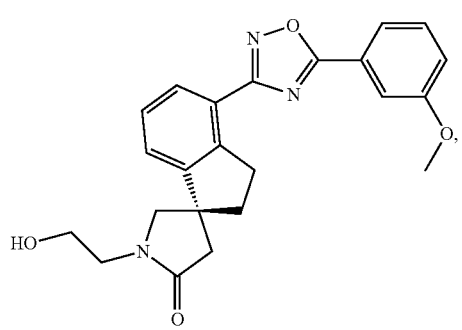,
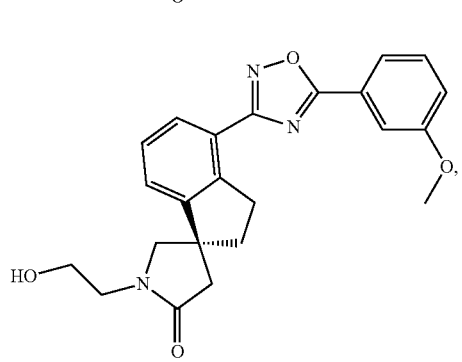,
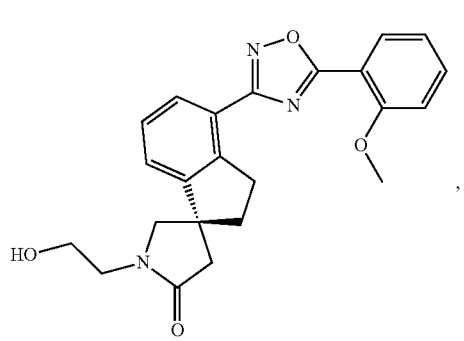,
72
-continued
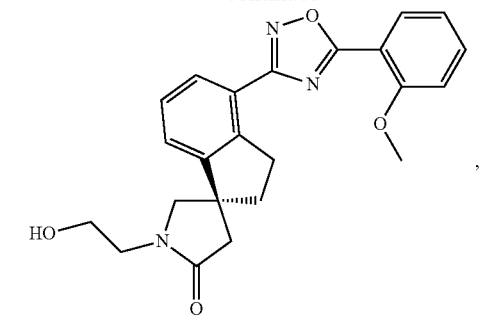,
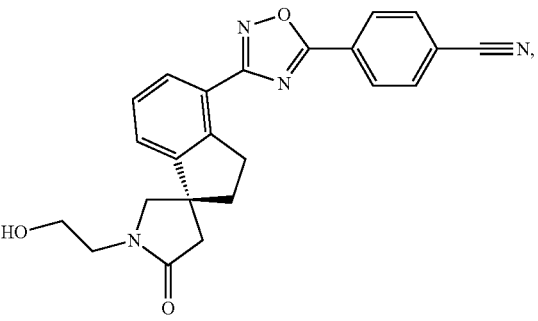,
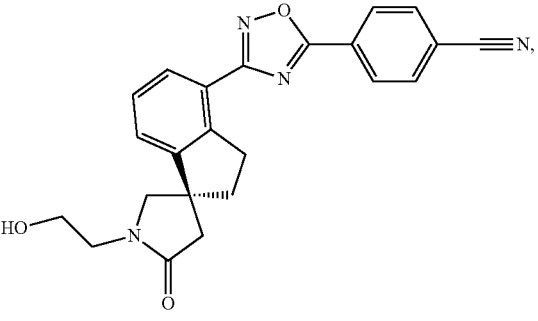,
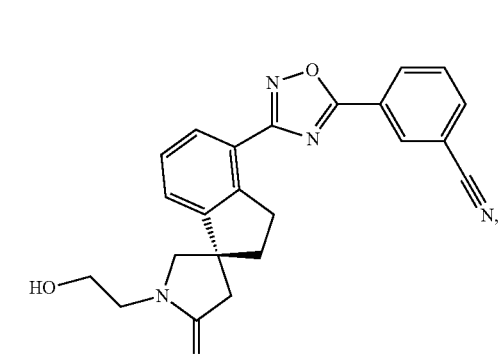,
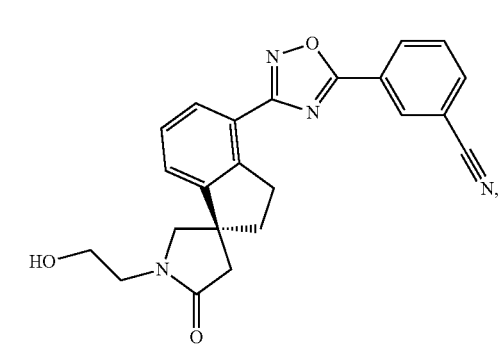, 73
-continued
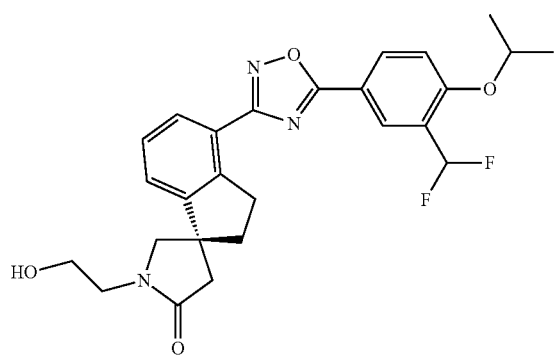
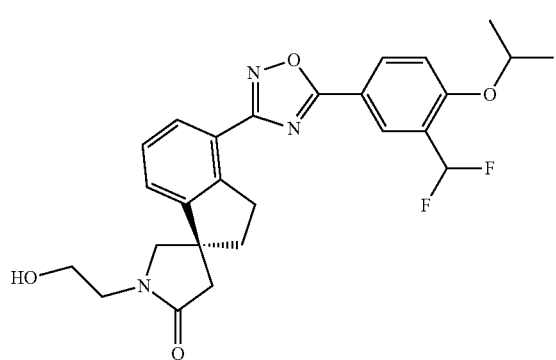
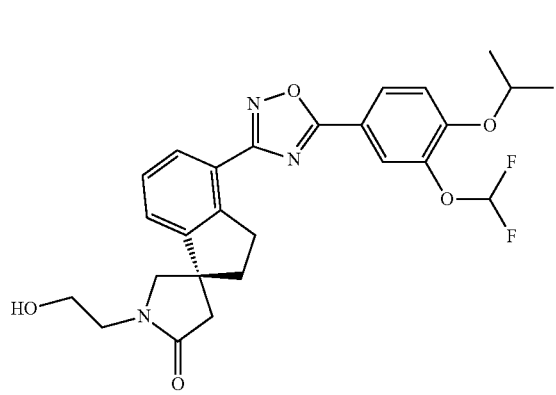
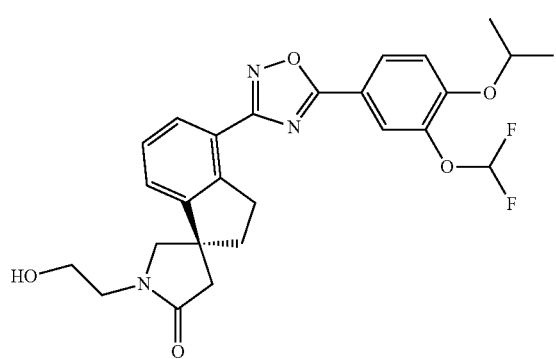
74
-continued
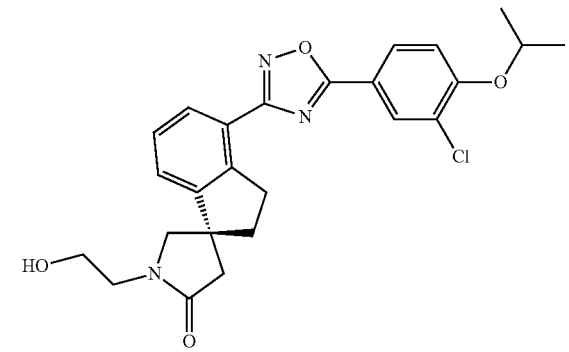
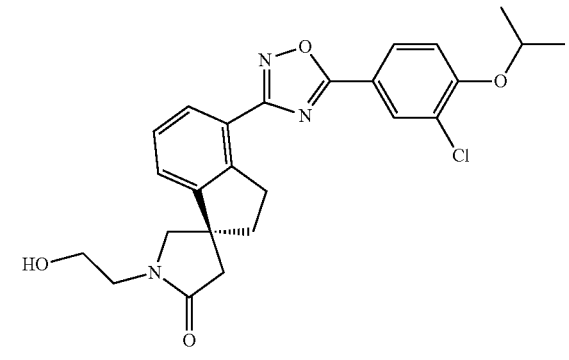
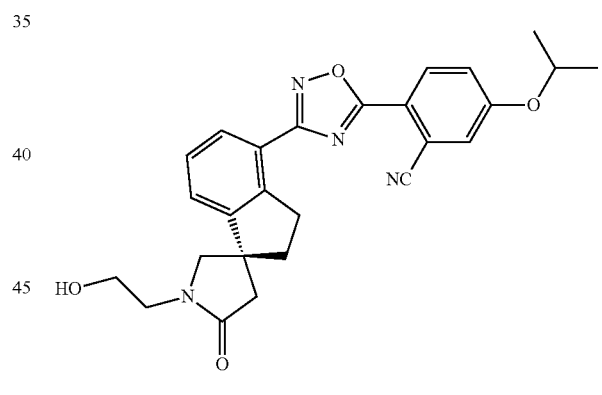
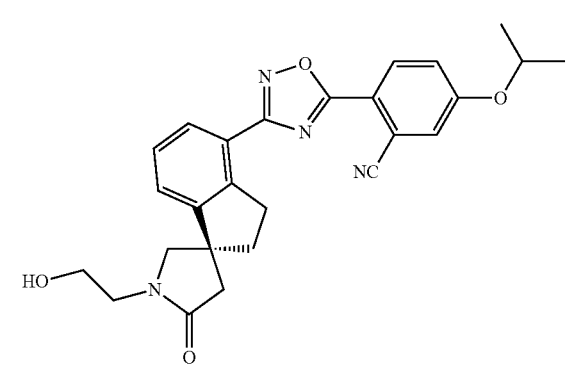

75
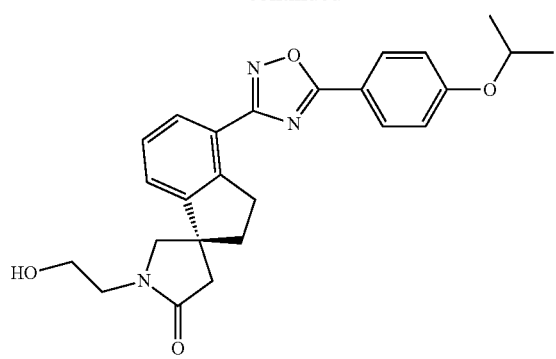
,
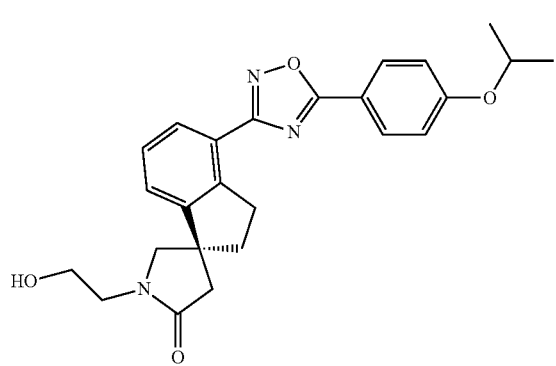
,
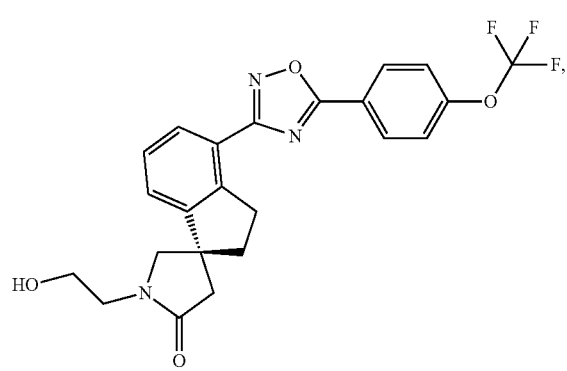
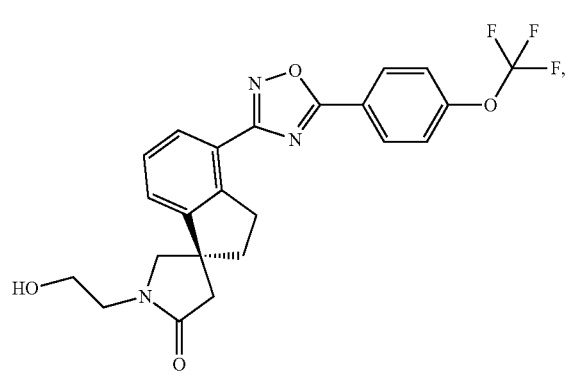
,
76
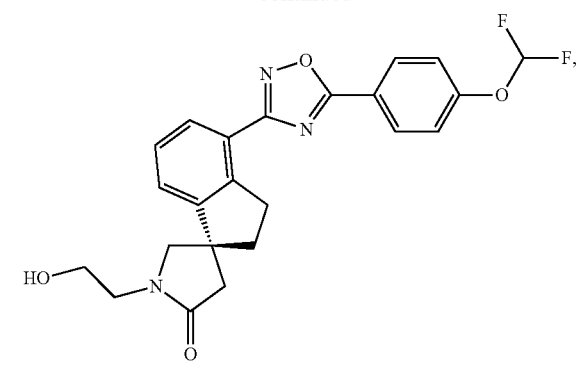
,
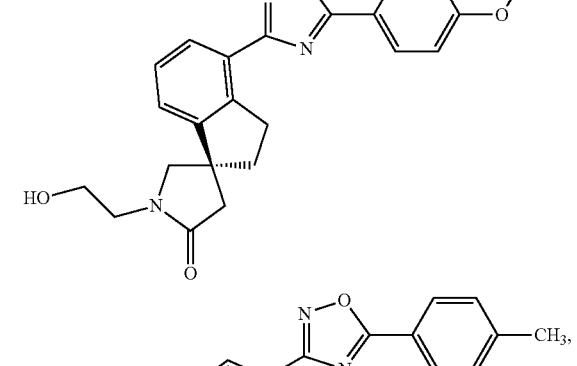
,
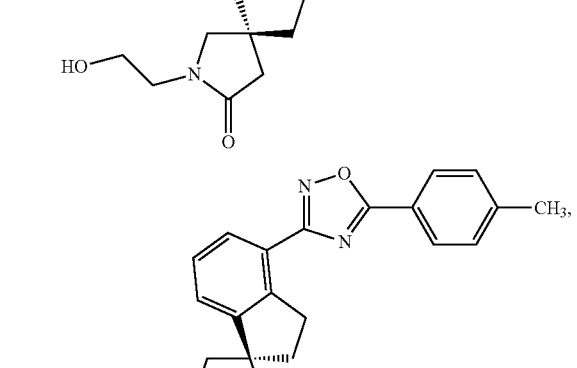
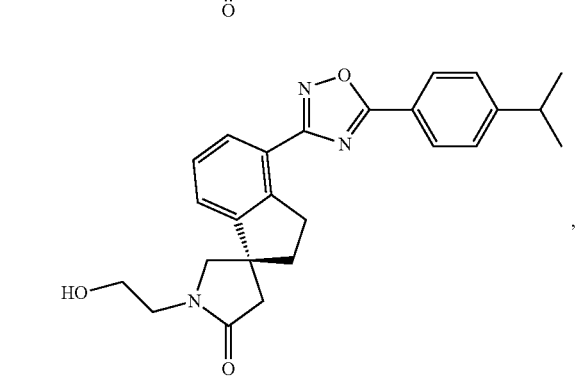
,

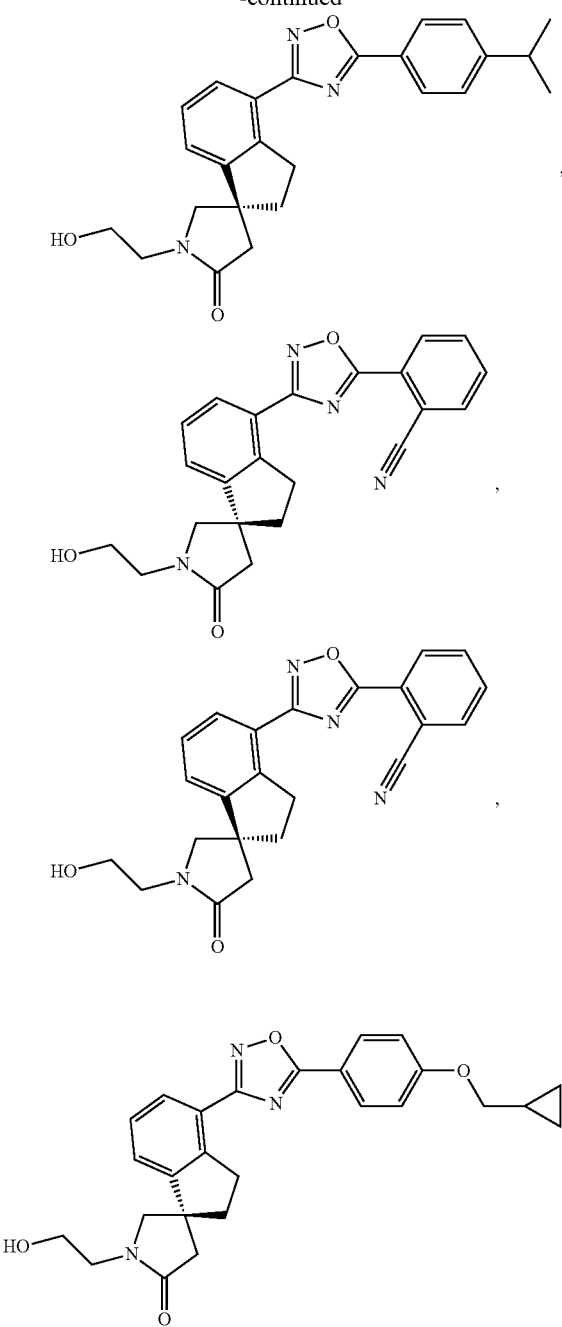
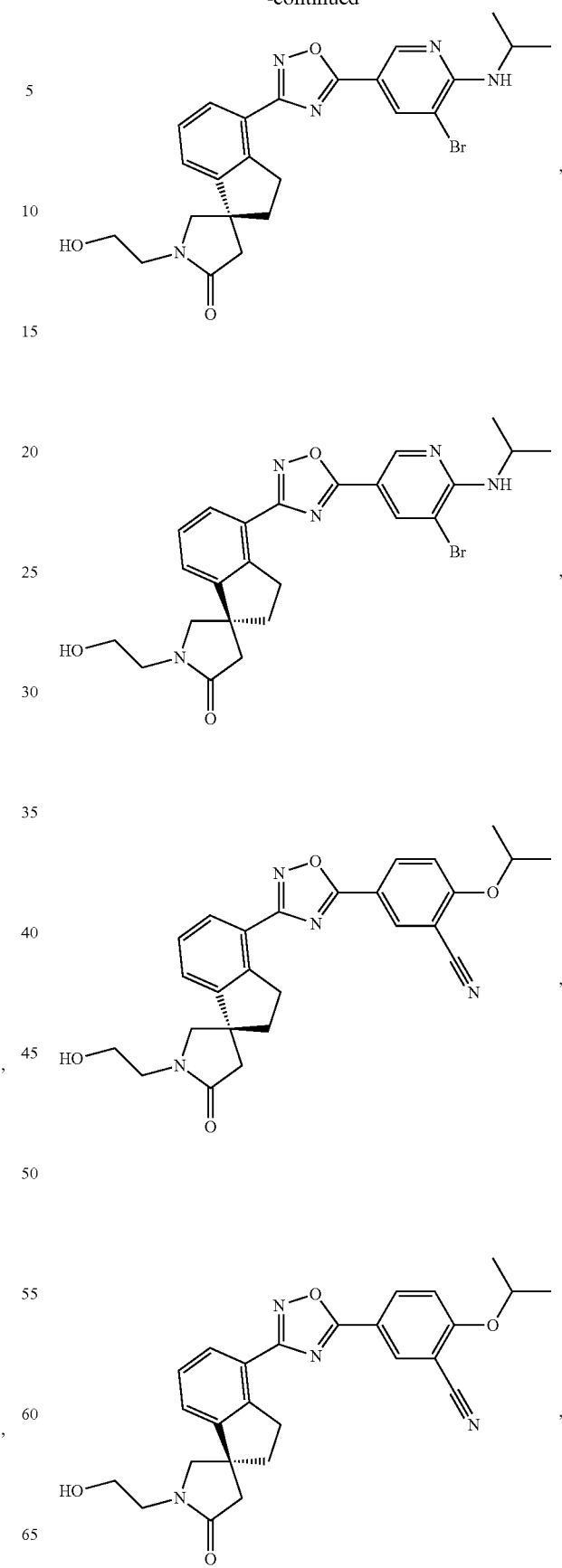

79
-continued
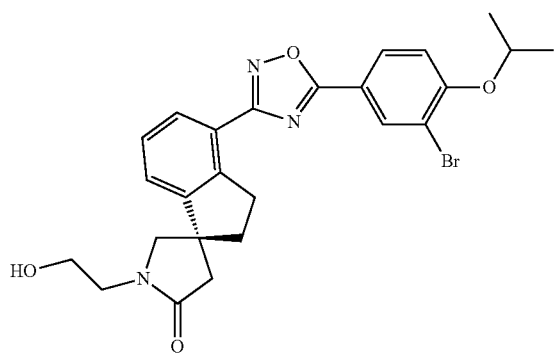
,
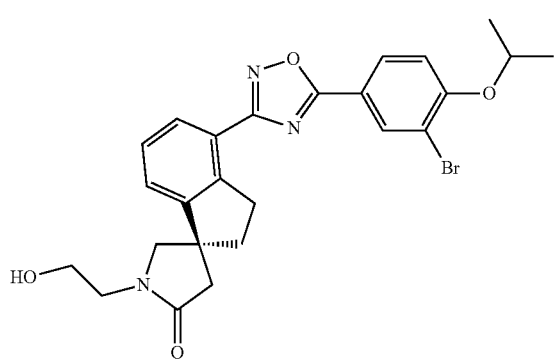
,
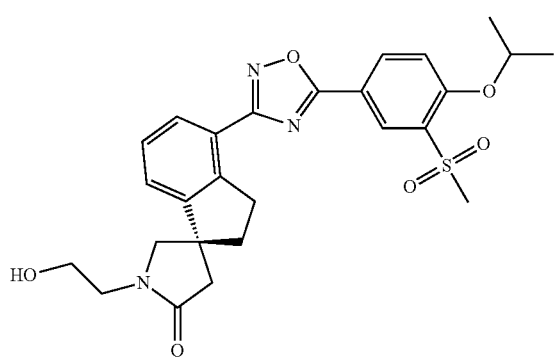
,
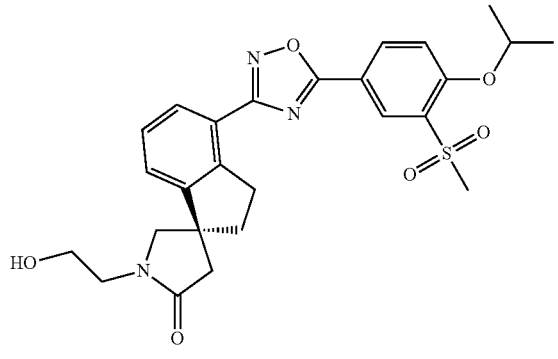
,
80
-continued
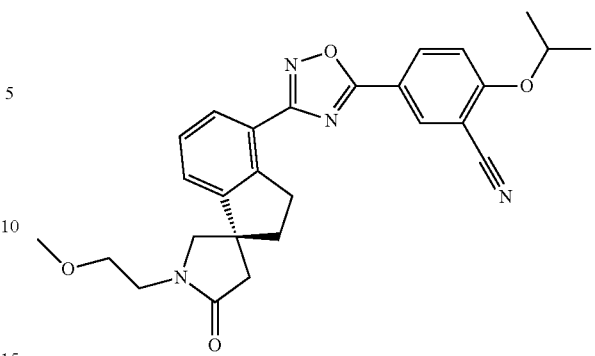
,
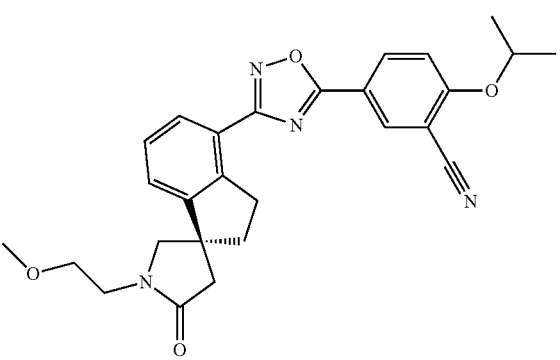
,
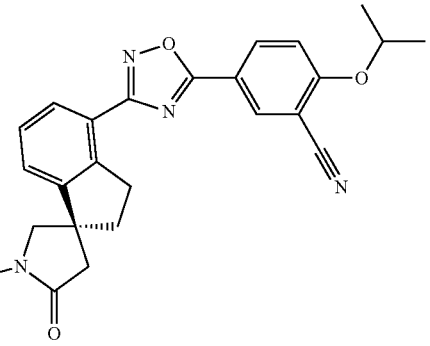
, 81
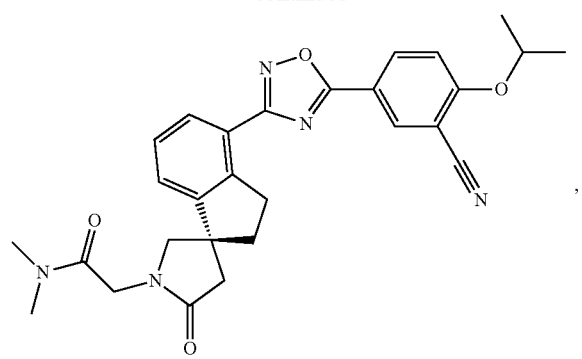
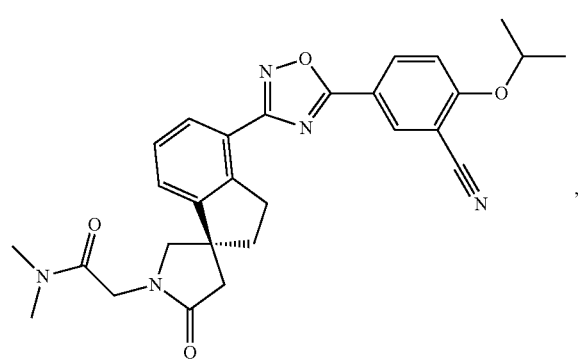
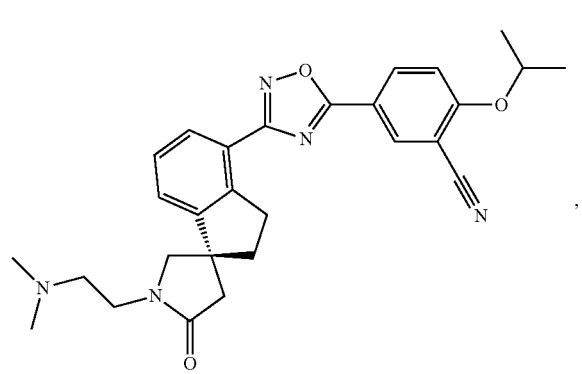
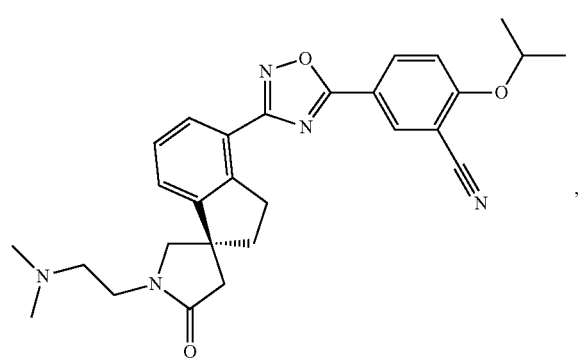
82
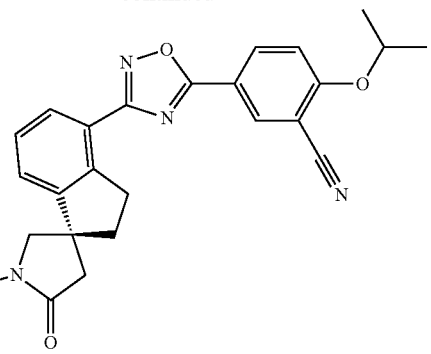
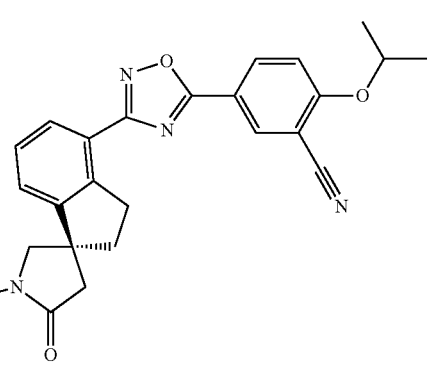
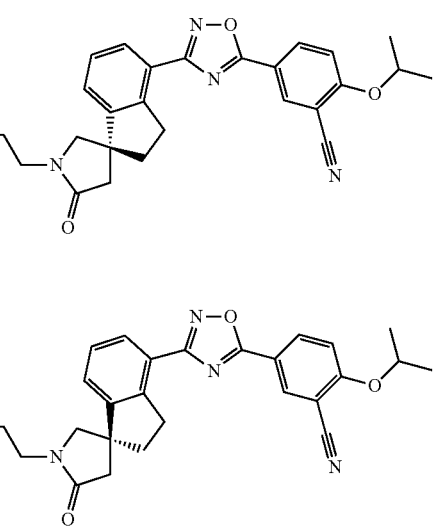
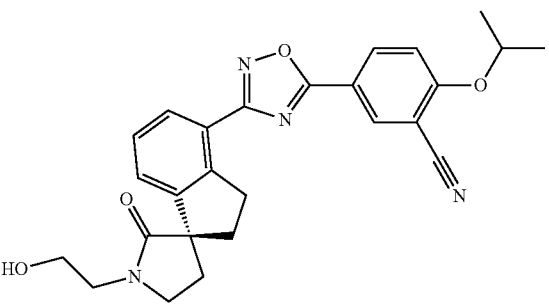

83
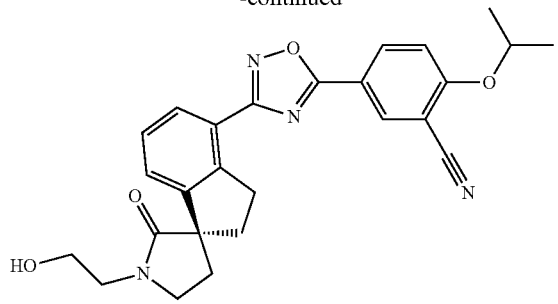
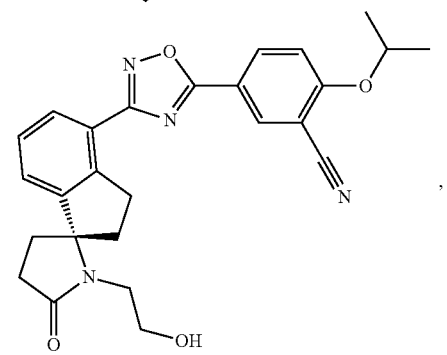
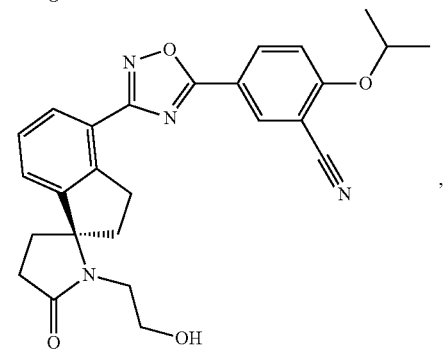
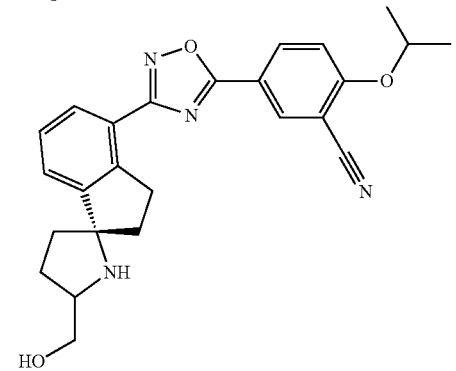
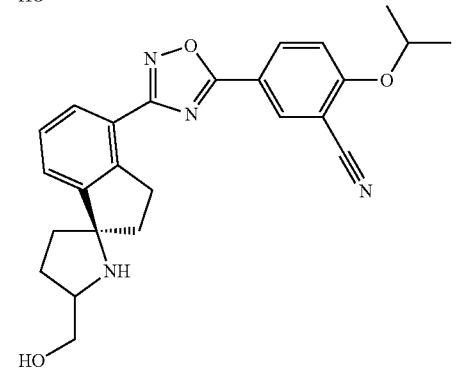
84
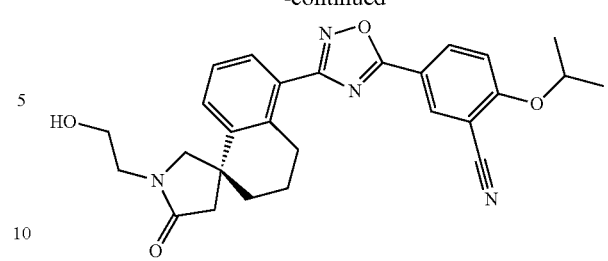
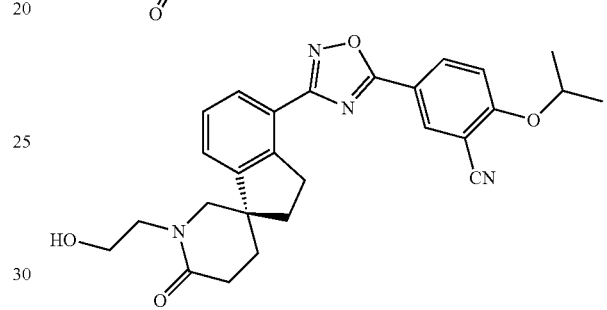
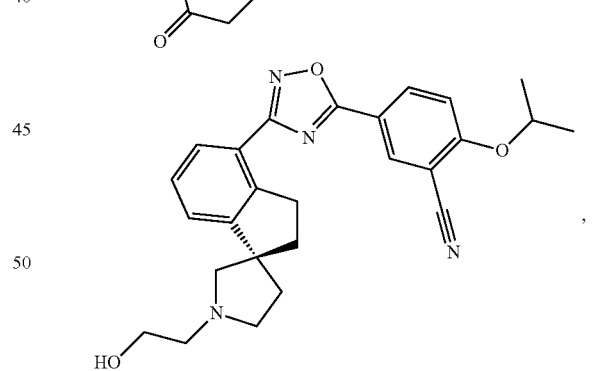
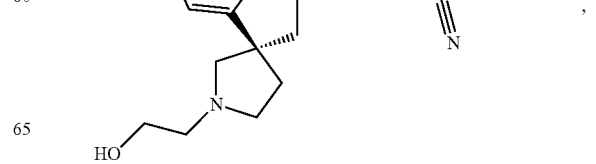

85
-continued
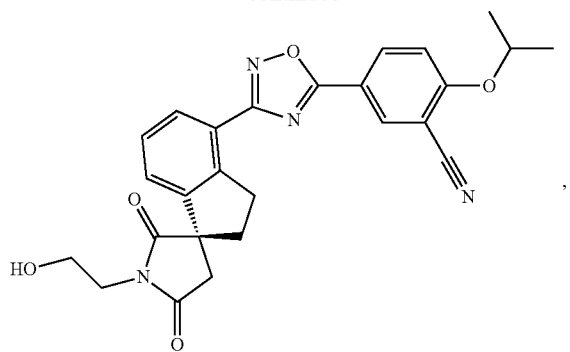
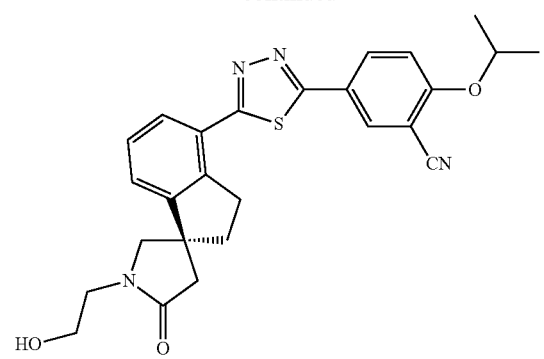
86
-continued
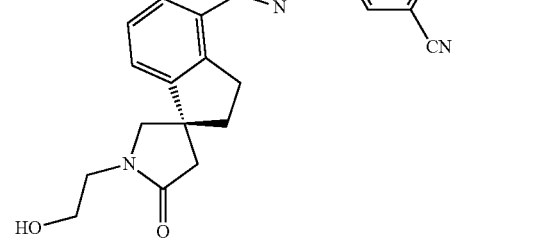
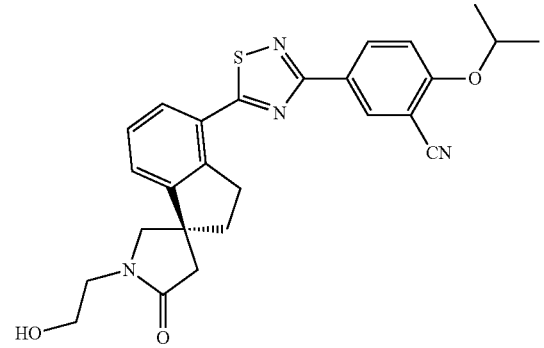
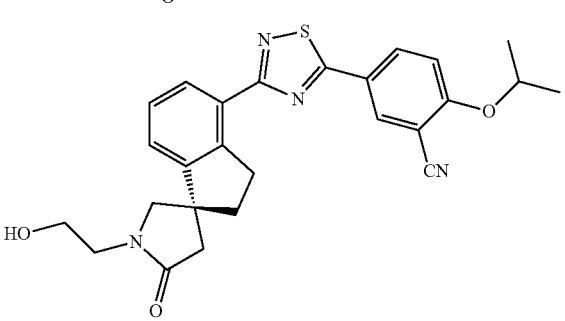
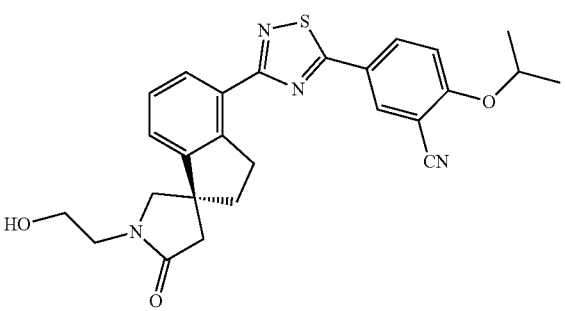

87
-continued
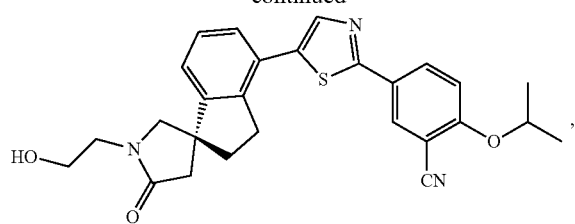
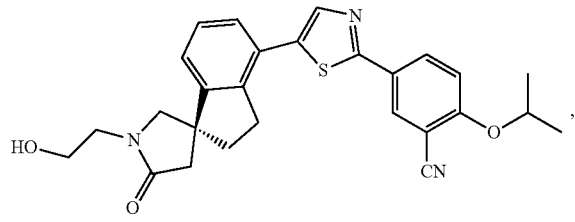
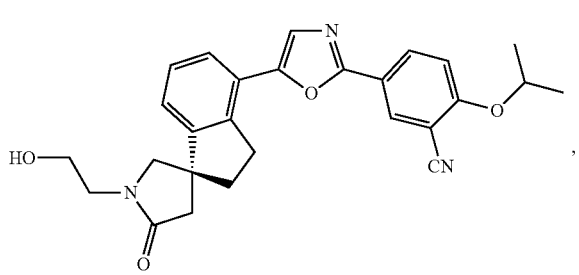
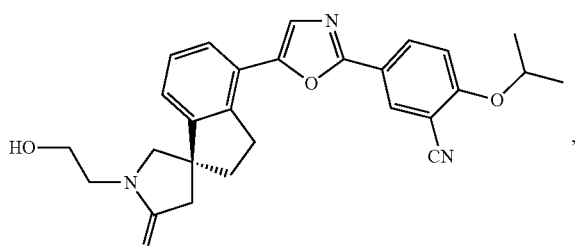
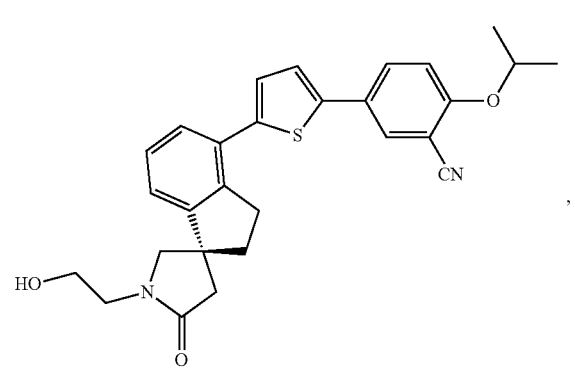
88
-continued
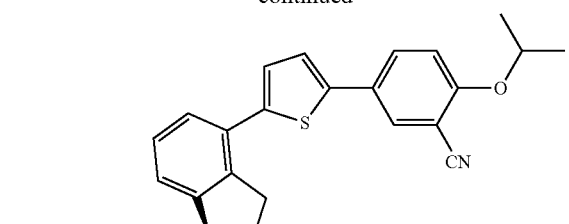
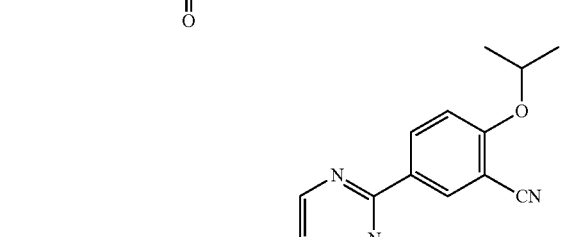
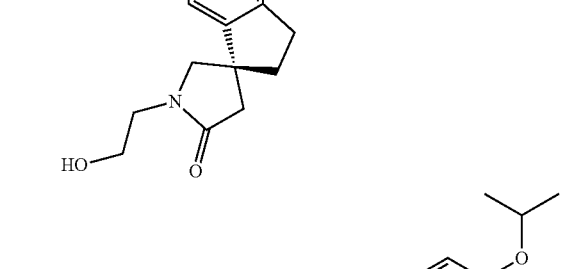
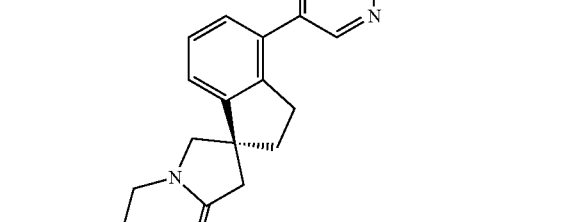
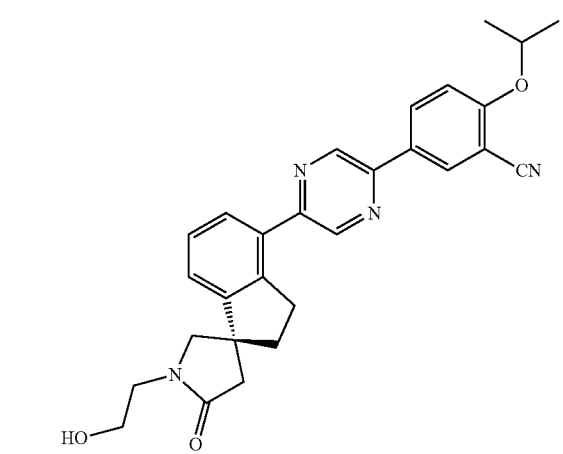

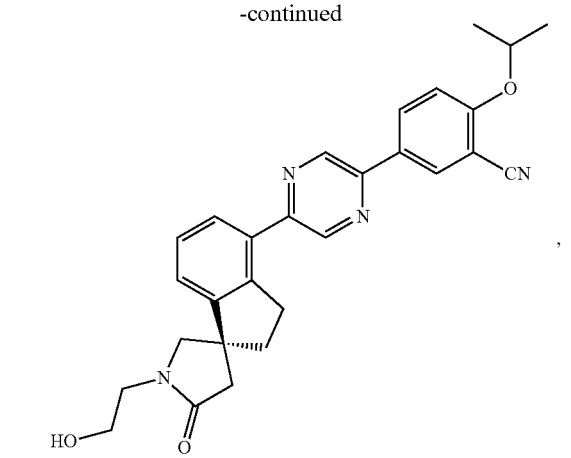

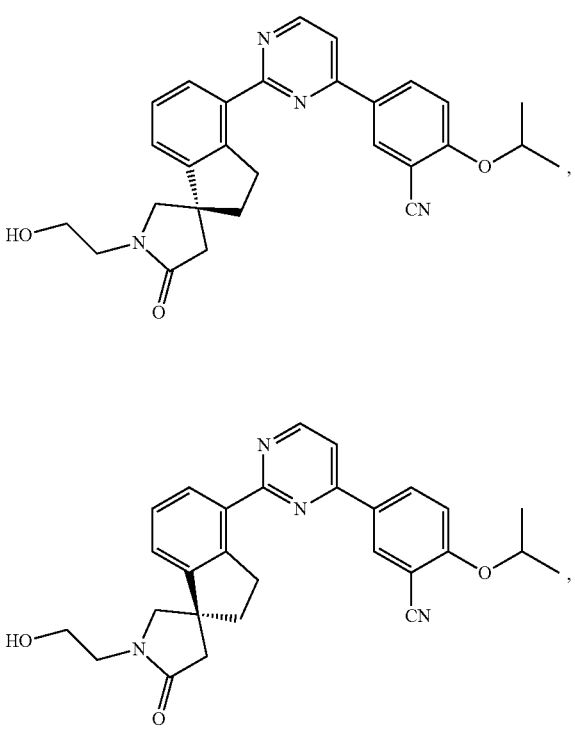

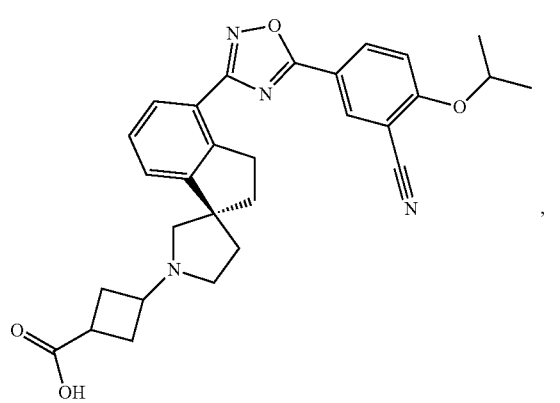

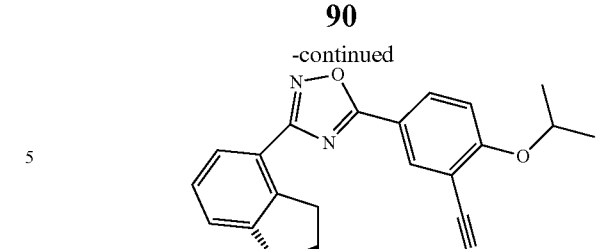

The present disclosure also provides a pharmaceutical composition comprising a therapeutically effective amount of the above compound, the optical isomer thereof or the pharmaceutically acceptable salt thereof as an active ingredient, and pharmaceutically acceptable carriers.

The present disclosure also provides use of the above compound, the optical isomer thereof or the pharmaceutically acceptable salt thereof or the above composition in the manufacture of a medicament for treating a disease associated with S1P1 receptor.

Technical Effects

The present disclosure synthesized a compound of formula (I) and its tautomers, obtaining a novel class of S1P1 receptor agonists. This class of compounds can reduce the number of lymphocytes in circulatory system and be used to treat related autoimmune diseases. At the same time, the compound disclosed herein has better activity, better pharmacokinetics, and good druggability.

Definitions and Terms

Unless otherwise indicated, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound disclosed herein that is prepared by reacting the compound having a specific substituent disclosed herein with a relatively non-toxic acid or base. When the compound disclosed herein contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound disclosed herein contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "Pharmaceutical Salts", Journal of Pharmaceutical Science 66: 1-19 (1977)). Certain specific compounds disclosed herein contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound disclosed herein, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided herein also exists in prodrug form. The prodrug of the compound described herein is the compound that readily undergoes chemical change under physiological condition to be converted into the compound disclosed herein. Additionally, the prodrug can be converted to the compound disclosed herein by a chemical or biochemical method in vivo environment.

Certain compounds disclosed herein can exist in an unsolvated form or a solvated form, including a hydrated form. Generally, the solvated form is equivalent to the unsolvated form, and both are encompassed within the scope disclosed herein.

Certain compounds disclosed herein can have an asymmetric carbon atom (optical center) or a double bond. The racemate, diastereomer, geometric isomer and individual isomer are all encompassed within the scope disclosed herein.

Unless otherwise stated, a wedged bond and a dashed bond ( ⟋ ⟍ ) are used to indicate the absolute configuration of a stereocenter, and the wavy line ⟿ is used to indicate the wedged bond and the dashed bond ( ⟋ or ⟍ ). ⟋ and ⟍ are used to indicate the relative configuration of a stereogenic center. When the compound described herein contains an olefinic double bond or other geometric asymmetric centers, E and Z geometric isomers are included unless otherwise specified. Likewise, all tautomeric forms are encompassed within the scope disclosed herein.

The compound disclosed herein may be present in a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope disclosed herein. The substituent such as alkyl may have an additional asymmetric carbon atom. All these isomers and mixtures thereof are encompassed within the scope disclosed herein.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound disclosed herein may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound disclosed herein, whether radioactive or not, are encompassed within the scope disclosed herein.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a substituent can be linked to more than one atoms on a ring, such substituent can be bonded to any atom on the ring. For example, a moiety

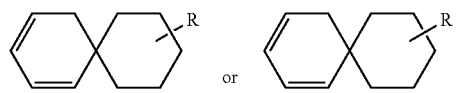

indicates that the substituent R can be positioned at any position on the cyclohexyl group or cyclohexadiene. When an enumerative substituent does not indicate through which atom it is linked to the substituted group, such substituent can be bonded through any of its atoms. For example, a pyridyl group as a substituent may be linked to the substituted group through any one of carbon atoms on the pyridine ring. When an enumerative linking group does not indicate its linking direction, its linking direction is arbitrary. For example, when the linking group L in

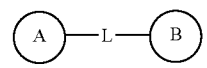

is -M-W—, the -M-W— can be linked to the ring A and the ring B in the same direction as the reading order from left to right to constitute

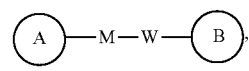, or can be linked to the ring A and the ring B in the reverse direction as the reading order from left to right to constitute

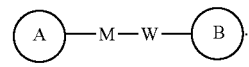.

A combination of the linking groups, substituents and/or variants thereof is allowed only when such combination can result in a stable compound.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and the group consisting of —C(=O)N(H)—, —N(H)—, —C(=NH)—, —S(=O)$_2$ N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidyl; on the other hand, the term "5-7 membered heterocycloalkyl ring" includes pyridyl and piperidyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from the group consisting of N, O and S, wherein any of the above heterocycle can be fused to a benzene ring to form a bicyclic ring. Nitrogen and sulfur heteroatoms can optionally be oxidized (i.e., NO and $S(O)_p$, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from the group consisting of N, O and S. Nitrogen atom can be substituted or unsubstituted (i.e., N or NR, wherein R is H or other substituents already defined herein). Nitrogen and sulfur heteroatoms may optionally be oxidized (i.e., NO and $S(O)_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuryl, benzomercaptofuryl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuryl, furyl, furazanyl, imidazolidinyl, imidazolinyl, imidazolyl, 1H-indazolyl, indolenyl, indolinyl, indolizinyl, indolyl, 3H-indolyl, isobenzofuryl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Fused-ring compounds and spiro compounds are also included.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from the group consisting of $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1, 4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from the group consisting of B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or hyponyms thereof (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclohydrocarbyl include 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuran-3-yl, tetrahydrothiophen-2-yl, tetrahydrothiophen-3-yl, 1-piperazinyl and 2-piperazinyl.

Unless otherwise specified, the term "alkyl" refers to a linear chain or branched saturated hydrocarbon group, can be mono-substituted (e.g. —CH$_2$F) or poly-substituted (e.g. —CF$_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom thereof is saturated. Cycloalkyl can be mono-substituted or poly-substituted, and can be monovalent, divalent or multivalent. Examples of cycloalkyl include, but are not limited to, cyclopropyl, norbomanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon double bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like.

Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and s-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from the group consisting of B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridyl, pyrimidinyl, benzothiazolyl, purinyl, benzimidazolyl, indolyl, isoquinolyl, quinoxalinyl, quinolinyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the group consisting of the acceptable substituents described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxymethyl, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)

methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound disclosed herein can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment disclosed herein.

All of the solvents used in the present disclosure are commercially available. The present disclosure employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyldicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide.

Compounds are named manually or by ChemDraw® software, and the commercially available compounds use their vendor directory names.

DETAILED DESCRIPTION

The present disclosure is illustrated below by the examples, but the present disclosure is not limited thereto. The present disclosure has been described in detail herein, including the embodiments disclosed herein, and various modifications and changes made to the embodiments disclosed herein, without departing from the spirit and scope of the invention, are obvious to a person skilled in the art.

Example 1

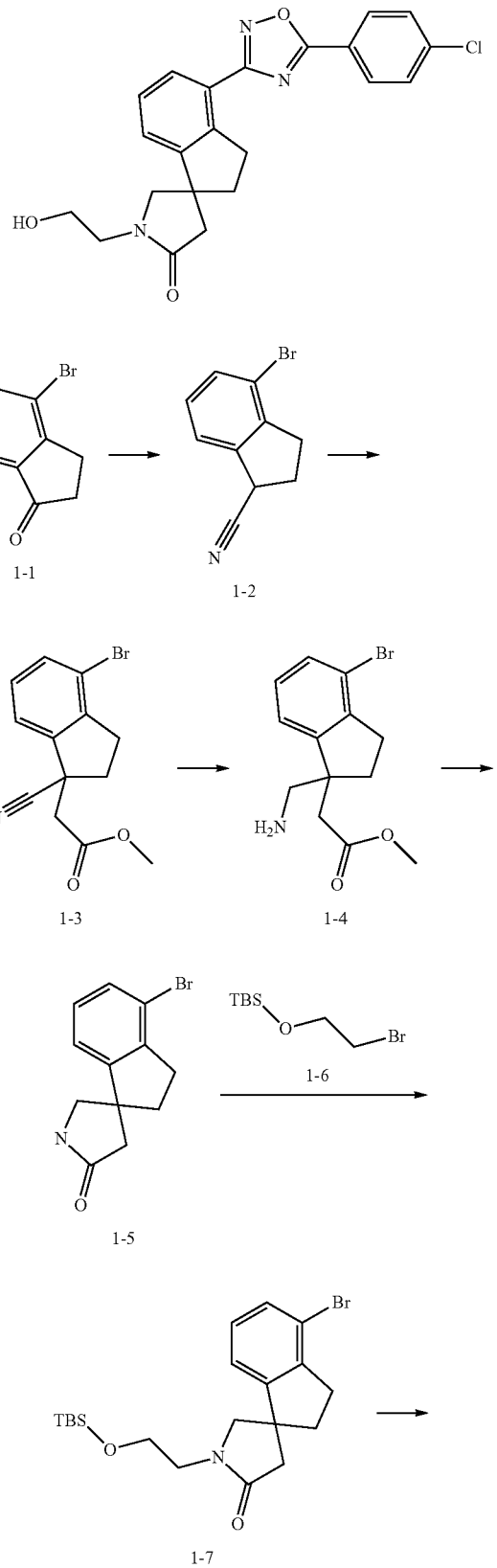

-continued

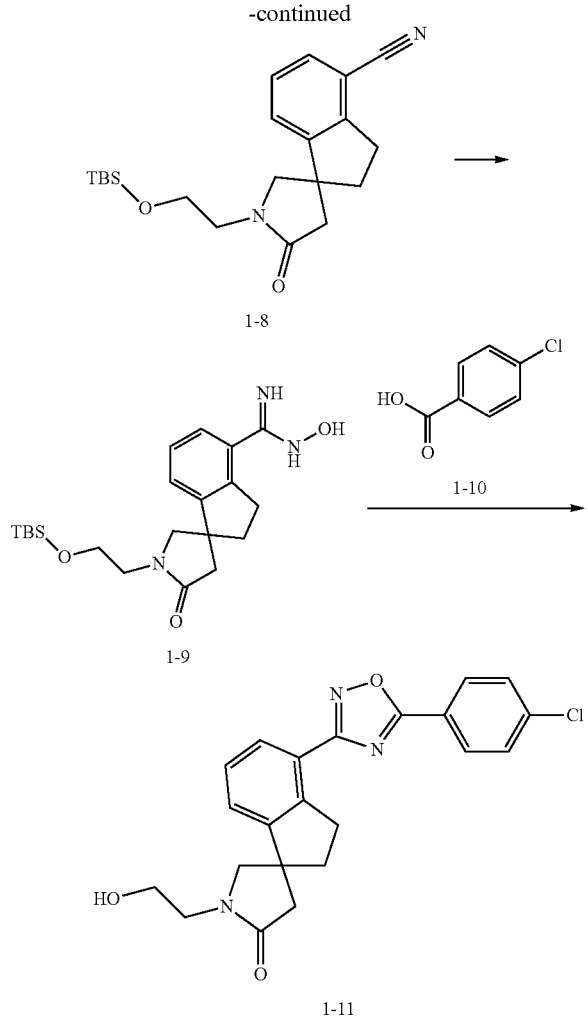

Step 1

Compound 1-1 (40.6 g, 192 mmol) and tosylmethyl isocyanide were dissolved in ethylene glycol monomethyl ether (1.30 L) and ethanol (69.0 mL). Potassium tert-butoxide (23.7 g, 212 mmol) was added to the reaction solution at 0° C. The reaction solution was stirred at 16° C. for 15 hours. Water (1 L) was added to the reaction solution, and the mixture was extracted with ethyl acetate (800 mL×3). The organic phases were combined, dried over anhydrous sodium sulfate, and filtered. The filtrate was concentrated under reduced pressure. The crude product was isolated by silica gel column chromatography (silica, petroleum ether:ethyl acetate=50:1) to afford compound 1-2.

$^1$H NMR: (400 MHz, CDCl$_3$) δ 7.45 (d, J=8.0 Hz, 1H), 7.38 (d, J=8.0 Hz, 1H), 7.16 (t, J=8.0 Hz, 1H), 4.21 (t, J=8.4 Hz, 1H), 3.22-3.07 (m, 1H), 3.05-2.95 (m, 1H), 2.65-2.55 (m, 1H), 2.47-2.33 (m, 1H).

Step 2

Compound 1-2 (16.8 g, 75.7 mmol) was dissolved in anhydrous tetrahydrofuran (160 mL), lithium diisopropylamide (2 M, 49.2 mL) was added dropwise to the reaction mixture at −78° C., and the reaction mixture was stirred at that temperature for 1 hour. Methyl bromoacetate (16.2 g, 106 mmol, 10.0 mL) was then added to the reaction solution, and the reaction solution was stirred at 16° C. for 16 hours. Water (150 mL) was added to the reaction solution, and the mixture was extracted with ethyl acetate (200 mL×3). The organic phases were combined, washed with saturated brine (500 mL×1), dried over anhydrous sodium sulfate, and filtered. The filtrate was concentrated under reduced pressure. The crude product was isolated by silica gel column chromatography (silica, petroleum ether:ethyl acetate=50:1 to 40:1) to afford compound 1-3.

$^1$H NMR: (400 MHz, CDCl$_3$) δ 7.40 (d, J=8.0 Hz, 1H), 7.30 (d, J=8.0 Hz, 1H), 7.13-7.06 (m, 1H), 3.68 (s, 3H), 3.06-2.88 (m, 3H), 2.75-2.63 (m, 2H), 2.45-2.34 (m, 1H).

Step 3

Compound 1-3 (14.2 g, 48.3 mmol) was dissolved in methanol (400 mL) and water (4.00 mL). Cobalt dichloride (25.1 g, 193 mmol) and sodium borohydride (3.65 g, 96.6 mmol) were added portionwise to the reaction solution at −20° C. The reaction solution was stirred at −20° C. to 0° C. for 4 hours. After the reaction solution was filtered, water (400 mL) was added to the filtrate. The mixture was extracted with ethyl acetate (400 mL×3). The organic phases were combined, washed with saturated brine (600 mL×1), dried over anhydrous sodium sulfate (20 g), and filtered. The filtrate was concentrated under reduced pressure to afford compound 1-4. The crude product was used in the next step directly without purification.

MS-ESI calculated for [M+]$^+$: 298 and 300, found: 298 and 300.

Step 4

Compound 1-4 (12.0 g, 40.1 mmol) was dissolved in methanol (120 mL). Sodium hydroxide (3.21 g, 80.3 mmol) was added to the reaction solution. The reaction solution was stirred at 16° C. for 15 hours. Water (200 mL) was added to the reaction solution, and the mixture was extracted with ethyl acetate (200 mL×3). The organic phases were combined, washed with saturated brine (500 mL×1), dried over anhydrous sodium sulfate, and filtered. The filtrate was concentrated under reduced pressure. The crude product was isolated by silica gel column chromatography (silica, petroleum ether:ethyl acetate=3:1 to 0:1) to afford compound 1-5.

$^1$H NMR: (400 MHz, DMSO-d$_6$) δ 7.74 (s, 1H), 7.40 (d, J=7.6 Hz, 1H), 7.35 (d, J=7.6 Hz, 1H), 7.18-7.13 (m, 1H), 3.31-3.29 (m, 2H), 2.89-2.80 (m, 2H), 2.34-1.94 (m, 4H). MS-ESI calculated for [M+H]$^+$: 266 and 268, found: 266 and 268.

Step 5

Compound 1-5 (8.33 g, 27.2 mmol) was dissolved in anhydrous N,N-dimethylformamide (85.0 mL). Sodium hydride (2.17 g, 54.4 mmol, 60% purity) was added portionwise to the mixture at 0° C., and the reaction was stirred at that temperature for 1 hour. Compound 1-6 (13.0 g, 54.4 mmol) was then added to the reaction solution, and the reaction solution was stirred at 16° C. for 16 hours. Water (200 mL) was added to the reaction solution, and the mixture was extracted with ethyl acetate (200 mL×3). The organic phases were combined, washed with saturated brine (400 mL×1), dried over anhydrous sodium sulfate (20 g), and filtered. The filtrate was concentrated under reduced pressure. The crude product was isolated by silica gel column chromatography (silica, petroleum ether:ethyl acetate=10:1) to afford compound 1-7.

$^1$H NMR: (400 MHz, CDCl$_3$) δ 7.32 (d, J=7.6 Hz, 1H), 7.10 (d, J=7.6 Hz, 1H), 7.04 (t, J=7.6 Hz, 1H), 3.74 (t, J=5.2 Hz, 2H), 3.60-3.53 (m, 2H), 3.41 (t, J=5.2 Hz, 2H), 2.91 (t, J=7.2 Hz, 2H), 2.66-2.47 (m, 2H), 2.24-2.08 (m, 2H), 0.82 (s, 9H), 0.00 (s, 6H). MS-ESI calculated for [M+H]$^+$: 424 and 426, found: 424 and 426.

Step 6

Compound 1-7 (5.00 g, 10.6 mmol) was dissolved in acetonitrile (130 mL). Zinc cyanide (3.75 g, 31.9 mmol), tris(dibenzylideneacetone)dipalladium (1.95 g, 2.13 mmol) and 2-dicyclohexylphosphino-2',4',6'-triisopropylbiphenyl (2.03 g, 4.26 mmol) were added to the reaction solution. The reaction solution was stirred at 90° C. for 16 hours under nitrogen. The reaction solution was cooled to room temperature, and filtered. The filter cake was washed with dichloromethane (100 mL×3) and the filtrate was concentrated under reduced pressure. The crude product was isolated by silica gel column chromatography (silica, petroleum ether:ethyl acetate=8:1 to 2:1) to afford compound 1-8.

$^1$H NMR: (400 MHz, CDCl$_3$) δ 7.50 (d, J=7.6 Hz, 1H), 7.45 (d, J=7.6, 1H), 7.33-7.28 (m, 1H), 3.79 (t, J=5.2 Hz, 2H), 3.64 (d, J=0.8 Hz, 2H), 3.53-3.41 (m, 2H), 3.13 (t, J=7.2 Hz, 2H), 2.72-2.58 (m, 2H), 2.37-2.20 (m, 2H), 0.86 (s, 9H), 0.00 (s, 6H).

MS-ESI calculated for [M+H]$^+$: 371, found: 371.

Step 7

Compound 1-8 (2.70 g, 7.29 mmol) was dissolved in ethanol (70.0 mL). Hydroxylamine hydrochloride (1.52 g, 21.9 mmol) and triethylamine (2.95 g, 29.2 mmol) were added to the reaction solution. The reaction solution was stirred at 60° C. for 15 hours under nitrogen. The reaction solution was concentrated under reduced pressure, and water (100 ml) was then added. The mixture was extracted with ethyl acetate (150 mL×3). The organic phases were combined, washed with saturated brine (300 mL×1), dried over anhydrous sodium sulfate, and filtered. The filtrate was concentrated under reduced pressure to afford compound 1-9.

$^1$H NMR: (400 MHz, CDCl$_3$) δ 7.34 (d, J=6.8 Hz, 1H), 7.24-7.17 (m, 2H), 4.81 (s, 2H), 3.74 (t, J=5.2 Hz, 2H), 3.65-3.52 (m, 2H), 3.41 (t, J=5.2 Hz, 2H), 3.06 (t, J=7.2 Hz, 2H), 2.70-2.46 (m, 2H), 2.15-2.05 (m, 2H), 0.82 (s, 9H), 0.00 (s, 6H).

MS-ESI calculated for [M+H]$^+$: 404, found: 404.

Step 8

Compound 1-10 (38.8 mg, 0.248 mmol) was dissolved in N,N-dimethylformamide (3 mL). To the reaction solution were added 1-hydroxybenzotriazole (67.0 mg, 0.496 mmol) and 1-(3-dimethylaminopropyl)-3-ethylcarbodiimide hydrochloride (71.3 mg, 0.372 mmol). The reaction solution was stirred at 25° C. for 1 hour. Compound 1-9 (100 mg, 0.248 mmol) was then added to the reaction solution, and the reaction solution was stirred at 25° C. for 1 hour. The reaction solution was then heated to 85° C., and stirred at 85° C. for 15 hours. The reaction solution was cooled to room temperature and isolated by high performance liquid chromatography (formic acid system) to afford compound 1-11 (i.e., Example 1).

$^1$H NMR: (400 MHz, Methanol-d$_4$) δ 8.22 (d, J=8.8 Hz, 2H), 8.07 (d, J=7.6 Hz, 1H), 7.65 (d, J=8.8 Hz, 2H), 7.53 (d, J=7.6 Hz, 1H), 7.47-7.39 (m, 1H), 3.76-3.72 (m, 2H), 3.71 (s, 2H), 3.57-3.44 (m, 2H), 3.38 (t, J=7.2 Hz, 2H), 2.81-2.61 (m, 2H), 2.42-2.19 (m, 2H).

MS-ESI calculated for [M+H]$^+$: 410, found: 410.

Example 2

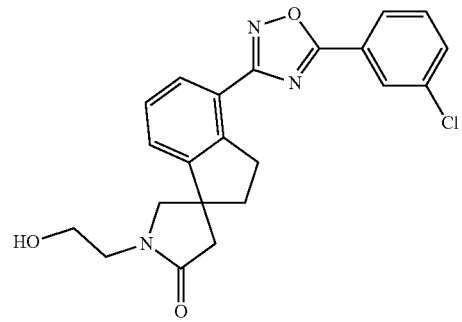

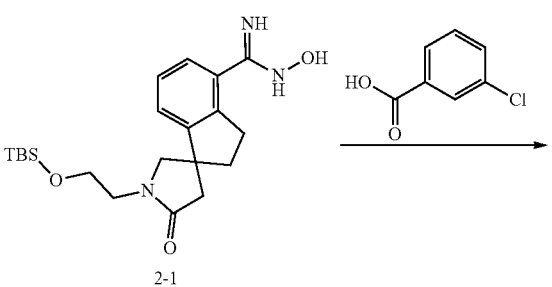

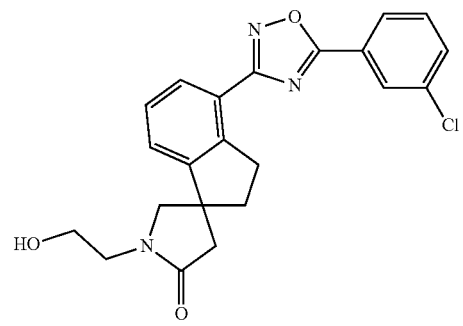

The reaction procedure was similar to that of the Step 8 of Example 1. The crude product was isolated by high performance liquid chromatography (formic acid system) to afford compound 2-2 (i.e., Example 2).

$^1$H NMR: (400 MHz, Methanol-d$_4$) δ 8.22 (s, 1H), 8.16 (d, J=7.6 Hz, 1H), 8.08 (d, J=7.6 Hz, 1H), 7.73-7.68 (m, 1H), 7.63 (t, J=7.6 Hz, 1H), 7.56-7.51 (m, 1H), 7.44 (t, J=7.6 Hz, 1H), 3.77-3.72 (m, 2H), 3.71 (s, 2H), 3.56-3.45 (m, 2H), 3.37 (t, J=7.2 Hz, 2H), 2.81-2.61 (m, 2H), 2.42-2.20 (m, 2H).

MS-ESI calculated for [M+H]$^+$: 410, found: 410.

105
Example 3

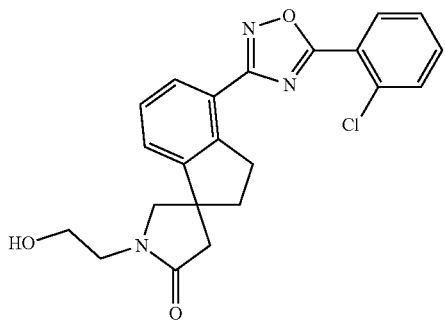

106
Example 4

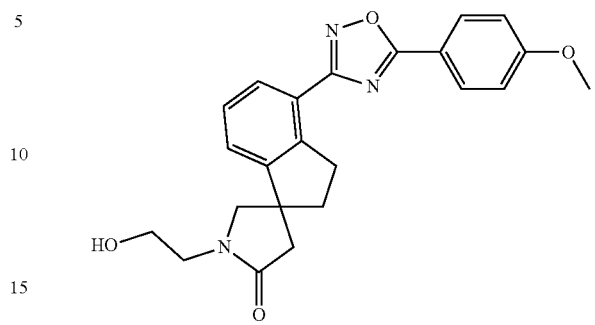

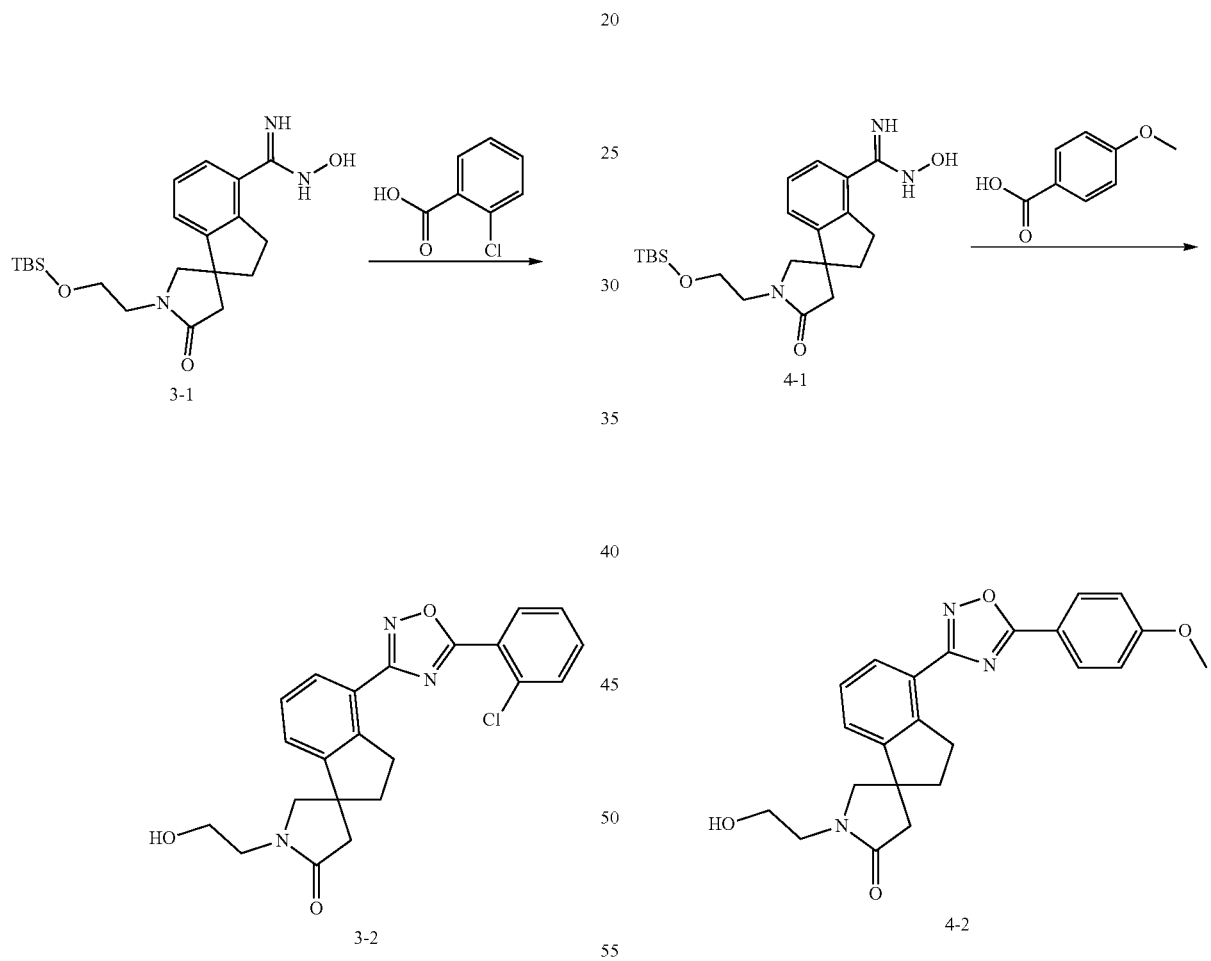

The reaction procedure was similar to that of the Step 8 of Example 1. The crude product was isolated by high performance liquid chromatography (formic acid system) to afford compound 3-2 (i.e., Example 3).

$^1$H NMR: (400 MHz, Methanol-d$_4$) δ 8.18 (dd, J=1.6, 7.6 Hz, 1H), 8.08 (dd, J=1.6, 7.6 Hz, 1H), 7.72-7.62 (m, 2H), 7.60-7.52 (m, 2H), 7.44 (t, J=7.6 Hz, 1H), 3.7-3.72 (m, 4H), 3.55-3.45 (m, 2H), 3.40 (t, J=7.2 Hz, 2H), 2.90-2.60 (m, 2H), 2.42-2.21 (m, 2H).

MS-ESI calculated for [M+H]$^+$: 410, found: 410.

The reaction procedure was similar to that of the Step 8 of Example 1. The crude product was isolated by high performance liquid chromatography (formic acid system) to afford compound 4-2 (i.e., Example 4).

$^1$H NMR: (400 MHz, Methanol-d$_4$) δ 8.18 (d, J=8.8 Hz, 2H), 8.07 (d, J=7.6 Hz, 1H), 7.53 (d, J=7.6 Hz, 1H), 7.49-7.40 (m, 1H), 7.17 (d, J=8.8 Hz, 2H), 3.93 (s, 3H), 3.79-3.74 (m, 2H), 3.73 (s, 2H), 3.55-3.46 (m, 2H), 3.38 (t, J=7.2 Hz, 2H), 2.83-2.61 (m, 2H), 2.43-2.22 (m, 2H).

MS-ESI calculated for [M+H]$^+$: 406, found: 406.

Example 5

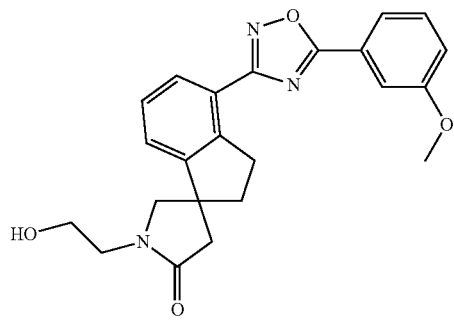

Example 6

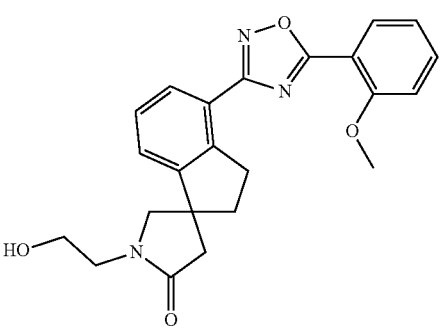

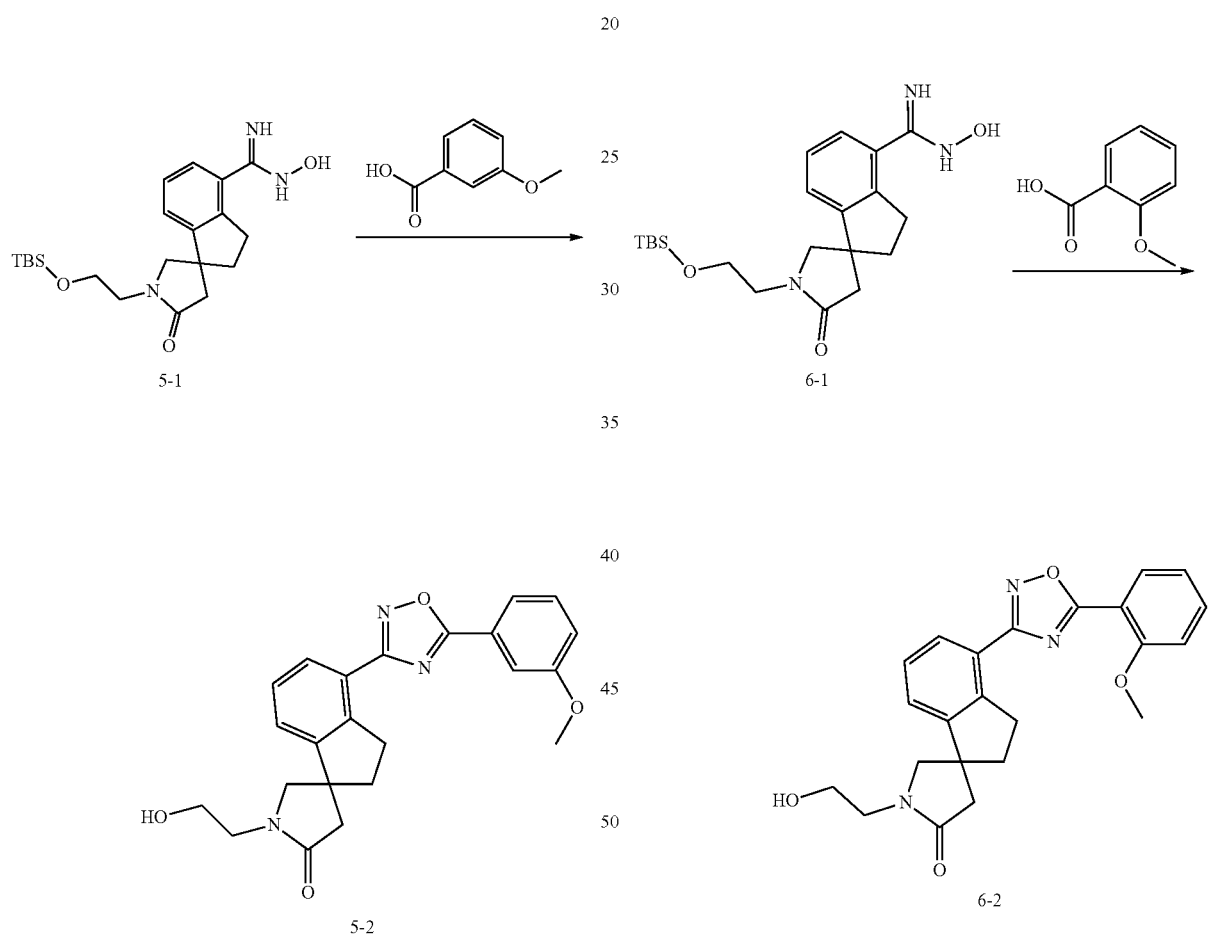

The reaction procedure was similar to that of the Step 8 of Example 1. The crude product was isolated by high performance liquid chromatography (formic acid system) to afford compound 5-2 (i.e., Example 5).

$^1$H NMR: (400 MHz, Methanol-$d_4$) δ 8.09 (d, J=7.6 Hz, 1H), 7.82 (d, J=7.6 Hz, 1H), 7.76 (s, 1H), 7.59-7.52 (m, 2H), 7.45 (t, J=7.6 Hz, 1H), 7.27 (d, J=7.6 Hz, 1H), 3.94 (s, 3H), 3.76-3.73 (m, 4H), 3.57-3.46 (m, 2H), 3.39 (t, J=7.2 Hz, 2H), 2.85-2.61 (m, 2H), 2.45-2.22 (m, 2H).

MS-ESI calculated for [M+H]$^+$: 406, found: 406.

The reaction procedure was similar to that of the Step 8 of Example 1. The crude product was isolated by high performance liquid chromatography (formic acid system) to afford compound 6-2 (i.e., Example 6).

$^1$H NMR: (400 MHz, Methanol-$d_4$) δ 8.11 (d, J=7.6 Hz, 1H), 8.05 (d, J=7.6 Hz, 1H), 7.65 (t, J=7.6 Hz, 1H), 7.52 (d, J=7.6 Hz, 1H), 7.43 (t, J=7.6 Hz, 1H), 7.27 (d, J=7.6 Hz, 1H), 7.16 (t, J=7.6 Hz, 1H), 4.01 (s, 3H), 3.74-3.71 (m, 4H), 3.55-3.44 (m, 2H), 3.37 (t, J=7.2 Hz, 2H), 2.82-2.61 (m, 2H), 2.43-2.20 (m, 2H).

MS-ESI calculated for [M+H]$^+$: 406, found: 406.

Example 7

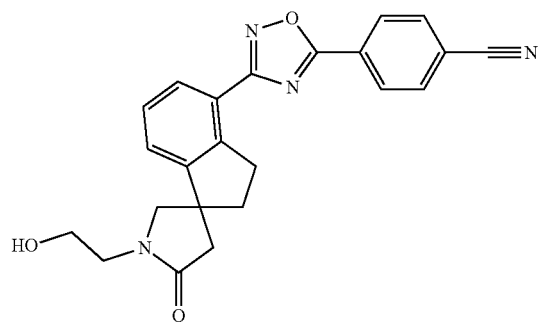

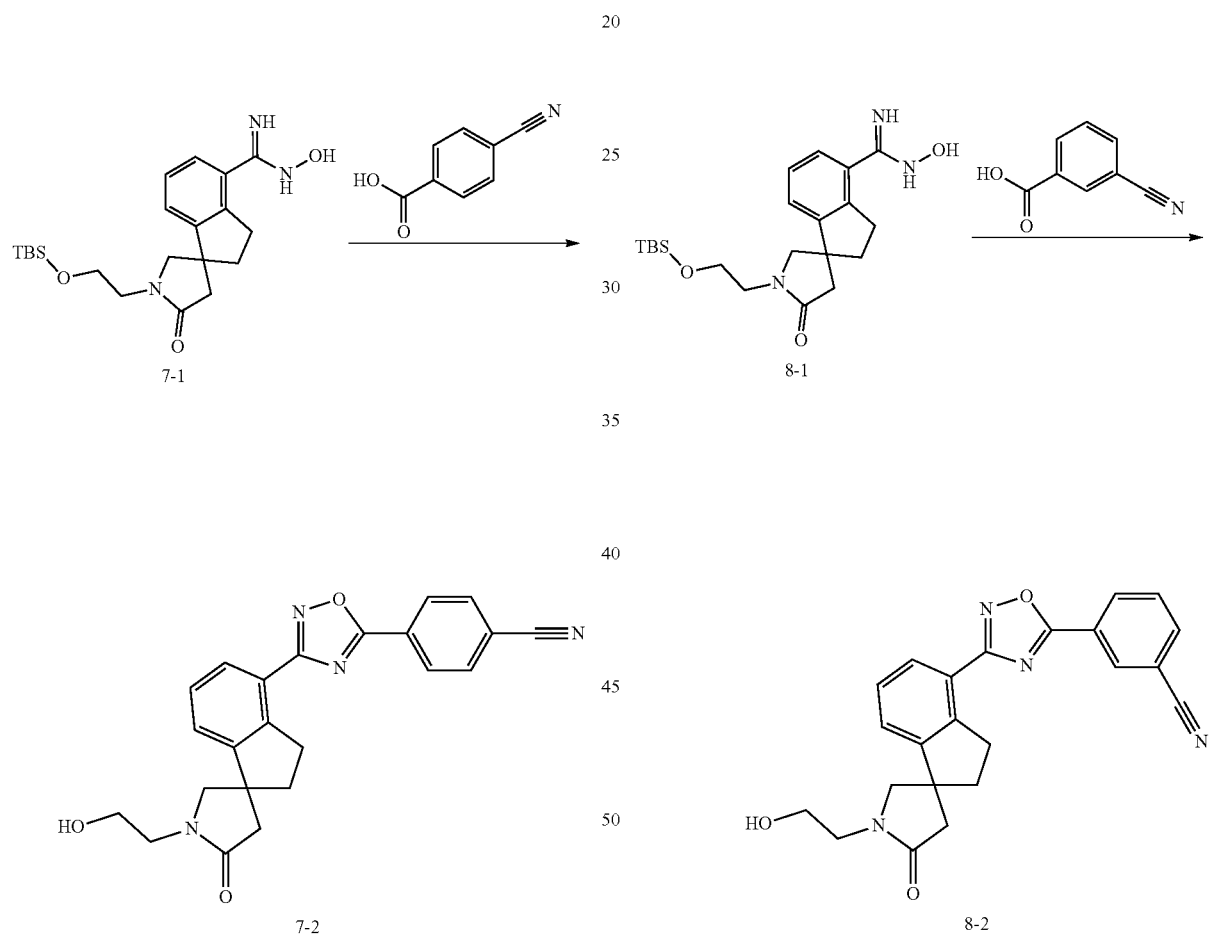

The reaction procedure was similar to that of the Step 8 of Example 1. The crude product was isolated by high performance liquid chromatography (formic acid system) to afford compound 7-2 (i.e., Example 7).

$^1$H NMR: (400 MHz, Methanol-$d_4$) δ 8.38 (d, J=8.4 Hz, 2H), 8.09 (d, 7.6 Hz, 1H), 8.03 (d, J=8.4 Hz, 2H), 7.54 (d, J=7.6 Hz, 1H), 7.44 (t, J=7.6 Hz, 1H), 3.74-3.71 (m, 4H), 3.53-3.46 (m, 2H), 3.38-3.34 (m, 2H), 2.81-2.61 (m, 2H), 2.31-2.21 (m, 2H).

MS-ESI calculated for [M+H]$^+$: 401, found: 401.

Example 8

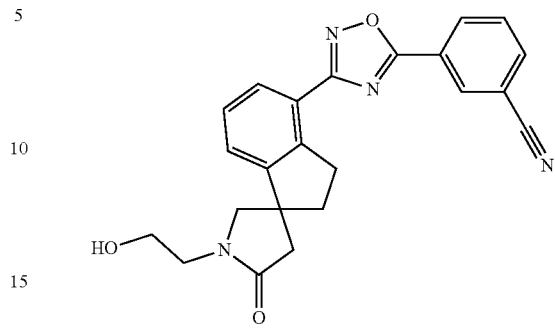

The reaction procedure was similar to that of the Step 8 of Example 1. The crude product was isolated by high performance liquid chromatography (formic acid system) to afford compound 8-2 (i.e., Example 8).

$^1$H NMR: (400 MHz, Methanol-$d_4$) δ 8.55 (s, 1H), 8.52-8.47 (m, 1H), 8.11-8.02 (m, 2H), 7.82 (t, J=8.0 Hz, 1H), 7.53 (d, J=7.6 Hz, 1H), 7.43 (t, J=7.6 Hz, 1H), 3.74 (t, J=5.6 Hz, 2H), 3.71 (s, 2H), 3.54-3.44 (m, 2H), 3.37 (t, J=7.2 Hz, 2H), 2.81-2.60 (m, 2H), 2.46-2.20 (m, 2H).

MS-ESI calculated for [M+H]$^+$: 401, found: 401.

Example 9

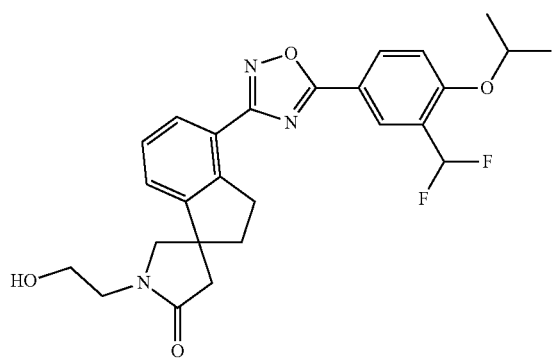

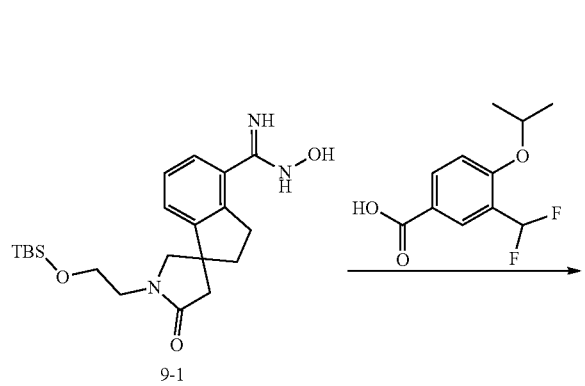

Example 10

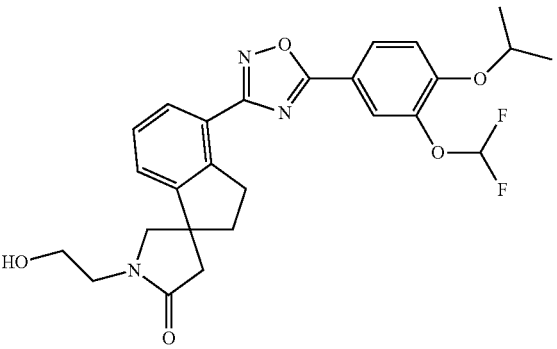

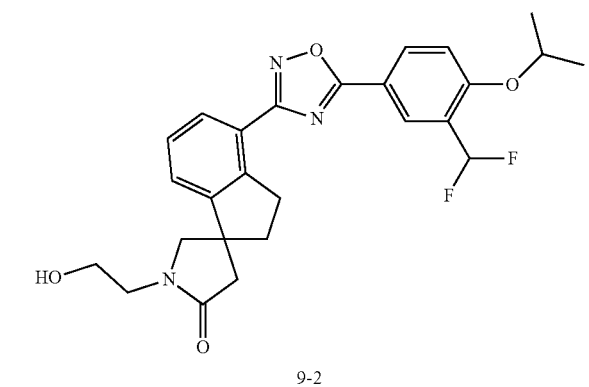

The reaction procedure was similar to that of the Step 8 of Example 1. The crude product was isolated by high performance liquid chromatography (formic acid system) to afford compound 9-2 (i.e., Example 9).

$^1$H NMR: (400 MHz, Methanol-$d_4$) δ 8.36-8.28 (m, 2H), 8.11-8.04 (m, 1H), 7.53 (d, J=7.6 Hz, 1H), 7.44 (t, J=7.6 Hz, 1H), 7.36 (d, J=7.6 Hz, 1H), 7.03 (t, J=55.2 Hz, 1H), 4.97-4.90 (m, 1H) 3.75 (t, J=1.0 Hz, 2H), 3.72 (s, 2H), 3.56-3.43 (m, 2H), 3.38 (t, J=7.2 Hz, 2H), 2.83-2.61 (m, 2H), 2.42-2.18 (m, 2H), 1.42 (d, J=6.0 Hz, 6H).

MS-ESI calculated for [M+H]$^+$: 484, found: 484.

The reaction procedure was similar to that of the Step 8 of Example 1. The crude product was isolated by high performance liquid chromatography (formic acid system) to afford compound 10-2 (i.e., Example 10).

$^1$H NMR: (400 MHz, Methanol-$d_4$) δ 8.12-8.03 (m, 2H), 7.95 (s, 1H), 7.52 (d, J=7.6 Hz, 1H), 7.43 (t, J=7.6 Hz, 1H), 7.34 (d, J=7.6 Hz, 1H), 7.03-6.65 (t, J=74.4 Hz, 1H), 4.86-4.81 (m, 1H), 3.74-3.71 (m, 4H), 3.56-3.44 (m, 2H), 3.36 (t, J=7.2 Hz, 2H), 2.82-2.59 (m, 2H), 2.42-2.19 (m, 2H), 1.42 (d, J=6.0 Hz, 6H).

MS-ESI calculated for [M+H]$^+$: 500, found: 500.

Example 11

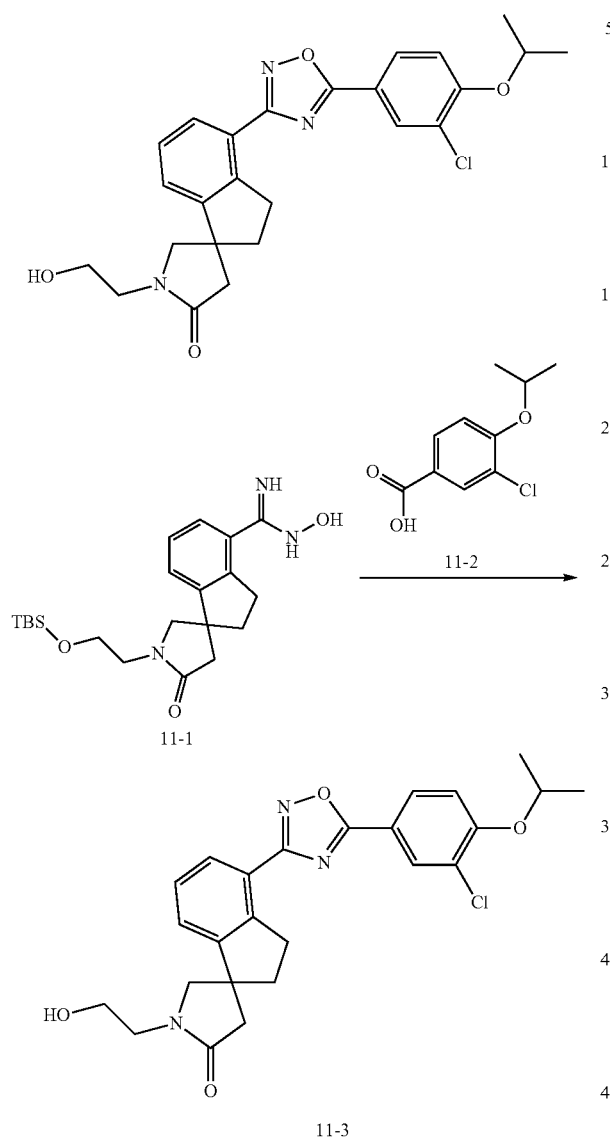

Step 1

Compound 11-2 (53.2 mg, 0.248 mmol) was dissolved in DMF (4.00 mL). HOBt (67.0 mg, 0.496 mmol) and 1-ethyl-3-(3-dimethylaminopropyl)carbodiimide hydrochloride (71.3 mg, 0.372 mmol) were added to the reaction solution. The reaction solution was stirred at 15° C. for 1 hour. Compound 11-1 (100 mg, 0.248 mmol) was then added to the reaction solution. The mixture was stirred at 15° C. for 1 hour, and finally heated to 85° C. and stirred for 12 hours. The reaction solution was cooled to room temperature, and isolated by high performance liquid chromatography (formic acid system) to afford compound 11-3 (i.e., Example 11).

$^1$H NMR: (400 MHz, CDCl$_3$) δ 8.24 (d, J=2.0 Hz, 1H), 8.12-8.04 (m, 2H), 7.40 (d, J=4.4 Hz, 2H), 7.06 (d, J=9.0 Hz, 1H), 4.76-4.68 (m, 1H), 3.85-3.81 (m, 2H), 3.67-3.49 (m, 4H), 3.42-3.34 (m, 2H), 2.82-2.75 (m, 1H), 2.72-2.64 (m, 1H), 2.72-2.64 (m, 1H), 2.38-2.23 (m, 2H), 1.45 (d, J=6.0 Hz, 6H).

MS-ESI calculated for [M+H]$^+$: 468, found: 468.

Example 12

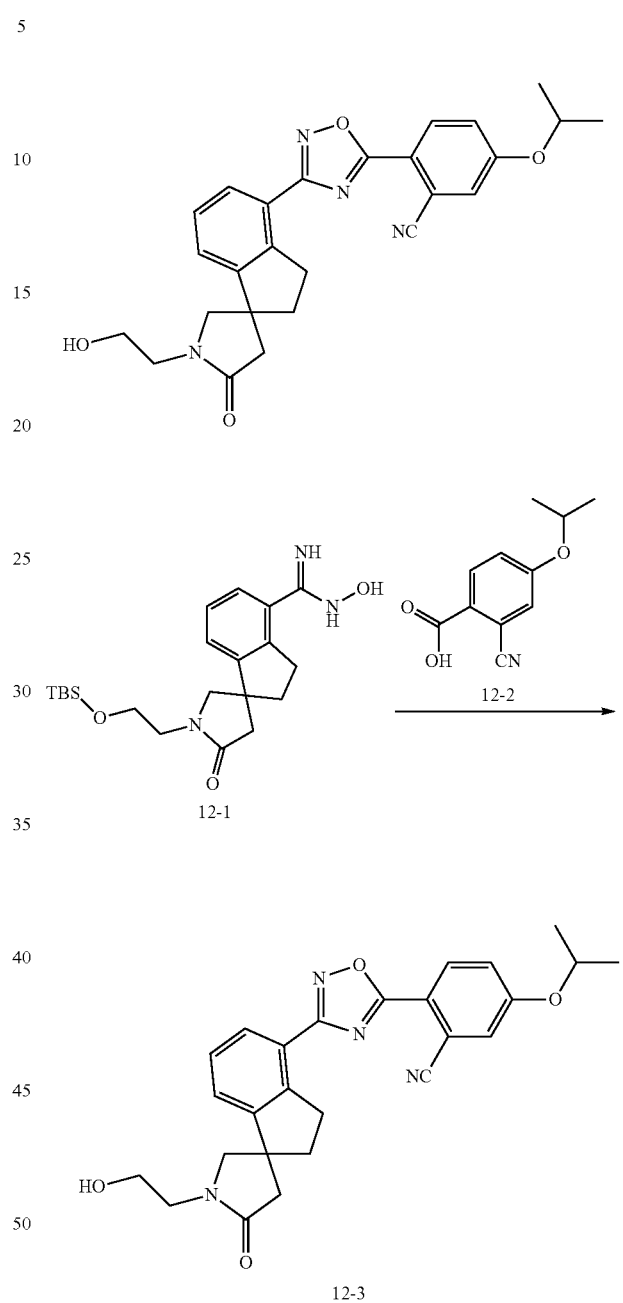

Step 1

The reaction procedure was similar to that of the Step 1 of Example 11. The residue was isolated by high performance liquid chromatography (formic acid system) to afford compound 12-3 (i.e., Example 12).

$^1$H NMR: (400 MHz, Methanol-d$_4$) δ 8.26 (d, J=8.8 Hz, 1H), 8.05 (d, J=7.6 Hz, 1H), 7.52-7.48 (m, 2H), 7.43-7.37 (m, 2H), 4.86-4.82 (m, 1H), 3.74-3.70 (m, 4H), 3.56-3.43 (m, 2H), 3.39 (t, J=7.2 Hz, 2H), 2.75-2.64 (m, 2H), 2.40-2.31 (m, 1H), 2.28-2.19 (m, 1H), 1.39 (d, J=6.0 Hz, 6H).

MS-ESI calculated for [M+H]$^+$: 459, found: 459.

115
Example 13

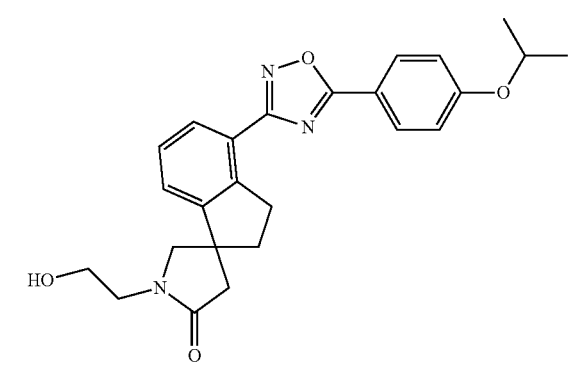

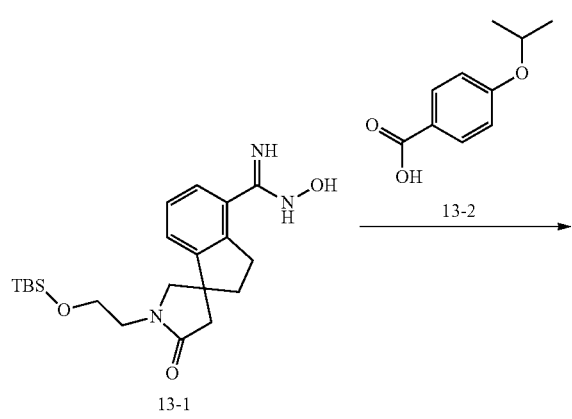

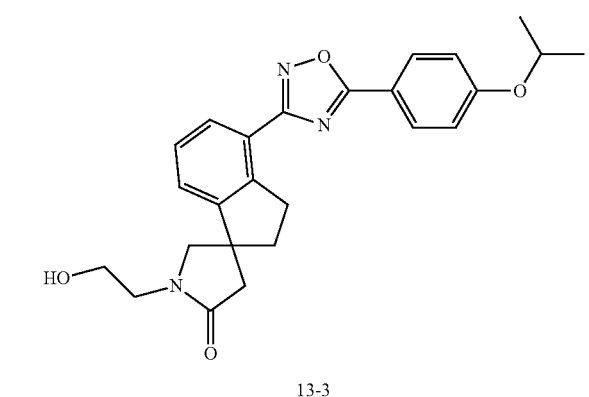

116
Example 14

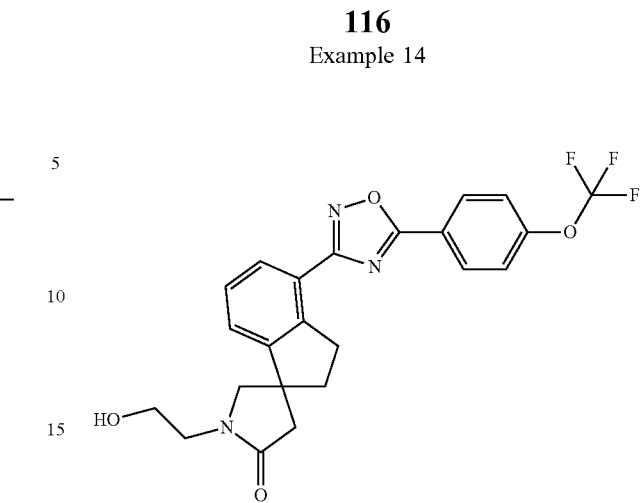

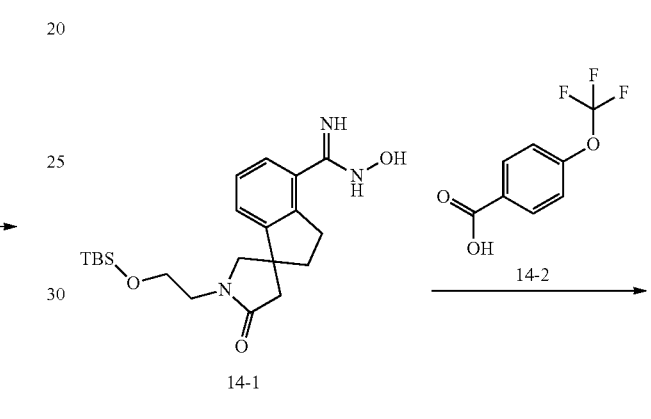

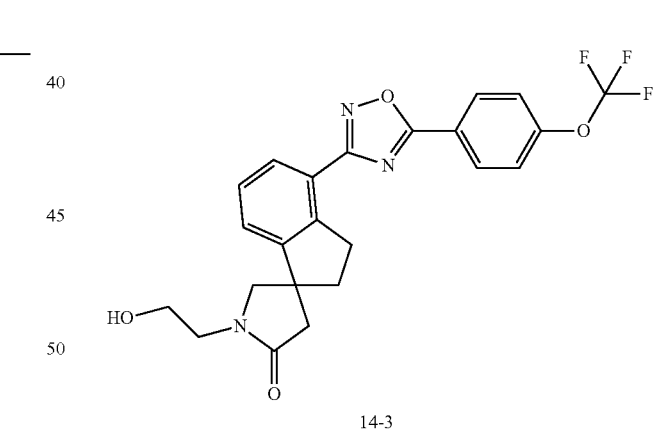

Step 1

The reaction procedure was similar to that of the Step 1 of Example 11. The residue was isolated by high performance liquid chromatography (formic acid system) to afford compound 13-3 (i.e., Example 13).

$^1$H NMR: (400 MHz, Methanol-d$_4$) δ 8.12 (d, J=8.8 Hz, 2H), 8.03 (d, J=7.6 Hz, 1H), 7.49 (d, J=7.6 Hz, 1H), 7.41 (t, J=7.6 Hz, 1H), 7.10 (d, J=8.8 Hz, 2H), 4.78-4.72 (m, 1H), 3.77-3.69 (m, 4H), 3.56-3.44 (m, 2H), 3.35 (t, J=7.2 Hz, 2H), 2.75-2.64 (m, 2H), 2.39-2.31 (m, 1H), 2.28-2.19 (m, 1H), 1.37 (d, J=6.0 Hz, 6H).

MS-ESI calculated for [M+H]$^+$: 434, found: 434.

Step 1

The reaction procedure was similar to that of the Step 1 of Example 11. The residue was isolated by high performance liquid chromatography (formic acid system) to afford compound 14-3 (i.e., Example 14).

$^1$H NMR: (400 MHz, Methanol-d$_4$) δ 8.36-8.31 (m, 2H), 8.06 (d, J=7.6 Hz, 1H), 7.53 (t, J=7.6 Hz, 3H), 7.42 (t, J=7.6 Hz, 1H), 3.77-3.69 (m, 4H), 3.56-3.44 (m, 2H), 3.37 (t, J=7.2 Hz, 2H), 2.7-2.65 (m, 2H), 2.41-2.32 (m, 1H), 2.29-2.20 (m, 1H).

MS-ESI calculated for [M+H]$^+$: 460, found: 460.

Example 15

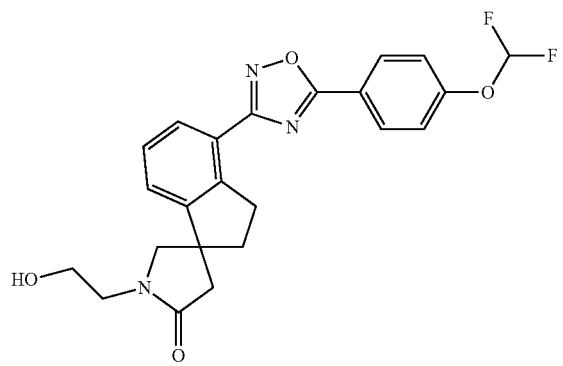

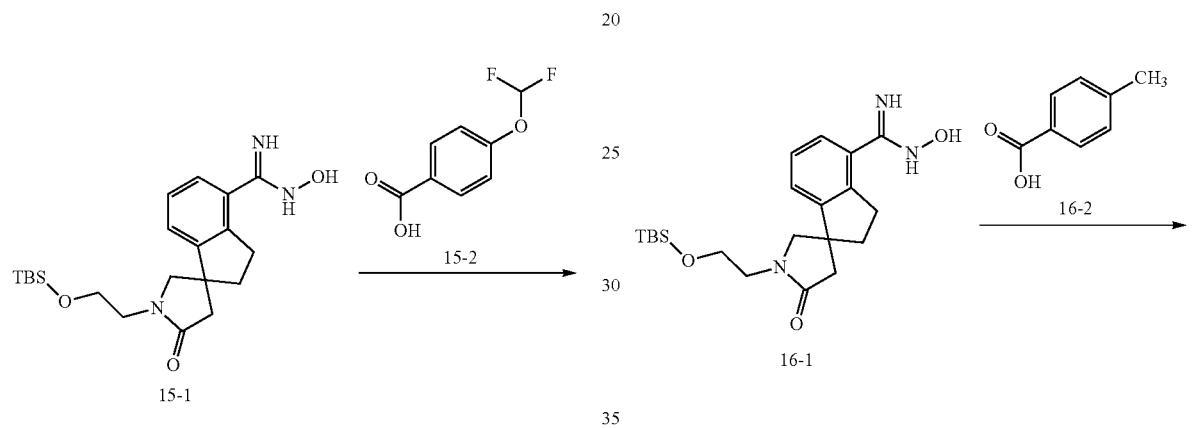

Step 1

The reaction procedure was similar to that of the Step 1 of Example 11. The residue was isolated by high performance liquid chromatography (formic acid system) to afford compound 15-3 (i.e., Example 15).

$^1$H NMR: (400 MHz, Methanol-$d_4$) δ 8.27 (d, J=8.8 Hz, 2H), 8.09-8.02 (m, 1H), 7.56 (d, J=7.6 Hz, 1H), 7.45-7.35 (m, 3H), 7.03 (t, J=73.2 Hz, 1H), 3.80-3.67 (m, 4H), 3.58-3.44 (m, 2H), 3.37 (t, J=7.2 Hz, 2H), 2.71 (q, J=1.0 Hz, 2H), 2.41-2.32 (m, 1H), 2.30-2.19 (m, 1H).

MS-ESI calculated for [M+H]$^+$: 442, found: 442.

Example 16

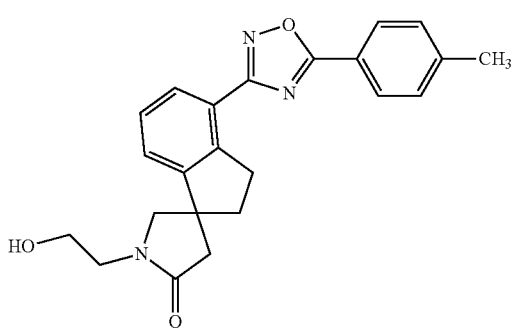

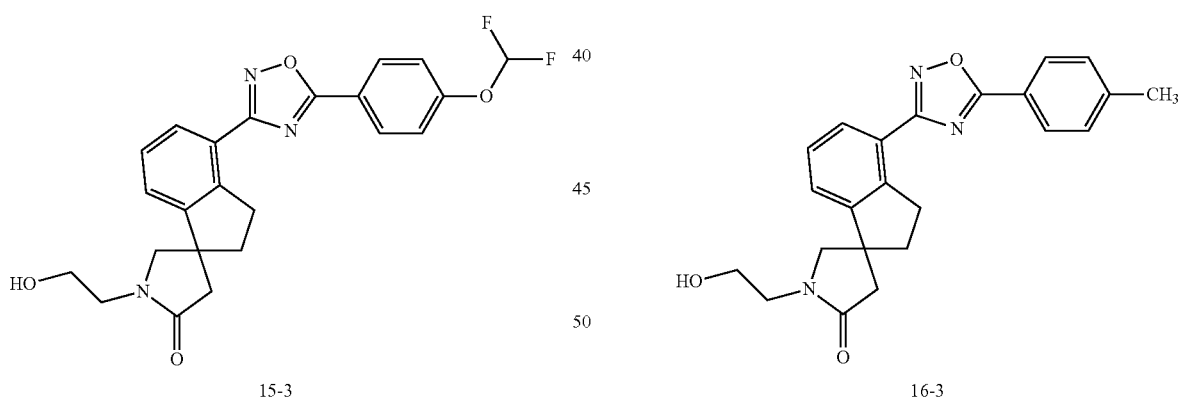

Step 1

The reaction procedure was similar to that of the Step 1 of Example 11. The residue was isolated by high performance liquid chromatography (formic acid system) to afford compound 16-3 (i.e., Example 16).

$^1$H NMR: (400 MHz, Methanol-$d_4$) δ 8.11 (d, J=8.4 Hz, 2H), 8.06 (d, J=7.6 Hz, 1H), 7.52 (d, J=7.6 Hz, 1H), 7.47-7.40 (m, 3H), 3.74-3.71 (m, 4H), 3.56-3.44 (m, 2H), 3.37 (t, J=7.2 Hz, 2H), 2.76-2.65 (m, 2H), 2.47 (s, 3H), 2.41-2.33 (m, 1H), 2.30-2.21 (m, 1H).

MS-ESI calculated for [M+H]$^+$: 390, found: 390.

Example 17

Example 18

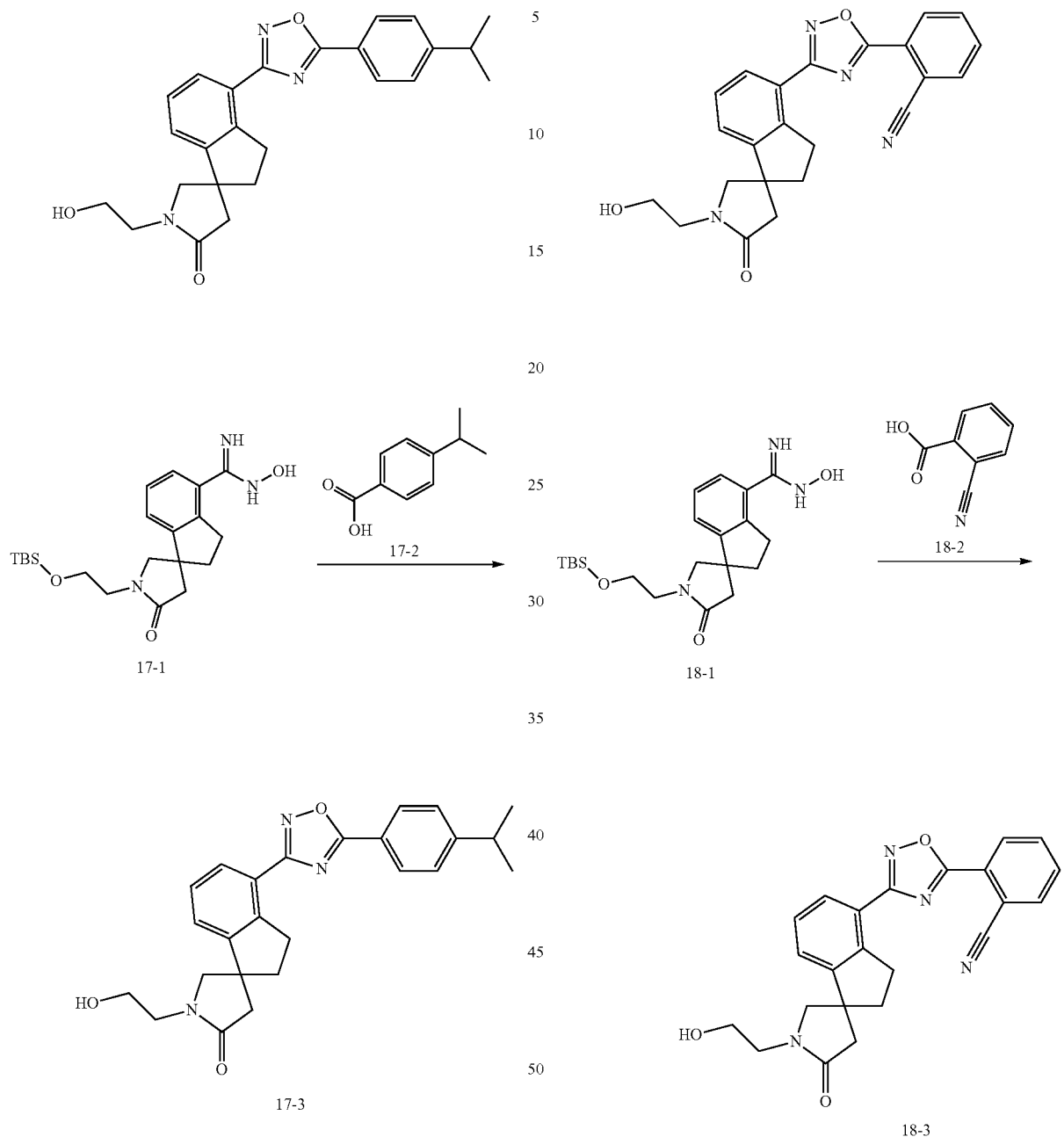

Step 1

The reaction procedure was similar to that of the Step 1 of Example 11. The residue was isolated by high performance liquid chromatography (formic acid system) to afford compound 17-3 (i.e., Example 17).

$^1$H NMR: (400 MHz, Methanol-$d_4$) δ 8.14 (d, J=8.4 Hz, 2H), 8.06 (d, J=6.8 Hz, 1H), 7.54-7.47 (m, 3H), 7.43 (t, J=6.8 Hz, 1H), 3.78-3.69 (m, 4H), 3.56-3.43 (m, 2H), 3.37 (t, J=7.2 Hz, 2H), 3.09-2.99 (m, 1H), 2.76-2.65 (m, 2H), 2.41-2.32 (m, 1H), 2.30-2.20 (m, 1H), 1.32 (d, J=6.8 Hz, 6H).

MS-ESI calculated for [M+H]$^+$: 418, found: 418.

Step 1

The reaction procedure was similar to that of the Step 1 of Example 11. The residue was isolated by high performance liquid chromatography (formic acid system) to afford compound 18-3 (i.e., Example 18).

$^1$H NMR: (400 MHz, CDCl$_3$) δ 8.34 (d, J=7.6 Hz, 1H), 8.15 (d, J=7.6 Hz, 1H), 7.95 (d, J=7.6 Hz, 1H), 7.82 (t, J=7.6 Hz, 1H), 7.75 (t, J=7.6 Hz, 1H), 7.45-7.40 (m, 2H), 3.85 (s, 2H), 3.67-3.61 (m, 2H), 3.58-3.49 (m, 2H), 3.48-3.40 (m, 2H), 2.78-2.64 (m, 2H), 2.40-2.24 (m, 2H).

MS-ESI calculated for [M+H]$^+$: 401, found: 401.

Example 19
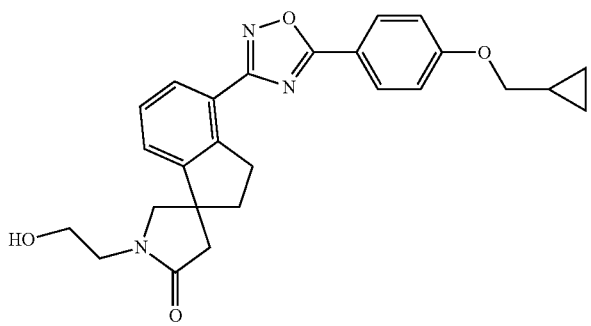
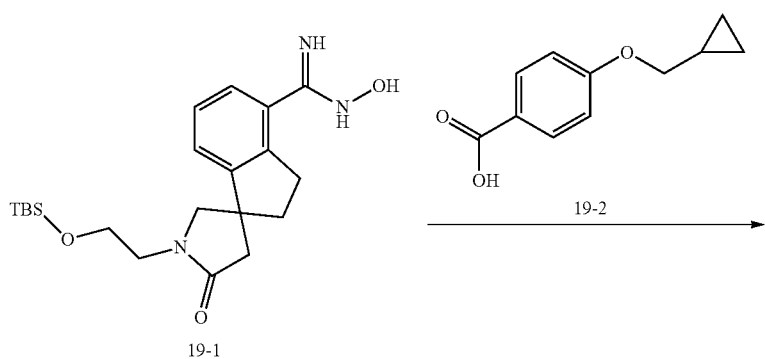
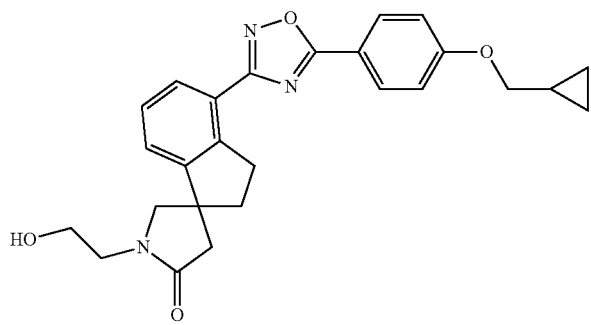
Step 1
The reaction procedure was similar to that of the Step 1 of Example 11. The residue was isolated by high performance liquid chromatography (formic acid system) to afford compound 19-3 (i.e., Example 19).
$^1$H NMR: (400 MHz, Methanol-$d_4$) δ 8.14 (d, J=8.8 Hz, 2H), 8.04 (d, J=7.6 Hz, 1H), 7.50 (d, J=7.6 Hz, 1H), 7.42 (t, J=7.6 Hz, 1H), 7.12 (d, J=8.8 Hz, 2H), 3.94 (d, J=6.8 Hz, 2H), 3.80-3.67 (m, 4H), 3.57-3.44 (m, 2H), 3.36-3.33 (m, 2H), 2.7-2.64 (m, 2H), 2.40-2.31 (m, 1H), 2.29-2.19 (m, 1H), 1.34-1.28 (m, 1H), 0.69-0.61 (m, 2H), 0.44-0.36 (m, 2H).
MS-ESI calculated for [M+H]$^+$: 446, found: 446.

Example 20
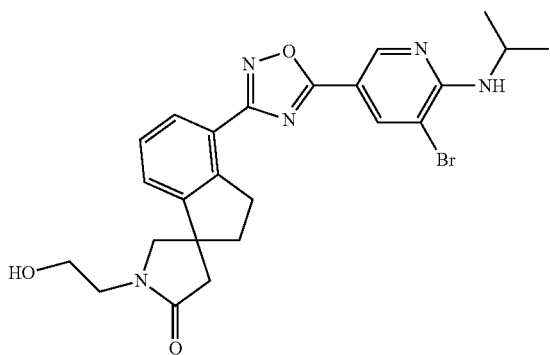
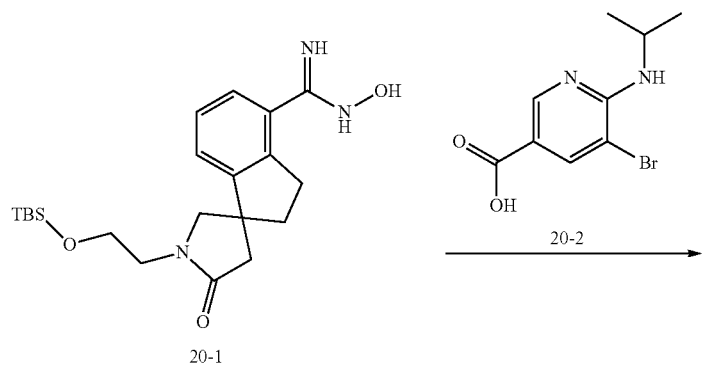
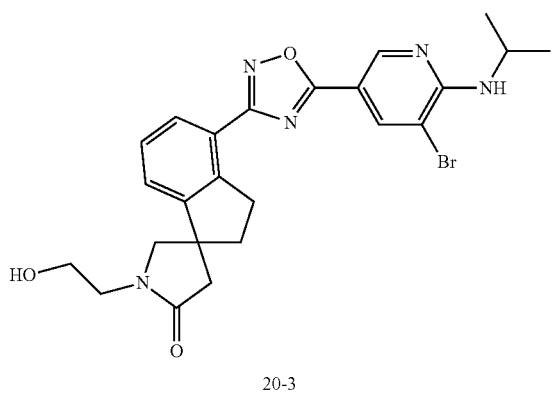
Step 1
The reaction procedure was similar to that of the Step 1 of Example 11. The residue was isolated by high performance liquid chromatography (formic acid system) to afford compound 20-3 (i.e., Example 20).
$^1$H NMR: (400 MHz, Methanol-$d_4$) δ 8.80 (d, J=2.0 Hz, 1H), 8.34 (d, J=2.0 Hz, 1H), 8.01 (d, J=7.6 Hz, 1H), 7.50 (d, J=7.6 Hz, 1H), 7.40 (t, J=7.6 Hz, 1H), 4.49-4.33 (m, 1H), 3.74-3.70 (m, 2H), 3.70 (s, 2H), 3.55-3.43 (m, 2H), 3.37-3.33 (m, 2H), 2.75-2.64 (m, 2H), 2.40-2.30 (m, 1H), 2.27-2.17 (m, 1H), 1.30 (d, J=6.8 Hz, 6H).
MS-ESI calculated for [M+H]$^+$: 512 and 514, found: 512 and 514.

Example 21
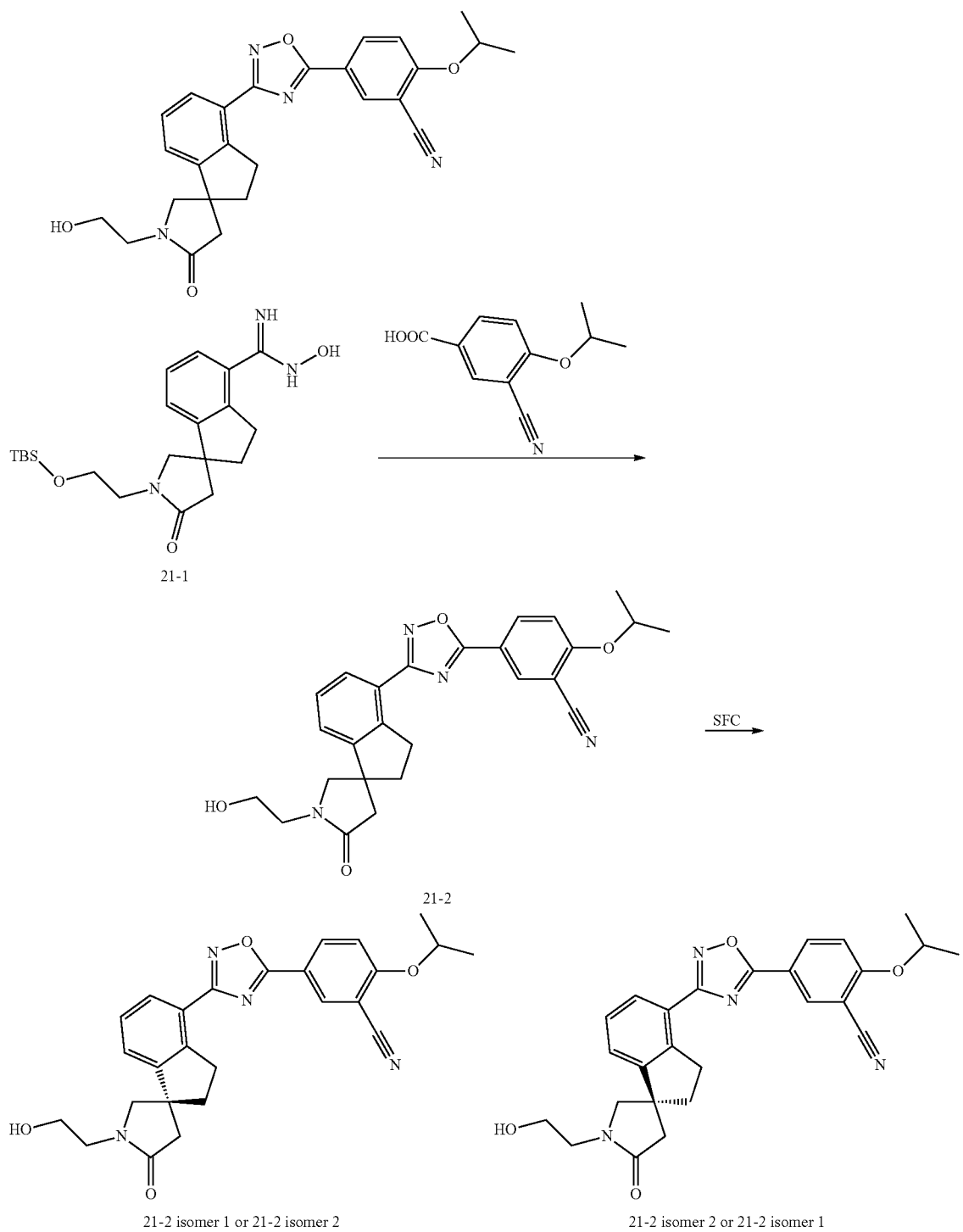
Step 1
By referring to the Step 8 of Example 1, compound 21-2 (i.e., Example 21) was obtained.
$^1$H NMR: (400 MHz, Methanol-$d_4$) δ 8.48-8.36 (m, 2H), 8.06-8.04 (m, 1H), 7.52 (d, J=7.2 Hz, 1H), 7.45-7.38 (m, 2H), 4.94-4.92 (m, 1H), 3.79-3.68 (m, 4H), 3.56-3.43 (m, 2H), 3.37-3.33 (m, 2H), 2.79-2.61 (m, 2H), 2.45-2.16 (m, 2H), 1.45 (d, J=6.0 Hz, 6H).
MS-ESI calculated for [M+H]$^+$: 459, found: 459.

Step 2

Chiral resolution of compound 21-2 afforded compound 21-2 isomer 1 and compound 21-2 isomer 2

SFC isolation method:

Chromatography column: Chiralpak AD-3 50 mm*4.6 mm I.D., 3 μm;

Mobile phase: A: carbon dioxide; B: 40% ethanol (containing 0.05% diethylamine);

Flow rate: 4 mL/min;

Column temperature: 40° C.

Compound 21-2 Isomer 1, retention time: 1.173 minutes. $^1$H NMR: (400 MHz, Methanol-$d_4$) δ 8.42-8.28 (m, 2H), 7.99 (d, J=7.6 Hz, 1H), 7.54-7.33 (m, 3H), 4.93-4.91 (m, 1H), 3.82-3.60 (m, 4H), 3.56-3.40 (m, 2H), 3.37-3.31 (m, 2H), 2.81-2.57 (m, 2H), 2.41-2.16 (m, 2H), 1.45 (d, J=5.6 Hz, 6H).

MS-ESI calculated for [M+H]$^+$: 459, found: 459.

Compound 21-2 isomer 2, retention time: 1.460 minutes. $^1$H NMR: (400 MHz, Methanol-$d_4$) δ 8.42-8.38 (m, 2H), 8.06-8.02 (m, 1H), 7.55-7.36 (m, 3H), 5.01-4.91 (m, 1H), 3.78-3.68 (m, 4H), 3.56-3.44 (m, 2H), 3.34 (s, 2H), 2.79-2.59 (m, 2H), 2.41-2.19 (m, 2H), 1.46 (d, J=6.0 Hz, 6H).

MS-ESI calculated for [M+H]$^+$: 459, found: 459.

Example 22

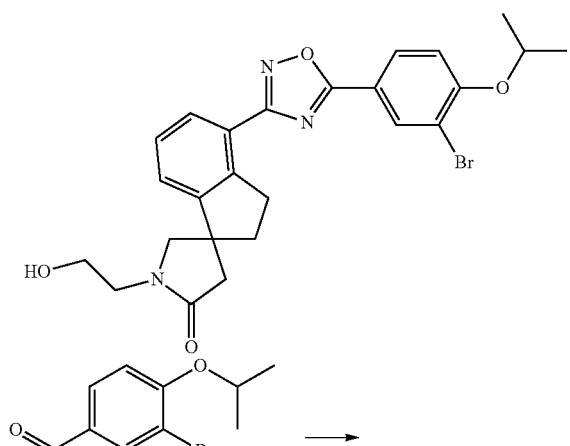

22-1

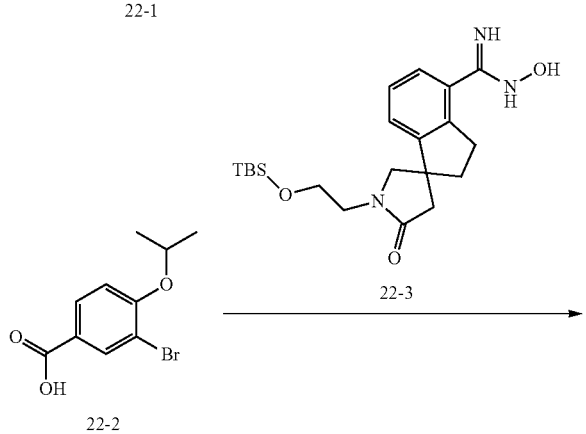

22-2

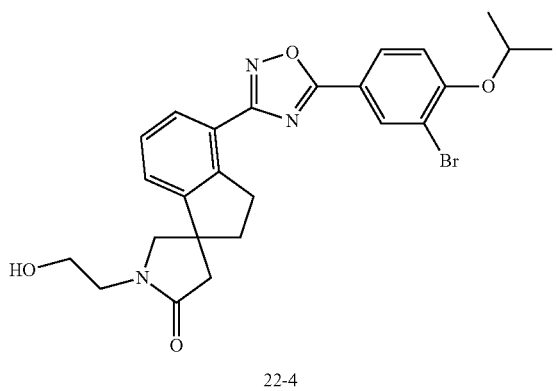

22-4

Step 1

Compound 22-1 (200 mg, 0.732 mmol) was dissolved in MeOH (5.00 mL). Lithium hydroxide monohydrate (61.5 mg, 1.46 mmol) and water (1.00 mL) were added. The mixture was stirred at 10° C. for 16 hours. The reaction solution was concentrated. The residue was added in water (3 mL) and extracted with dichloromethane (5 mL×1). The organic phase was discarded. The aqueous phase was adjusted to pH 5-6 with hydrochloric acid (1 mol/L), and extracted with dichloromethane (5 mL×2). The organic phase was dried over anhydrous sodium sulfate, filtered and concentrated to afford compound 22-2.

$^1$H NMR: (400 MHz, CDCl$_3$) δ 8.31 (d, J=2.0 Hz, 1H), 8.02 (dd, J=2.0, 8.8 Hz, 1H), 6.94 (d, J=8.8 Hz, 1H), 4.81-4.61 (m, 1H), 1.44 (d, J=6.0 Hz, 6H).

Step 2

Compound 22-2 (70.0 mg, 0.270 mmol) was dissolved in N,N-dimethylformamide (2.00 mL), and 1-hydroxybenzotriazole (73.0 mg, 0.540 mmol) and 1-(3-dimethylaminopropyl)-3-ethylcarbodiimide hydrochloride (77.7 mg, 0.405 mmol) were added. The mixture was stirred at 15° C. for 1 hour. Compound 22-3 (109 mg, 0.270 mmol) was added and the mixture was stirred at 15° C. for 1 hour. Hydrochloride/ethyl acetate (1.00 mL, 4 mol/L) was added and the mixture was stirred at 15° C. for 1 hour. Triethylamine was added to adjust the pH to 10 and the mixture was stirred at 85° C. for 12 hours. The reaction solution was concentrated, and the residue was isolated by high performance liquid chromatography (formic acid system) to afford compound 22-4 (i.e., Example 22).

$^1$H NMR: (400 MHz, Methanol-$d_4$) δ 8.40 (d, J=2.4 Hz, 1H), 8.18 (dd, J=2.4, 8.8 Hz, 1H), 8.08 (dd, J=7.6 Hz, 1H), 7.54 (d, J=7.6 Hz, 1H), 7.45 (t, J=7.6 Hz, 1H), 7.29 (d, J=8.8 Hz, 1H), 4.95-4.92 (m, 1H), 3.76 (t, J=5.6 Hz, 2H), 3.73 (s, 2H), 3.53-3.48 (m, 2H), 3.42-3.38 (m, 2H), 2.83-2.61 (m, 2H), 2.44-2.35 (m, 1H), 2.31-2.23 (m, 1H), 1.44 (d, J=6.0 Hz, 6H).

MS-ESI calculated for [M+H]$^+$: 512 and 514, found: 512 and 514.

Example 23

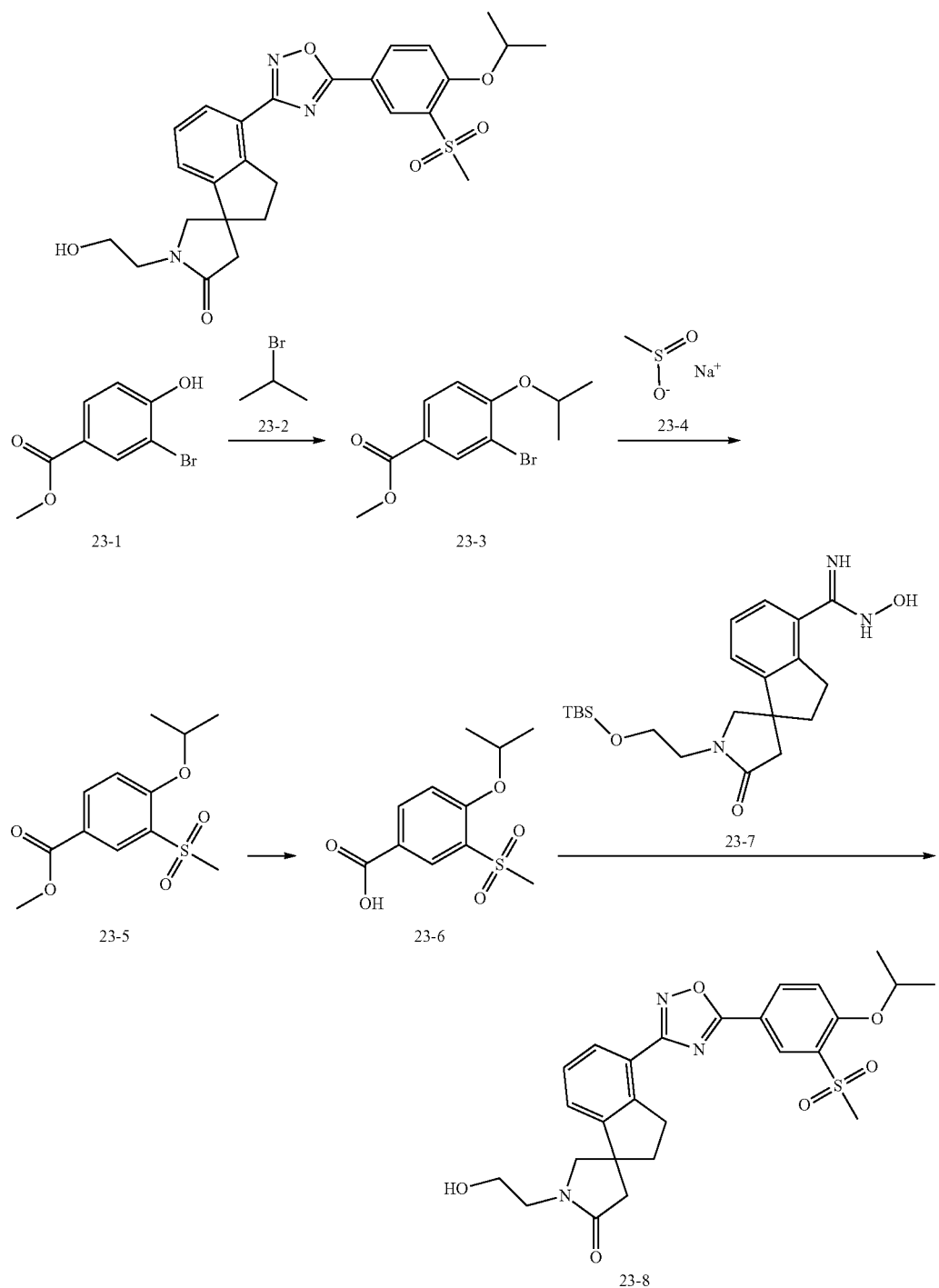

Step 1

Compound 23-1 (6.00 g, 26.0 mmol) was dissolved in N,N-dimethylformamide (100 mL). Compound 23-2 (3.83 g, 31.2 mmol) and potassium carbonate (10.8 g, 77.9 mmol) were added at 10° C. The mixture was stirred at this temperature for 16 hours. The reaction solution was concentrated. The residue was added into dichloromethane (100 mL) and stirred for 1 hour. The mixture was filtered. The filtrate was concentrated to afford compound 23-3.

$^1$H NMR: (400 MHz, CDCl$_3$) δ 8.23 (d, J=2.0 Hz, 1H), 7.94 (dd, J=2.0, 8.8 Hz, 1H), 6.90 (d, J=8.8 Hz, 1H), 4.75-4.61 (m, 1H), 3.89 (s, 3H), 1.42 (d, J=6.0 Hz, 6H).

Step 2

Compound 23-3 (2.00 g, 7.32 mmol) was dissolved in dimethyl sulfoxide (20.0 mL). Compound 23-4 (2.24 g, 22.0 mmol), cuprous iodide (697 mg, 3.66 mmol), L-proline (843 mg, 7.32 mmol) and sodium hydroxide (293 mg, 7.32 mmol) were added. The mixture was stirred at 100° C. for 16 hours under nitrogen. The reaction solution was poured into water (100 mL), and extracted with EtOAc (100 mL×1). The organic phase was dried over anhydrous sodium sulfate (5 g) and filtered. The crude product was isolated by silica gel column chromatography (silica, petroleum ether: ethyl acetate=3:1 to 1:1) to afford compound 23-5.

$^1$H NMR: (400 MHz, CDCl$_3$) δ 8.66 (d, J=2.0 Hz, 1H), 8.25 (dd, J=2.0, 8.8 Hz, 1H), 7.08 (d, J=8.8 Hz, 1H), 4.94-4.78 (m, 1H), 3.92 (s, 3H), 3.23 (s, 3H), 1.49 (d, J=6.0 Hz, 6H).

Step 3

Compound 23-5 (130 mg, 0.477 mmol) was dissolved in tetrahydrofuran (5.00 mL). Lithium hydroxide monohydrate (40.1 mg, 0.955 mmol) and water (1.00 mL) were added. The mixture was stirred at 15° C. for 2 hours. The reaction solution was concentrated. The residue was added into water (3 mL) and extracted with dichloromethane (5 mL×1). The organic phase was discarded. The aqueous phase was adjusted to pH 5 to 6 with hydrochloric acid (1 mol/L), and extracted again with dichloromethane (5 mL×2). The organic phase was dried over anhydrous sodium sulfate, filtered and concentrated to afford compound 23-6.

Step 4

Compound 23-6 (50.0 mg, 0.194 mmol) was dissolved in N,N-dimethylformamide (2.00 mL). 1-hydroxybenzotriazole (52.3 mg, 0.387 mmol) and 1-(3-dimethylaminopropyl)-3-ethylcarbodiimide hydrochloride (55.7 mg, 0.290 mmol) were added, and the mixture was stirred at 15° C. for 1 hour. Compound 23-7 (78.1 mg, 0.194 mmol) was then added and the mixture was stirred at 15° C. for 1 hour. The mixture was then heated to 80° C. and stirred for 16 hours. The reaction solution was concentrated, and the residue was isolated by high performance liquid chromatography (formic acid system) to afford compound 23-8 (i.e., Example 23).

$^1$H NMR: (400 MHz, Methanol-d$_4$) δ 8.73 (d, J=2.4 Hz, 1H), 8.50 (dd, J=2.4, 8.8 Hz, 1H), 8.10 (d, J=7.6 Hz, 1H), 7.59-7.51 (m, 2H), 7.46 (t, J=7.6 Hz, 1H), 5.10-5.01 (m, 1H), 3.79-3.72 (m, 4H), 3.55-3.48 (m, 2H), 3.40 (t, J=7.2 Hz, 2H), 3.34 (s, 3H), 2.85-2.61 (m, 2H), 2.45-2.22 (m, 2H), 1.52 (d, J=6.0 Hz, 6H).

MS-ESI calculated for [M+H]$^+$: 512, found: 512.

Example 24

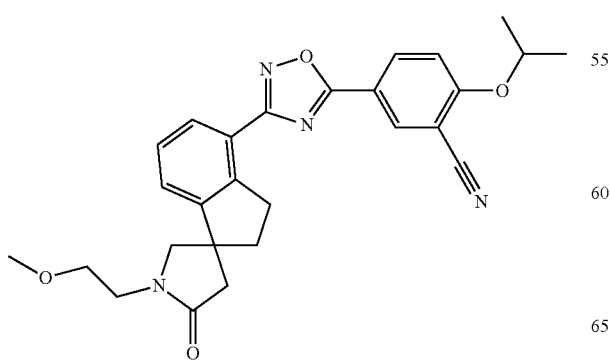

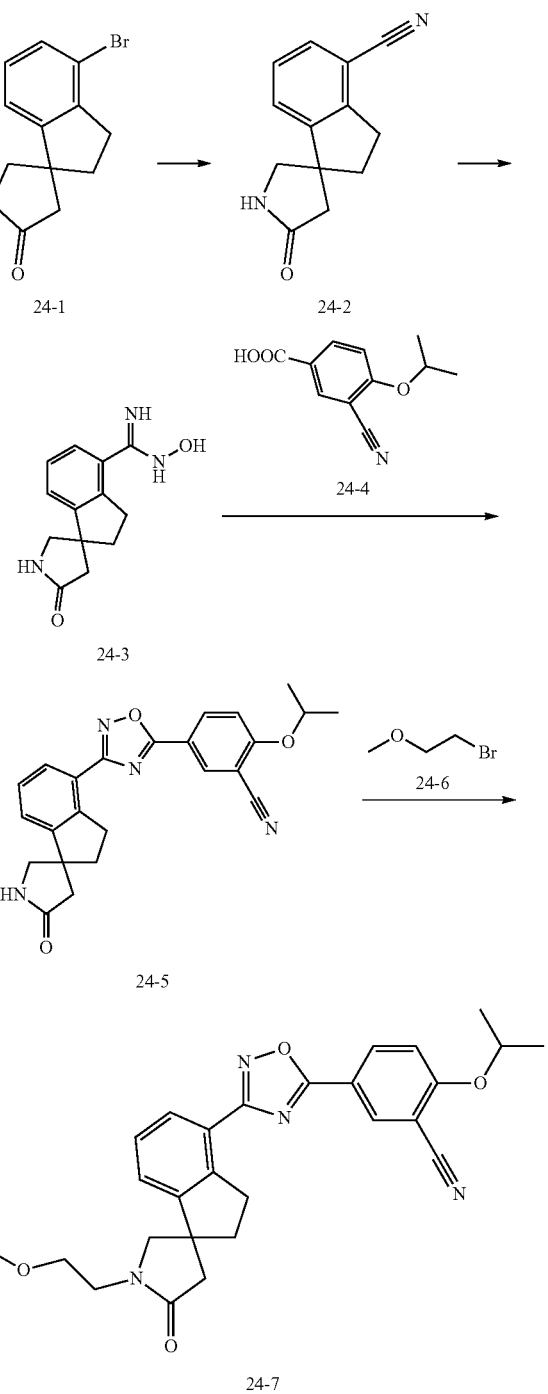

Step 1

Compound 24-1 (2.00 g, 7.52 mmol) was dissolved in acetonitrile (75.00 mL). Zinc cyanide (2.65 g, 22.6 mmol), tris(dibenzylideneacetone)dipalladium (1.38 g, 1.50 mmol) and 2-dicyclohexylphosphino-2',4',6'-triisopropylbiphenyl (1.43 g, 3.01 mmol) were added to the reaction solution. The reaction solution was stirred at 90° C. for 16 hours under nitrogen. The reaction solution was cooled to room temperature, and filtered. The filtrate was concentrated under reduced pressure. The crude product was isolated by silica gel column chromatography (silica, petroleum ether:ethyl acetate=1:1 to dichloromethane:methanol=6:1) to afford compound 24-2.

$^1$H NMR: (400 MHz, Methanol-$d_4$) δ 7.62 (d, J=7.6 Hz, 1H), 7.56 (d, J=7.6 Hz, 1H), 7.40 (t, J=1.0 Hz, 1H), 3.58-3.46 (m, 2H), 3.12 (t, J=7.2 Hz, 2H), 2.68-2.47 (m, 2H), 2.43-2.21 (m, 2H).

MS-ESI calculated for [M+H]$^+$: 213, found: 213.

Step 2

Compound 24-2 (1.20 g, 5.65 mmol) was dissolved in ethanol (30.0 mL). Hydroxylamine hydrochloride (1.18 g, 17.0 mmol) and triethylamine (2.29 g, 22.6 mmol, 3.13 mL) were added to the reaction solution. The reaction solution was stirred at 60° C. for 15 hours under nitrogen. The reaction solution was concentrated under reduced pressure. Water (100 mL) was then added. The mixture was extracted with ethyl acetate (150 mL×3) and filtered to afford a part of the product. The filtrate was concentrated to afford a crude product. Compound 24-3 was afforded. The crude product was used directly in the next reaction.

MS-ESI calculated for [M+H]$^+$: 246, found: 246.

Step 3

Compound 24-4 (637 mg, 3.06 mmol) was dissolved in N,N-dimethylformamide (5.00 mL). To the reaction solution were added 1-hydroxybenzotriazole (826 mg, 6.12 mmol) and 1-(3-dimethylaminopropyl)-3-ethylcarbodiimide hydrochloride (899 mg, 4.69 mmol). The reaction solution was stirred at 25° C. for 1 hour. Compound 24-3 (500.00 mg, 2.04 mmol) was then added to the reaction solution, and the reaction solution was stirred at 25° C. for 1 hour. The reaction solution was then heated to 85° C., and stirred at 85° C. for 15 hours. Water (20 mL) was added to the reaction solution. The mixture was extracted with ethyl acetate (20 mL×3). The organic phases were combined, washed with saturated brine (30 mL×1), dried over anhydrous sodium sulfate (5 g), filtered and concentrated. The crude product was isolated by silica gel column chromatography (silica, petroleum ether:ethyl acetate=1:1 to dichloromethane:methanol=10:1) to afford compound 24-5.

MS-ESI calculated for [M+H]+415, found: 415.

Step 4

Compound 24-5 (70.0 mg, 0.122 mmol) was dissolved in anhydrous N,N-dimethylformamide (1.00 mL). Sodium hydride (9.77 mg, 0.244 mmol, 60% purity) was added at 0° C. The reaction was stirred at this temperature for 1 hour. Compound 24-6 (33.9 mg, 0.244 mmol) was then added to the reaction solution, and the reaction solution was stirred at 16° C. for 3 hours. The reaction solution was isolated by high performance liquid chromatography (formic acid system) to afford compound 24-7 (i.e., Example 24).

$^1$H NMR: (400 MHz, Methanol-$d_4$) δ 8.42-8.29 (m, 2H), 8.02 (d, J=7.6 Hz, 1H), 7.52-7.45 (m, 1H), 7.43-7.36 (m, 2H), 4.98-4.89 (m, 1H), 3.67 (s, 2H), 3.63-3.47 (m, 4H), 3.37 (s, 3H), 3.35-3.32 (m, 2H), 2.77-2.60 (m, 2H), 2.36-2.14 (m, 2H), 1.46 (d, J=6.0 Hz, 6H).

MS-ESI calculated for [M+H]$^+$: 473, found: 473.

Example 25

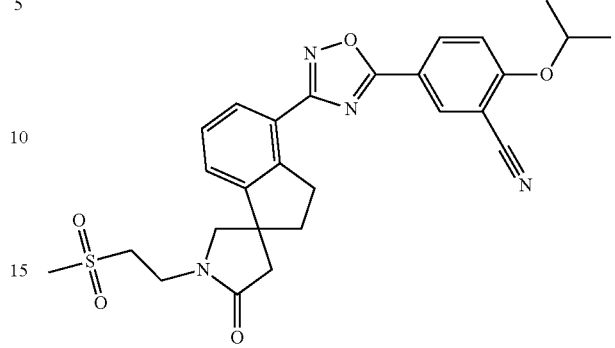

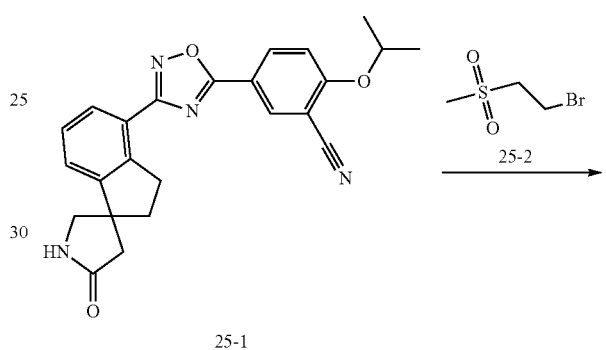

25-1

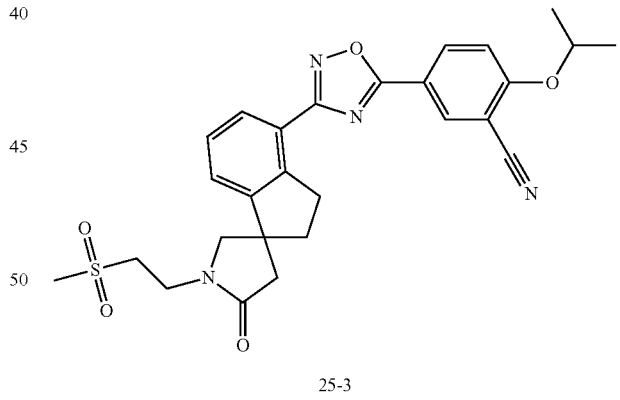

25-3

The reaction procedure was similar to that of Step 4 of Example 24, and the crude product was isolated by high performance liquid chromatography (formic acid system) to afford compound 25-3 (i.e., Example 25).

$^1$H NMR: (400 MHz, Methanol-$d_4$) δ 8.47-8.39 (m, 2H), 8.07 (d, J=6.8 Hz, 1H), 7.57-7.40 (m, 3H), 5.00-4.93 (m, 1H), 3.95-3.82 (m, 2H), 3.70 (s, 2H), 3.47 (t, J=6.8 Hz, 2H), 3.37 (t, J=6.8 Hz, 2H), 3.08 (s, 3H), 2.85-2.56 (m, 2H), 2.46-2.16 (m, 2H), 1.47 (d, J=6.0 Hz, 6H).

MS-ESI calculated for [M+H]$^+$: 521, found: 521.

Example 26

Example 27

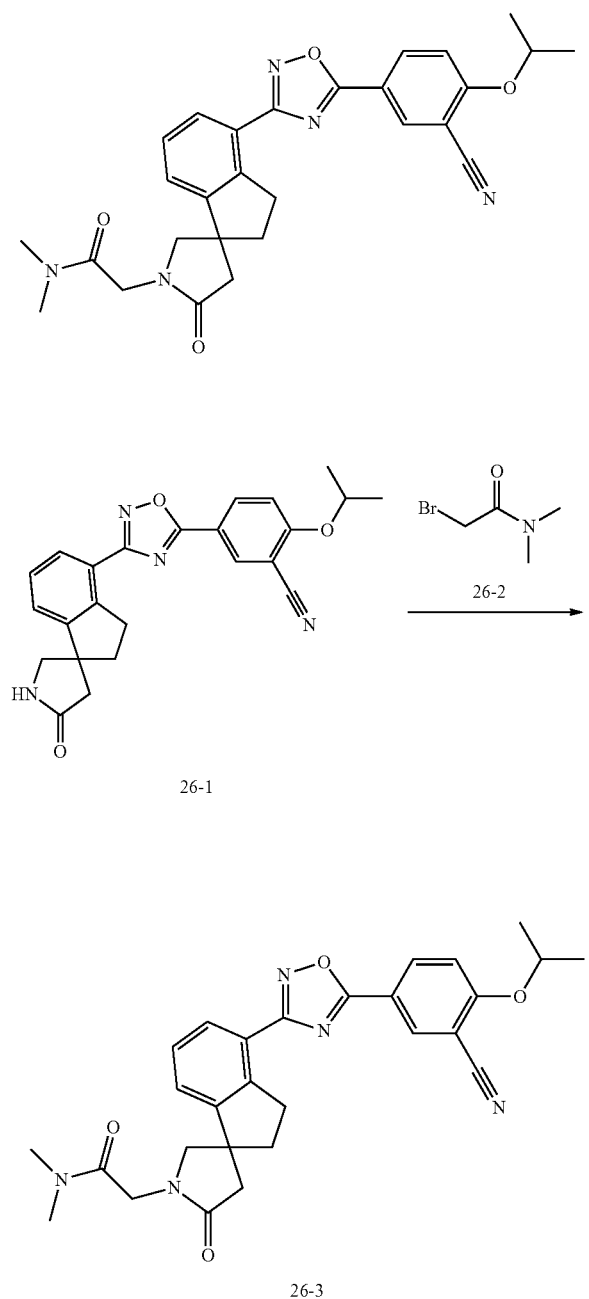

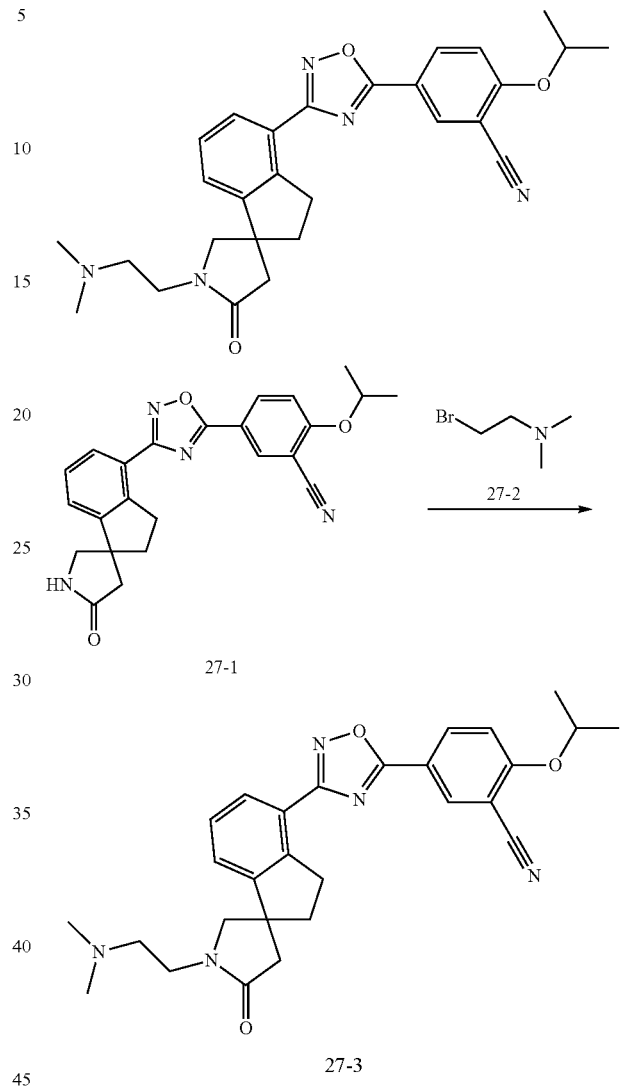

Compound 27-1 (50.0 mg, 0.0876 mmol) was dissolved in anhydrous N,N-dimethylformamide (1.00 mL). Sodium hydride (7.01 mg, 0.175 mmol, 60% purity) was added at 0° C., and the mixture was stirred at this temperature for 1 hour. Compound 27-2 (26.6 mg, 0.175 mmol) was then added to the reaction solution, and the reaction solution was stirred at 16° C. for 3 hours. Water (3 mL) was added to the reaction solution, and the pH of the reaction solution was adjusted to 6 with hydrochloric acid (2 mol/L). The reaction solution was isolated by high performance liquid chromatography (formic acid system) to afford compound 27-3 (i.e., Example 27).

$^1$H NMR: (400 MHz, Methanol-$d_4$) δ 8.41-8.32 (m, 2H), 8.03 (d, J=7.6 Hz, 1H), 7.53-7.47 (m, 1H), 7.45-7.38 (m, 2H), 4.97-4.92 (m, 1H), 3.75-3.67 (m, 2H), 3.65 (s, 2H), 3.34 (t, J=7.2 Hz, 2H), 3.18-3.10 (m, 2H), 2.85-2.77 (m, 7H), 2.73-2.57 (m, 1H), 2.41-2.18 (m, 2H), 1.45 (d, J=6.0 Hz, 6H).

MS-ESI calculated for [M+H]$^+$: 486, found: 486.

The reaction procedure was similar to that of Step 4 of Example 24, and the crude product was isolated by high performance liquid chromatography (formic acid system) to afford compound 26-3 (i.e., Example 26).

$^1$H NMR: (400 MHz, Methanol-$d_4$) δ 8.47-8.37 (m, 2H), 8.06 (d, J=6.8 Hz, 1H), 7.64 (d, J=6.8 Hz, 1H), 7.50-7.39 (m, 2H), 4.98-4.92 (m, 1H), 4.38-4.17 (m, 2H), 3.74-3.62 (m, 2H), 3.37 (t, J=7.2 Hz, 2H), 3.08 (s, 3H), 2.98 (s, 3H), 2.88-2.63 (m, 2H), 2.52-2.20 (m, 2H), 1.46 (d, J=6.0 Hz, 6H).

MS-ESI calculated for [M+H]$^+$: 500, found: 500.

Example 28

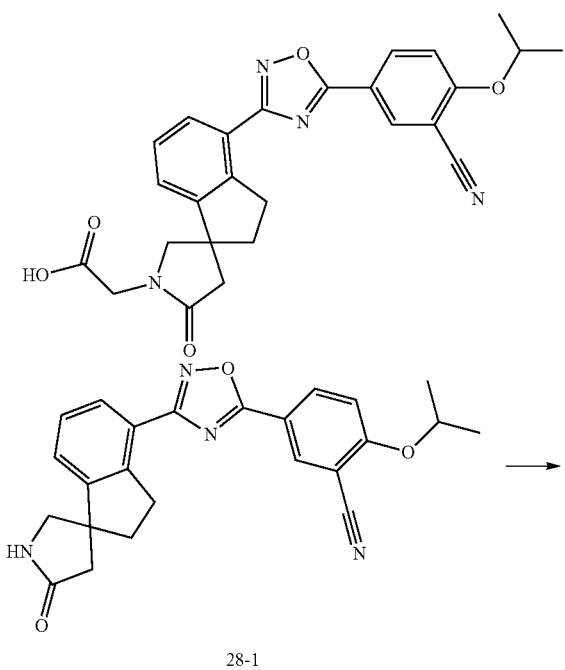

acetate (10 mL×3). The organic phases were combined, washed with water (20 mL×1), dried over anhydrous sodium sulfate (2 g) and filtered. The filtrate was concentrated under reduced pressure to afford a crude product. The crude product was isolated by thin layer chromatography (silica, petroleum ether:ethyl acetate=1:1) to afford compound 28-2.

MS-ESI calculated for [M+H]$^+$: 487, found: 487.

Step 2

Compound 28-2 (30.0 mg, 0.0617 mmol) was dissolved in methanol (3 mL) and water (1 mL). Lithium hydroxide monohydrate (5.17 mg, 0.123 mmol) was added at 16° C. The reaction solution was stirred at this temperature for 16 hours. The reaction solution was concentrated under reduced pressure to afford a crude product. The crude product was dissolved in methanol (3 mL) and adjusted to pH 6 with 2 mol/L hydrochloric acid. The reaction solution was isolated by high performance liquid chromatography (formic acid system) to afford compound 28-3 (i.e., Example 28).

$^1$H NMR: (400 MHz, Methanol-d$_4$) δ 8.46-8.40 (m, 2H), 8.06 (d, J=7.6 Hz, 1H), 7.63 (d, J=7.2 Hz, 1H), 7.48-7.39 (m, 2H), 4.97-4.93 (m, 1H), 4.15-4.00 (m, 2H), 3.77-3.64 (m, 2H), 3.39-3.34 (m, 2H), 2.85-2.62 (m, 2H), 2.48-2.20 (m, 2H), 1.47 (d, J=6.0 Hz, 6H).

MS-ESI calculated for [M+H]$^+$: 473, found: 473.

Example 29

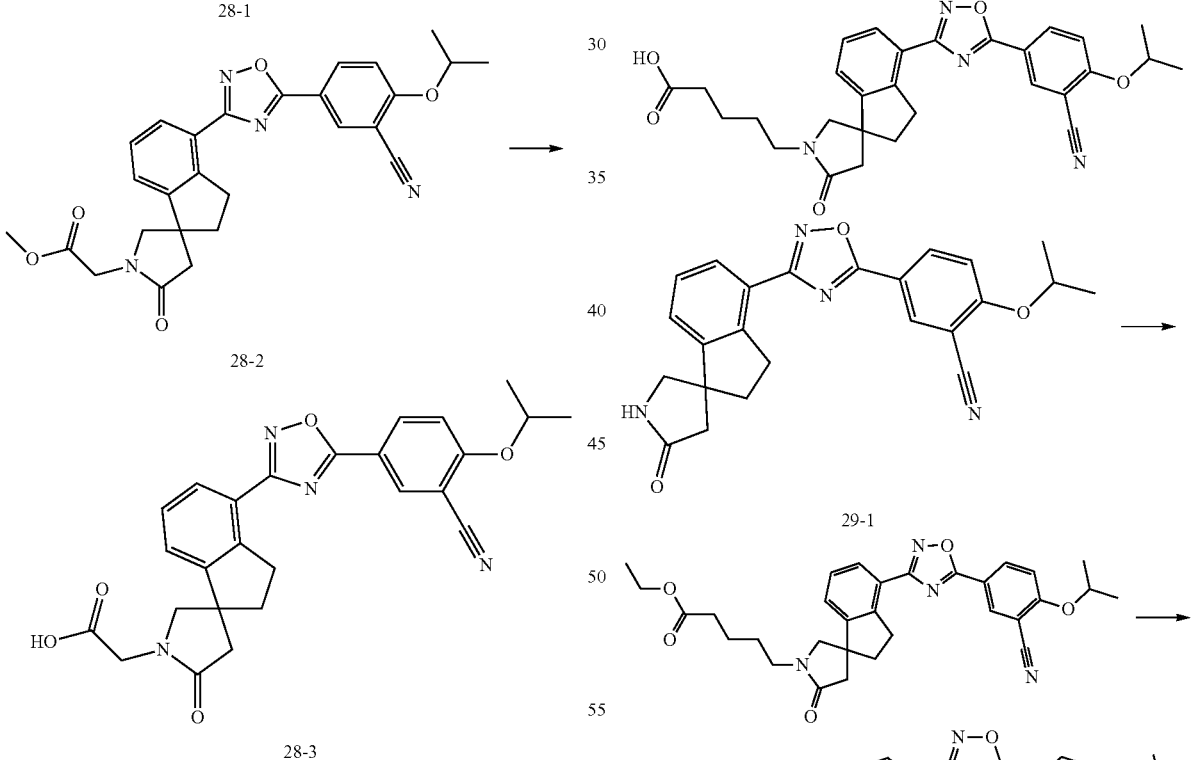

Step 1

Compound 28-1 (70.0 mg, 0.122 mmol) was dissolved in anhydrous N,N-dimethylformamide (1.00 mL). Sodium hydride (9.77 mg, 0.244 mmol, 60% purity) was added at 0° C., and the reaction was stirred at this temperature for 1 hour. Methyl bromoacetate (18.7 mg, 0.122 mmol) was then added to the reaction solution. The reaction solution was stirred at 16° C. for 16 hours. Water (10 mL) was added to the reaction solution. The mixture was extracted with ethyl Step 1

Compound 29-1 (70.0 mg, 0.122 mmol) was dissolved in anhydrous N,N-dimethylformamide (1.00 mL). Sodium hydride (9.77 mg, 0.244 mmol, 60% purity) was added at 0° C., and the reaction was stirred at this temperature for 1 hour. Ethyl 5-bromopentanoate (25.5 mg, 0.122 mmol) was then added to the reaction solution, and the reaction solution was stirred at 16° C. for 4 hours. Water (10 mL) was added to the reaction solution. The mixture was extracted with ethyl acetate (10 mL×3). The organic phases were combined, washed with water (20 mL×1), dried over anhydrous sodium sulfate (2 g) and filtered. The filtrate was concentrated under reduced pressure to afford a crude product. The crude product was isolated by thin layer chromatography (silica, petroleum ether:ethyl acetate=1:1) to afford compound 29-2.

MS-ESI calculated for [M+H]$^+$: 543, found: 543.

Step 2

The reaction procedure was similar to that of the Step 2 of Example 28, and the crude product was isolated by high performance liquid chromatography (formic acid system) to afford compound 29-3 (i.e., Example 29).

$^1$H NMR: (400 MHz, CDCl$_3$) δ 8.52-8.22 (m, 2H), 8.11-8.02 (m, 1H), 7.45-7.33 (m, 2H), 7.13 (d, J=7.6 Hz, 1H), 4.80 (s, 1H), 3.90-3.20 (m, 10H), 2.90-2.56 (m, 2H), 2.54-2.18 (m, 4H), 1.48 (d, J=3.6 Hz, 6H).

MS-ESI calculated for [M+h]$^+$: 515, found: 515.

Example 30

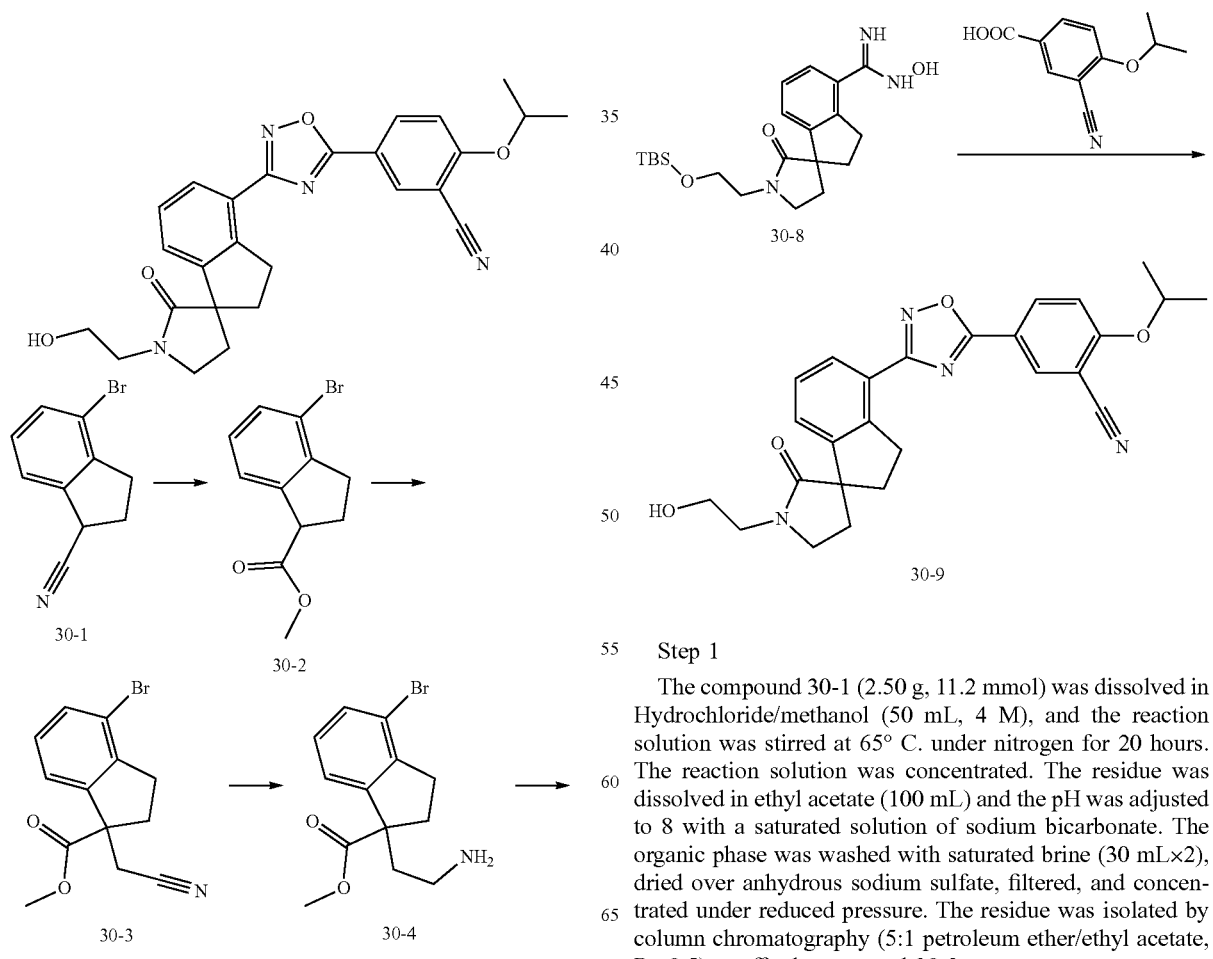

Step 1

The compound 30-1 (2.50 g, 11.2 mmol) was dissolved in Hydrochloride/methanol (50 mL, 4 M), and the reaction solution was stirred at 65° C. under nitrogen for 20 hours. The reaction solution was concentrated. The residue was dissolved in ethyl acetate (100 mL) and the pH was adjusted to 8 with a saturated solution of sodium bicarbonate. The organic phase was washed with saturated brine (30 mL×2), dried over anhydrous sodium sulfate, filtered, and concentrated under reduced pressure. The residue was isolated by column chromatography (5:1 petroleum ether/ethyl acetate, R$_f$=0.5) to afford compound 30-2.

¹H NMR: (400 MHz, CDCl₃) δ 7.38 (d, J=7.6 Hz, 1H), 7.31 (d, J=7.6 Hz, 1H), 7.07 (t, J=7.6 Hz, 1H), 4.23-4.10 (m, 1H), 3.74 (s, 3H), 3.19-3.08 (m, 1H), 3.01-2.88 (m, 1H), 2.54-2.29 (m, 2H).

MS-ESI calculated for [M+H]⁺: 255 and 257, found: 255 and 257.

Step 2

Compound 30-2 (2.30 g, 9.02 mmol) was dissolved in tetrahydrofuran (30 mL). Lithium diisopropylamide (2 M, 5.86 mL) was slowly added dropwise at −78° C. under nitrogen. The reaction solution was stirred at −78° C. for 1 hour, and 2-bromoacetonitrile (1.62 g, 13.5 mmol) was then added. The reaction solution was stirred at 25° C. for 12 hours. Water (5 mL) was added to the reaction solution, and the mixture was extracted with ethyl acetate (50 mL×2). The organic phases were combined, washed with saturated brine (20 mL×2), dried over anhydrous sodium sulfate, and concentrated under reduced pressure. The residue was isolated by column chromatography (10:1 petroleum ether/ethyl acetate, R$_f$=0.4) to afford compound 30-3.

¹H NMR: (400 MHz, CDCl₃) δ 7.47 (d, J=7.6 Hz, 1H), 7.21 (d, J=7.6 Hz, 1H), 7.16-7.10 (m, 1H), 3.75 (s, 3H), 3.23-3.01 (m, 3H), 2.91-2.80 (m, 2H), 2.29-2.23 (m, 1H).

Step 3

By referring to the Step 3 of Example 1, compound 30-4 was obtained.

MS-ESI calculated for [M+H]⁺: 298 and 300, found: 298 and 300.

Step 4

By referring to Step 4 of Example 1, compound 30-5 was obtained.

¹H NMR: (400 MHz, CDCl₃) δ 7.42-7.34 (m, 1H), 7.13-7.04 (m, 2H), 6.33 (s, 1H), 3.58-3.40 (m, 2H), 3.25-3.10 (m, 1H), 3.06-2.91 (m, 1H), 2.59-2.54 (m, 1H), 2.40-2.27 (m, 2H), 2.11-2.07 (m, 1H).

MS-ESI calculated for [M+H]⁺: 266 and 268, found: 266 and 268.

Step 5

In the same manner as in Step 5 of Example 1, compound 30-6 was obtained.

¹H NMR: (400 MHz, CDCl₃) δ 7.38-7.34 (m, 1H), 7.07-7.03 (m, 2H), 3.87-3.79 (m, 2H), 3.70-3.68 (m, 1H), 3.63-3.50 (m, 2H), 3.46-3.35 (m, 1H), 3.23-3.10 (m, 1H), 2.98-2.94 (m, 1H), 2.62-2.55 (m, 1H), 2.22 (t, J=6.8 Hz, 2H), 2.06-2.00 (m, 1H), 0.93 (s, 9H), 0.09 (s, 6H).

MS-ESI calculated for [M+H]⁺: 424 and 426, found: 424 and 426.

Step 6

By referring to the Step 6 of Example 1, compound 30-7 was obtained.

¹H NMR: (400 MHz, CDCl₃) δ 7.49 (d, J=7.6 Hz, 1H), 7.34 (d, J=7.6 Hz, 1H), 7.29-7.25 (m, 1H), 3.86-3.79 (m, 2H), 3.70-3.68 (m, 1H), 3.62-3.52 (m, 2H), 3.47-3.27 (m, 2H), 3.17-3.15 (m, 1H), 2.63-2.61 (m, 1H), 2.30-2.20 (m, 2H), 2.14-2.08 (m, 1H), 0.92 (s, 9H), 0.09 (d, J=1.2 Hz, 6H).

MS-ESI calculated for [M+H]⁺: 371, found: 371.

Step 7

By referring to the Step 7 of Example 1, compound 30-8 was obtained as a crude product.

MS-ESI calculated for [M+H]⁺: 404, found: 404.

Step 8

By referring to the Step 8 of Example 1, compound 30-9 (i.e., Example 30) was obtained.

¹H NMR: (400 MHz, Methanol-d₄) δ 8.46-8.27 (m, 2H), 8.05-7.95 (m, 1H), 7.43-7.33 (m, 3H), 4.97-4.90 (m, 1H), 3.83-3.69 (m, 3H), 3.66-3.43 (m, 4H), 3.38-3.32 (m, 1H), 2.56-2.50 (m, 1H), 2.39-2.27 (m, 2H), 2.19-2.15 (m, 1H), 1.45 (d, J=6.0 Hz, 6H).

MS-ESI calculated for [M+H]⁺: 459, found: 459.

Example 31

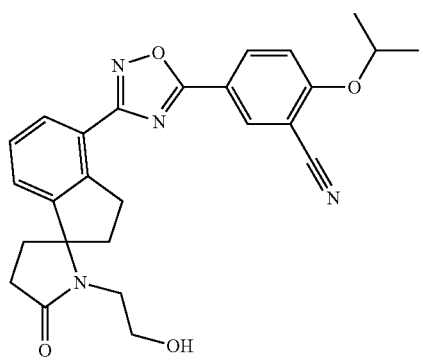

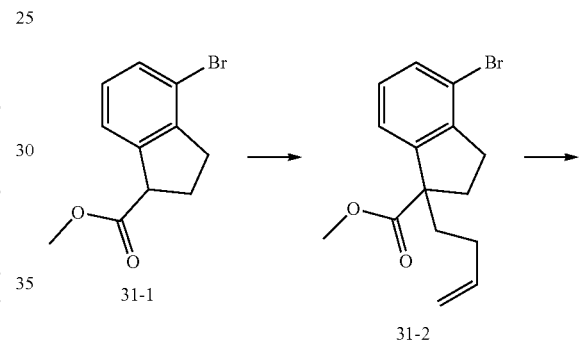

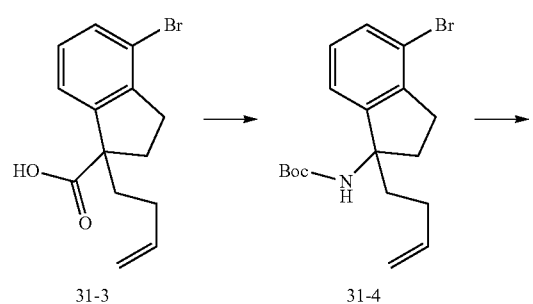

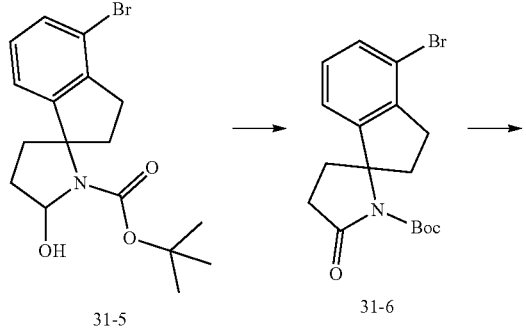

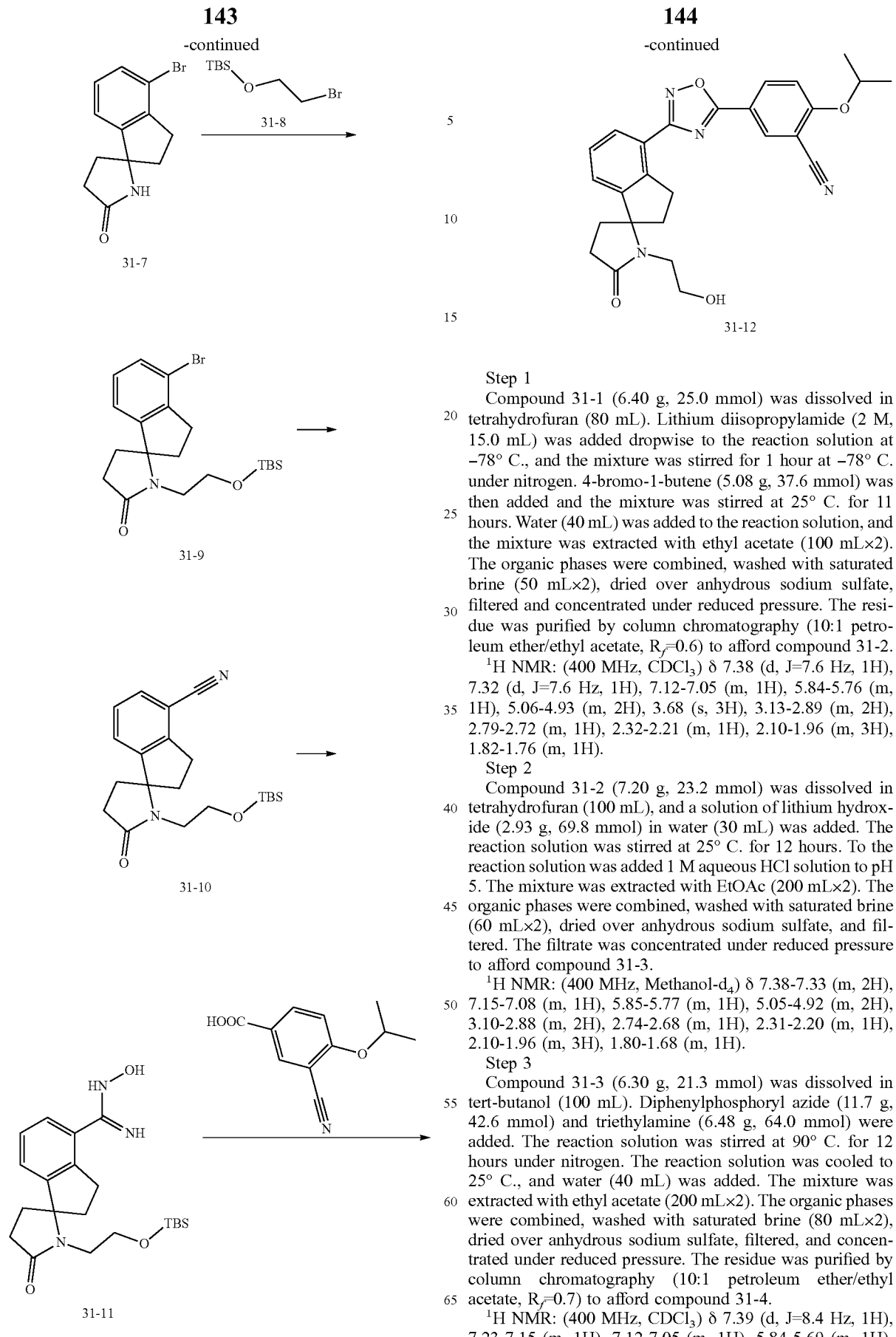

Step 1

Compound 31-1 (6.40 g, 25.0 mmol) was dissolved in tetrahydrofuran (80 mL). Lithium diisopropylamide (2 M, 15.0 mL) was added dropwise to the reaction solution at −78° C., and the mixture was stirred for 1 hour at −78° C. under nitrogen. 4-bromo-1-butene (5.08 g, 37.6 mmol) was then added and the mixture was stirred at 25° C. for 11 hours. Water (40 mL) was added to the reaction solution, and the mixture was extracted with ethyl acetate (100 mL×2). The organic phases were combined, washed with saturated brine (50 mL×2), dried over anhydrous sodium sulfate, filtered and concentrated under reduced pressure. The residue was purified by column chromatography (10:1 petroleum ether/ethyl acetate, $R_f$=0.6) to afford compound 31-2.

$^1$H NMR: (400 MHz, CDCl$_3$) δ 7.38 (d, J=7.6 Hz, 1H), 7.32 (d, J=7.6 Hz, 1H), 7.12-7.05 (m, 1H), 5.84-5.76 (m, 1H), 5.06-4.93 (m, 2H), 3.68 (s, 3H), 3.13-2.89 (m, 2H), 2.79-2.72 (m, 1H), 2.32-2.21 (m, 1H), 2.10-1.96 (m, 3H), 1.82-1.76 (m, 1H).

Step 2

Compound 31-2 (7.20 g, 23.2 mmol) was dissolved in tetrahydrofuran (100 mL), and a solution of lithium hydroxide (2.93 g, 69.8 mmol) in water (30 mL) was added. The reaction solution was stirred at 25° C. for 12 hours. To the reaction solution was added 1 M aqueous HCl solution to pH 5. The mixture was extracted with EtOAc (200 mL×2). The organic phases were combined, washed with saturated brine (60 mL×2), dried over anhydrous sodium sulfate, and filtered. The filtrate was concentrated under reduced pressure to afford compound 31-3.

$^1$H NMR: (400 MHz, Methanol-d$_4$) δ 7.38-7.33 (m, 2H), 7.15-7.08 (m, 1H), 5.85-5.77 (m, 1H), 5.05-4.92 (m, 2H), 3.10-2.88 (m, 2H), 2.74-2.68 (m, 1H), 2.31-2.20 (m, 1H), 2.10-1.96 (m, 3H), 1.80-1.68 (m, 1H).

Step 3

Compound 31-3 (6.30 g, 21.3 mmol) was dissolved in tert-butanol (100 mL). Diphenylphosphoryl azide (11.7 g, 42.6 mmol) and triethylamine (6.48 g, 64.0 mmol) were added. The reaction solution was stirred at 90° C. for 12 hours under nitrogen. The reaction solution was cooled to 25° C., and water (40 mL) was added. The mixture was extracted with ethyl acetate (200 mL×2). The organic phases were combined, washed with saturated brine (80 mL×2), dried over anhydrous sodium sulfate, filtered, and concentrated under reduced pressure. The residue was purified by column chromatography (10:1 petroleum ether/ethyl acetate, $R_f$=0.7) to afford compound 31-4.

$^1$H NMR: (400 MHz, CDCl$_3$) δ 7.39 (d, J=8.4 Hz, 1H), 7.23-7.15 (m, 1H), 7.12-7.05 (m, 1H), 5.84-5.69 (m, 1H), 5.05-4.85 (m, 3H), 3.12-2.96 (m, 1H), 2.88-2.82 (m, 1H), 2.58-2.43 (m, 1H), 2.39-2.20 (m, 1H), 2.14-1.80 (m, 4H), 1.53-1.08 (m, 9H).

MS-ESI calculated for [M+H]$^+$: 366, 368, found: 366, 368.

Step 4

Compound 31-4 (1.00 g, 2.73 mmol) was dissolved in methanol (12 mL) and water (4 mL). Osmium tetroxide (69.4 mg, 0.273 mmol) and sodium periodate (1.75 g, 8.19 mmol) were added at 0° C. The reaction solution was stirred at 30° C. for 4 hours under nitrogen. Water (30 mL) was added to the reaction solution. The mixture was extracted with ethyl acetate (30 mL×2). The organic phases were combined, washed with saturated sodium sulfite solution (20 mL×2) and then saturated brine (20 mL×2), dried over anhydrous sodium sulfate, filtered and concentrated under reduced pressure to afford compound 31-5.

MS-ESI calculated for [M+H]$^+$: 368 and 370, found: 368 and 370.

Step 5

Compound 31-5 (860 mg, 2.34 mmol) was dissolved in tetrahydrofuran (10 mL). Water (2 mL), sulfamic acid (318 mg, 3.28 mmol) and sodium chlorite (275 mg, 3.04 mmol) were added at 0° C. The reaction solution was stirred at 25° C. for 12 hours under nitrogen. Ethyl acetate (60 mL) was added to the reaction solution. The mixture was washed with water (20 mL×2) and then saturated brine (20 mL×2), dried over anhydrous sodium sulfate, filtered and concentrated under reduced pressure. The residue was purified by column chromatography (3:1 petroleum ether/ethyl acetate, R$_f$=0.2) to afford compound 31-6.

$^1$H NMR: (400 MHz, CDCl$_3$) δ 7.44-7.42 (m, 1H), 7.18-7.08 (m, 2H), 3.16-3.05 (m, 1H), 2.98-2.91 (m, 1H), 2.72-2.53 (m, 3H), 2.34-2.31 (m, 1H), 2.23-2.17 (m, 1H), 2.07-1.98 (m, 1H), 1.15 (s, 9H).

MS-ESI calculated for [M+H]$^+$: 366, 368, found: 366, 368.

Step 6

Compound 31-6 (188 mg, 0.513 mmol) was dissolved in dichloromethane (5 mL). Trifluoroacetic acid (2 mL) was added at 0° C., and the reaction solution was stirred at 25° C. for 2 hours. The reaction solution was concentrated under reduced pressure. The residue was dissolved in ethyl acetate (40 mL), washed with saturated sodium bicarbonate (20 mL×2) and then saturated brine (20 mL×2), dried over anhydrous sodium sulfate, filtered and concentrated under reduced pressure to afford compound 31-7.

$^1$H NMR: (400 MHz, CDCl$_3$) δ 7.44 (d, J=7.6 Hz, 1H), 7.25-7.21 (m, 1H), 7.18-7.12 (m, 1H), 5.89 (s, 1H), 3.05-2.96 (m, 1H), 2.93-2.83 (m, 1H), 2.58-2.50 (m, 2H), 2.44-2.28 (m, 2H), 2.20-2.10 (m, 2H).

MS-ESI calculated for [M+H]$^+$: 266, 268, found: 266, 268.

Step 7

The compound 31-7 (130 mg, 0.488 mmol) was dissolved in N,N-dimethylformamide (3 mL). Sodium hydride (39.0 mg, 0.976 mmol, purity 60%) was added at 0° C. The reaction solution was stirred at 0° C. for 1 hour. Compound 31-8 (233 mg, 0.976 mmol) was added, and the reaction solution was stirred at 25° C. under nitrogen for 12 hr. Water (10 mL) was added to the reaction solution and extracted with ethyl acetate (30 mL×3). The organic phases were combined, washed with saturated brine (20 mL×4), dried over anhydrous sodium sulfate, filtered and concentrated under reduced pressure. The residue was purified by preparative TLC (2:1 petroleum ether/ethyl acetate, R$_f$=0.5) to afford compound 31-9.

$^1$H NMR: (400 MHz, CDCl$_3$) δ 7.44 (d, J=7.6 Hz, 1H), 7.15-7.10 (m, 1H), 7.07-7.03 (m, 1H), 3.84-3.80 (m, 1H), 3.60-3.56 (m, 1H), 3.28-3.23 (m, 1H), 3.10-2.83 (m, 3H), 2.58-2.44 (m, 3H), 2.28-2.02 (m, 3H), 0.85 (s, 9H), 0.01 (d, J=3.2 Hz, 6H).

MS-ESI calculated for [M+H]$^+$: 424, 426, found: 424, 426.

Step 8

By referring to the Step 1 of Example 1, compound 31-10 was obtained.

MS-ESI calculated for [M+H]$^+$: 371, found: 371.

Step 9

By referring to the Step 2 of Example 1, compound 31-11 was obtained.

MS-ESI calculated for [M+H]$^+$: 404, found: 404.

Step 10

By referring to the Step 3 of Example 1, compound 31-12 (i.e., Example 31) was obtained.

$^1$H NMR: (400 MHz, Methanol-d$_4$) δ 8.48-8.38 (m, 2H), 8.15 (d, J=7.6 Hz, 1H), 7.52-7.40 (m, 3H), 4.98-4.94 (m, 1H), 3.69-3.60 (m, 1H), 3.56-3.46 (m, 2H), 3.29-3.17 (m, 2H), 3.09-3.04 (m, 1H), 2.67-2.55 (m, 2H), 2.50-2.44 (m, 1H), 2.42-2.33 (m, 2H), 2.28-2.17 (m, 1H), 1.46 (d, J=5.6 Hz, 6H).

MS-ESI calculated for [M+H]$^+$: 459, found: 459.

Example 32

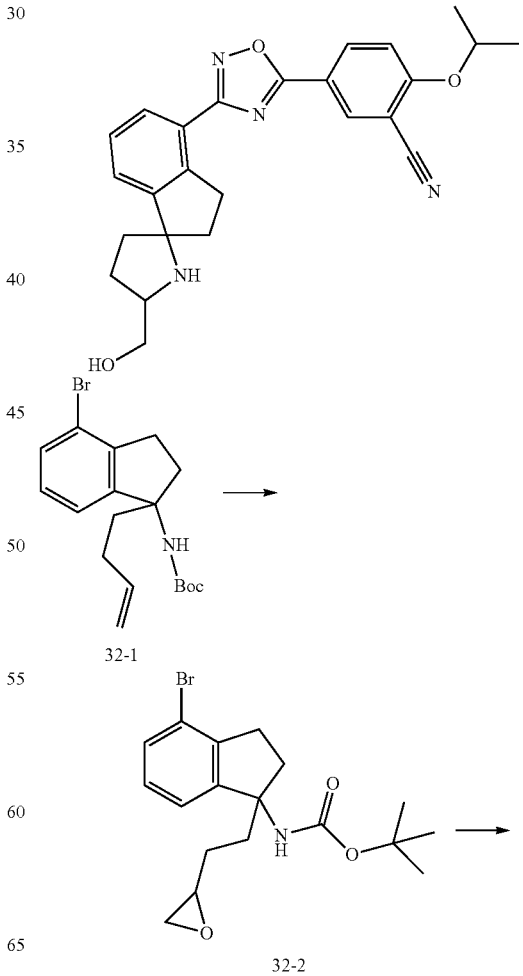

-continued

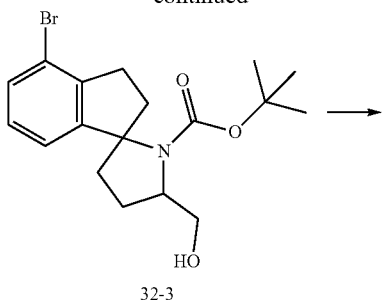
32-3

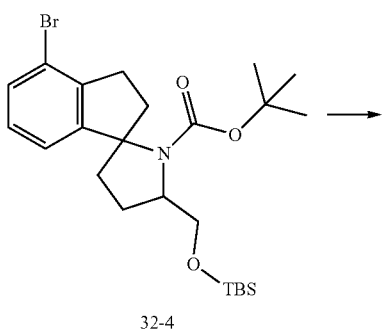
32-4

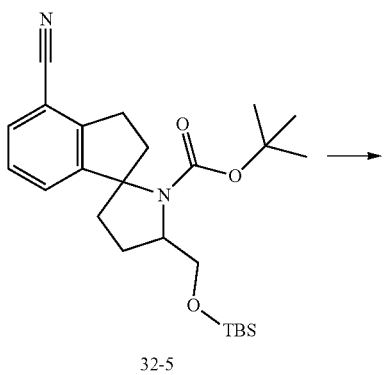
32-5

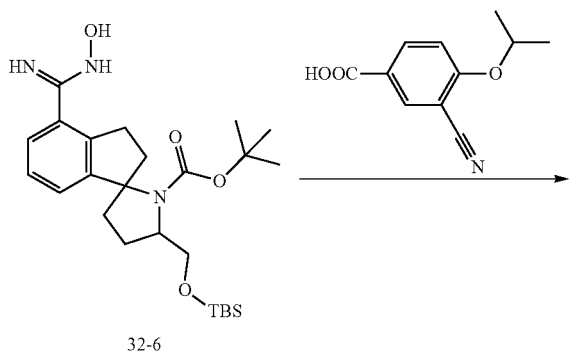
32-6

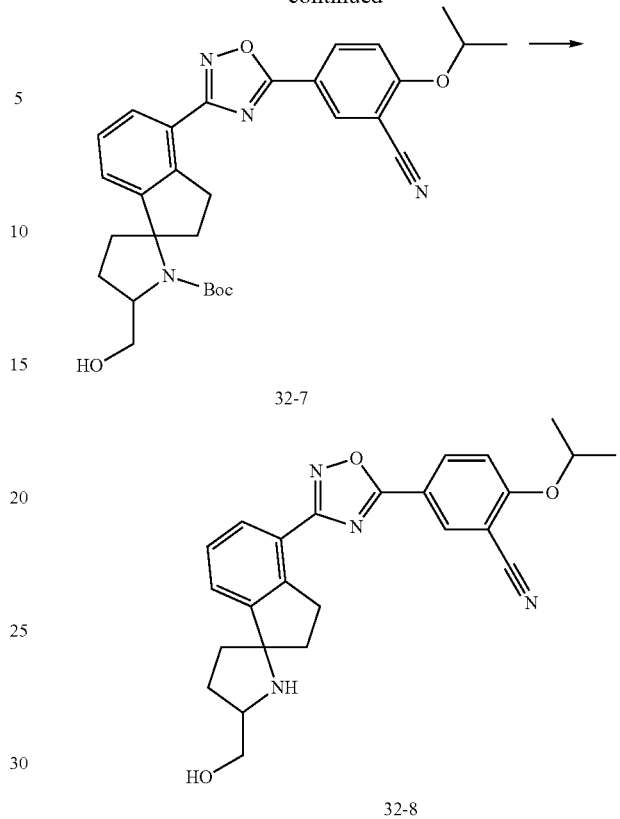

Step 1

Compound 32-1 (1.00 g, 2.73 mmol) was dissolved in dichloromethane (20 mL). To the reaction solution was added m-chloroperoxybenzoic acid (1.11 g, 5.46 mmol). The reaction solution was stirred at 25° C. for 3 hours under nitrogen. Saturated sodium sulfite (20 mL) was added to the reaction solution, and the mixture was extracted with dichloromethane (50 mL×2). The organic phases were combined, washed with saturated sodium sulfate (10 mL×3), saturated sodium bicarbonate (10 mL×3), and then saturated brine (10 mL×2), dried over anhydrous sodium sulfate, filtered, and concentrated under reduced pressure. The residue was purified by column chromatography (5:1 petroleum ether/ethyl acetate, $R_f$=0.5) to afford compound 32-2.

$^1$H NMR: (400 MHz, CDCl$_3$) δ 7.39 (d, J=8.4 Hz, 1H), 7.18 (d, J=8.4 Hz, 1H), 7.12-7.06 (m, 1H), 4.91 (d, J=12.8 Hz, 1H), 3.11-2.97 (m, 1H), 2.91-2.79 (m, 2H), 2.75-2.68 (m, 1H), 2.55-2.40 (m, 2H), 2.34-2.19 (m, 1H), 2.04-1.91 (m, 1H), 1.51 (s, 2H), 1.45-1.26 (m, 9H).

Step 2

Compound 32-2 (940 mg, 2.46 mmol) was dissolved in tetrahydrofuran (15 mL). Sodium hydride (393 mg, 9.84 mmol) was added. The reaction solution was stirred at 25° C. for 12 hours under nitrogen. Water (15 mL) was added to the reaction solution to quench the reaction. The mixture was extracted with ethyl acetate (50 mL×2). The organic phases were combined, washed with saturated brine (20 mL×2), dried over anhydrous sodium sulfate, filtered, and concentrated under reduced pressure. The residue was purified by column chromatography (3:1 petroleum ether/ethyl acetate, $R_f$=0.4) to afford compound 32-3.

$^1$H NMR: (400 MHz, CDCl$_3$) δ 7.38-7.36 (m, 1H), 7.15-7.07 (m, 2H), 4.43-4.23 (m, 2H), 3.96-3.87 (m, 1H), 3.82-3.71 (m, 1H), 3.08-2.96 (m, 1H), 2.84-2.82 (m, 1H), 2.61-2.45 (m, 1H), 2.18-1.94 (m, 4H), 1.77-1.73 (m, 1H), 1.05 (s, 9H).

Step 3

Compound 32-3 (190 mg, 0.497 mmol) was dissolved in N,N-dimethylformamide (6.00 mL). Tert-butyldimethylchlorosilane (149 mg, 0.994 mmol) and imidazole (101 mg, 1.49 mmol) were added. The reaction solution was stirred at 25° C. for 12 hours under nitrogen. Water (10 mL) was added to the reaction solution and the mixture was extracted with ethyl acetate (40 mL×2). The organic phases were combined, washed with saturated brine (20 mL×3), dried over anhydrous sodium sulfate, filtered, and concentrated under reduced pressure. The residue was purified by column chromatography (10:1 petroleum ether/ethyl acetate, $R_f$=0.4) to afford compound 32-4.

MS-ESI calculated for [M+H]$^+$: 496, 498, found: 496, 498.

Step 4

By referring to the Step 6 of Example 1, compound 32-5 was obtained.

MS-ESI calculated for [M+H]$^+$: 443, found: 443.

Step 5

By referring to the Step 7 of Example 1, compound 32-6 was obtained.

MS-ESI calculated for [M+H]$^+$: 476, found: 476.

Step 6

By referring to the Step 8 of Example 1, compound 32-7 was obtained as a crude product.

MS-ESI calculated for [M+H]$^+$: 531, found: 531.

Step 7

Compound 32-7 (50.0 mg, 0.0942 mmol) was dissolved in dioxane (2 mL). Hydrochloride/dioxane (4 M, 235.58 μL) was added. The reaction solution was stirred at 50° C. for 2 hours. The reaction solution was concentrated under reduced pressure. The residue was isolated by high performance liquid chromatography (hydrochloric acid system) to afford compound 32-8 (i.e., Example 32).

$^1$H NMR: (400 MHz, Methanol-d$_4$) δ 8.46-8.37 (m, 2H), 8.25 (d, J=7.6 Hz, 1H), 7.83 (d, J=7.6 Hz, 1H), 7.58 (t, J=7.6 Hz, 1H), 7.44 (d, J=8.8 Hz, 1H), 5.00-4.92 (m, 1H), 4.00-3.82 (m, 2H), 3.59-3.44 (m, 2H), 2.70-2.52 (m, 2H), 2.48-2.36 (m, 2H), 2.35-2.26 (m, 1H), 2.24-2.12 (m, 1H), 1.46 (d, J=6.0 Hz, 6H), 1.36-1.26 (m, 1H).

MS-ESI calculated for [M+H]$^+$: 431, found: 431.

Example 33

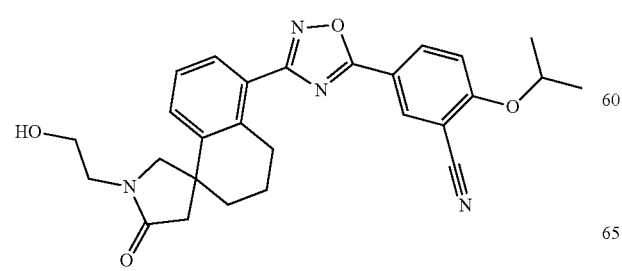

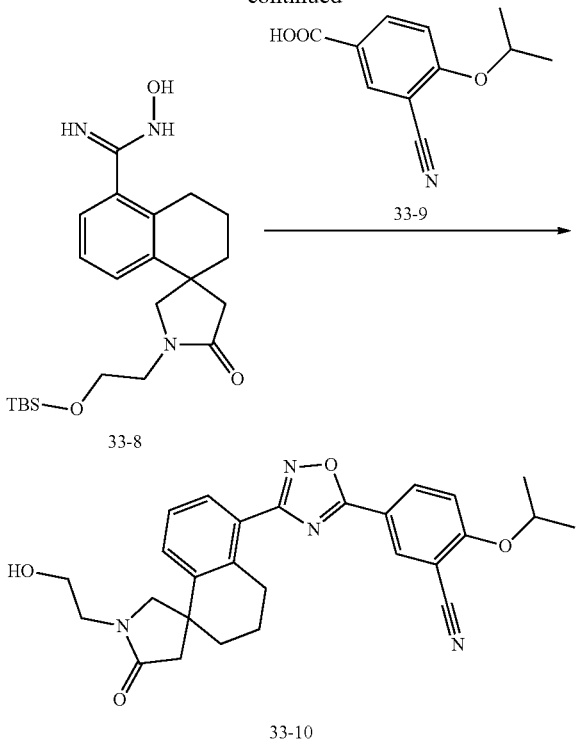

Step 1

Compound 33-1 (7.50 g, 33.3 mmol) and tosylmethyl isocyanide (19.5 g, 100 mmol) were dissolved in ethanol (10.00 mL) and ethylene glycol dimethyl ether (150 mL). Potassium tert-butoxide (11.2 g, 100 mmol) was added at 0° C., and the mixture was stirred at 40° C. for 20 hours. The reaction solution was poured into water (100 mL) and extracted with ethyl acetate (100 mL×1). The organic phase was concentrated to afford a crude product. The crude product was isolated by silica gel column chromatography (silica, petroleum ether:ethyl acetate=400:1 to 200:1) to afford compound 33-2.

$^1$H NMR: (400 MHz, CDCl$_3$) δ 7.54 (d, J=7.6 Hz, 1H), 7.35 (d, J=7.6 Hz, 1H), 7.11 (t, J=7.6 Hz, 1H), 4.00 (t, J=5.6 Hz, 1H), 2.93-2.70 (m, 2H), 2.21-2.02 (m, 3H), 1.99-1.83 (m, 1H).

Step 2

Compound 33-2 (1.50 g, 6.35 mmol) was dissolved in tetrahydrofuran (20.0 mL). Lithium diisopropylamide (2 M, 4.13 mL) was added at −70° C., and the mixture was stirred at this temperature for 1 hour. Methyl bromoacetate (1.36 g, 8.89 mmol) was added at −70° C. and the mixture was stirred at 20° C. for 16 h. The reaction was quenched by the addition of water (100 mL) and extracted with ethyl acetate (100 mL×1). The organic phase was dried over anhydrous sodium sulfate (1 g), filtered and concentrated to afford a crude product. The crude product was isolated by silica gel column chromatography (silica, petroleum ether:ethyl acetate=40:1, 30:1, 10:1) to afford compound 33-3.

$^1$H NMR: (400 MHz, CDCl$_3$) δ 7.55 (d, J=7.6 Hz, 1H), 7.47 (d, J=7.6 Hz, 1H), 7.13 (t, J=7.6 Hz, 1H), 3.73 (s, 3H), 3.09-2.87 (m, 2H), 2.86-2.79 (m, 2H), 2.39-2.24 (m, 2H), 2.09-1.88 (m, 2H).

Step 3

Compound 33-3 (1.46 g, 4.74 mmol) was dissolved in methanol (30.0 mL) and water (3.00 mL). Sodium borohydride (716.90 mg, 19.0 mmol) and cobalt chloride hexahydrate (4.51 g, 19.0 mmol) were slowly added at 0° C. The mixture was stirred at 0° C. for 5 hours. The reaction solution was filtered and the filtrate was concentrated. The residue was isolated by silica gel column chromatography (silica, petroleum ether:ethyl acetate=20:1, 10:1, 1:1) to afford compound 33-4.

$^1$H NMR: (400 MHz, CDCl$_3$) δ 7.46 (d, J=7.6 Hz, 1H), 7.35 (d, J=7.6 Hz, 1H), 7.08 (t, J=7.6 Hz, 1H), 5.94 (s, 1H), 3.63-3.44 (m, 2H), 2.84-2.80 (m, 2H), 2.74-2.46 (m, 2H), 1.95-1.79 (m, 4H).

Step 4

Compound 33-4 (420 mg, 1.50 mmol) was dissolved in N,N-dimethylformamide (10.0 mL). Sodium hydride (69.1 mg, 1.73 mmol, purity 60%) was added portionwise at 0° C. under nitrogen. The mixture was stirred at 0° C. for 1 hour. Compound 33-5 (675 mg, 3.00 mmol) was then added and the mixture was stirred at 25° C. under nitrogen for 16 h. The reaction was quenched with water (50 mL) and extracted with ethyl acetate (50 mL×1). The organic phase was dried over anhydrous sodium sulfate (500 mg), filtered and concentrated to afford a crude product. The crude product was purified by preparative TLC to afford compound 33-6.

$^1$H NMR: (400 MHz, CDCl$_3$) δ 7.45 (d, J=7.6 Hz, 1H), 7.30 (d, J=7.6 Hz, 1H), 7.06 (t, J=7.6 Hz, 1H), 3.81 (t, J=5.2 Hz, 2H), 3.76-3.60 (m, 2H), 3.48 (t, J=5.2 Hz, 2H), 2.87-2.79 (m, 2H), 2.77-2.57 (m, 2H), 1.94-1.77 (m, 4H), 0.89 (s, 9H), 0.07 (s, 6H).

Step 5

Compound 33-6 (400 mg, 0.912 mmol) was dissolved in acetonitrile (10.0 mL). Zinc cyanide (321 mg, 2.74 mmol), 2-dicyclohexylphosphino-2',4',6'-triisopropylbiphenyl (174 mg, 0.365 mmol) and tris(dibenzylideneacetone)dipalladium (167 mg, 0.182 mmol) were added. The mixture was stirred at 90° C. for 16 h under nitrogen. The reaction solution was concentrated. The residue was added into dichloromethane (100 mL) and filtered. The filter cake was washed with dichloromethane (50 mL). The filtrates were combined and concentrated to afford a crude product. The crude product was purified by preparative TLC to afford compound 33-7.

$^1$H NMR: (400 MHz, CDCl$_3$) δ 7.53-7.44 (m, 2H), 7.27-7.23 (m, 1H), 3.76 (t, J=5.2 Hz, 2H), 3.71-3.53 (m, 2H), 3.49-3.36 (m, 2H), 3.04-2.90 (m, 2H), 2.74-2.43 (m, 2H), 1.93-1.76 (m, 4H), 0.82 (s, 9H), 0.01 (s, 6H).

Step 6

Compound 33-7 (320 mg, 0.832 mmol) was dissolved in ethanol (10.0 mL). Hydroxyamine hydrochloride (173 mg, 2.50 mmol) and triethylamine (337 mg, 3.33 mmol) were added. The mixture was stirred at 80° C. for 40 hours. The mixture was concentrated. The residue was added into water (20 mL) and extracted with ethyl acetate (20 mL×2). The organic phase was dried over anhydrous sodium sulfate (1 g), filtered and concentrated to afford compound 33-8.

MS-ESI calculated for [M+H]$^+$: 418, found: 418.

Step 7

Compound 33-9 (107 mg, 0.512 mmol) was dissolved in N,N-dimethylformamide (5.00 mL). To the reaction solution were added 1-hydroxybenzotriazole (76.2 mg, 0.564 mmol) and 1-(3-dimethylaminopropyl)-3-ethylcarbodiimide hydrochloride (123 mg, 0.641 mmol), and the mixture was stirred at 15° C. for 1 hour. Compound 33-8 (200 mg, 0.256 mmol) was then added, the mixture was stirred at 15° C. for 1 hour, and heated to 85° C. and stirred for 16 hours. The reaction solution was concentrated to afford a crude product. The crude product was isolated by high performance liquid chromatography (formic acid system) to afford compound 33-10 (i.e., Example 33).

¹H NMR: (400 MHz, Methanol-d₄) δ 8.45-8.37 (m, 2H), 7.83 (d, J=7.6 Hz, 1H), 7.63 (d, J=7.6 Hz, 1H), 7.44 (d, J=8.0 Hz, 1H), 7.39 (t, J=8.0 Hz, 1H), 5.00-4.91 (m, 1H), 3.85 (d, J=10.4 Hz, 1H), 3.77 (t, J=5.6 Hz, 2H), 3.69 (d, J=10.4 Hz, 1H), 3.59-3.45 (m, 2H), 3.10 (t, J=6.2 Hz, 2H), 2.89-2.55 (m, 2H), 2.09-1.83 (m, 4H), 1.47 (d, J=6.2 Hz, 6H).

MS-ESI calculated for [M+H]⁺: 473, found: 473.

Example 34

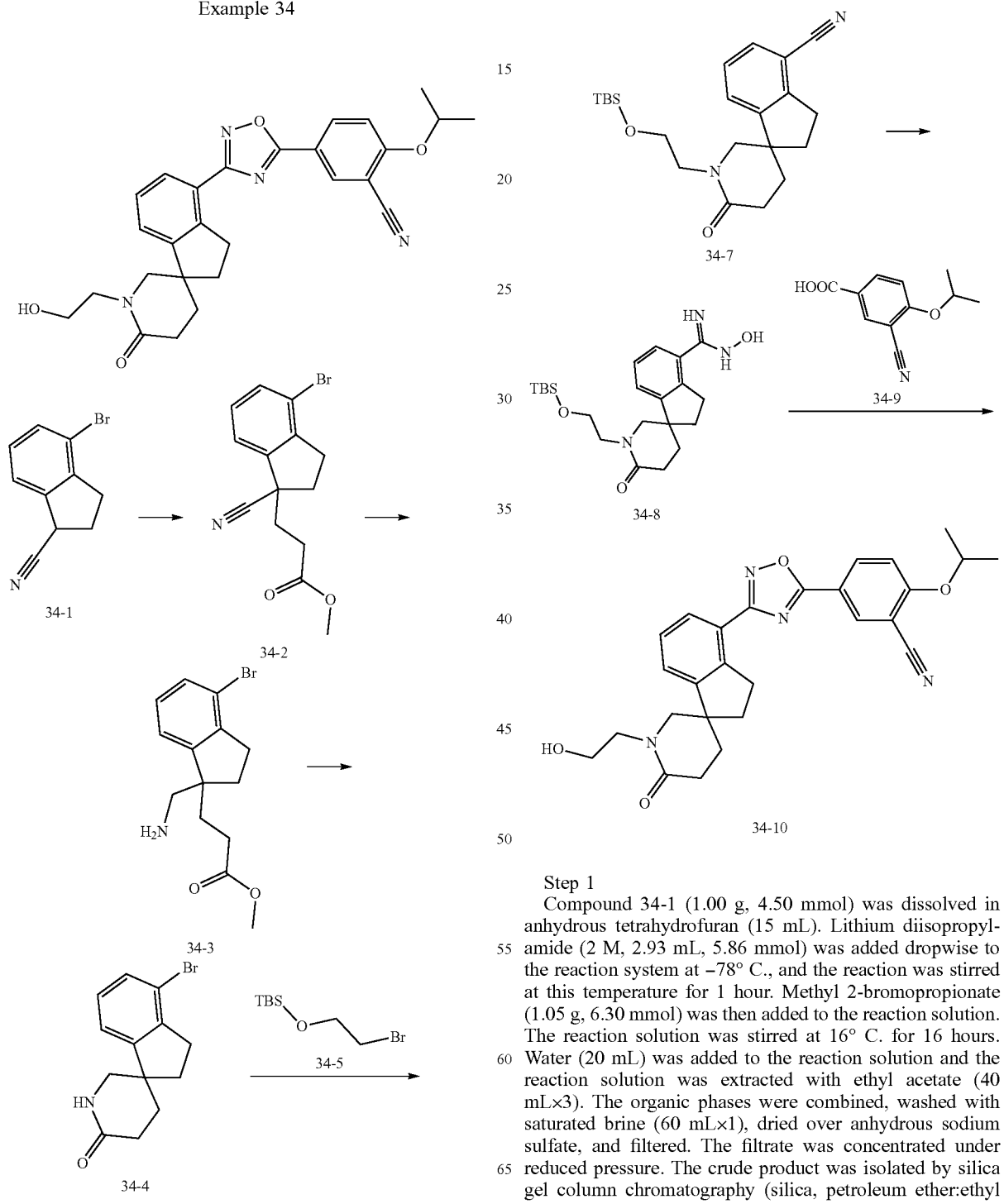

Step 1

Compound 34-1 (1.00 g, 4.50 mmol) was dissolved in anhydrous tetrahydrofuran (15 mL). Lithium diisopropylamide (2 M, 2.93 mL, 5.86 mmol) was added dropwise to the reaction system at −78° C., and the reaction was stirred at this temperature for 1 hour. Methyl 2-bromopropionate (1.05 g, 6.30 mmol) was then added to the reaction solution. The reaction solution was stirred at 16° C. for 16 hours. Water (20 mL) was added to the reaction solution and the reaction solution was extracted with ethyl acetate (40 mL×3). The organic phases were combined, washed with saturated brine (60 mL×1), dried over anhydrous sodium sulfate, and filtered. The filtrate was concentrated under reduced pressure. The crude product was isolated by silica gel column chromatography (silica, petroleum ether:ethyl acetate=50:1 to 40:1) to afford compound 34-2.

1H NMR: (400 MHz, CDCl$_3$) δ 7.47 (d, J=7.6 Hz, 1H), 7.32 (d, J=7.6 Hz, 1H), 7.17 (t, J=7.6 Hz, 1H), 3.68 (s, 3H), 3.22-2.93 (m, 2H), 2.70-2.50 (m, 3H), 2.34-2.21 (m, 2H), 2.18-2.03 (m, 1H).

Step 2

Compound 34-2 (700 mg, 2.27 mmol) was dissolved in methanol (20 mL) and water (0.2 mL). Cobalt dichloride (1.18 g, 9.08 mmol) and sodium borohydride (172 mg, 4.54 mmol) were added portionwise to the reaction solution at −20° C. The reaction solution was reacted at −20° C. to 0° C. for 4 hours. After filtering the reaction solution, the filter cake was washed with dichloromethane (100 mL×2). The filtrate was concentrated under reduced pressure to afford compound 34-3. The crude product was used in the next step directly without purification.

MS-ESI calculated for [M+H]$^-$: 312 and 314, found: 312 and 314.

Step 3

Compound 34-3 (600 mg, 1.92 mmol) was dissolved in methanol (6 mL). Sodium hydroxide (154 mg, 3.84 mmol) was added to the reaction solution. The reaction solution was reacted at 16° C. for 2 hours. Water (20 mL) was added to the reaction solution and the reaction solution was extracted with ethyl acetate (30 mL×3). The organic phases were combined, dried over anhydrous sodium sulfate, and filtered. The filtrate was concentrated under reduced pressure. The crude product was isolated by a preparative TLC plate (silica, petroleum ether:ethyl acetate=0:1) to afford compound 11-4.

MS-ESI calculated for [M+H]$^+$: 280 and 282, found: 280 and 282.

Step 4

Compound 34-4 (320 mg, 1.14 mmol) was dissolved in anhydrous N,N-dimethylformamide (5 mL). Sodium hydride (91.2 mg, 2.28 mmol, 60% purity) was added portionwise at 0° C., and the reaction was stirred at this temperature for 1 hour. Compound 34-5 (545 mg, 2.28 mmol) was then added to the reaction solution, and the reaction solution was stirred at 16° C. for 16 hours. Water (20 mL) was added to the reaction solution, and the reaction solution was extracted with ethyl acetate (30 mL×3). The organic phases were combined, washed with saturated brine (50 mL×1), dried over anhydrous sodium sulfate, and filtered. The filtrate was concentrated under reduced pressure. The crude product was isolated by thin layer chromatography (silica, petroleum ether:ethyl acetate=1:1) to afford compound 34-6.

$^1$H NMR: (400 MHz, CDCl$_3$) δ 7.40 (d, J=7.6 Hz, 1H, 1H), 7.13-7.05 (m, 2H), 3.85-3.77 (m, 2H), 3.55-3.46 (m, 3H), 3.39-3.31 (m, 1H), 3.03-2.95 (m, 2H), 2.58-2.52 (m, 2H), 2.28-2.12 (m, 2H), 2.03-1.78 (m, 2H), 0.87 (s, 9H), 0.05 (s, 6H).

MS-ESI calculated for [M+H]$^+$: 438 and 440, found: 438 and 440.

Step 5

Compound 34-6 (340 mg, 0.775 mmol) was dissolved in acetonitrile (10 mL). Zinc cyanide (273 mg, 2.33 mmol), tris(dibenzylideneacetone)dipalladium (142 mg, 0.155 mmol) and 2-dicyclohexylphosphino-2',4',6'-triisopropylbiphenyl (148 mg, 0.310 mmol) was added to the reaction solution. The reaction solution was stirred at 90° C. for 16 hours under nitrogen. The reaction solution was cooled to room temperature, and filtered. The filtrate was concentrated under reduced pressure. The crude product was isolated by silica gel column chromatography (silica, petroleum ether: ethyl acetate=1:2) to afford compound 34-7.

$^1$H NMR: (400 MHz, CDCl$_3$) δ 7.52 (d, J=7.6 Hz, 1H), 7.41-7.37 (d, J=7.6 Hz, 1H), 7.31 (s, 1H), 3.87-3.78 (m, 2H), 3.57-3.43 (m, 3H), 3.40-3.36 (m, 1H), 3.26-3.09 (m, 2H), 2.58-2.51 (m, 2H), 2.36-2.25 (m, 1H), 2.22-2.12 (m, 1H), 2.10-2.00 (m, 1H), 1.89-1.78 (m, 1H), 0.85 (s, 9H), 0.02 (s, 6H).

MS-ESI calculated for [M+H]$^+$: 385, found: 385.

Step 6

Compound 34-7 (240 mg, 0.624 mmol) was dissolved in ethanol (6 mL). Hydroxylamine hydrochloride (130 mg, 1.87 mmol) and triethylamine (253 mg, 2.50 mmol) were added to the reaction solution. The solution was stirred at 60° C. for 15 hours under nitrogen. The reaction solution was concentrated under reduced pressure. Water (20 mL) was then added to the reaction solution. The reaction solution was extracted with ethyl acetate (20 mL×3). The organic phases were combined, washed with saturated brine (30 mL×1), dried over anhydrous sodium sulfate, and filtered. The filtrate was concentrated under reduced pressure to afford compound 34-8.

MS-ESI calculated for [M+H]$^+$: 418, found: 418.

Step 7

Compound 34-9 (49.1 mg, 0.239 mmol) was dissolved in N,N-dimethylformamide (3 mL). To the reaction solution were added 1-hydroxybenzotriazole (32.4 mg, 0.239 mmol) and 1-(3-dimethylaminopropyl)-3-ethylcarbodiimide hydrochloride (45.9 mg, 0.239 mmol). The reaction solution was stirred at 25° C. for 1 hour. Compound 34-8 (100 mg, 0.239 mmol) was then added to the reaction solution, and the reaction solution was stirred at 25° C. for 1 hour. After the temperature was raised to 85° C., the reaction solution was stirred at 85° C. for 15 hours. The reaction solution was cooled to room temperature and isolated by high performance liquid chromatography (formic acid system) to afford compound 34-10 (i.e., Example 34).

$^1$H NMR: (400 MHz, Methanol-d$_4$) δ 8.47-8.36 (m, 2H), 8.09-8.02 (m, 2H), 7.49-7.36 (m, 2H), 5.00-4.91 (m, 1H), 3.78-3.72 (m, 2H), 3.63-3.33 (m, 6H), 2.64-2.50 (m, 2H), 2.41-2.26 (m, 2H), 2.14-2.03 (m, 1H), 1.91-1.77 (m, 1H), 1.46 (d, J=6.0 Hz, 6H).

MS-ESI calculated for [M+H]+473, found: 473.

Example 35

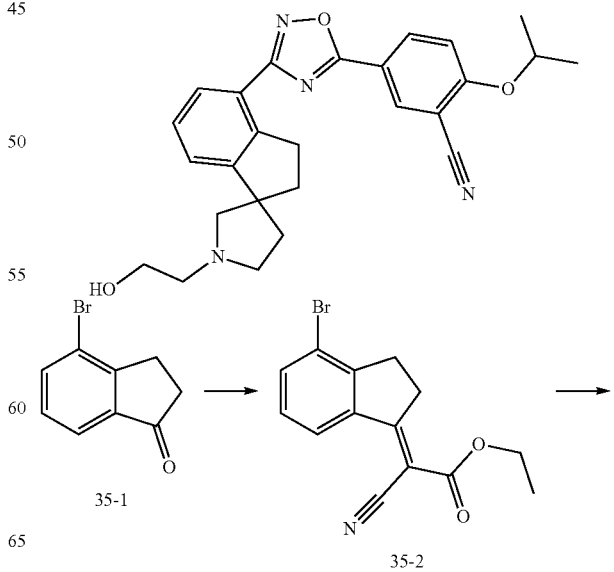

157

-continued

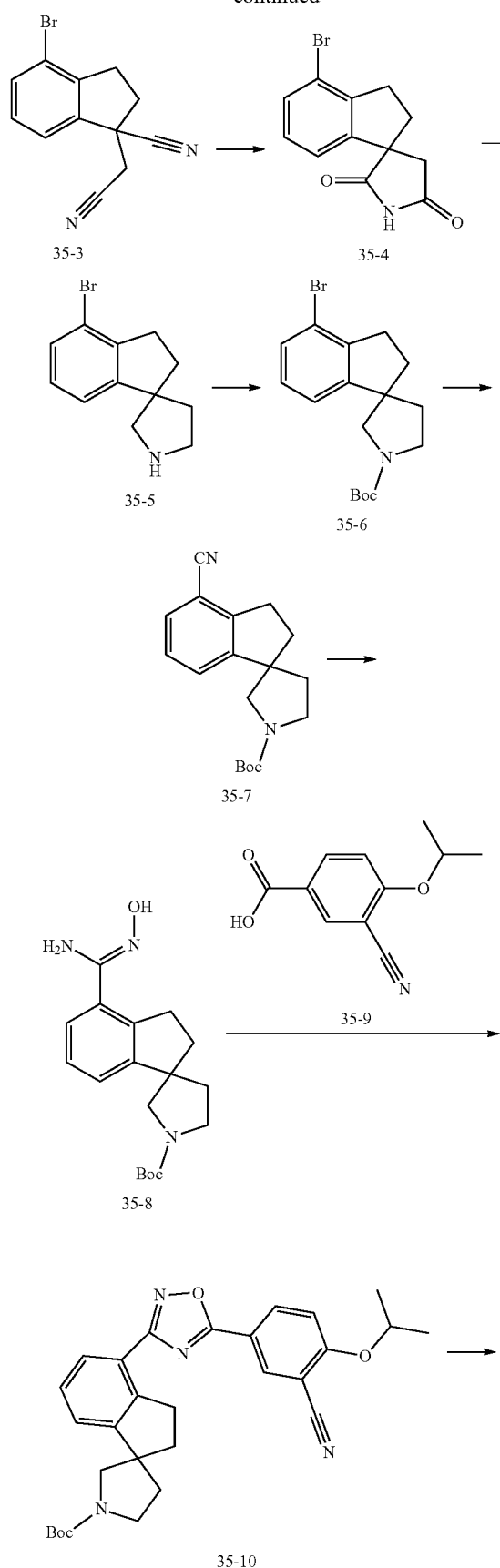

35-3

35-4

35-5

35-6

35-7

35-8

35-9

35-10

158

-continued

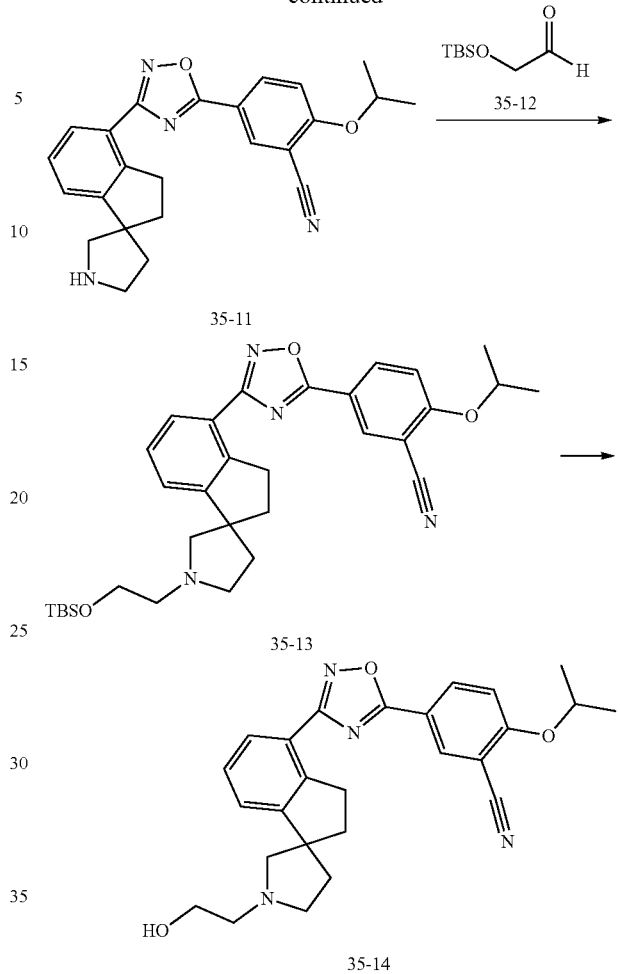

35-11

35-12

35-13

35-14

Step 1

To a 100 ml reaction flask containing compound 35-1 (10.0 g, 47.4 mmol) was added toluene (48.0 mL), ethyl cyanoacetate (6.27 g, 55.4 mmol), ammonium acetate (7.3 g, 97.7 mmol) and acetic acid (22.0 mL). The reaction solution was heated to reflux and water was separated with a water separator for 24 hours. Once the reaction was complete, the reaction solution was concentrated until a large amount of solid precipitated. The solid was collected by filteration and dried to afford compound 35-2.

MS-ESI calculated for [M+H]$^+$: 306 and 308, found: 306 and 308.

$^1$H NMR: (400 MHz, CDCl$_3$) δ 8.63 (d, J=8.0 Hz, 1H), 7.71 (d, J=8.0 Hz, 1H), 7.31 (t, J=8.0 Hz, 1H), 4.35 (q, J=7.2 Hz, 2H), 3.63-3.42 (m, 2H), 3.24-2.99 (m, 2H), 1.40 (t, J=7.2 Hz, 3H).

Step 2

Ethanol (50.0 mL) was added to a 100 ml reaction flask containing compound 35-2 (6.80 g, 22.2 mmol). A solution of potassium cyanide (3.62 g, 55.5 mmol) in water (15 mL) was added dropwise to the mixture at 20° C., and the reaction solution was reacted at 65° C. for 48 hours. After the reaction was completed, ethanol was evaporated under reduced pressure. Water (50.0 mL) was added to the residue, and the mixture was extracted with ethyl acetate (50 mL×3). The organic phases were combined, dried, filtered and concentrated. The evaporated residue was isolated by silica gel column chromatography (eluent gradient: petroleum ether/ethyl acetate=100:1 to 1:1) to afford compound 35-3.

$^1$H NMR: (400 MHz, CDCl$_3$) δ 7.56 (d, J=8.0 Hz, 1H), 7.47 (d, J=8.0 Hz, 1H), 7.27-7.21 (t, J=8.0 Hz 1H), 3.26-3.06 (m, 2H), 2.95-2.92 (m, 2H), 2.85-2.78 (m, 1H), 2.51-2.45 (m, 1H).

MS-ESI calculated for [M+H]$^+$: 261 and 263, found: 261 and 263.

Step 3

To a 40 ml reaction flask containing compound 35-3 (2.80 g, 22.2 mmol) was added acetic acid (6.0 mL) and 78% sulfuric acid (2.1 mL). The mixture was reacted at 125° C. for 1.5 hours. After the reaction was completed, the reaction solution was cooled, poured into 50 ml of water and a large amount of solid was precipitated. The solid was collected by filtration, and dried to afford compound 35-4.

$^1$H NMR: (400 MHz, CDCl$_3$) δ 7.93 (s, 1H), 7.45 (d, J=8.0 Hz, 1H), 7.17-7.10 (m, 1H), 7.07 (s, 1H), 3.33-3.21 (m, 1H), 3.13-3.03 (m, 1H), 3.01 (d, J=9.2 Hz, 2H), 2.82-2.77 (m, 1H), 2.25-2.19 (m, 1H).

MS-ESI calculated for [M+H]$^+$: 280 and 282, found: 280 and 282.

Step 4

Compound 35-4 (800 mg, 2.86 mmol) was dissolved in anhydrous tetrahydrofuran (20 mL). Borane dimethyl sulfide complex (10 M, 1.14 mL) was slowly added dropwise at 0° C. The reaction solution was then stirred at 70° C. for 18 hours. To the reaction solution, methanol (20 mL) was slowly added dropwise, and the reaction was then stirred at 25° C. for 1 hour. Hydrochloric acid (1 M, 50 mL) was then added, and the reaction was stirred at 80° C. for 3 hours. The mixture was extracted with tert-butyl methyl ether (30 mL×3). An aqueous sodium hydroxide (1 M, 60 mL) was then added to the aqueous phase, and the mixture was extracted with chloroform/isopropanol (3:1 by volume) (50 mL×3). The organic phases were combined, dried over anhydrous sodium sulfate, and filtered. The filtrate was concentrated under reduced pressure. The residue is compound 35-5.

$^1$H NMR: (400 MHz, CDCl$_3$) δ 7.27-7.19 (m, 1H), 7.05-6.98 (m, 2H), 3.09-3.07 (m, 2H), 2.94-2.84 (m, 4H), 2.04-1.82 (m, 4H).

MS-ESI calculated for [M+H]$^+$: 252 and 254, found: 252 and 254.

Step 5

Compound 35-5 (300 mg, 1.19 mmol) was dissolved in dichloromethane (5 mL). Di-tert-butyl dicarbonate (519 mg, 2.38 mmol) and triethylamine (241 mg, 2.38 mmol) were added to the reaction solution. The reaction solution was stirred at 25° C. for 12 hours under nitrogen. Water (30 mL) was added to the reaction solution. The mixture was extracted with dichloromethane (30 mL×3). The organic phases were combined, washed with saturated brine (20 mL×3), dried over anhydrous sodium sulfate, and filtered. The filtrate was concentrated under reduced pressure. The residue was isolated by a preparative TLC plate (10:1 petroleum ether/ethyl acetate, R$_f$=0.7) to afford compound 35-6.

$^1$H NMR: (400 MHz, CDCl$_3$) δ 7.30-7.28 (m, 1H), 7.19-6.99 (m, 2H), 3.57-3.42 (m, 4H), 2.92-2.88 (m, 2H), 2.07-2.01 (m, 1H), 1.99-1.97 (m, 2H), 1.89-1.86 (m, 1H), 1.43 (s, 9H).

MS-ESI calculated for [M+H]$^+$: 352 and 354, found: 352 and 354.

Step 6

Compound 35-6 (350 mg, 0.994 mmol) was dissolved in acetonitrile (5 mL). Zinc cyanide (233 mg, 1.99 mmol), 2-dicyclohexylphosphino-2',4',6'-triisopropylbiphenyl (98.1 mg, 0.199 mmol) and tris(dibenzylideneacetone)dipalladium (91.0 mg, 0.0994 mmol) were added to the reaction solution, and the reaction solution was stirred at 90° C. for 16 hours under nitrogen. The reaction solution was cooled to room temperature. Water (20 mL) was added to the reaction solution. The mixture was extracted with ethyl acetate (20 mL×3). The organic phases were combined, washed with saturated brine (20 mL×2), dried over anhydrous sodium sulfate, and filtered. The filtrate was concentrated under reduced pressure. The residue was isolated by a preparative TLC plate (5:1 petroleum ether/ethyl acetate, R$_f$=0.5) to afford compound 35-7.

$^1$H NMR: (400 MHz, CDCl$_3$) δ 7.43-7.41 (m, 1H), 7.31-7.29 (m, 1H), 7.25-7.21 (m, 1H), 3.47-3.32 (m, 4H), 3.09-3.06 (m, 2H), 2.07-1.97 (m, 3H), 1.91-1.89 (m, 1H), 1.43 (s, 9H).

MS-ESI calculated for [M+H]$^+$: 299, found: 299.

Step 7

Compound 35-7 (280 mg, 0.938 mmol) was dissolved in ethanol (2 mL). Hydroxylamine hydrochloride (196 mg, 2.82 mmol) and triethylamine (379 mg, 3.75 mmol) were added to the reaction solution. The reaction solution was stirred at 80° C. for 12 hours under nitrogen. The reaction solution was cooled to room temperature. Water (20 mL) was added. The mixture was extracted with ethyl acetate (10 mL×3). The organic phases were combined, washed with saturated brine (10 mL×2), dried over anhydrous sodium sulfate, and filtered. The filtrate was concentrated under reduced pressure. The residue was isolated by a preparative TLC plate (1:1 petroleum ether/ethyl acetate, R$_f$=0.3) to afford compound 35-8.

$^1$H NMR: (400 MHz, CDCl$_3$) δ 7.32-7.30 (m, 1H), 7.17-7.14 (m, 2H), 4.74 (s, 2H), 3.59-3.35 (m, 6H), 2.07-1.85 (m, 4H), 1.43 (s, 9H).

MS-ESI calculated for [M+H]$^-$: 332, found: 332.

Step 8

Compound 35-9 (111 mg, 0.543 mmol) was dissolved in N,N-dimethylformamide (5 mL). To the reaction solution were added 1-hydroxybenzotriazole (147 mg, 1.09 mmol) and 1-(3-dimethylaminopropyl)-3-ethylcarbodiimide hydrochloride (208 mg, 1.09 mmol). The reaction solution was stirred at 25° C. for 0.5 hour under nitrogen. Compound 35-8 (180 mg, 0.543 mmol) was then added to the reaction solution, and the reaction solution was stirred at 25° C. for 1 hour. Then, the temperature was raised to 80° C., and the reaction solution was stirred at 80° C. for 12 hours. The reaction solution was cooled to room temperature, and water (30 mL) was added. The mixture was extracted with ethyl acetate (30 mL×3). The organic phases were combined, washed with saturated brine (20 mL×2), dried over anhydrous sodium sulfate, and filtered. The filtrate was concentrated under reduced pressure. The residue was isolated by a preparative TLC plate (1:1 petroleum ether/ethyl acetate, R$_f$=0.8) to afford compound 35-10.

$^1$H NMR: (400 MHz, CDCl$_3$) δ 8.45 (s, 1H), 8.38-8.35 (m, 1H), 8.09-8.07 (m, 1H), 7.43-7.39 (m, 2H), 7.16-7.13 (m, 1H), 4.85-4.79 (m, 1H), 3.59-3.38 (m, 6H), 2.24-2.18 (m, 3H), 2.01-2.00 (m, 1H), 1.53-1.49 (m, 15H).

MS-ESI calculated for [M+H]$^+$: 501, found: 501.

Step 9

Compound 35-10 (170 mg, 0.340 mmol) was dissolved in dioxane (3 mL). Hydrochloride/dioxane (4 M, 1 mL) was added to the reaction solution, and the reaction solution was stirred at 25° C. for 12 hours under nitrogen. A saturated aqueous solution of sodium bicarbonate (20 mL) was added to the reaction solution. The mixture was extracted with dichloromethane (20 mL×3). The organic phases were combined, washed with saturated brine (20 mL×2), dried over anhydrous sodium sulfate, and filtered. The filtrate was concentrated under reduced pressure. The residue is compound 35-11.

¹H NMR: (400 MHz, CDCl₃) δ 8.36 (s, 1H), 8.29-8.26 (m, 1H), 8.02-8.00 (m, 1H), 7.40-7.36 (m, 2H), 7.07-7.05 (m, 1H), 4.75-4.72 (m, 1H), 3.32-3.25 (m, 4H), 2.28-2.07 (m, 6H), 1.38 (d, J=6.0 Hz, 6H).

MS-ESI calculated for [M+H]⁺: 401, found: 401.

Step 10

Compound 35-11 (70.0 mg, 0.175 mmol) was dissolved in 1,2-dichloroethane (5 mL). Compound 35-12 (30.5 mg, 0.175 mmol) and titanium tetraisopropoxide (99.4 mg, 0.350 mmol) were added to the reaction solution, and the reaction solution was stirred at 50° C. for 1 hour under nitrogen. Sodium triacetoxyborohydride (74.1 mg, 0.350 mmol) was then added to the reaction solution, and the reaction solution was stirred at 80° C. for 12 hours. After the temperature was raised to 80° C., the reaction solution was stirred at 80° C. for 12 hours. The reaction solution was cooled to room temperature, and water (20 mL) was added. The mixture was filtered, and the filtrate was extracted with ethyl acetate (20 mL×3). The organic phases were combined, washed with saturated brine (20 mL×2), dried over anhydrous sodium sulfate, and filtered. The filtrate was concentrated under reduced pressure. The residue was isolated by a preparative TLC plate (1:1 petroleum ether/ethyl acetate, R_f=0.4) to afford compound 35-13.

MS-ESI calculated for [M+H]⁺: 559, found: 559.

Step 11

Compound 35-13 (12.0 mg, 0.0215 mmol) was dissolved in dioxane (3 mL). Hydrochloride/dioxane (4 M, 1 mL) was added to the reaction solution, and the reaction solution was stirred at 25° C. for 10 min under nitrogen. The reaction solution was cooled and concentrated under reduced pressure. The residue was isolated by high performance liquid chromatography to afford compound 35-14 (i.e., Example 35).

¹H NMR: (400 MHz, CD₃OD) δ 8.48-8.43 (m, 2H), 8.15-8.12 (m, 1H), 7.54-7.52 (m, 1H), 7.48-7.46 (m, 2H), 5.00-4.99 (m, 1H), 3.97-3.91 (m, 4H), 3.62-3.44 (m, 6H), 2.44-2.24 (m, 4H), 1.47 (d, J=6.0 Hz, 6H).

MS-ESI calculated for [M+H]⁺: 445, found: 445.

Example 36

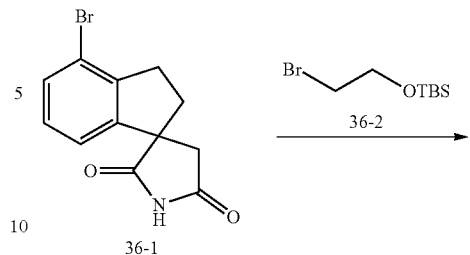

36-1

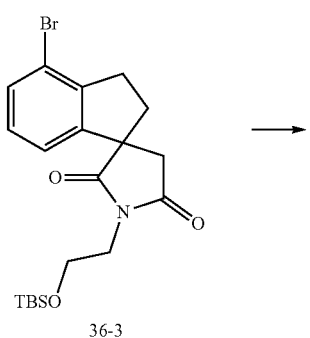

36-3

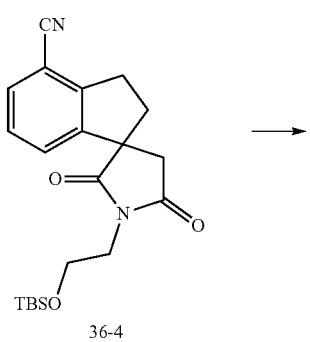

36-4

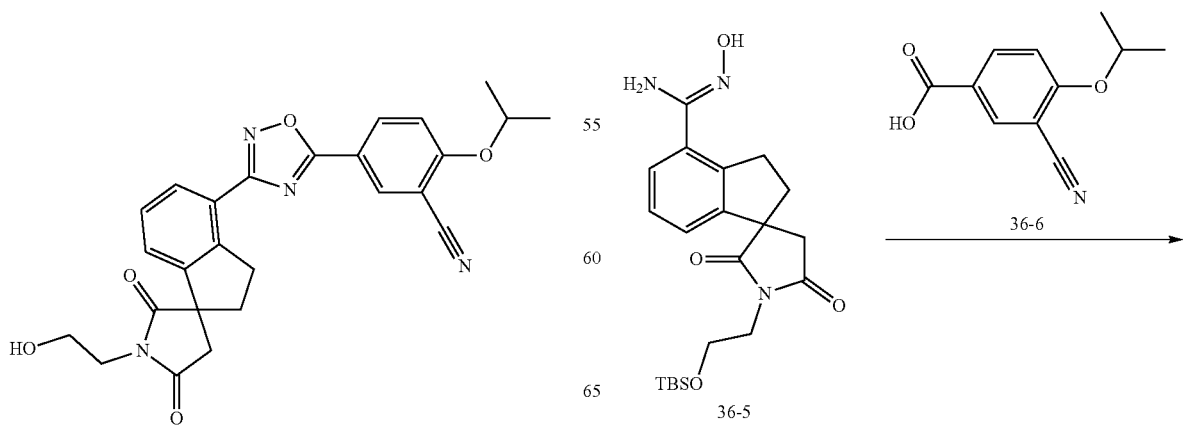

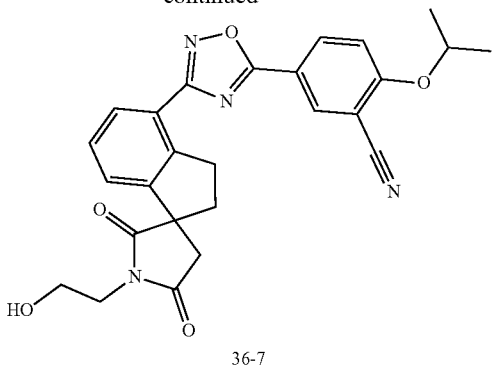

36-7

Step 1

Compound 36-1 (300 mg, 1.07 mmol) was dissolved in anhydrous N,N-dimethylformamide (5 mL). Sodium hydride (64.3 mg, 1.61 mmol, 60% purity) was added portionwise at 0° C., and the reaction was stirred at this temperature for 30 min. Compound 36-2 (307 mg, 1.28 mmol) was then added to the reaction solution, and the reaction solution was stirred at 60° C. for 12 hours. Water (20 mL) was added to the reaction solution, and the mixture was extracted with ethyl acetate (20 mL×3). The organic phases were combined, washed with saturated brine (30 mL×2), dried over anhydrous sodium sulfate, and filtered. The filtrate was concentrated under reduced pressure. The residue was isolated by a preparative TLC plate (3:1 petroleum ether/ethyl acetate, $R_f$=0.3) to afford compound 36-3.

$^1$H NMR: (400 MHz, CDCl$_3$) δ 7.39-7.37 (m, 1H), 7.06-7.02 (m, 1H), 6.96-6.95 (m, 1H), 3.78-3.76 (m, 2H), 3.69-3.68 (m, 2H), 3.25-3.22 (m, 1H), 3.03-2.97 (m, 1H), 2.90-2.88 (m, 2H), 2.72-2.69 (m, 1H), 2.14-2.01 (m, 1H), 0.81 (s, 9H), 0.05-0.00 (m, 6H).

MS-ESI calculated for [M+H]$^+$: 438 and 440, found: 438 and 440.

Step 2

Compound 36-3 (150 mg, 0.342 mmol) was dissolved in N,N-dimethylformamide (5 mL). Zinc cyanide (80.4 mg, 0.684 mmol) and tetrakis(triphenylphosphino)palladium (39.5 mg, 0.0342 mmol) were added to the reaction solution. The reaction solution was stirred at 100° C. for 16 hours under nitrogen. The reaction solution was cooled to room temperature, and water (10 mL) was added. The mixture was extracted with ethyl acetate (20 mL×3). The organic phases were combined, washed with saturated brine (20 mL×3), dried over anhydrous sodium sulfate, and filtered. The filtrate was concentrated under reduced pressure. The residue was isolated by a preparative TLC plate (1:1 petroleum ether/ethyl acetate, $R_f$=0.4) to afford compound 36-4.

$^1$H NMR: (400 MHz, CD$_3$OD) δ 7.58-7.56 (m, 1H), 7.40-7.30 (m, 2H), 3.78-3.75 (m, 2H), 3.64-3.61 (m, 2H), 3.34-3.33 (m, 1H), 3.28-3.26 (m, 1H), 2.98-2.96 (m, 2H), 2.69-2.67 (m, 1H), 2.29-2.26 (m, 1H), 0.82 (s, 9H), 0.03-0.00 (m, 6H).

MS-ESI calculated for [M+H]$^+$: 385, found: 385.

Step 3

Compound 36-4 (40.0 mg, 0.104 mmol) was dissolved in ethanol (2 mL). Hydroxylamine hydrochloride (21.7 mg, 0.312 mmol) and triethylamine (42.1 mg, 0.416 mmol) were added to the reaction solution. The solution was stirred at 60° C. for 12 hours under nitrogen. The reaction solution was cooled to room temperature, and water (10 mL) was added. The mixture was extracted with ethyl acetate (10 mL×3). The organic phases were combined, washed with saturated brine (10 mL×2), dried over anhydrous sodium sulfate, and filtered. The filtrate was concentrated under reduced pressure. The residue is compound 36-5.

MS-ESI calculated for [M+H]$^+$: 418, found: 418.

Step 4

Compound 36-6 (14.7 mg, 0.0718 mmol) was dissolved in N,N-dimethylformamide (3 mL). To the reaction solution were added 1-hydroxybenzotriazole (19.4 mg, 0.144 mmol) and 1-(3-dimethylaminopropyl)-3-ethylcarbodiimide hydrochloride (27.6 mg, 0.144 mmol). The reaction solution was stirred at 25° C. for 0.5 hour under nitrogen. Compound 36-5 (30.0 mg, 0.0718 mmol) was then added to the reaction solution, and the mixture was stirred at 25° C. for 1 hour. After the temperature was raised to 80° C., the reaction solution was stirred at 80° C. for 12 hours. The reaction solution was cooled to room temperature, and water (10 mL) was added. The mixture was extracted with ethyl acetate (20 mL×3). The organic phases were combined, washed with saturated brine (10 mL×2), dried over anhydrous sodium sulfate, and filtered. The filtrate was concentrated under reduced pressure. The residue was isolated by high performance liquid chromatography to afford compound 36-7 (i.e., Example 36).

$^1$H NMR: (400 MHz, DMSO-d$_6$) δ 8.53 (s, 1H), 8.43-8.40 (m, 1H), 8.06-8.03 (m, 1H), 7.57-7.55 (m, 1H), 7.47-7.45 (m, 2H), 5.01-4.95 (m, 1H), 3.56-3.54 (m, 4H), 3.43-3.41 (m, 2H), 3.12-3.08 (m, 1H), 3.01-2.96 (m, 1H), 2.63-2.62 (m, 1H), 2.32-2.30 (m, 1H), 1.39 (d, J=6.0 Hz, 6H).

MS-ESI calculated for [M+H]$^+$: 473, found: 473.

Example 37

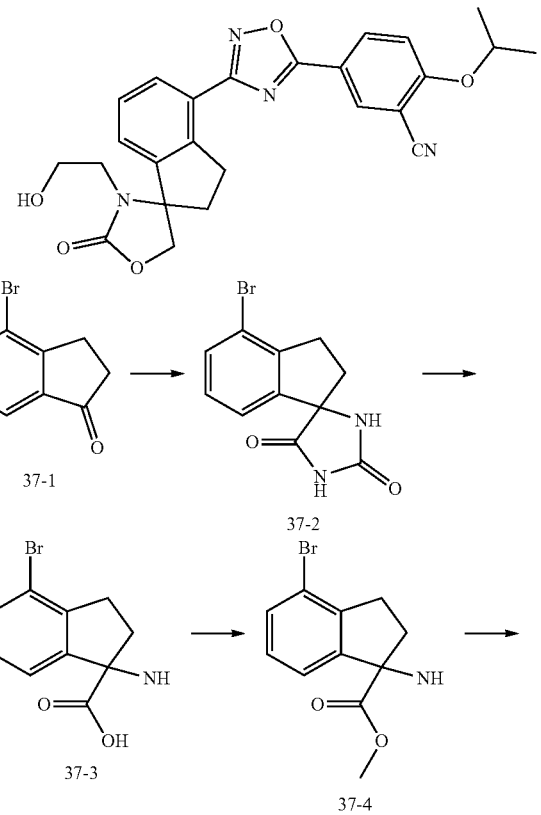

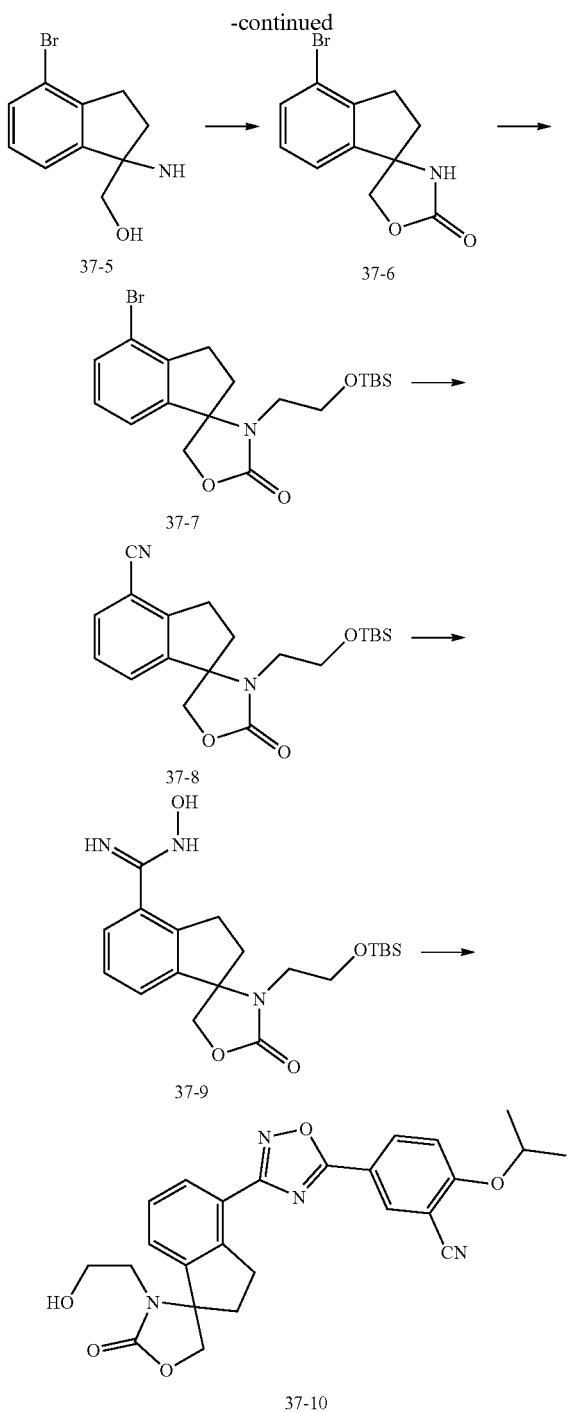

¹H NMR: (400 MHz, DMSO-d₆) δ 8.45 (s, 1H), 7.56 (d, J=7.6 Hz, 1H), 7.23 (d, J=7.6 Hz, 1H), 7.18 (d, J=7.6 Hz, 1H), 3.01-2.95 (m, 2H), 2.60-2.53 (m, 1H), 2.23-2.15 (m, 1H). MS-ESI calculated for [M+H]⁺: 281 and 283, found: 281 and 283.

Step 2

To a solution of compound 37-2 (1.00 g, 3.56 mmol) in water (10 mL) was added sodium hydroxide (997 mg, 24.92 mmol). The reaction solution was heated to 100° C. and stirred for 15 hours. The reaction solution was cooled to room temperature, and adjusted to pH 7 with diluted hydrochloric acid (1 M) to afford a white solid. After filtration, the filter cake was washed with cold water (10 mL×3) and then acetone (5 mL) to afford compound 37-3.

¹H NMR: (400 MHz, DMSO-d₆) δ 7.47 (d, J=7.6 Hz, 1H), 7.35 (d, J=7.6 Hz, 1H), 7.16 (t, J=7.6 Hz, 1H), 3.04-2.96 (m, 2H), 2.73-2.67 (m, 1H), 2.11-2.01 (m, 1H).

MS-ESI calculated for [M+H]⁺: 256 and 258, found: 256 and 258.

Step 3

To a solution of compound 37-3 (300 mg, 1.17 mmol) in methanol (8 mL) was added hydrochloride/methanol (2 mL, 4 M). The reaction solution was heated to 60° C. and stirred for 15 hours. The reaction solution was cooled to room temperature and concentrated under reduced pressure. The residue was washed with water (10 mL) and adjusted to pH 7 with a saturated aqueous solution of potassium carbonate. The aqueous phase was extracted with ethyl acetate (20 mL×3). The organic phase was dried over anhydrous sodium sulfate, filtered and concentrated to afford compound 37-4.

¹H NMR: (400 MHz, DMSO-d₆) δ 7.51 (d, J=7.6 Hz, 1H), 7.38 (d, J=7.6 Hz, 1H), 7.23 (t, J=7.6 Hz, 1H), 3.66 (s, 3H), 3.02-2.92 (m, 2H), 2.68-2.64 (m, 1H), 2.12-2.02 (m, 1H).

MS-ESI calculated for [M+H]⁺: 270 and 272, found: 270 and 272.

Step 4

To a solution of compound 37-4 (2.60 g, 9.63 mmol) in methanol (20 mL) was added sodium borohydride (729 mg, 19.26 mmol). The reaction solution was stirred at 25° C. for 3 hours. The reaction was quenched with water (20 mL). The methanol was removed by concentration under reduced pressure. The aqueous phase was extracted with dichloromethane (30 mL×3). The organic phase was dried over anhydrous sodium sulfate, filtered and concentrated. The residue was purified by column chromatography (petroleum ether:ethyl acetate=10:1 to 1:1, R_f=0.08) to afford compound 37-5.

¹H NMR: (400 MHz, Methanol-d₄) δ 7.40 (d, J=7.6 Hz, 1H), 7.36 (d, J=7.6 Hz, 1H), 7.15 (t, J=7.6 Hz, 1H), 3.61-3.52 (m, 2H), 3.07-2.95 (m, 1H), 2.92-2.79 (m, 1H), 2.41-2.31 (m, 1H), 2.02-1.89 (m, 1H).

Step 5

To a solution of compound 37-5 (2.20 g, 9.09 mmol) in dichloromethane (30 mL) was added carbonyldiimidazole (2.21 g, 13.63 mmol) and triethylamine (5.04 mL, 36.36 mmol) at 0° C. The reaction solution was warmed to 25° C. and stirred for 15 hours. The reaction solution was quenched with water (20 mL) and extracted with dichloromethane (20 mL×3). The organic phases were combined, dried over anhydrous sodium sulfate, filtered and concentrated. The residue was purified by column chromatography (petroleum ether:ethyl acetate=10:1 to 1:1, R_f=0.63) to afford compound 37-6.

¹H NMR: (400 MHz, Methanol-d₄) δ 7.50 (d, J=7.6 Hz, 1H), 7.40 (d, J=7.6 Hz, 1H), 7.26 (t, J=7.6 Hz, 1H), 4.53 (d, J=8.4 Hz, 1H), 4.38 (d, J=8.4 Hz, 1H), 2.98-3.07 (m, 1H), 2.97-2.88 (m, 1H), 2.53-2.45 (m, 1H), 2.37-2.28 (m, 1H).

Step 1

Compound 37-1 (10.0 g, 47.3 mmol), potassium cyanide (6.17 g, 94.7 mmol), and ammonium carbonate (18.2 g, 189.5 mmol) were dissolved in ethanol (70 mL), and water (70 mL). The atmosphere of the reaction solution was replaced with nitrogen for three times, and the reaction solution was heated to 60° C., and stirred for 8 hours. The reaction solution was cooled to room temperature and concentrated to 2/3 of the original volume. A white solid was precipitated. The solid was filtered, and the filter cake was washed with cold water (10 mL×3) and recrystallized from ethanol (30 mL) to afford compound 37-2.

MS-ESI calculated for [M+H]$^+$: 268 and 270, found: 268 and 270.

Step 6

Compound 37-6 (1.50 g, 5.59 mmol) was dissolved in anhydrous N,N-dimethylformamide (25 mL). The solution was cooled to 0° C. To the solution was added sodium hydride (447 mg, 11.18 mmol, purity 60%), and the reaction solution was stirred for 15 min. (2-bromoethoxy)-dimethyl-tert-butylsilane (2.01 g, 8.39 mmol) was slowly added to the reaction solution. The solution was slowly warmed to 25° C. and stirred for 2 hours. The reaction solution was quenched with water (10 mL) and extracted with ethyl acetate (20 mL×3). The organic phases were combined, dried over anhydrous sodium sulfate, filtered and concentrated. The residue was purified by column chromatography (petroleum ether:ethyl acetate=10:1 to 1:1, R$_f$=0.42) to afford compound 37-7.

$^1$H NMR: (400 MHz, Methanol-d$_4$) δ 7.54 (d, J=7.6 Hz, 1H), 7.32 (d, J=7.6 Hz, 1H), 7.25 (t, J=7.6 Hz, 1H), 4.49-4.34 (m, 2H), 3.73-3.64 (m, 1H), 3.49-3.42 (m, 1H), 3.17-2.88 (m, 4H), 2.66-2.58 (m, 1H), 2.38-2.31 (m, 1H), 0.86 (s, 9H), 0.00 (d, J=2.0 Hz, 6H).

MS-ESI calculated for [M+H]$^+$: 426 and 428, found: 426 and 428.

Step 7

Compound 37-7 (1.00 g, 2.35 mmol), zinc cyanide (552 mg, 4.70 mmol), tris(dibenzylideneacetone)dipalladium (107 mg, 0.12 mmol), 2-dicyclohexylphosphino-2',4',6'-tri-isopropylbiphenyl (112 mg, 0.23 mmol) were dissolved in acetonitrile (15 mL). The atmosphere of the reaction solution was replaced with nitrogen for three times, the reaction solution was heated to 80° C., and stirred for 15 hours. The reaction solution was cooled to room temperature and filtered. The filtrate was concentrated under reduced pressure. The residue was washed with water (10 mL) and ethyl acetate (10 mL×3). The organic phases were combined, dried over anhydrous sodium sulfate, filtered and concentrated. The residue was purified by column chromatography (petroleum ether:ethyl acetate=10:1 to 4:1, R$_f$=0.38) to afford compound 37-8.

$^1$H NMR: (400 MHz, Methanol-d$_4$) δ 7.71 (d, J=7.6 Hz, 1H), 7.65 (d, J=7.6 Hz, 1H), 7.49 (t, J=7.6 Hz, 1H), 4.48-4.36 (m, 2H), 3.72-3.67 (m, 1H), 3.56-3.45 (m, 1H), 3.25-3.07 (m, 3H), 3.05-2.94 (m, 1H), 2.70-2.64 (m, 1H), 2.44-2.39 (m, 1H), 0.85 (s, 9H), 0.00 (d, J=2.0 Hz, 6H).

MS-ESI calculated for [M+H]$^+$: 373, found: 373.

Step 8

Compound 37-8 (700 mg, 1.88 mmol) was dissolved in ethanol (10 mL). Triethylamine (1.04 mL, 7.52 mmol) and hydroxylamine hydrochloride (392 mg, 5.64 mmol) was added dropwise to the reaction solution. The reaction solution was heated to 80° C. and stirred for 15 hours. The reaction solution was concentrated under reduced pressure. The residue was dissolved in ethyl acetate (10 mL) and washed with water (5 mL). The aqueous phase was extracted with ethyl acetate (20 mL×3). The organic phase was dried over anhydrous sodium sulfate, filtered and concentrated. The residue was purified by column chromatography (petroleum ether:ethyl acetate=10:1 to 1:1, R$_f$=0.17) to afford compound 37-9.

$^1$H NMR: (400 MHz, Methanol-d$_4$) δ 7.50-7.43 (m, 1H), 7.38-7.31 (m, 2H), 4.43 (d, J=8.8 Hz, 1H), 4.31 (d, J=8.8 Hz, 1H), 3.72-3.38 (m, 1H), 3.61-3.51 (m, 1H), 3.23-3.00 (m, 3H), 2.96-2.93 (m, 1H), 2.56-2.50 (m, 1H), 2.29-2.24 (m, 1H), 0.85 (s, 9H), 0.00 (d, J=2.0 Hz, 6H).

MS-ESI calculated for [M+H]$^+$: 406, found: 406.

Step 9

3-cyano-4-isopropoxybenzoic acid (101 mg, 0.49 mmol), 1-hydroxybenzotriazole (133 mg, 0.99 mmol), and 1-(3-dimethylaminopropyl)-3-ethylcarbodiimide hydrochloride (187 mg, 0.99 mmol) were dissolved in anhydrous N,N-dimethylformamide (4 mL). The atmosphere of the reaction solution was replaced with nitrogen for three times and the reaction solution was stirred at 25° C. for 1 hour. Compound 37-9 (200 mg, 0.49 mmol) was added to this solution and the mixture was stirred at 25° C. for 1 hour. The reaction solution was then heated to 90° C. and stirring was continued for 13 hours. The reaction solution was concentrated under reduced pressure. The residue was purified by preparative high performance liquid chromatography (hydrochloric acid system) to afford compound 37-10 (i.e., Example 37).

$^1$H NMR: (400 MHz, Methanol-d$_4$) δ 8.49-8.41 (m, 2H), 8.23 (d, J=7.2 Hz, 1H), 7.62-7.53 (m, 2H), 7.46 (d, J=8.8 Hz, 1H), 4.99-4.93 (m, 1H), 4.59-4.45 (m, 2H), 3.69-3.58 (m, 1H), 3.58-3.44 (m, 2H), 3.40-3.34 (m, 1H), 3.24-3.14 (m, 1H), 3.10-3.00 (m, 1H), 2.73-2.61 (m, 1H), 2.48-2.42 (m, 1H), 1.48 (d, J=6.0 Hz, 6H).

MS-ESI calculated for [M+H]$^+$: 461, found: 461.

Example 38

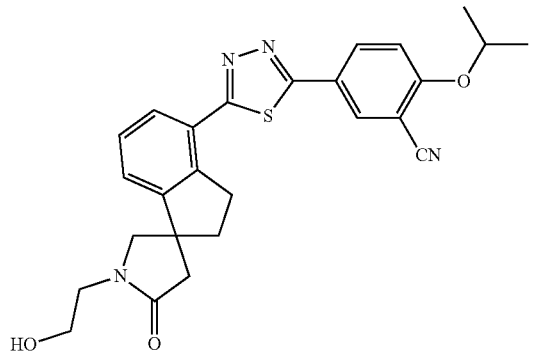

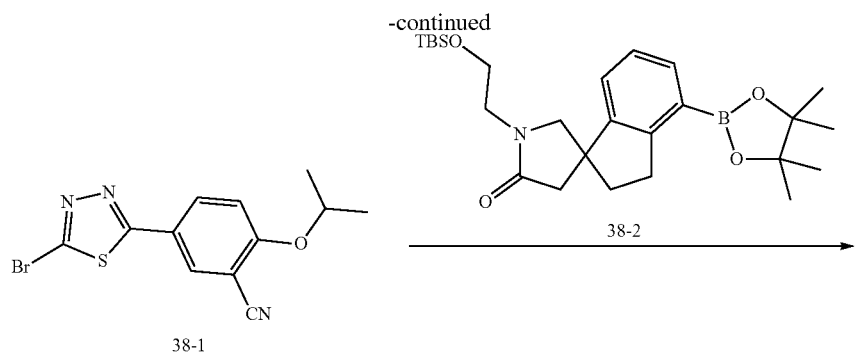

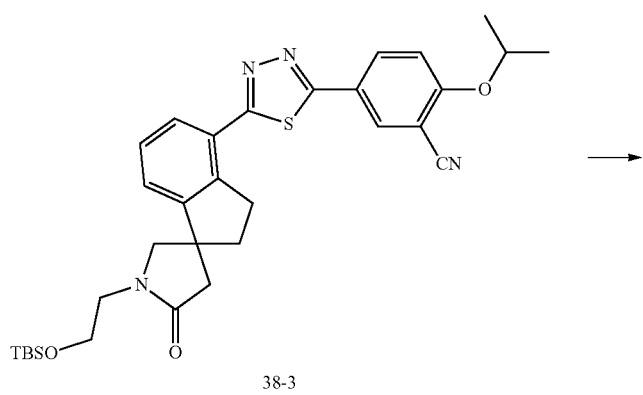

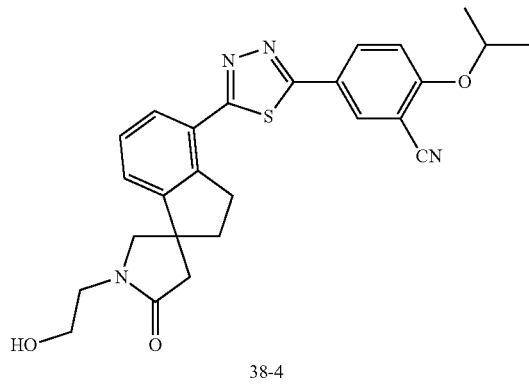

Step 1

Compound 38-1 (110 mg, 0.246 mmol) and compound 38-2 (125 mg, 0.258 mmol) were dissolved in 1,4-dioxane (5.00 mL). 1,1'-bis(diphenylphosphino)ferrocene palladium dichloride (18.0 mg, 0.0246 mmol), potassium carbonate (102 mg, 0.738 mmol) and water (1.00 mL) were added. The mixture was stirred at 80° C. for 16 hours under nitrogen. The reaction solution was concentrated. The residue was added into water (30 mL) and extracted with ethyl acetate (30 mL×2). The organic phase was dried over anhydrous sodium sulfate, filtered and concentrated. The crude product was isolated by a preparative TLC plate to afford compound 38-3.

MS-ESI calculated for [M+H]$^+$: 589, found: 589.

Step 2

Compound 38-3 (55.0 mg, 0.0934 mmol) was dissolved in ethyl acetate (5.00 mL). Hydrochloride/ethyl acetate (5.00 mL, 4 mol/L) was added. The mixture was stirred at 15° C. for 1 hour. The reaction solution was concentrated, and the residue was isolated by high performance liquid chromatography (formic acid system) to afford compound 38-4 (i.e., Example 38).

$^1$H NMR: (400 MHz, Methanol-d$_4$) δ 8.36-8.21 (m, 2H), 7.86 (d, J=7.6 Hz, 1H), 7.53 (d, J=7.6 Hz, 1H), 7.47-7.34 (m, 2H), 4.93-4.89 (m, 1H), 3.83-3.66 (m, 4H), 3.54-3.45 (m, 2H), 3.40-3.34 (m, 2H), 2.83-2.58 (m, 2H), 2.44-2.18 (m, 2H), 1.45 (d, J=6.0 Hz, 6H).

MS-ESI calculated for [M+H]$^+$: 475, found: 475.

Example 39

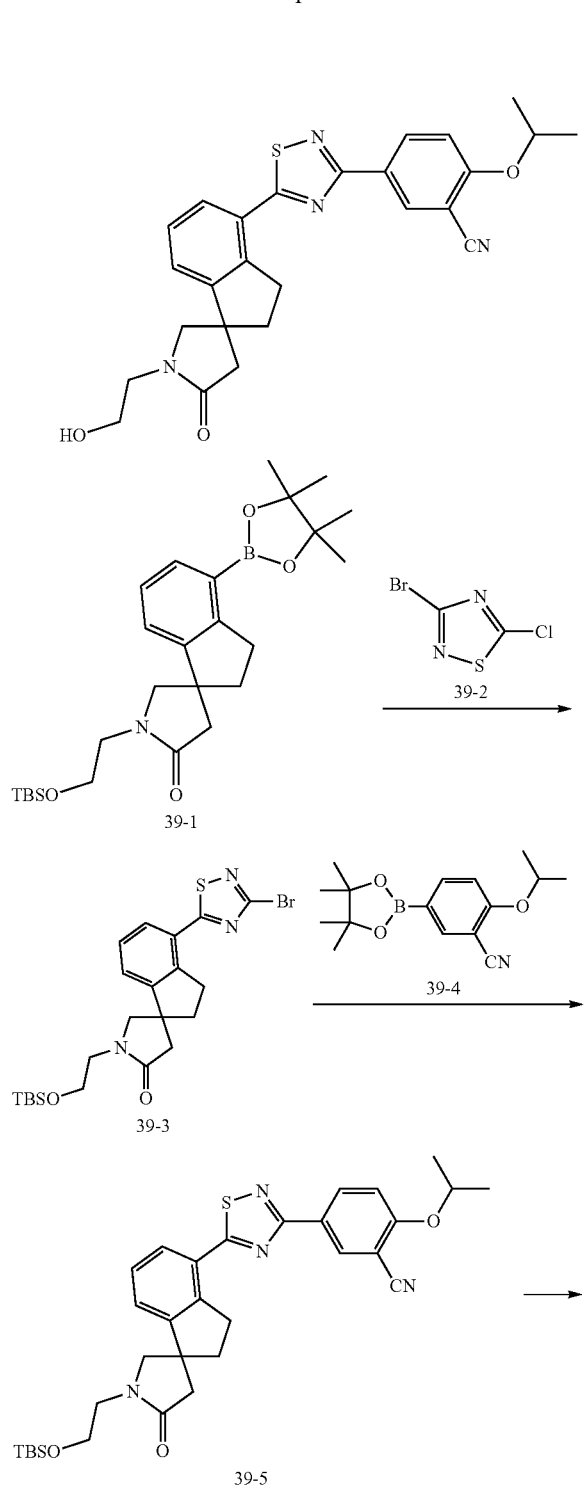

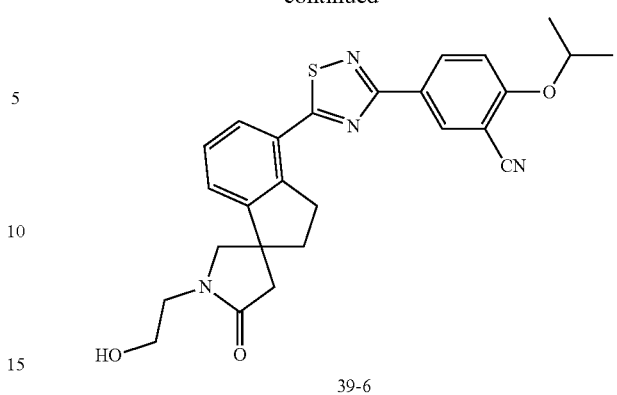

Step 1

Compound 39-1 (200 mg, 0.412 mmol) and compound 39-2 (82.2 mg, 0.412 mmol) were dissolved in 1,4-dioxane (5.00 mL). 1,1'-bis(diphenylphosphino)ferrocene palladium dichloride (30.2 mg, 0.0412 mmol), potassium phosphate (175 mg, 0.825 mmol) and water (1.00 mL) were added. The mixture was stirred at 100° C. for 16 hours under nitrogen. The reaction solution was concentrated to afford compound 39-3, and the crude product was used in the next step directly.

Step 2

Compound 39-3 (460 mg, crude) was dissolved in 1,4-dioxane (4.00 mL). Compound 39-4 (130 mg, 0.452 mmol), potassium phosphate (384 mg, 1.81 mmol), 1,1'-bis(diphenylphosphino)ferrocene palladium dichloride (66.2 mg, 0.0905 mmol) and water (1.00 mL) were added. The mixture was stirred at 80° C. for 16 hours. The reaction solution was concentrated. The residue was isolated by preparative TLC to afford compound 39-5.

MS-ESI calculated for [M+H]$^+$: 589, found: 589.

Step 3

Compound 39-5 (98.0 mg, 0.163 mmol) was dissolved in EtOAc (5.00 mL). Hydrochloride/ethyl acetate (5.00 mL, 4N) was added. The mixture was stirred at 15° C. for 16 hours. The reaction solution was concentrated. The residue was isolated by high performance liquid chromatography (formic acid system) to afford compound 39-6 (i.e., Example 39).

$^1$H NMR: (400 MHz, Methanol-d$_4$) δ 8.61-8.48 (m, 2H), 8.08 (d, J=7.6 Hz, 1H), 7.57 (d, J=7.6 Hz, 1H), 7.46 (t, J=7.6 Hz, 1H), 7.34 (d, J=7.6 Hz, 1H), 4.93-4.89 (m, 1H), 3.79-3.69 (m, 4H), 3.58-3.44 (m, 2H), 3.39-3.33 (m, 2H), 2.86-2.60 (m, 2H), 2.50-2.23 (m, 2H), 1.45 (d, J=6.0 Hz, 6H).

MS-ESI calculated for [M+H]$^+$: 475, found: 475.

Example 40
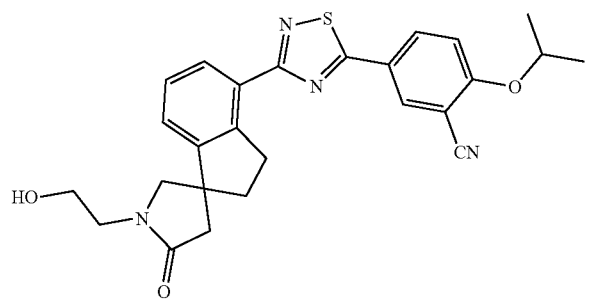
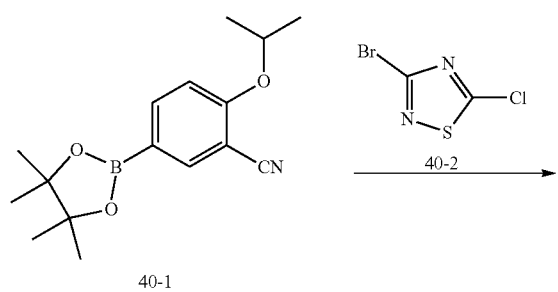
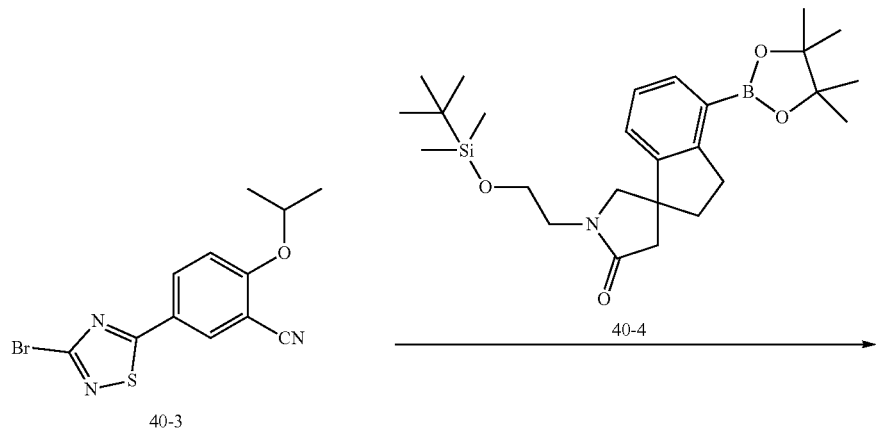
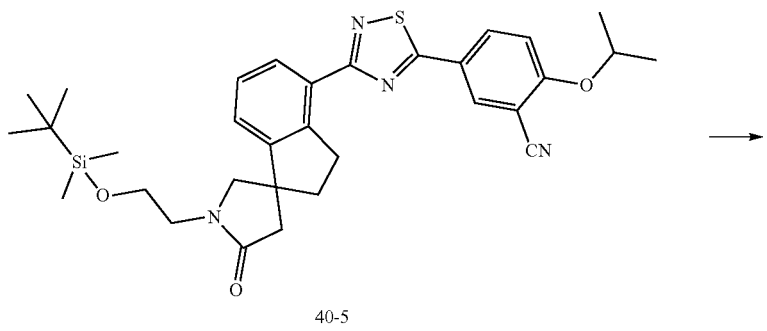

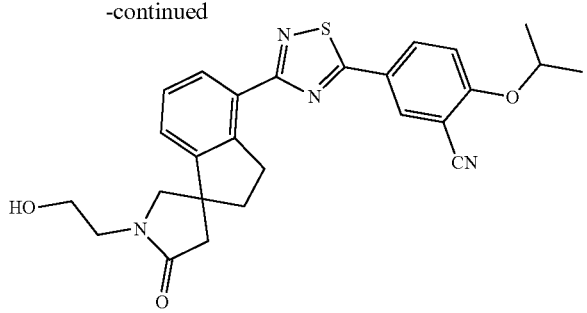

40-6

Step 1

Compound 40-1 (200 mg, 0.696 mmol) and compound 40-2 (139 mg, 0.696 mmol) were dissolved in 1,4-dioxane (5.00 mL). 1,1'-bis(diphenylphosphino)ferrocene palladium dichloride (51.0 mg, 0.0697 mmol), potassium phosphate (296 mg, 1.39 mmol) and water (1.00 mL) were added. The mixture was stirred at 80° C. for 16 hours under nitrogen. The reaction solution was concentrated to afford the compound 40-3, and the crude product was used in the next step directly.

MS-ESI calculated for [M+H]$^+$: 324 and 326, found: 324 and 326.

Step 2

Compound 40-3 (225 mg, crude) was dissolved in 1,4-dioxane (4.00 mL). Compound 40-4 (327 mg, 0.694 mmol), potassium phosphate (147 mg, 0.694 mmol), 1,1'-bis(diphenylphosphino)ferrocene palladium dichloride (50.8 mg, 0.0694 mmol) and water (1.00 mL) were added. The mixture was stirred at 90° C. for 16 hours. The reaction solution was filtered, and the filter cake was washed with dichloromethane (20 mL). The filtrate was concentrated. The residue was isolated by thin layer chromatography (silica, petroleum ether:ethyl acetate=1:1) to afford compound 40-5.

MS-ESI calculated for [M+H]$^+$: 589, found: 589.

Step 3

Compound 40-5 (130 mg, 0.221 mmol) was dissolved in ethyl acetate (2.00 mL). Hydrochloride/ethyl acetate (2.00 mL, 4N) was added. The mixture was stirred at 16° C. for 1 hour. The reaction solution was concentrated, and the residue was isolated by high performance liquid chromatography (formic acid system) to afford compound 40-6 (i.e., Example 40).

$^1$H NMR: (400 MHz, Methanol-d$_4$) δ 8.36 (d, J=2.4 Hz, 1H), 8.31 (dd, J=2.4, 8.8 Hz, 1H), 8.24 (d, J=8.0 Hz, 1H), 7.49-7.45 (m, 1H), 7.43-7.36 (m, 2H), 4.97-4.90 (m, 1H), 3.75-3.71 (m, 4H), 3.55-3.45 (m, 4H), 2.83-2.57 (m, 2H), 2.43-2.16 (m, 2H), 1.45 (d, J=6.0 Hz, 6H).

MS-ESI calculated for [M+H]$^+$: 475, found: 475.

Example 41

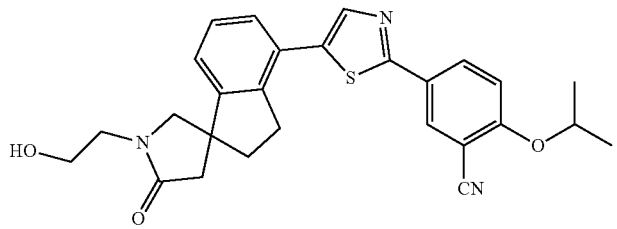

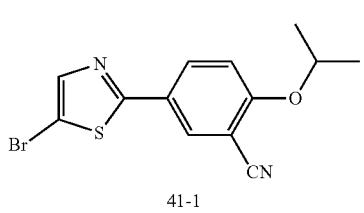

41-1

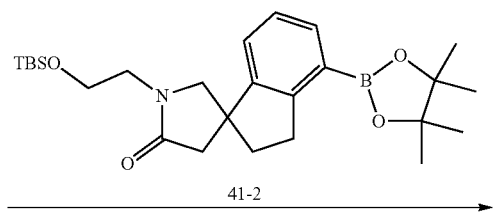

41-2

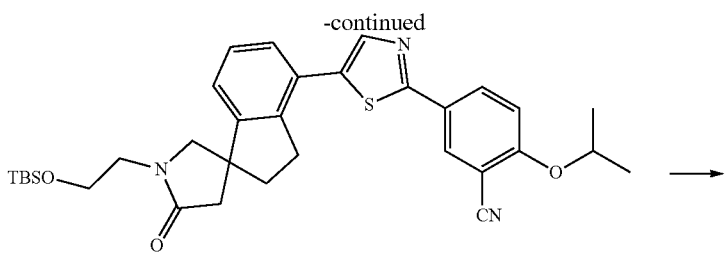

41-3

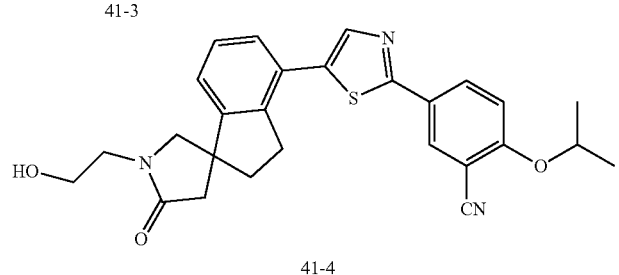

41-4

Step 1

Compound 41-1 (85.0 mg, 0.263 mmol) and compound 41-2 (126 mg, 0.263 mmol) were dissolved in 1,4-dioxane (4 mL). 1,1'-bis(diphenylphosphino)ferrocene palladium dichloride (19.2 mg, 0.0263 mmol), potassium phosphate (112 mg, 0.526 mmol) and water (1 mL) were added. The mixture was stirred at 80° C. for 16 hours under nitrogen. The reaction solution was concentrated, and the residue was purified by preparative TLC to afford compound 41-3.

MS-ESI calculated for [M+H]$^+$: 588, found: 588.

Step 2

Compound 41-3 (105 mg, 0.0179 mmol) was dissolved in ethyl acetate (5 mL). Hydrochloride/ethyl acetate (5 mL, 4N) was added. The mixture was stirred at 10° C. for 24 hours. The reaction solution was concentrated, and the residue was isolated by high performance liquid chromatography (formic acid system) to afford compound 41-4 (i.e., Example 41).

$^1$H NMR: (400 MHz, Methanol-d$_4$) δ 8.24-8.15 (m, 2H), 7.99 (s, 1H), 7.50 (d, J=6.8 Hz, 1H), 7.40-7.28 (m, 3H), 4.94-4.87 (m, 1H), 3.80-3.66 (m, 4H), 3.56-3.42 (m, 2H), 3.22-3.11 (m, 1H), 3.17 (t, J=7.2 Hz, 1H), 2.82-2.57 (m, 2H), 2.42-2.16 (m, 2H), 1.43 (d, J=6.0 Hz, 6H).

MS-ESI calculated for [M+H]$^+$: 474, found: 474.

Example 42

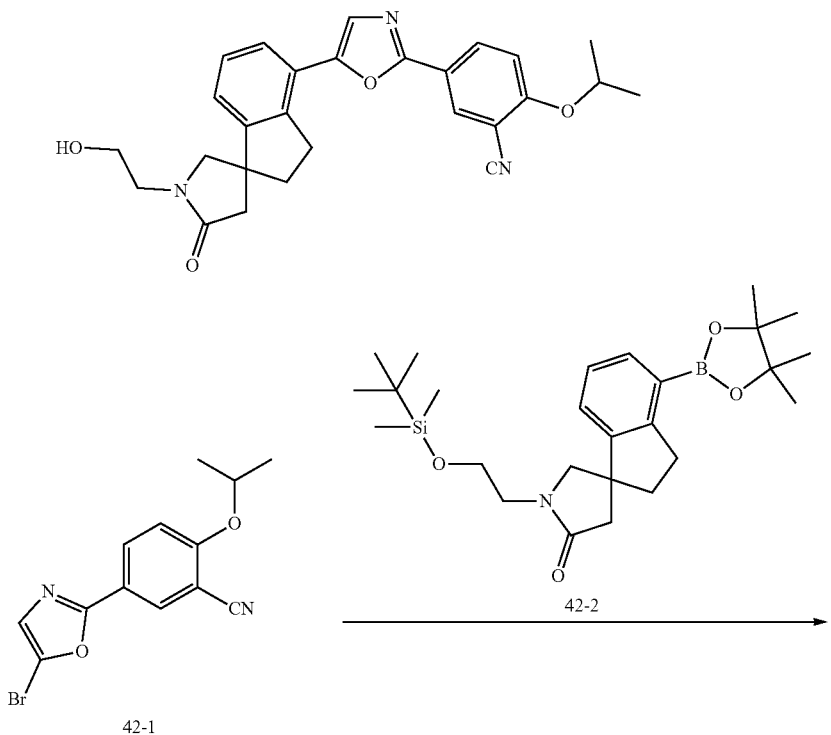

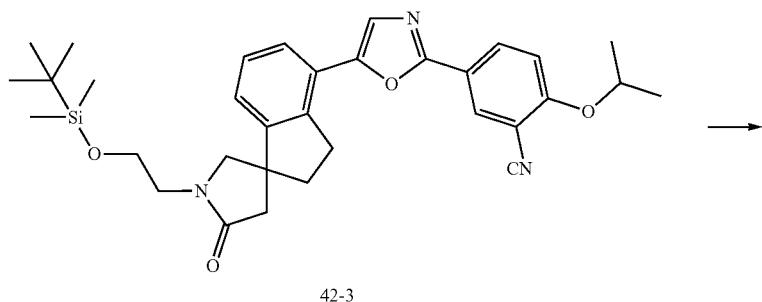

42-3

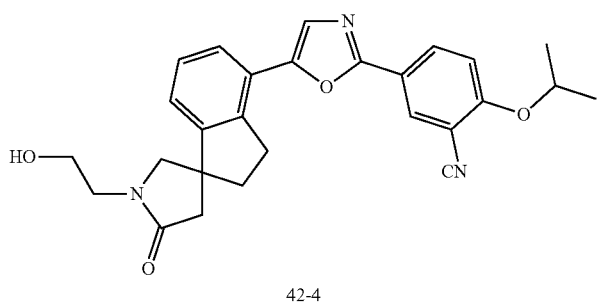

42-4

Step 1

Compound 42-1 (270 mg, 0.707 mmol) and compound 42-2 were dissolved in 1,4-dioxane (5.00 mL) and water (1 mL) at 16° C. Potassium phosphate (300 mg, 1.41 mmol), and 1,1'-bis(diphenylphosphino)ferrocene palladium dichloride (51.7 mg, 0.0707 mmol) were added. The mixture was stirred at 90° C. for 16 hours. The reaction solution was filtered, and the filter cake was washed with dichloromethane (60 mL). The filtrate was concentrated. The residue was isolated by silica gel chromatography column (silica, petroleum ether:ethyl acetate=2:1 to 0:1) to afford compound 42-3.

MS-ESI calculated for [M+H]$^+$: 572, found: 572.

Step 2

Compound 42-3 (290 mg, 0.507 mmol) was dissolved in EtOAc (5.00 mL). Hydrochloride/ethyl acetate (10 mL, 4N) was added. The mixture was stirred at 16° C. for 1 hour. The reaction solution was concentrated, and the residue was isolated by high performance liquid chromatography (formic acid system) to afford compound 42-4 (i.e., Example 42).

$^1$H NMR: (400 MHz, Methanol-d$_4$) δ 8.34-8.20 (m, 2H), 7.79-7.70 (m, 1H), 7.49 (s, 1H), 7.41-7.31 (m, 3H), 4.80-4.75 (m, 1H), 3.77-3.72 (m, 2H), 3.70 (s, 2H), 3.52-3.45 (m, 2H), 3.22-3.15 (m, 2H), 2.81-2.58 (m, 2H), 2.46-2.21 (m, 2H), 1.44 (d, J=6.0 Hz, 6H). MS-ESI calculated for [M+H]$^+$: 458, found: 458.

Example 43

[Structure of compound - spiroindanone with hydroxyethyl-pyrrolidinone, linked to thiophene-phenyl-isopropoxy-CN]

[Structure of compound 43-1: bromothiophene-phenyl-isopropoxy-CN]

[Structure of compound 43-2: TBS-protected spiroindanone with pinacol boronate]

43-1

43-2

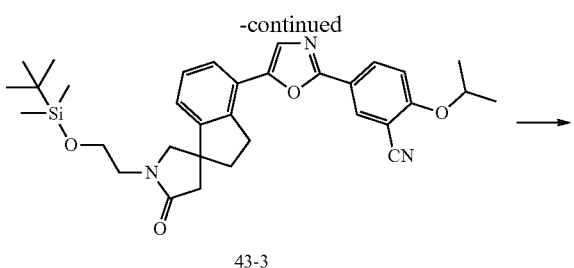

43-3

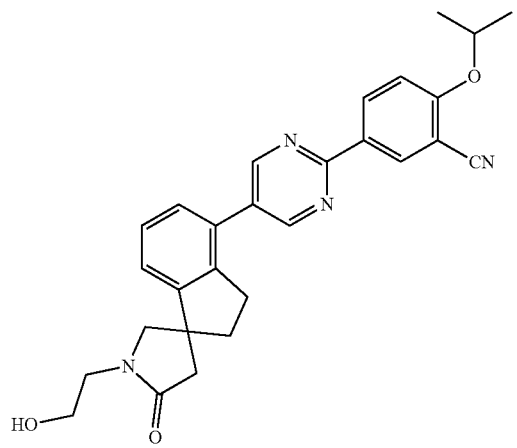

43-4

Step 1

Compound 43-2 (200 mg, 0.424 mmol) and compound 43-1 (137 mg, 0.424 mmol) were dissolved in 1,4-dioxane (5.00 mL) and water (1 mL). Potassium phosphate (180 mg, 0.848 mmol), and 1,1'-bis(diphenylphosphino)ferrocene palladium dichloride (31.0 mg, 0.0424 mmol) were added. The mixture was stirred at 90° C. for 16 hours. The reaction solution was filtered, and the filter cake was washed with dichloromethane (20 ml×2). The filtrate was concentrated. The residue was isolated by thin layer chromatography (silica, petroleum ether:ethyl acetate=1:1) to afford compound 43-3.

MS-ESI calculated for [M+H]⁺: 587, found: 587.

Step 2

Compound 43-3 (120 mg, 0.193 mmol) was dissolved in ethyl acetate (2.00 mL). Hydrochloride/ethyl acetate (5.00 mL, 4N) was added. The mixture was stirred at 16° C. for 10 minutes. The reaction solution was concentrated, and the residue was isolated by high performance liquid chromatography (formic acid system) to afford compound 43-4 (i.e., Example 43).

¹H NMR: (400 MHz, Methanol-d₄) δ 7.90-7.84 (m, 2H), 7.51-7.45 (m, 1H), 7.38 (d, J=3.6 Hz, 1H), 7.31-7.25 (m, 3H), 7.22 (d, J=8.8 Hz, 1H), 4.85-4.74 (m, 1H), 3.78-3.74 (m, 2H), 3.69 (s, 2H), 3.55-3.43 (m, 2H), 3.22-3.14 (m, 2H), 2.80-2.58 (m, 2H), 2.37-2.15 (m, 2H), 1.41 (d, J=6.0 Hz, 6H).

MS-ESI calculated for [M+H]⁺: 473, found: 473.

Example 44

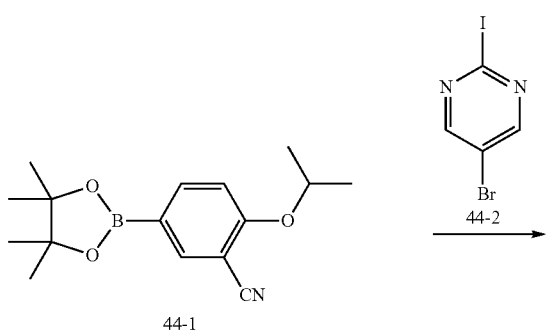

44-1     44-2

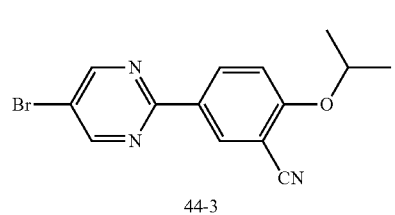
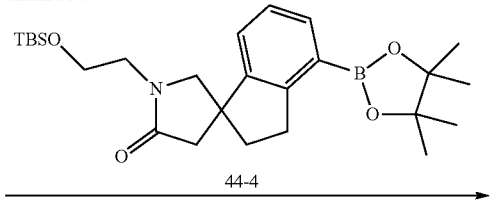

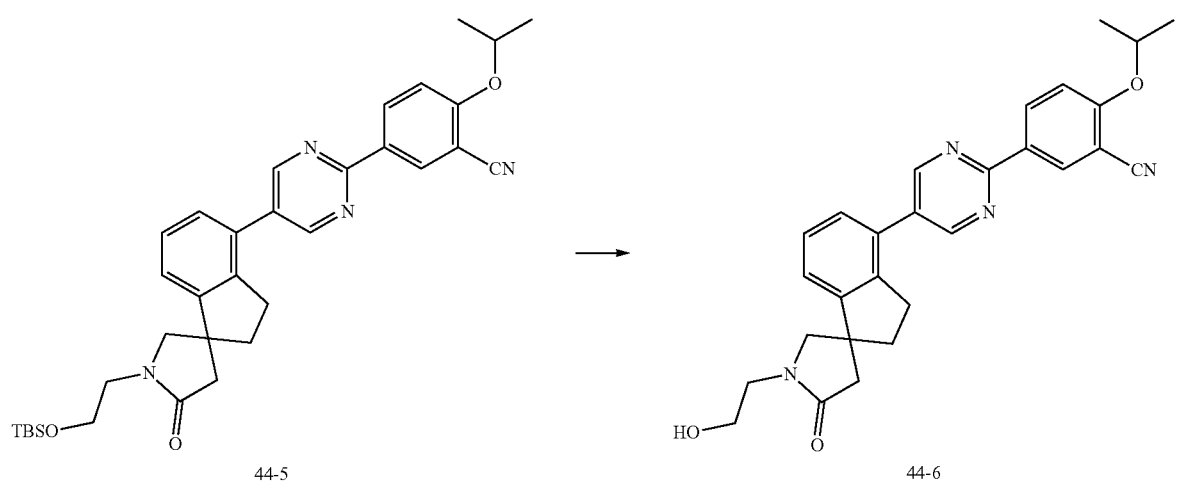

Step 1

Compound 44-1 (200 mg, 0.696 mmol) was dissolved in 1,4-dioxane (4.00 mL). Compound 44-2 (198 mg, 0.696 mmol), potassium phosphate (296 mg, 1.39 mmol), 1,1'-bis(diphenylphosphino)ferrocene palladium dichloride (51.0 mg, 0.0697 mmol) and water (1.00 mL) were added. The mixture was stirred at 80° C. for 16 hours under nitrogen. The mixture was concentrated. The residue was added into water (10 mL) and extracted with ethyl acetate (10 mL×2). The organic phase was dried over anhydrous sodium sulfate (0.2 g), filtered and concentrated to afford a crude product. The crude product was purified by preparative TLC to afford compound 44-3.

$^1$H NMR: (400 MHz, CDCl$_3$) δ 8.81 (s, 2H), 8.66 (d, J=2.0 Hz, 1H), 8.57 (d, J=2.0, 8.8 Hz, 1H), 7.05 (d, J=8.8 Hz, 1H), 4.82-4.71 (m, 1H), 1.46 (d, J=6.0 Hz, 6H).

MS-ESI calculated for [M+H]$^+$: 318 and 320, found: 318 and 320.

Step 2

Compound 44-3 (50.0 mg, 0.115 mmol) and compound 44-4 (56.0 mg, 0.115 mmol) were dissolved in 1,4-dioxane (8.00 mL). Potassium carbonate (31.9 mg, 0.231 mmol), 1,1-bis(di-tert-butylphosphino)ferrocene palladium dichloride (7.52 mg, 0.0115 mmol) and water (2.00 mL) were added. The mixture was stirred at 80° C. for 16 hours under nitrogen. The mixture was concentrated and the residue was purified by preparative TLC to afford compound 44-5.

MS-ESI calculated for [M+H]$^+$: 583, found: 583.

Step 3

Compound 44-5 (80.0 mg, 0.127 mmol) was dissolved in EtOAc (5.00 mL). Hydrochloride/ethyl acetate (5.00 mL, 4N) was added. The mixture was stirred at 10° C. for 16 hours. The reaction solution was concentrated. The residue was isolated by high performance liquid chromatography (formic acid system) to afford compound 44-6 (i.e., Example 44).

$^1$H NMR: (400 MHz, Methanol-d$_4$) δ 8.96 (s, 2H), 8.74-8.69 (m, 2H), 7.47-7.42 (m, 2H), 7.42-7.38 (m, 1H), 7.35 (d, J=8.8 Hz, 1H), 4.96-4.91 (m, 1H), 3.82-3.73 (m, 4H), 3.59-3.46 (m, 2H), 3.15-3.06 (m, 2H), 2.85-2.61 (m, 2H), 2.41-2.14 (m, 2H), 1.46 (d, J=6.0 Hz, 6H).

MS-ESI calculated for [M+H]$^+$: 469, found: 469.

Example 45

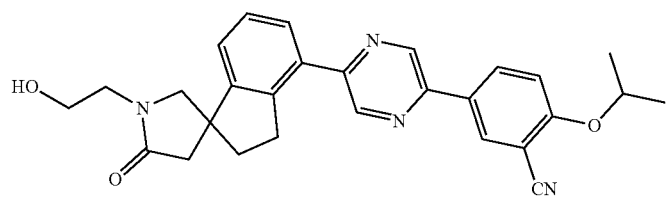

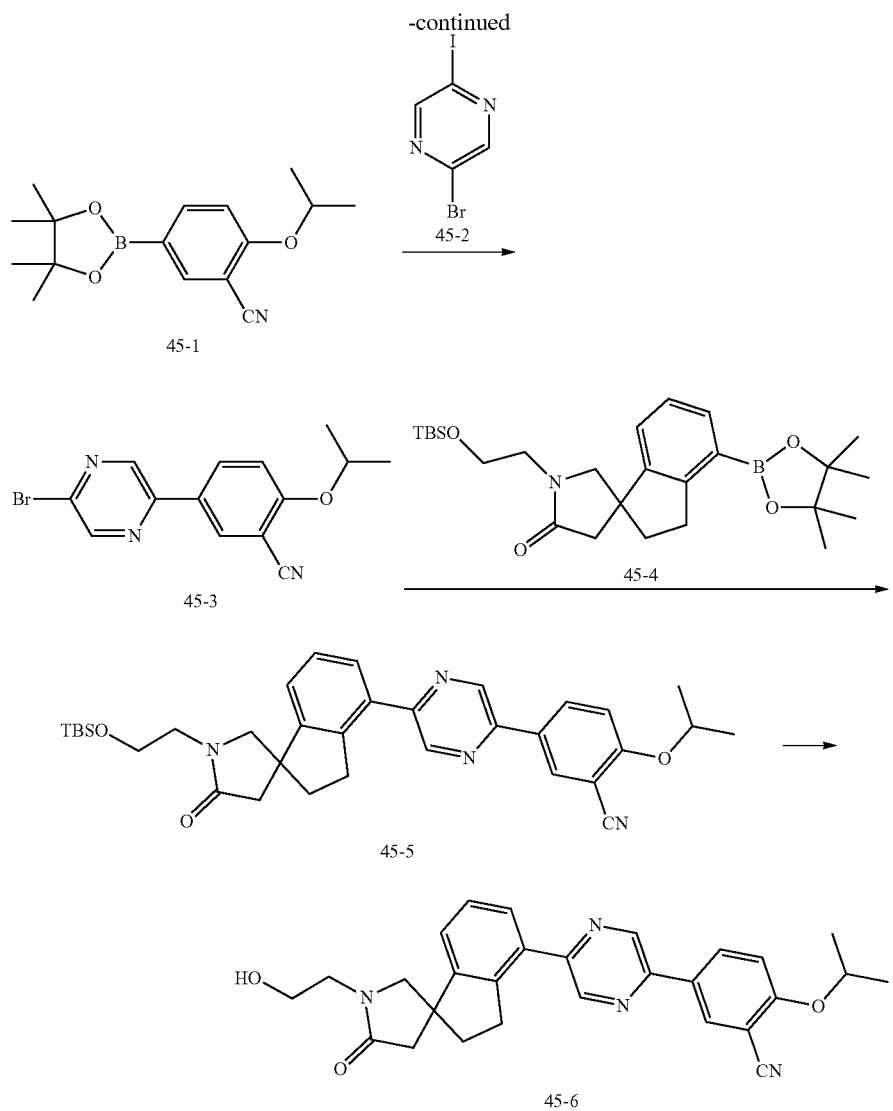

Step 1

Compound 45-1 (200 mg, 0.698 mmol) was dissolved in 1,4-dioxane (4 mL). Compound 45-2 (198 mg, 0.696 mmol), potassium carbonate (296 mg, 1.39 mmol), 1,1'-bis(diphenylphosphino)ferrocene palladium dichloride (51.0 mg, 0.0697 mmol) and water (1 mL) were added. The mixture was stirred at 60° C. for 16 hours under nitrogen. The reaction solution was concentrated, and the residue was dissolved in dichloromethane (30 mL) and washed once with water (20 mL). The organic phase was dried over anhydrous sodium sulfate, filtered and concentrated to afford a crude product. The crude product was purified by preparative TLC to afford compound 45-3.

MS-ESI calculated for [M+H]$^+$: 318 and 320, found: 318 and 320.

Step 2

Compound 45-3 (0.12 g, 0.377 mmol) and compound 45-4 (183 mg, 0.377 mmol) were dissolved in 1,4-dioxane (4 mL). 1,1'-bis(diphenylphosphino)ferrocene palladium dichloride (27.6 mg, 0.0377 mmol), potassium phosphate (160 mg, 0.754 mmol) and water (1 mL) were added. The mixture was stirred at 80° C. for 16 hours under nitrogen. The reaction solution was concentrated and the residue was dissolved in dichloromethane (30 mL) and washed with water (10 mL). The organic phase was dried over anhydrous sodium sulfate, filtered and concentrated to afford a crude product. The crude product was purified by preparative TLC to afford compound 45-5.

MS-ESI calculated for [M+H]$^+$: 583, found: 583.

Step 3

Compound 45-5 (72.0 mg, 0.124 mmol) was dissolved in ethyl acetate (4 mL). Hydrochloride/ethyl acetate (4 mL, 4 M) was added. The mixture was stirred at 5° C. for 24 hours. The reaction was concentrated to afford a crude product. The crude product was isolated by high performance liquid chromatography (formic acid system) to afford compound 45-6 (i.e., Example 45).

$^1$H NMR: (400 MHz, Methanol-d$_4$) δ 9.11 (d, J=1.6 Hz, 1H), 8.87 (d, J=1.6 Hz, 1H), 8.40-8.31 (m, 2H), 7.64 (d, J=7.6 Hz, 1H), 7.47-7.34 (m, 2H), 7.30 (d, J=8.8 Hz, 1H), 4.85-4.80 (m, 1H), 3.82-3.68 (m, 4H), 3.57-3.41 (m, 2H), 3.27-3.14 (m, 2H), 2.83-2.55 (m, 2H), 2.34-2.10 (m, 2H), 1.43 (d, J=6.0 Hz, 6H).

MS-ESI calculated for [M+H]$^+$: 469, found: 469.

Example 46

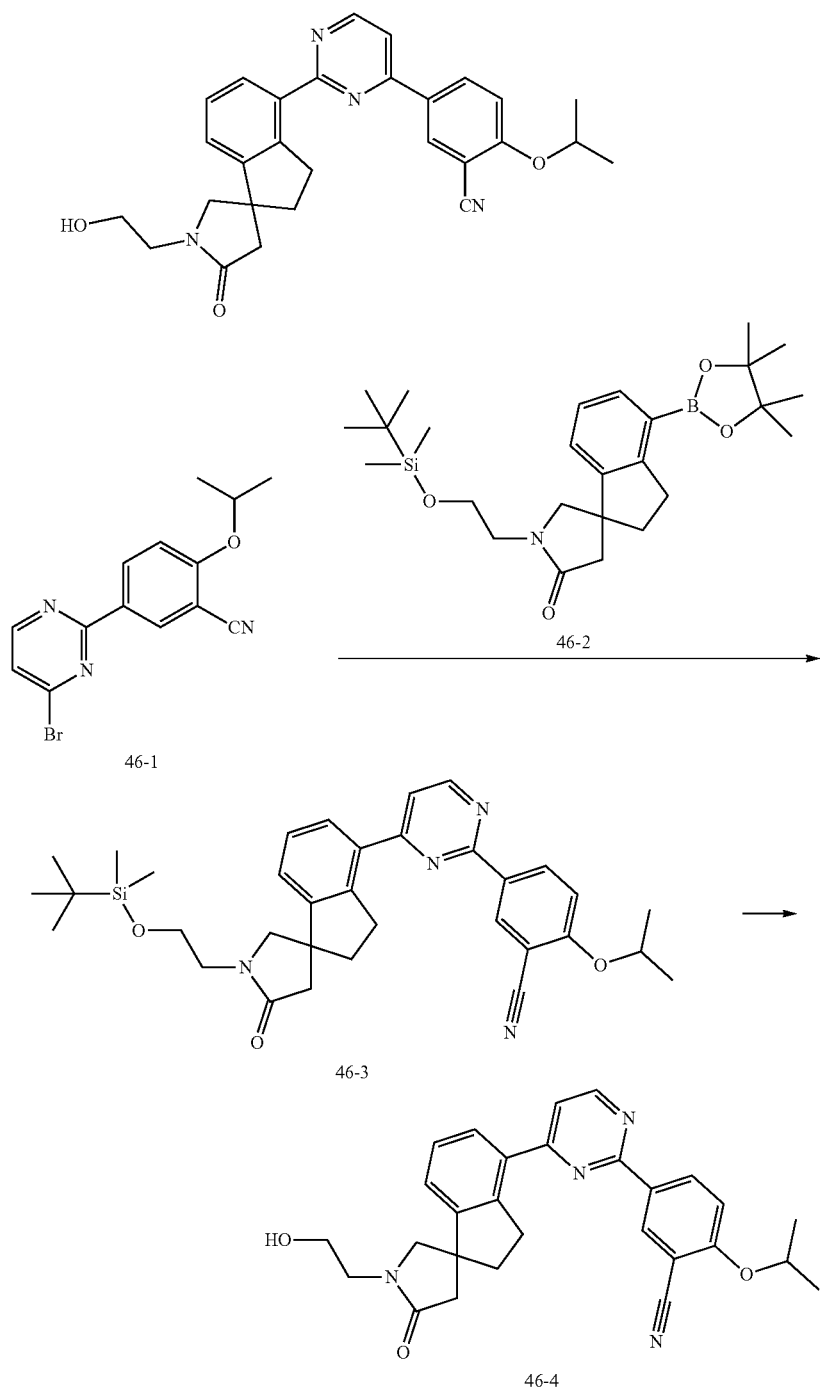

Step 1

Compound 46-2 (90.7 mg, 0.184 mmol) and compound 46-1 (60.0 mg, 0.184 mmol) were dissolved in dioxane (5 mL) and water (1 mL). 1,1'-bis(diphenylphosphino)ferrocene palladium dichloride (13.5 mg, 0.0184 mmol) and potassium phosphate (78.0 mg, 0.368 mmol) were added to the reaction solution in one portion. The reaction solution was stirred at 90° C. for 12 hours under nitrogen. The reaction solution was filtered, and the filter cake was washed with dichloromethane (20 mL×2), and the filtrate was concentrated under reduced pressure. The crude product was purified by preparative thin layer chromatography (petroleum ether:ethyl acetate=1:1, $R_f$=0.26) to afford compound 46-3.

MS-ESI calculated for [M+H]$^+$: 583, found: 583.

Step 2

Compound 46-3 (53.0 mg, 0.0863 mmol) was dissolved in ethyl acetate (2 mL). Hydrochloride/ethyl acetate (4 M, 5 mL) was added to the reaction solution. The reaction solution was stirred at 15° C. for 0.5 hours. The reaction solution was concentrated in vacuo and isolated by high performance liquid chromatography (formic acid system) to afford compound 46-4 (i.e., Example 46).

$^1$H NMR: (400 MHz, Methanol-$d_4$) δ 8.82 (d, J=5.2 Hz, 1H), 8.52-8.42 (m, 2H), 8.17 (d, J=7.6 Hz, 1H), 7.76 (d, J=5.2 Hz, 1H), 7.49-7.43 (m, 1H), 7.42-7.29 (m, 2H), 4.92-4.86 (m, 1H), 3.79-3.71 (m, 4H), 3.55-3.42 (m, 4H), 2.82-2.72 (m, 1H), 2.68-2.58 (m, 1H), 2.36-2.25 (m, 1H), 2.23-2.13 (m, 1H), 1.44 (d, J=6.0 Hz, 6H).

MS-ESI calculated for [M+H]$^+$: 469, found: 469.

Example 47

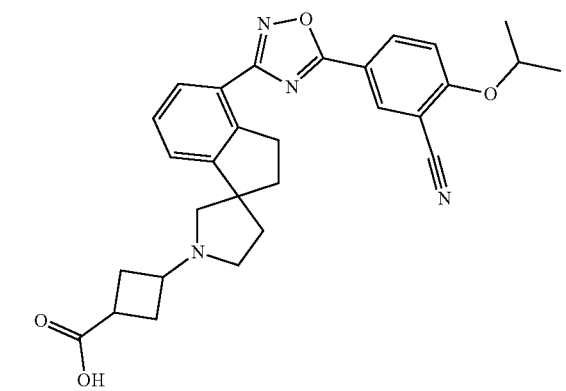

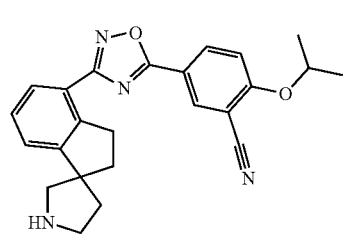
47-1

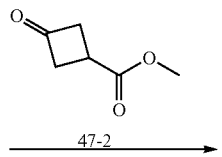
47-2

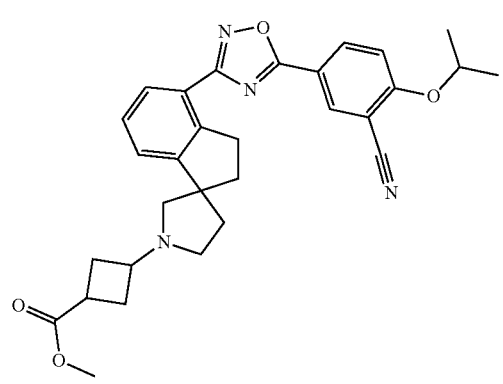
47-3

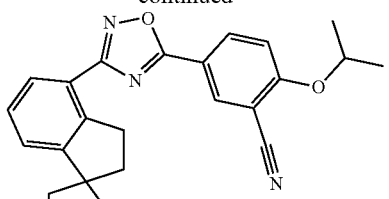
47-4

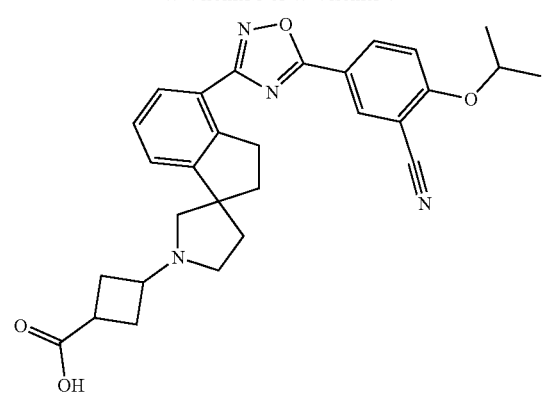
47-4 isomer 1 or 47-4 isomer 2 or 47-4 isomer 3 or 47-4 isomer 4

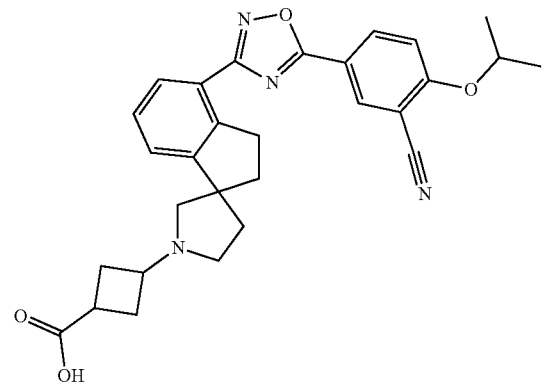
47-4 isomer 1 or 47-4 isomer 2 or 47-4 isomer 3 or 47-4 isomer 4

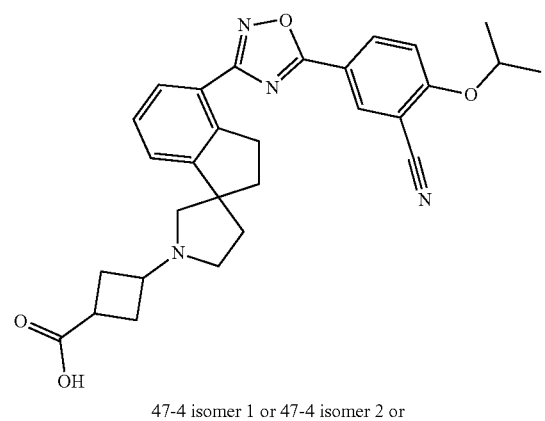
47-4 isomer 1 or 47-4 isomer 2 or 47-4 isomer 3 or 47-4 isomer 4

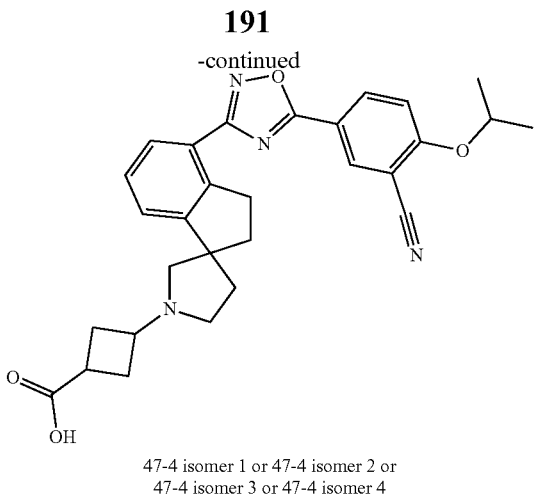

47-4 isomer 1 or 47-4 isomer 2 or
47-4 isomer 3 or 47-4 isomer 4

Step 1

Compound 47-1 (60.0 mg, 0.150 mmol) was dissolved in 1,2-dichloroethane (5 mL). Compound 47-2 (19.2 mg, 0.150 mmol) and titanium tetraisopropoxide (85.2 mg, 0.300 mmol) were added to the reaction solution, and the mixture was stirred at 50° C. for 1 hour under nitrogen. Sodium triacetoxyborohydride (63.5 mg, 0.300 mmol) was then added to the reaction solution, and the reaction solution was stirred at 80° C. for 12 hours. The reaction solution was cooled to room temperature, and water (20 mL) was added. The mixture was filtered and the filtrate was extracted with ethyl acetate (20 mL×3). The organic phases were combined, dried over anhydrous sodium sulfate and filtered. The filtrate was concentrated under reduced pressure. The residue was isolated by a preparative TLC plate (1:1 petroleum ether/ethyl acetate, $R_f$=0.6) to afford compound 47-3 (12.0 mg) in a yield of 12%.

MS-ESI calculated for [M+H]$^+$: 513, found: 513.

Step 2

Compound 47-3 (12.0 mg, 0.0234 mmol) was dissolved in tetrahydrofuran (2 mL) and water (0.5 mL). Lithium hydroxide (3.9 mg, 0.0936 mmol) was added. The mixture was stirred at 60° C. for 3 hours. The reaction solution was concentrated under reduced pressure, and the residue was purified by preparative high performance liquid chromatography (hydrochloric acid system) to afford compound 47-4 (i.e., Example 47).

1H NMR (400 MHz, Methanol-d$_4$) δ 8.36-8.32 (m, 2H), 8.02 (d, J=7.2 Hz, 1H), 7.51 (d, J=7.2 Hz, 1H), 7.42-7.34 (m, 2H), 4.86-4.85 (m, 1H), 3.93-3.84 (m, 1H), 3.54 (s, 1H), 3.40-3.28 (m, 3H), 3.22-3.20 (m, 3H), 2.99-2.90 (m, 1H), 2.65-2.57 (m, 2H), 2.47-2.37 (m, 2H), 2.26-2.18 (m, 3H), 1.37 (d, J=6.0 Hz, 6H).

MS-ESI calculated for [M+H]$^+$: 499, found: 499.

Step 3

The compound 47-4 was subjected to chiral resolution to afford the compound 47-4 isomer 1, the compound 47-4 isomer 2, the compound 47-4 isomer 3 and the compound 47-4 isomer 4.

SFC isolation method:

Chromatography column: DAICEL CHIRALPAK AD (250 mm*30 mm, 10 um)

Mobile phase: A: carbon dioxide; B: methanol (containing 0.1% NH3.H2O);

Flow rate: 70 mL/min;

Column temperature: 38° C.

Compound 47-4 isomer 1, retention time: 3.674 minutes.
$^1$H NMR: (400 MHz, DMSO-d$_6$) δ 8.52 (d, J=2.0 Hz, 1H), 8.41 (dd, J=2.0, 9.2 Hz, 1H), 8.02 (t, J=7.2 Hz, 1H), 7.69-7.89 (m, 1H), 7.57 (d, J=9.2 Hz, 1H), 7.51 (t, J=7.2 Hz, 1H), 4.95-5.02 (m, 1H), 4.11-4.17 (m, 1H), 3.67-3.87 (m, 2H), 3.02-3.32 (m, 6H), 2.63-2.79 (m, 2H), 2.20-2.43 (m, 3H), 1.96-2.18 (m, 2H), 1.39 (d, J=6.0 Hz, 6H).

MS-ESI calculated for [M+H]$^+$: 499, found: 499.

Compound 47-4 isomer 2, retention time: 5.124 minutes.
$^1$H NMR: (400 MHz, DMSO-d$_6$) δ 8.51 (d, J=2.0 Hz, 1H), 8.40 (dd, J=2.4, 9.2 Hz, 1H), 8.01 (t, J=5.2 Hz, 1H), 7.69-7.89 (m, 1H), 7.56 (d, J=9.2 Hz, 1H), 7.50 (t, J=7.6 Hz, 1H), 4.95-5.01 (m, 1H), 3.87-4.2 (m, 1H), 3.69-3.85 (m, 2H), 2.98-3.32 (m, 6H), 2.55-2.82 (m, 2H), 2.29-2.48 (m, 3H), 1.96-2.27 (m, 2H), 1.39 (d, J=6.0 Hz, 6H).

MS-ESI calculated for [M+H]$^+$: 499, found: 499.

Compound 47-4 isomer 3, retention time: 5.238 minutes.
$^1$H NMR: (400 MHz, DMSO-d$_6$) δ 8.51 (s, 1H), 8.40 (d, J=9.2 Hz, 1H), 8.02 (t, J=7.2 Hz, 1H), 7.69-7.88 (m, 1H), 7.57 (d, J=9.2 Hz, 1H), 7.45-7.54 (m, 1H), 4.95-5.01 (m, 1H), 3.81-3.99 (m, 1H), 3.69-3.76 (m, 2H), 2.91-3.32 (m, 6H), 2.55-2.68 (m, 2H), 2.21-2.48 (m, 3H), 1.96-2.19 (m, 2H), 1.39 (d, J=6.0 Hz, 6H).

MS-ESI calculated for [M+H]$^+$: 499, found: 499.

Compound 47-4 isomer 4, retention time: 7.157 minutes.
$^1$H NMR: (400 MHz, Methanol-d$_4$) δ 8.35-8.30 (m, 2H), 8.0 (d, J=7.2 Hz, 1H), 7.51 (d, J=7.2 Hz, 1H), 7.38 (t, J=7.2 Hz, 1H), 7.34 (d, J=9.2 Hz, 1H), 4.93-4.80 (m, 1H), 3.78-3.72 (m, 1H), 3.54-3.42 (m, 3H), 3.39-3.25 (m, 3H), 2.88-2.81 (m, 1H), 2.67-2.50 (m, 2H), 2.40-2.30 (m, 2H), 2.30-2.12 (m, 4H), 1.36 (d, J=6.0 Hz, 6H).

MS-ESI calculated for [M+H]$^+$: 499, found: 499.

Example 48

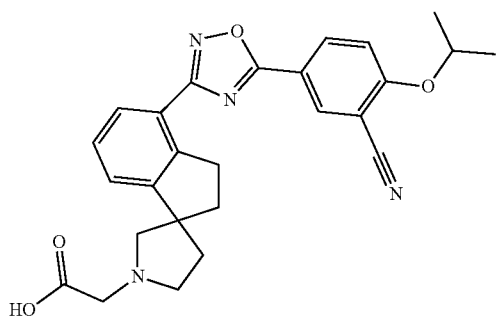

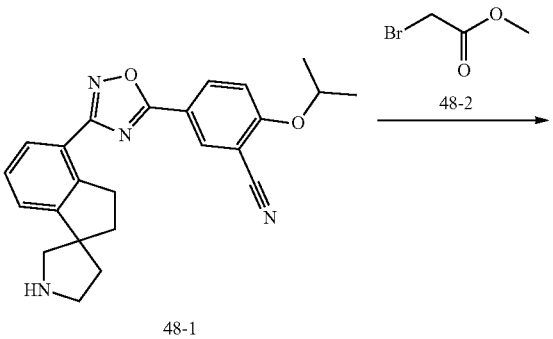

48-1

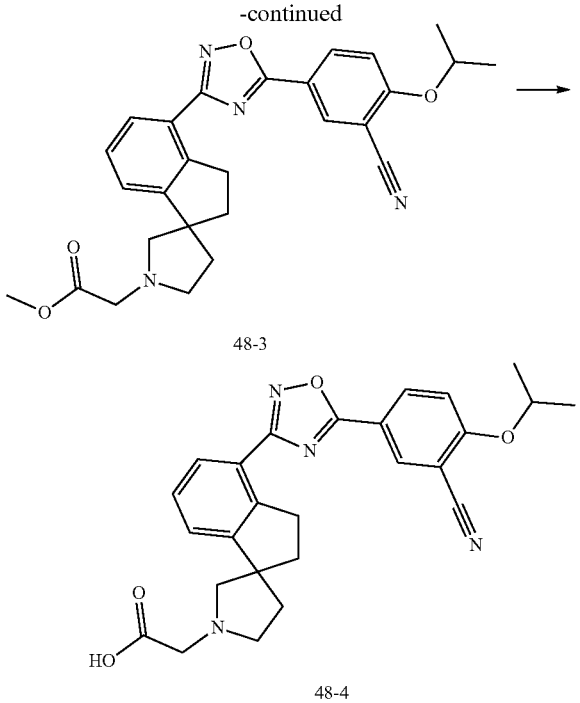

48-3

48-4

Step 1

Compound 48-1 (100 mg, 0.250 mmol) was dissolved in acetonitrile (6 mL). Compound 48-2 (38.2 mg, 0.250 mmol), potassium carbonate (104 mg, 0.749 mmol) and sodium iodide (112 mg, 0.749 mmol) were added to the reaction solution. The reaction solution was stirred at 90° C. for 2 hours under nitrogen. The reaction solution was cooled to room temperature, and water (10 mL) was added. The mixture was filtered and the filtrate was extracted with ethyl acetate (20 mL×3). The organic phases were combined, dried over anhydrous sodium sulfate and filtered. The filtrate was concentrated under reduced pressure. The residue was isolated by a preparative TLC plate (1:1 petroleum ether/ethyl acetate, $R_f$ 0.6) to afford compound 48-3.

$^1$H NMR (400 MHz, CDCl$_3$) δ 8.44 (d, J=2.0 Hz, 1H), 8.35 (dd, J=2.0, 8.8 Hz, 1H), 8.02 (d, J=8.8 Hz, 1H), 7.52 (d, J=7.6 Hz, 1H), 7.38 (t, J=7.6 Hz, 1H), 7.13 (d, J=7.6 Hz, 1H), 4.83-4.77 (m, 1H), 3.75 (s, 3H), 3.46 (s, 2H), 3.33-3.31 (m, 2H), 3.03-2.95 (m, 2H), 2.93-2.86 (m, 2H), 2.37-2.26 (m, 1H), 2.23-2.02 (m, 3H), 1.49 (d, J=6.0 Hz, 6H).

MS-ESI calculated for [M+H]$^+$: 473, found: 473.

Step 2

Compound 48-3 (40.0 mg, 0.0847 mmol) was dissolved in tetrahydrofuran (2 mL) and water (0.5 mL). Lithium hydroxide (14.2 mg, 0.339 mmol) was added. The mixture was stirred at 25° C. for 12 hours. The reaction solution was concentrated under reduced pressure, and the residue was purified by preparative high performance liquid chromatography (hydrochloric acid system) to afford compound 48-4 (i.e., Example 48).

$^1$H NMR (400 MHz, Methanol-d$_4$) δ 8.47-8.39 (m, 2H), 8.12 (d, J=7.2 Hz, 1H), 7.62 (d, J=7.2 Hz, 1H), 7.54-7.42 (m, 2H), 5.02-4.95 (m, 1H), 4.33 (s, 2H), 3.82-3.75 (m, 3H), 3.45-3.40 (m, 2H), 3.32-3.31 (m, 1H), 2.40-2.33 (m, 4H), 1.47 (d, J=6.0 Hz, 6H)

MS-ESI calculated for [M+H]$^+$: 459, found: 459.

Assay Example 1

Assay method:

I. Cell processing

1. A PathHunter cell strain was thawed according to standard procedures;

2. The cell was seeded in 20 μl 384-well microplates and incubated at 37° C. for an appropriate time.

II. Agonist

1. For an agonist assay, the cell was incubated with the sample to be tested to initiate a reaction;

2. The stock to be tested is diluted 5 folds to be a buffer solution;

3. The 5-fold diluted solution (5 μL) was added to the cells and incubated at 37° C. for 90-180 minutes. The solvent concentration was 1%.

III. Signal detection 1. 12.5 μL or 15 μL of PathHunter detection reagent (50 vol. %) was added in one portion and then incubated for 1 hour at room temperature to generate a detection signal;

2. The microplate was read using a PerkinElmer Envision™ instrument for chemiluminescent signal detection.

IV. Data analysis

1. Compound activity analysis was performed using a CBIS Data Analysis Kit;

2. Calculation formula:

% activity=100%×(average RLU of sample to be test-average RLU of solvents)/(average maximum control ligand-average RLU of solvents)

Assay Results:

TABLE 1 assay results of S1P1 receptor agonistic activity

| Assay sample (compounds prepared in each example) | S1P1 receptor agonistic activity |
|---|---|
| Example 1 | + |
| Example 2 | + |
| Example 3 | + |
| Example 4 | + |
| Example 5 | + |
| Example 6 | + |
| Example 7 | + |
| Example 8 | + |
| Example 9 | +++ |
| Example 10 | +++ |
| Example 11 | +++ |
| Example 12 | + |
| Example 13 | + |
| Example 14 | + |
| Example 15 | + |
| Example 16 | + |
| Example 17 | + |
| Example 18 | + |
| Example 19 | + |
| Example 20 | ++ |
| Example 21 mixture/isomer 1/isomer 2 | +++/+++/+++ |
| Example 22 | +++ |
| Example 23 | ++ |
| Example 24 | +++ |
| Example 25 | +++ |
| Example 26 | +++ |
| Example 27 | ++ |
| Example 28 | +++ |
| Example 29 | +++ |
| Example 30 | ++ |
| Example 31 | ++ |
| Example 32 | ++ |

TABLE 1-continued assay results of S1P1 receptor agonistic activity

| Assay sample (compounds prepared in each example) | S1P1 receptor agonistic activity |
|---|---|
| Example 33 | +++ |
| Example 34 | +++ |
| Example 35 | +++ |
| Example 36 | +++ |
| Example 37 | ++ |
| Example 38 | +++ |
| Example 39 | ++ |
| Example 40 | +++ |
| Example 41 | +++ |
| Example 42 | ++ |
| Example 43 | ++ |
| Example 44 | +++ |
| Example 45 | +++ |
| Example 46 | + |
| Example 47 | +++ |
| Example 48 | +++ |

Note:
"+" >100 nM;
100 nM ≥ "++" > 10 nM;
"+++" ≤10 nM

Conclusion: The compounds disclosed herein have significant and even unexpected S1P1 receptor agonistic activity.

Assay Example 2

Evaluation of Compounds' Pharmacokinetics

Objective: To test the pharmacokinetics of compounds in SD rats in vivo.

Assay Materials:
Sprague Dawley rats (male, 200-300 g, 7-9 weeks old, Shanghai Slack)

Assay Procedures:
The pharmacokinetics profile of the compound in rodent after intravenous injection and oral administrations was tested using a standard protocol. In the assay, the candidate compound was formulated into a clear solution, and was given to the rats through a single intravenous injection and oral administration. The vehicles for the intravenous injection and oral administration were an aqueous hydroxypropyl β-cyclodextrin solution or dimethyl sulfoxide in aqueous PEG400 solution in a proper proportion. The whole blood samples were collected within 24 hours, centrifuged at 3000 g for 15 minutes, and plasma samples were obtained by separating the supernatant. 4 times volume of acetonitrile solution containing an internal standard was added to precipitate proteins. After centrifugation, the supernatant was collected, to which an equal volume of water was added, and further centrifuged to collect the supernatant. The LC-MS/MS method was used to quantitatively analyze the plasma concentration, and the pharmacokinetics parameters, such as peak concentration, peak time, clearance rate, half-life, area under the curve, and bioavailability were calculated.

Assay results:

TABLE 2

Pharmacokinetic assay results

| Assay sample | Clearance (mL/min/kg) | Half life $T_{1/2}$ (h) | Concentration integral AUC (nM · hr) | Bioavailability F (%) |
|---|---|---|---|---|
| Ozanimod (3 mpk) | 46.3 | 5.24 | 1123 | 41.6 |
| Example 9 (2 mpk) | 2.52 | 99.3 | 4352 | 89.4 |
| Example 21 Isomer 1 (3 mpk) | 8.65 | 3.02 | 12636 | 100 |
| Example 21 Isomer 2 (3 mpk) | 11.6 | 3.22 | 8483 | 89.6 |
| Example 47 Isomer 3 (3 mpk) | 8.81 | 3.98 | 5656 | 48.7 |
| Example 47 Isomer 4 (3 mpk) | 11.6 | 3.22 | 8483 | 89.6 |

Conclusion: The compounds disclosed herein can significantly increase the single or multiple index of rat pharmacokinetics.

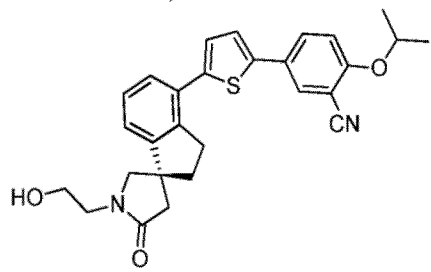

The invention claimed is:

1. A compound represented by formula (I), an optical isomer thereof or a pharmaceutically acceptable salt thereof,

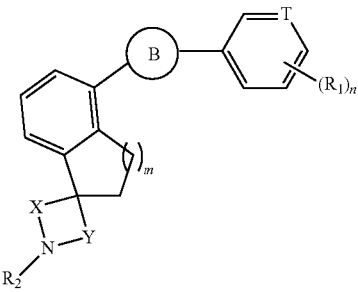

wherein each $R_1$ is independently selected from the group consisting of H, F, Cl, Br, I, OH, $NH_2$, and CN, or is independently selected from the group consisting of $C_{1-6}$ alkyl and $C_{1-6}$ heteroalkyl, each of which is optionally substituted by 1, 2 or 3 R;

$R_2$ is H, or is selected from the group consisting of $C_{1-6}$ alkyl, $C_{1-6}$ heteroalkyl and $C_{3-6}$ cycloalkyl, each of which is optionally substituted by 1, 2 or 3 R;

T is selected from the group consisting of N and CH;

moiety

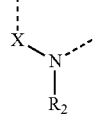

is selected from the group consisting of

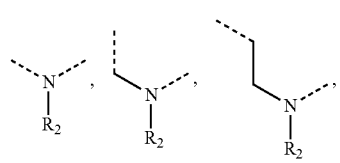

-continued

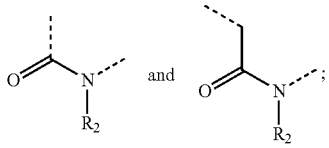

moiety

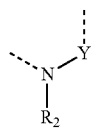

is selected from the group consisting of

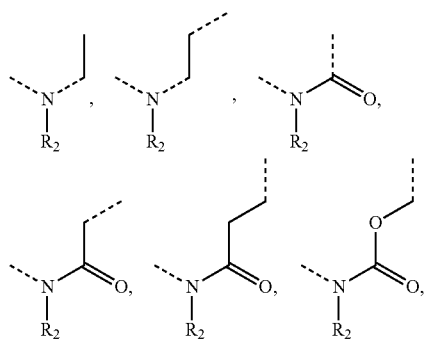

and

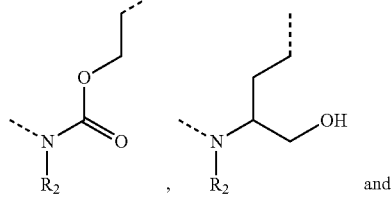

ring B is selected from the group consisting of phenyl and 5- to 6-membered heteroaryl;
m is 1 or 2;
n is 0, 1, 2 or 3;
R is selected from the group consisting of F, Cl, Br, I, OH, $NH_2$, CN, and COOH, or is selected from the group consisting of $C_{1-6}$ alkyl, $C_{1-6}$ alkoxy, N,N-di($C_{1-6}$ alkyl) amino, and $C_{3-6}$ cycloalkyl;
the heteroatom or the heteroatom group of the $C_{1-6}$ heteroalkyl and the 5- to 6-membered heteroaryl is each independently selected from the group consisting of N, O, S, NH, —NHC(=O)—, —S(=O)— and —S(=O)$_2$—; and
the number of the heteroatom or the heteroatom group is 1, 2, 3 or 4.

2. The compound, the optical isomer thereof or the pharmaceutically acceptable salt thereof according to claim 1, wherein R is selected from the group consisting of F, Cl, Br, I, OH, $NH_2$, CN, COOH, Me, Et, $N(CH_3)_2$,

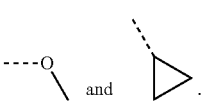

3. The compound, the optical isomer thereof or the pharmaceutically acceptable salt thereof according to claim 1, wherein each $R_1$ is independently selected from the group consisting of H, F, Cl, Br, I, OH, $NH_2$, and CN, or is independently selected from the group consisting of $C_{1-3}$ alkyl, $C_{1-3}$ alkoxy, $C_{1-3}$ alkylamino, and $C_{1-3}$ alkyl-S(=O)$_2$—, each of which is optionally substituted by 1, 2 or 3 R.

4. The compound, the optical isomer thereof or the pharmaceutically acceptable salt thereof according to claim 3, wherein each $R_1$ is independently selected from the group consisting of H, F, Cl, Br, I, OH, $NH_2$, and CN, or is independently selected from the group consisting of Me, Et,

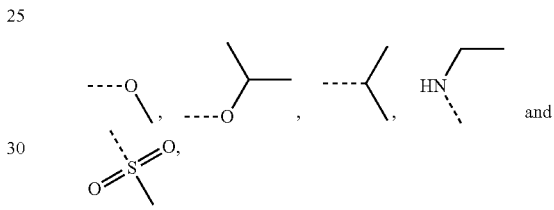

each of which is optionally substituted by 1, 2 or 3 R.

5. The compound, the optical isomer thereof or the pharmaceutically acceptable salt thereof according to claim 4, wherein each $R_1$ is independently selected from the group consisting of H, F, Cl, Br, I, OH, $NH_2$, CN, Me, Et,

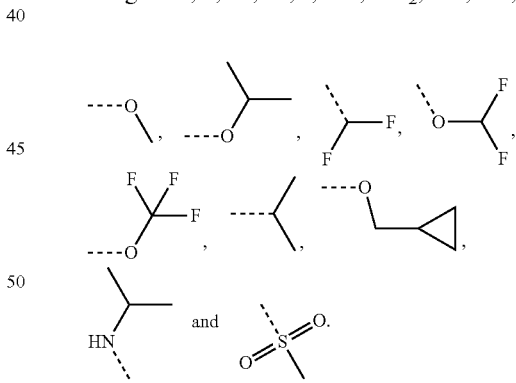

6. The compound, the optical isomer thereof or the pharmaceutically acceptable salt thereof according to claim 1, wherein $R_2$ is selected from the group consisting of $C_{1-4}$ alkyl, $C_{1-3}$ alkyl-O—$C_{1-3}$ alkyl-, $C_{1-3}$ alkyl-S(=O)$_2$—$C_{1-3}$ alkyl-, $C_{1-3}$ alkyl-NH—$C_{1-3}$ alkyl-, $C_{1-3}$ alkyl-NHC(=O)—$C_{1-3}$ alkyl- and $C_{3-6}$ cycloalkyl, each of which is optionally substituted by 1, 2 or 3 R.

7. The compound, the optical isomer thereof or the pharmaceutically acceptable salt thereof according to claim 6, wherein $R_2$ is selected from the group consisting of Me, Et,

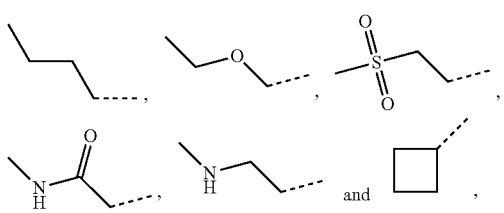

each of which is optionally substituted by 1, 2 or 3 R.

8. The compound, the optical isomer thereof or the pharmaceutically acceptable salt thereof according to claim 7, wherein $R_2$ is selected from the group consisting of

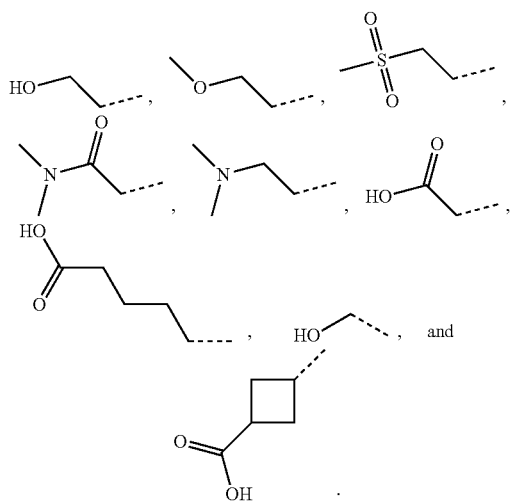

9. The compound, the optical isomer thereof or the pharmaceutically acceptable salt thereof according to claim 1, wherein the moiety ring

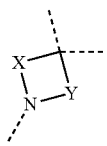

is selected from the group consisting of

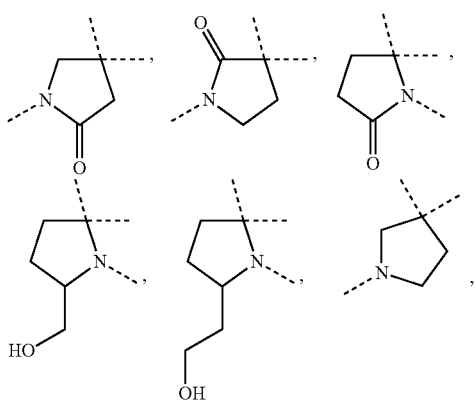

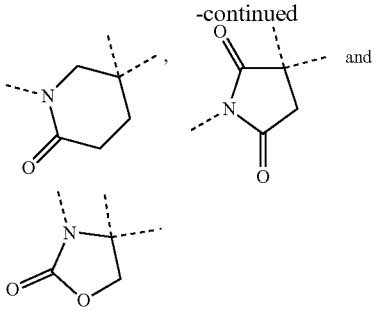

10. The compound, the optical isomer thereof or the pharmaceutically acceptable salt thereof according to claim 1, wherein ring B is selected from the group consisting of 1,2,4-oxadiazolyl, 1,2,4-thiadiazolyl, pyrazinyl, thiazolyl, oxazolyl and pyrimidinyl.

11. The compound, the optical isomer thereof or the pharmaceutically acceptable salt thereof according to claim 1, wherein ring B is selected from the group consisting of

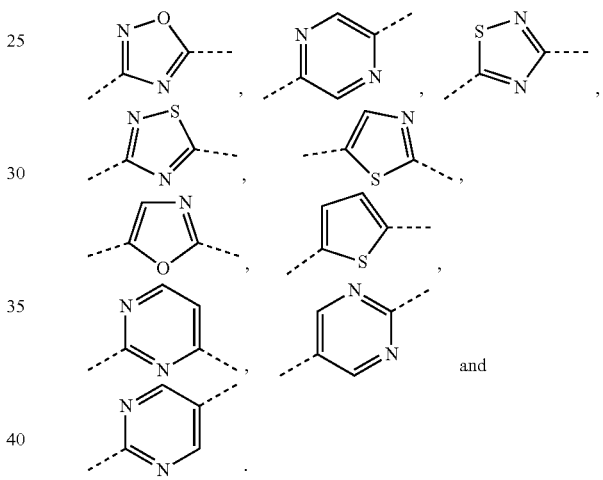

12. The compound, the optical isomer thereof, or the pharmaceutically acceptable salt thereof according to claim 1, wherein the moiety

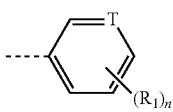

is selected from the group consisting of

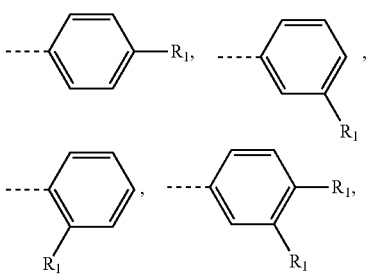

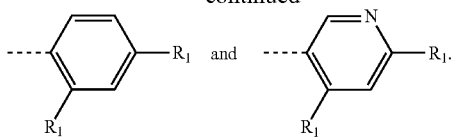
13. The compound, the optical isomer thereof or the pharmaceutically acceptable salt thereof according to claim 12, wherein the moiety
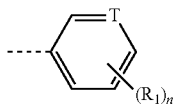
is selected from the group consisting of
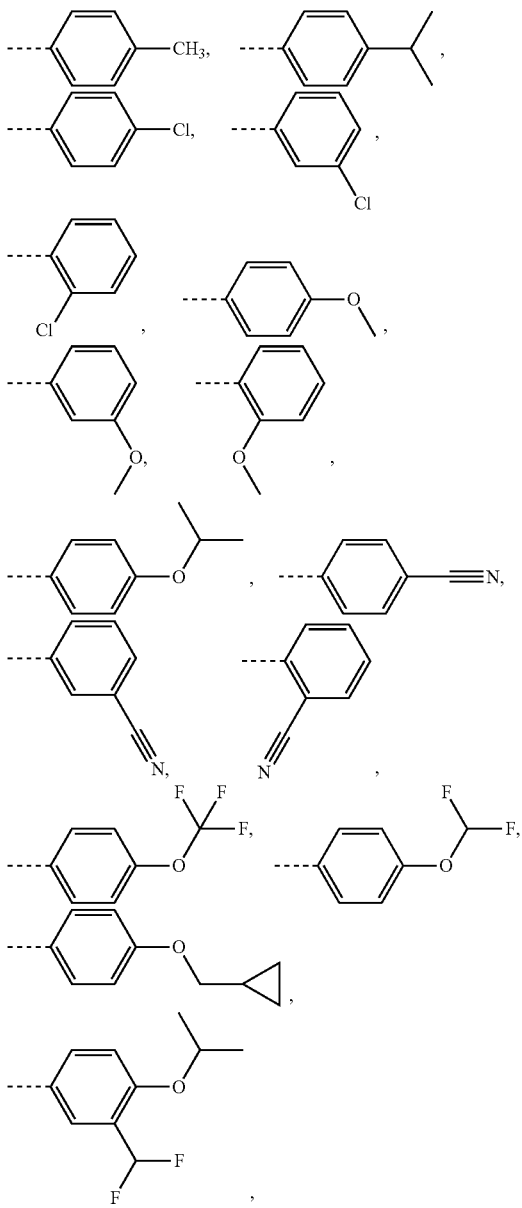
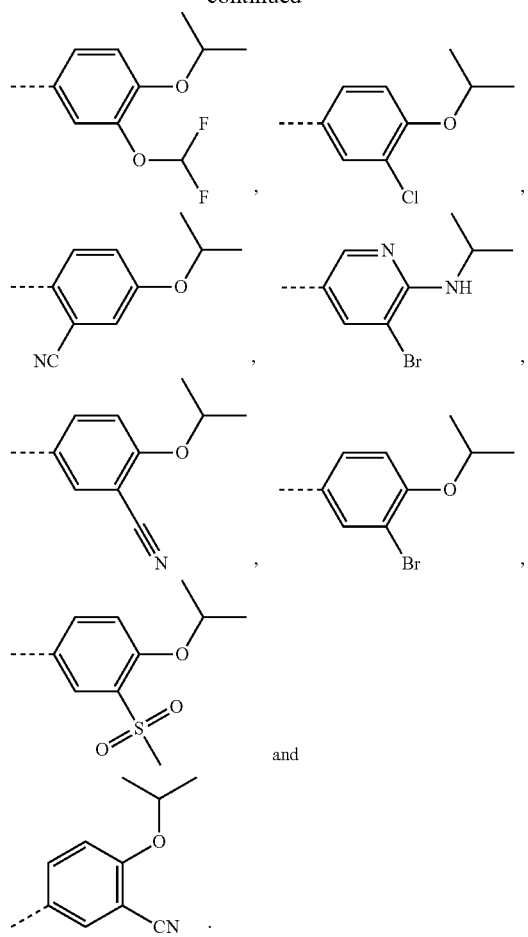
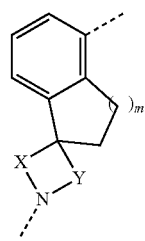
and
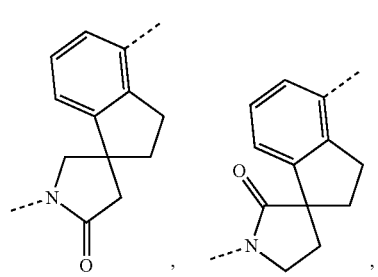
14. The compound, the optical isomer thereof or the pharmaceutically acceptable salt thereof according to claim 1, wherein the moiety
is selected from the group consisting of 203
-continued
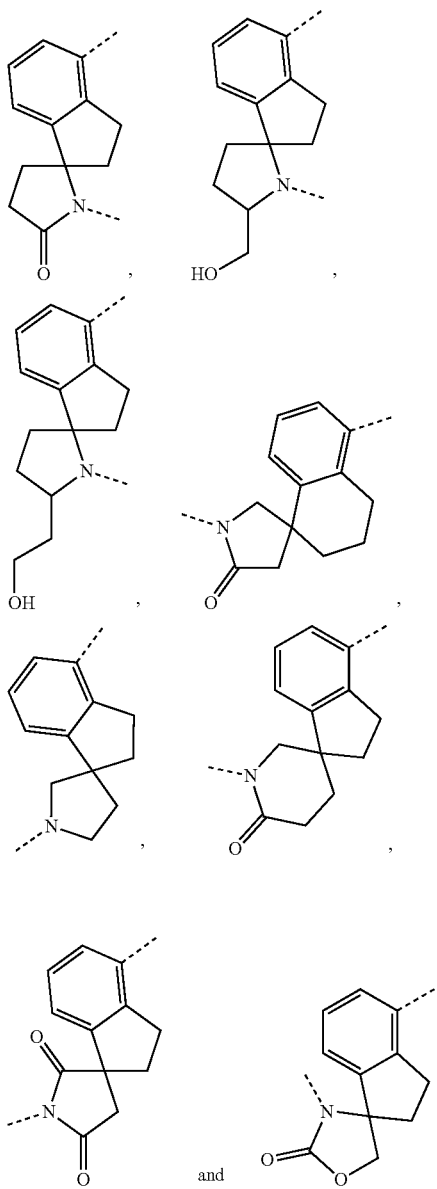
204
-continued
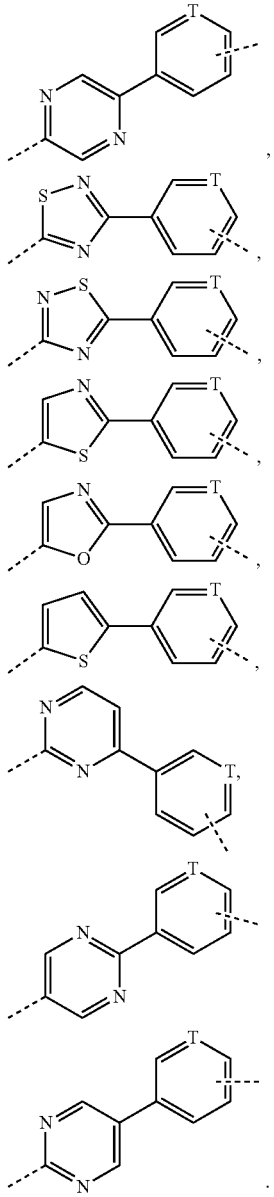
15. The compound, the optical isomer thereof or the pharmaceutically acceptable salt thereof according to claim 1, wherein the moiety
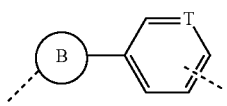
is selected from the group consisting of
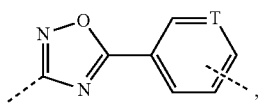
16. The compound, the optical isomer thereof or the pharmaceutically acceptable salt thereof according to claim 1, which is selected from the group consisting of
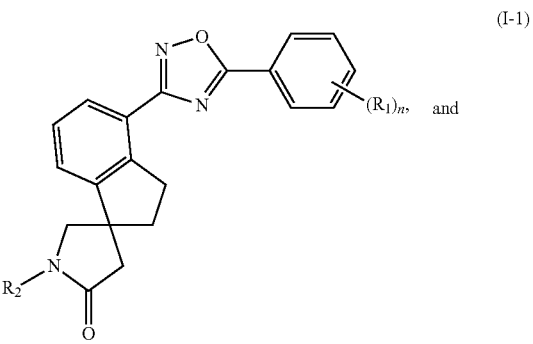

(1-2)
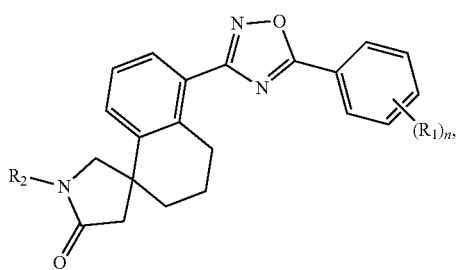
wherein n, $R_1$ and $R_2$ are as defined in claim 1.
17. The compound, the optical isomer thereof or the pharmaceutically acceptable salt thereof according to claim 16, which is selected from the group consisting of
(II-1)
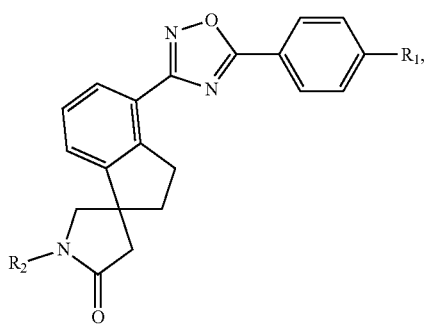
(II-2)
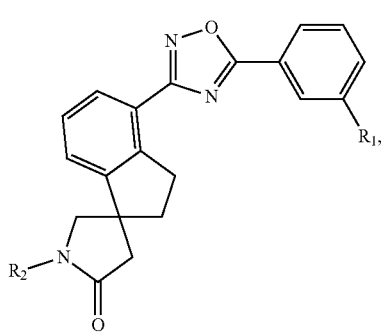
(II-3)
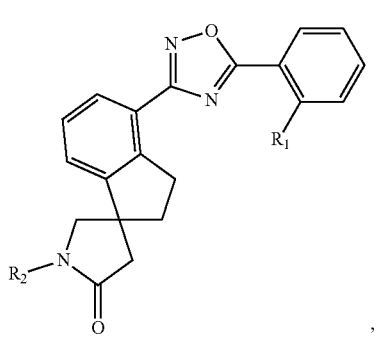
(II-4)
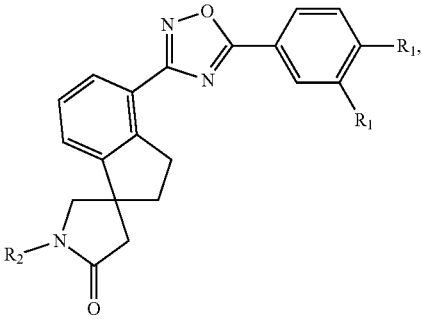
(II-5)
(II-6)
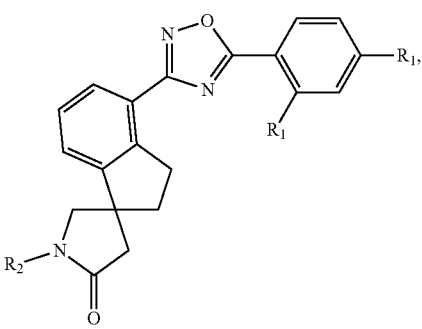
(II-7)
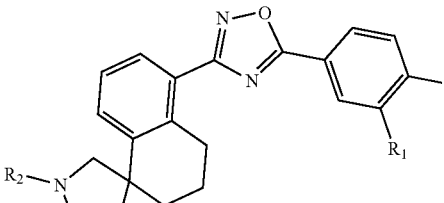
(II-8)
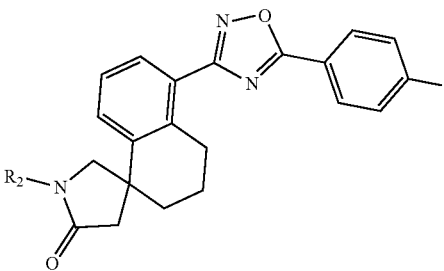

-continued
(II-9)
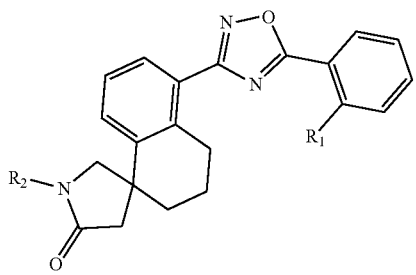
, and
(II-10)
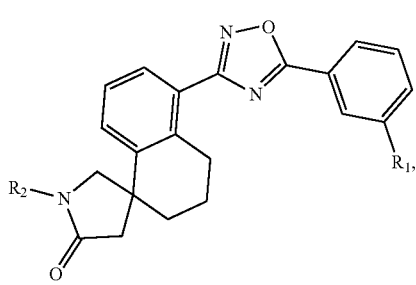
wherein R₁ and R₂ are as defined in claim 16.
18. A compound represented by the following formula, an optical isomer thereof or a pharmaceutically acceptable salt thereof, which is selected from the group consisting of
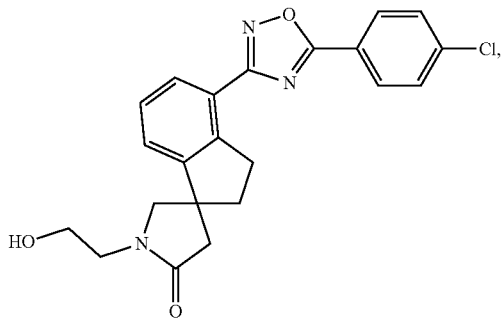
-continued
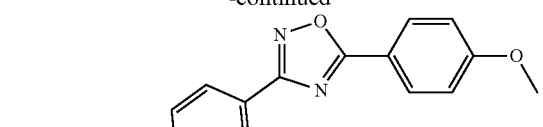
,
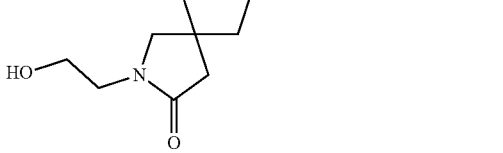
,
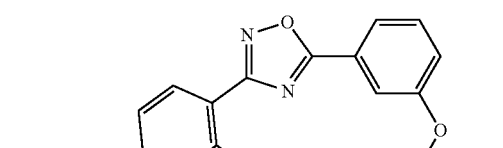
,
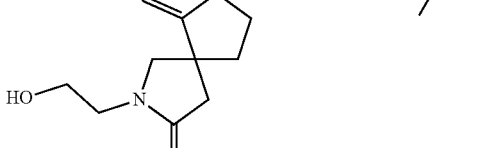
,
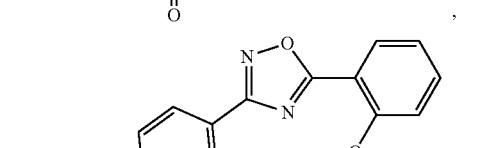
,
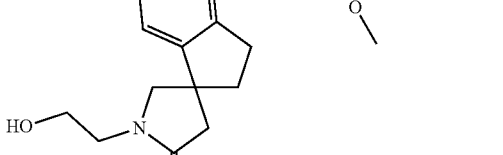
,
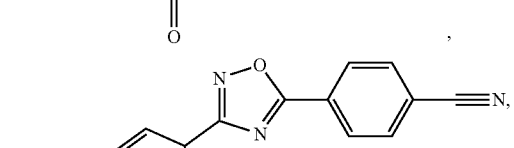
,
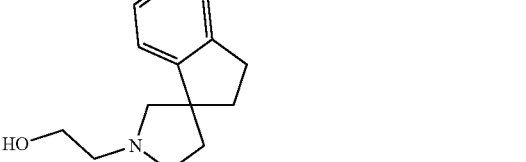
,
,
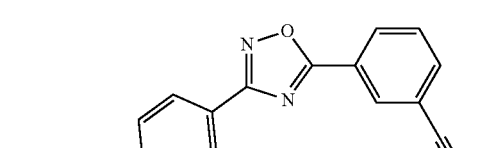
,
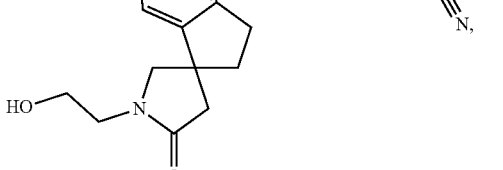
,

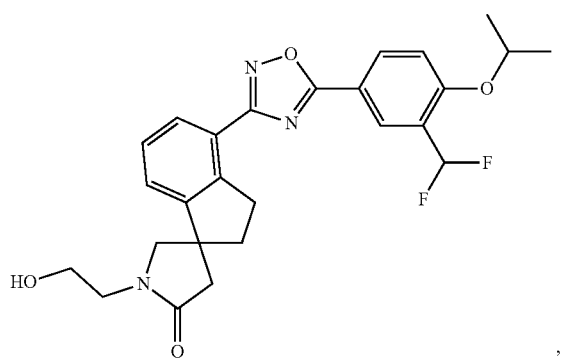
,
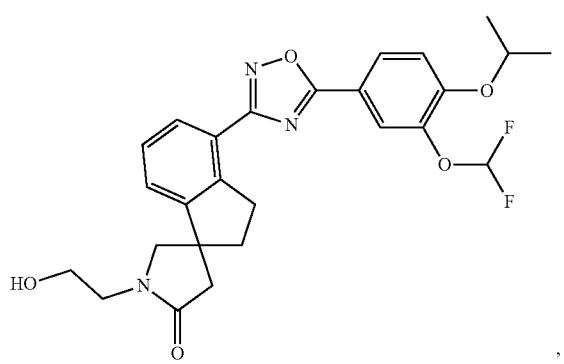
,
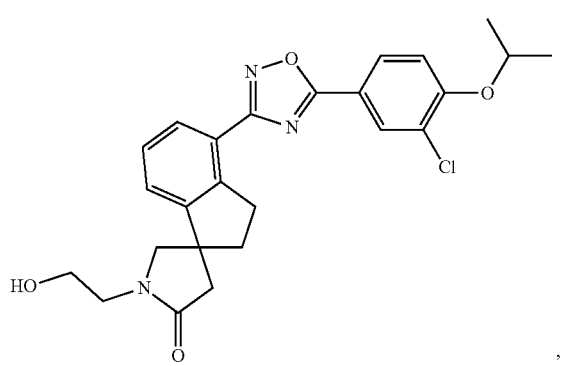
,
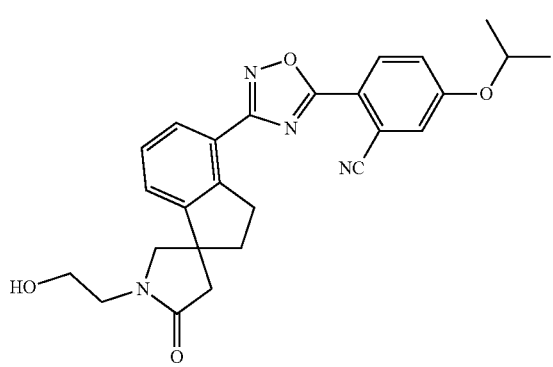
,
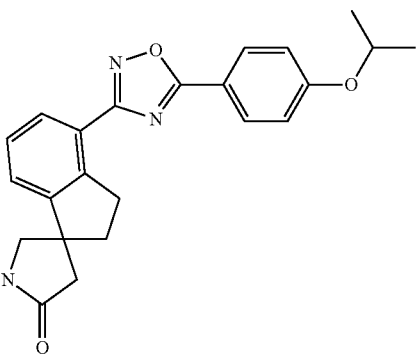
,
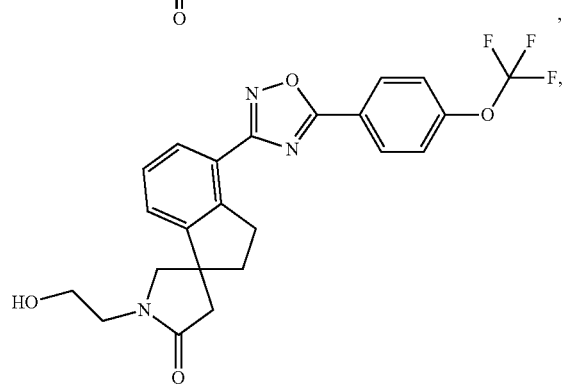
,
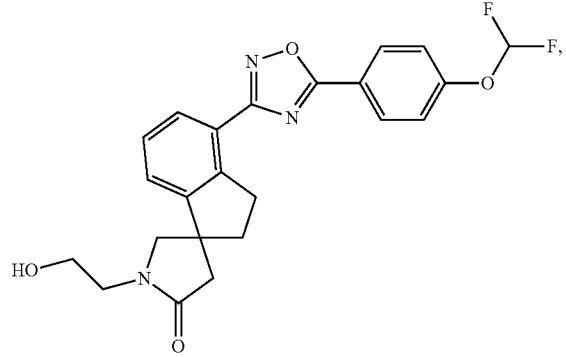
,
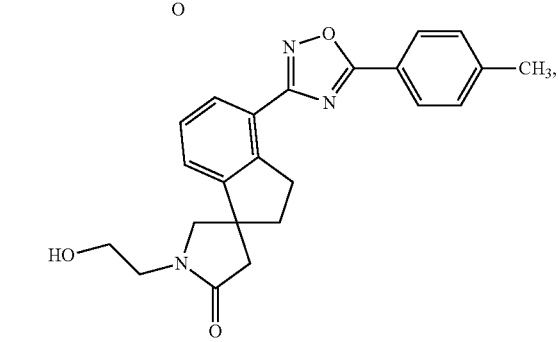
,
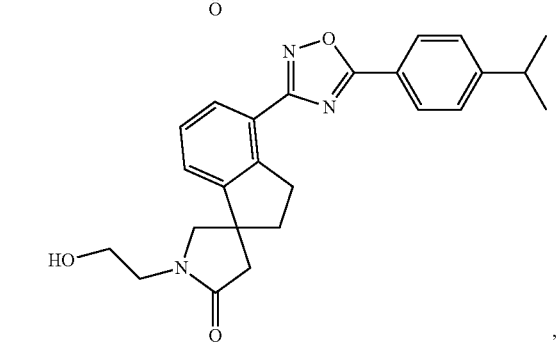
, 211
-continued
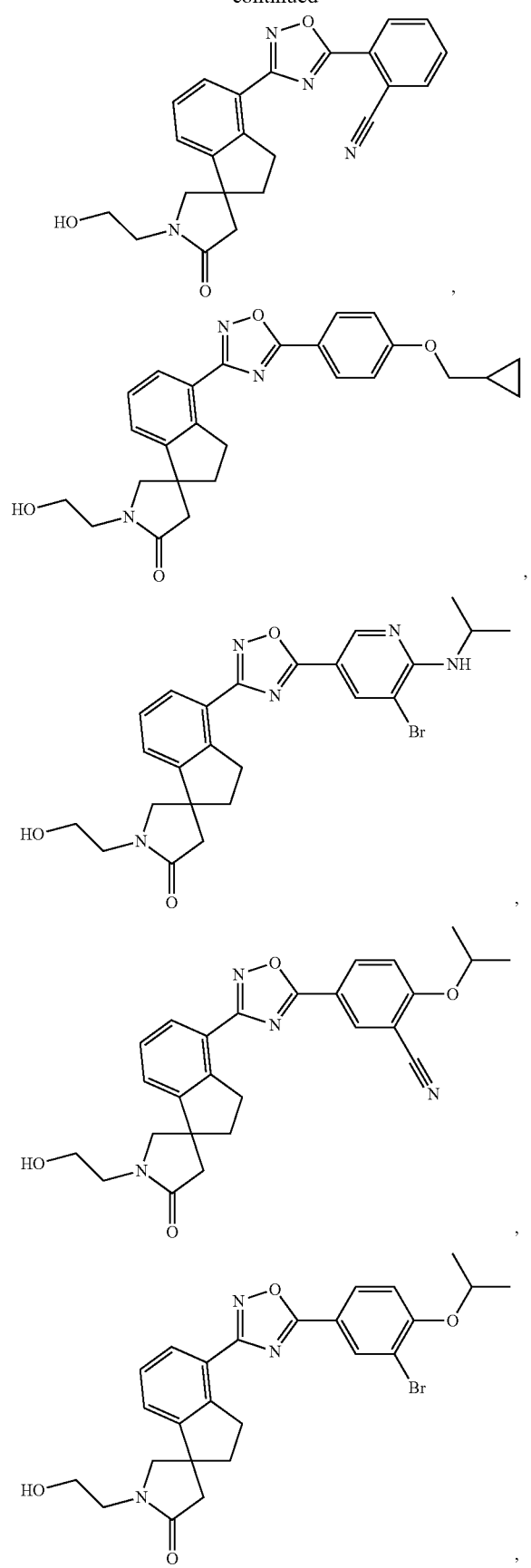
212
-continued
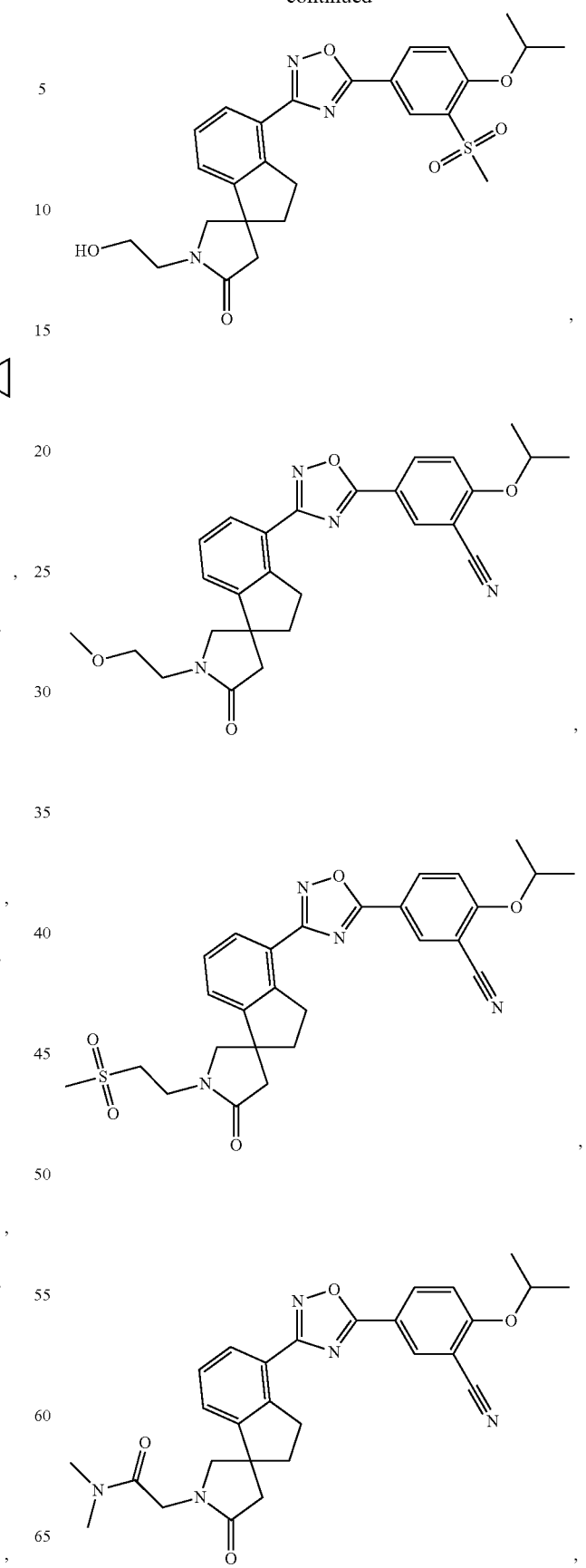

213
-continued
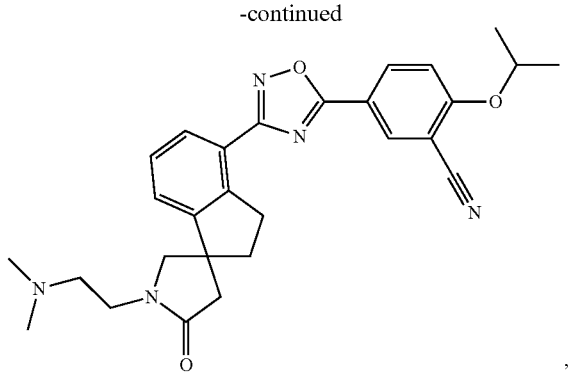
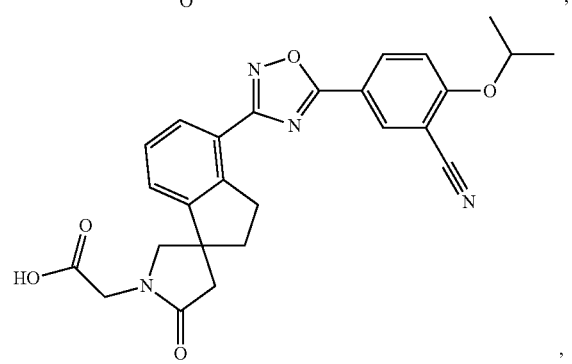
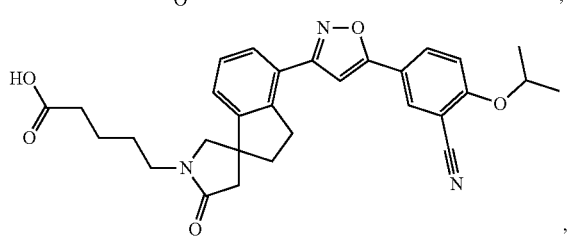
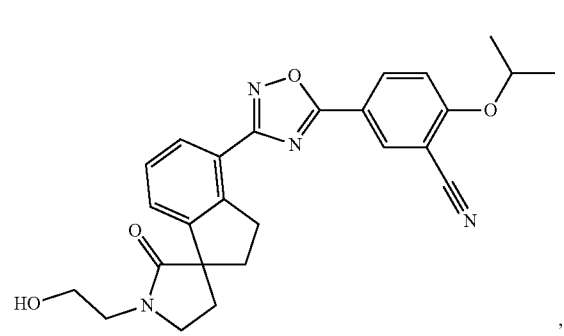
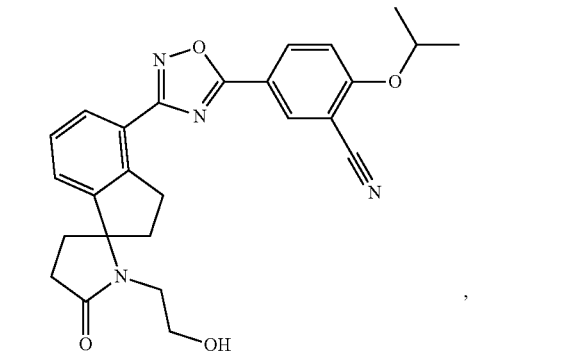
214
-continued
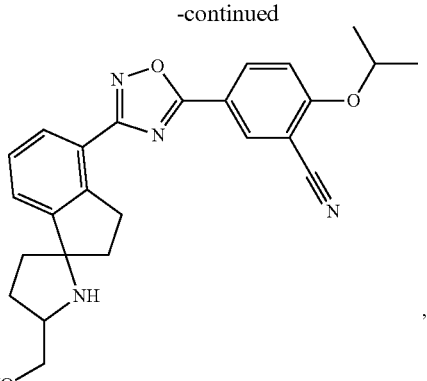
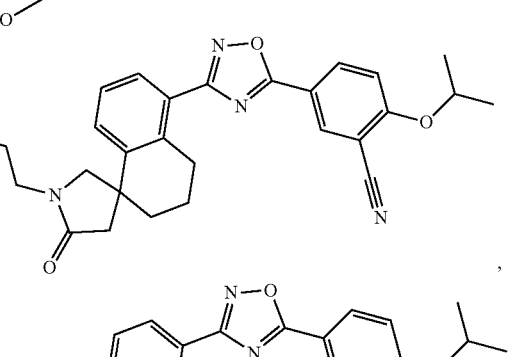
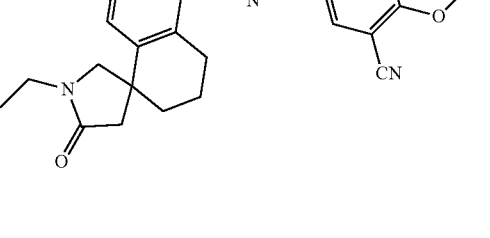
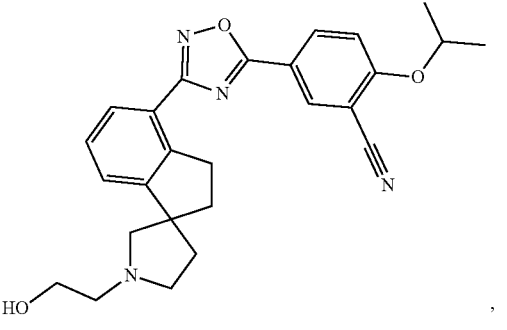
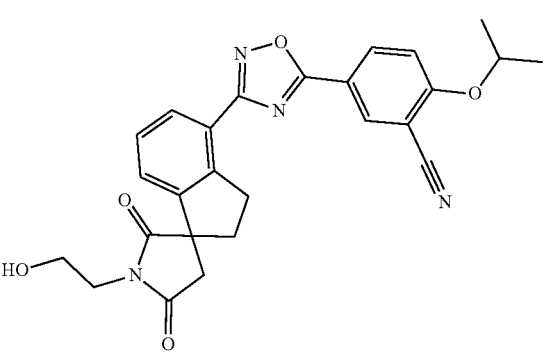

215
-continued
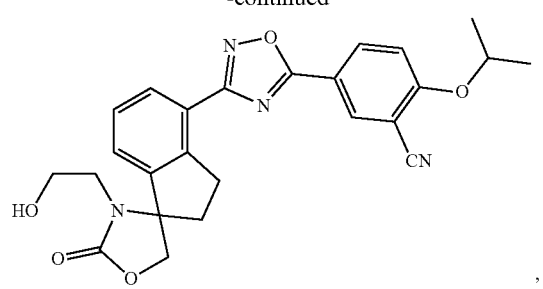
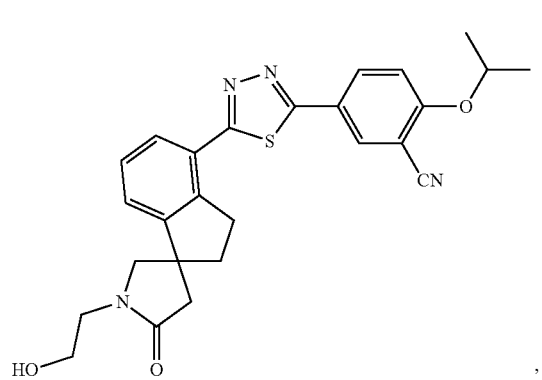
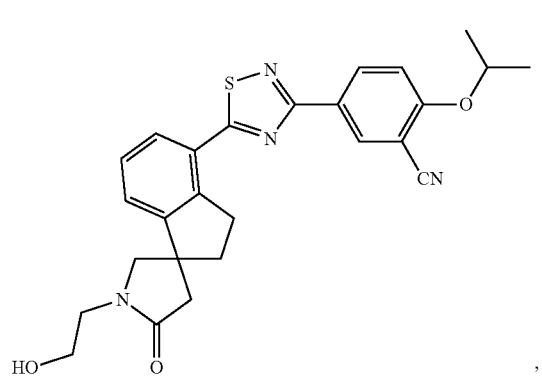
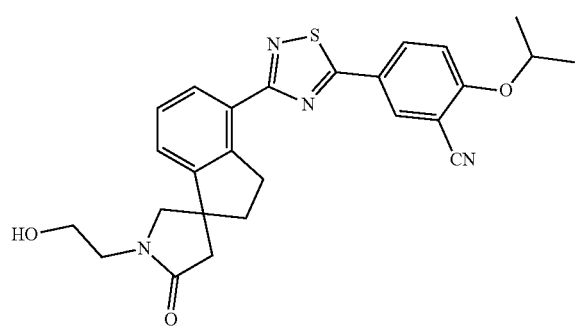
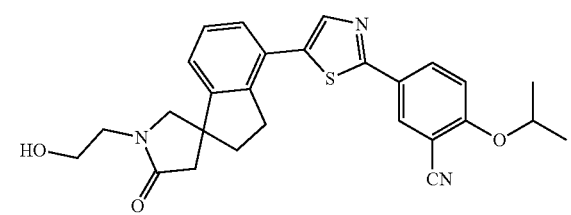
216
-continued
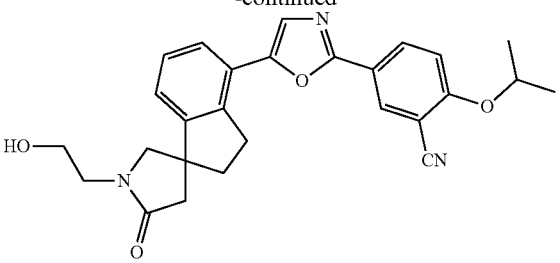
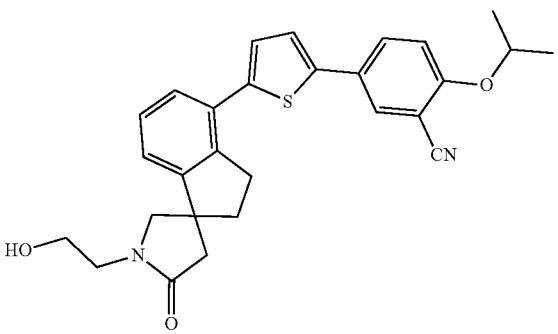
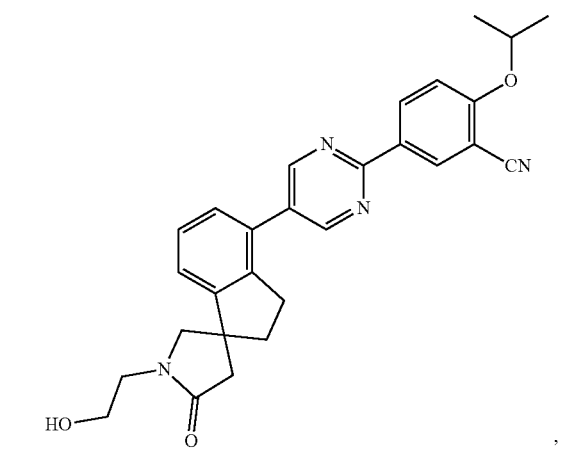
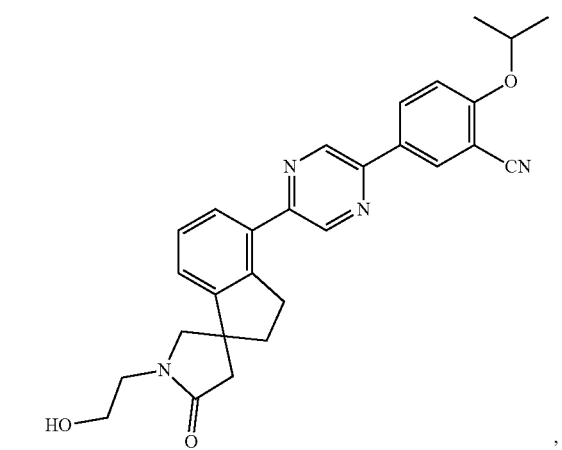

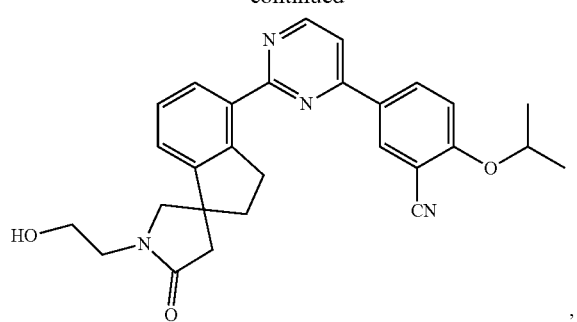
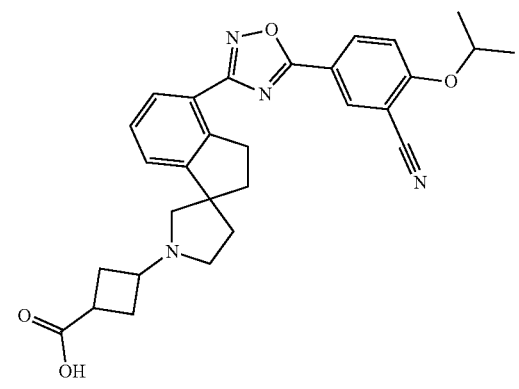
, and
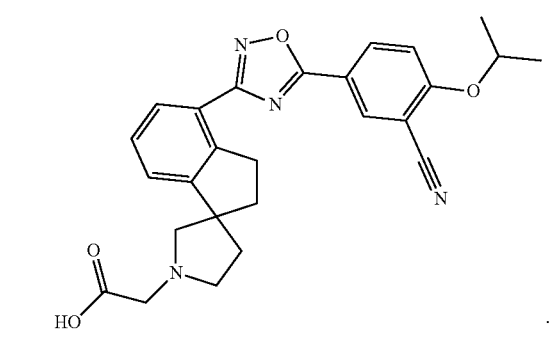
19. The compound, the optical isomer thereof or the pharmaceutically acceptable salt thereof according to claim 18, which is selected from the group consisting of
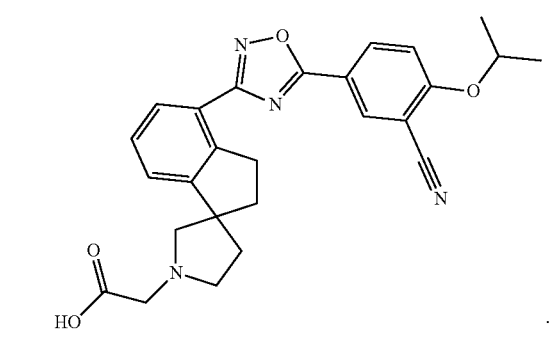

| 219 | 220 |
|---|---|
| -continued | -continued |
| 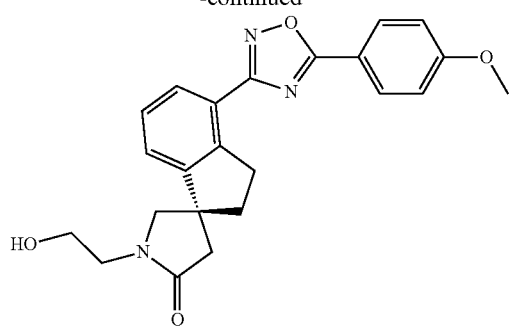 | 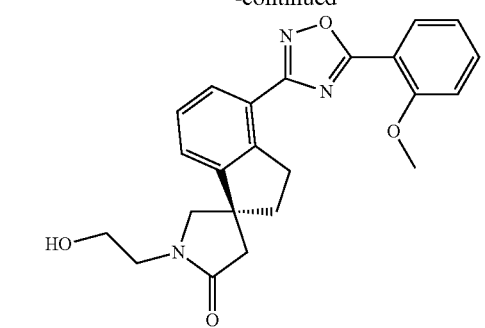 |
| 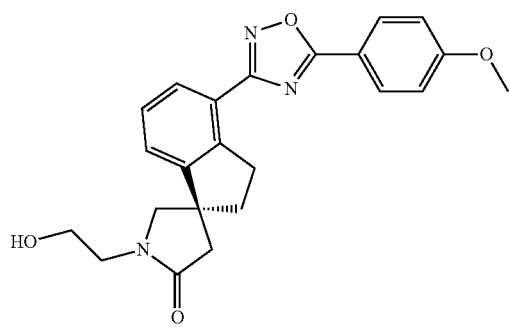 | 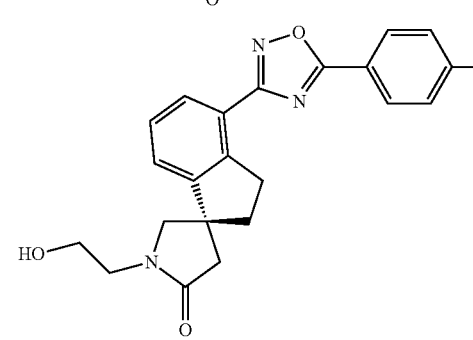 |
| 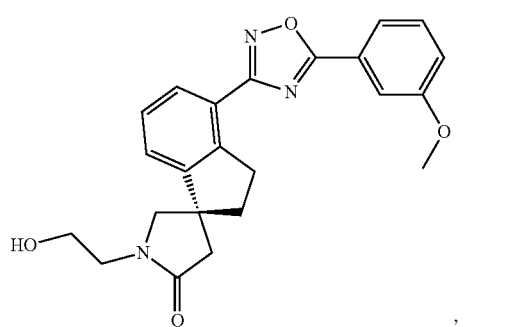 | 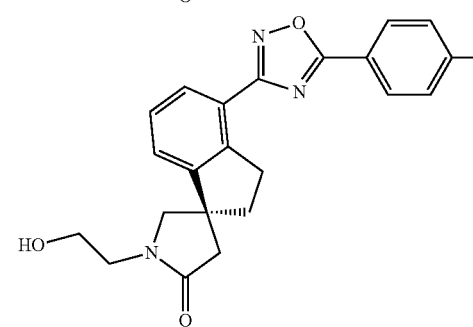 |
| 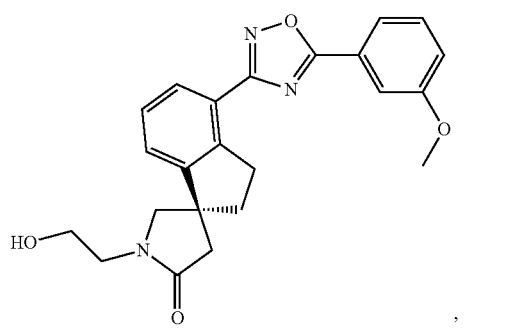 | 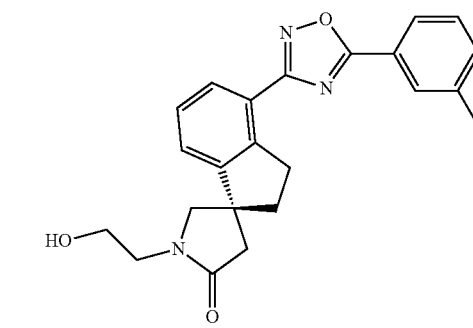 |
| 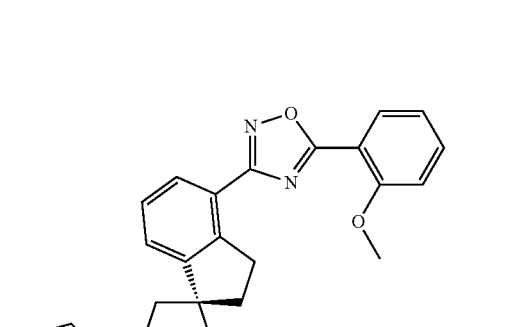 | 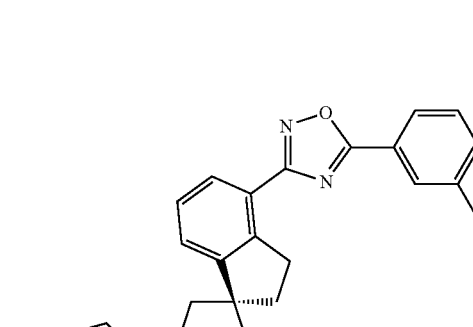 |

221
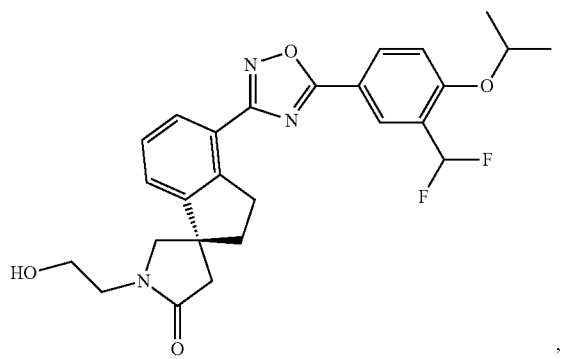
,
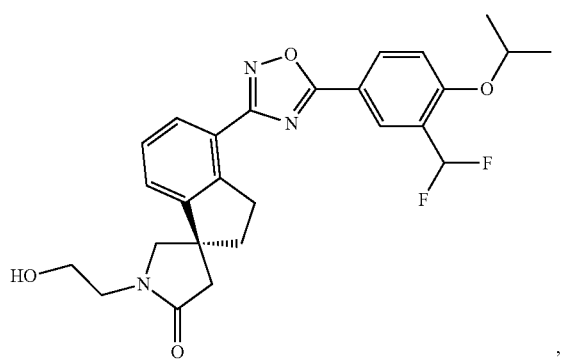
,
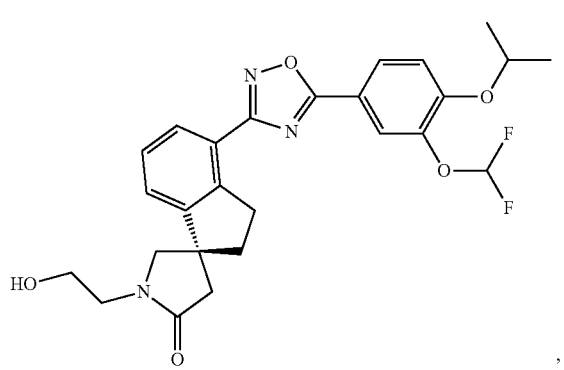
,
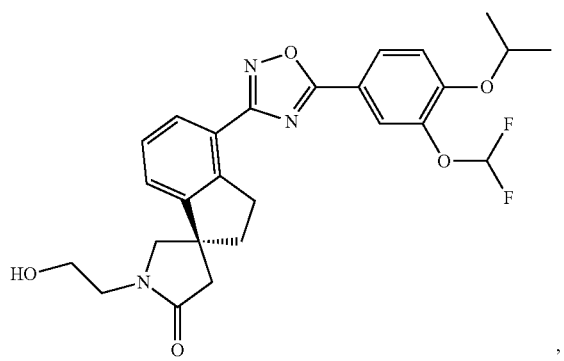
,
222
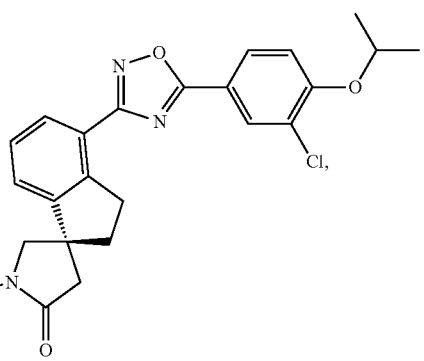
,
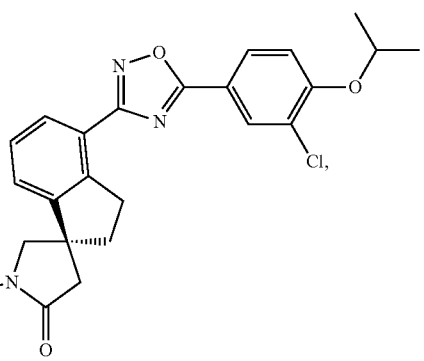
,
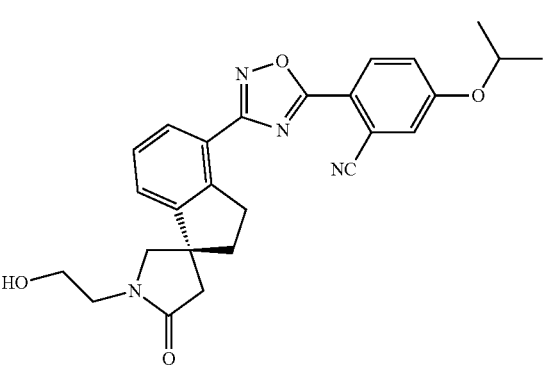
,
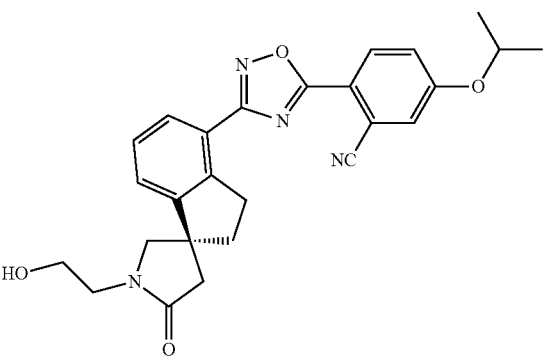
, 223
-continued
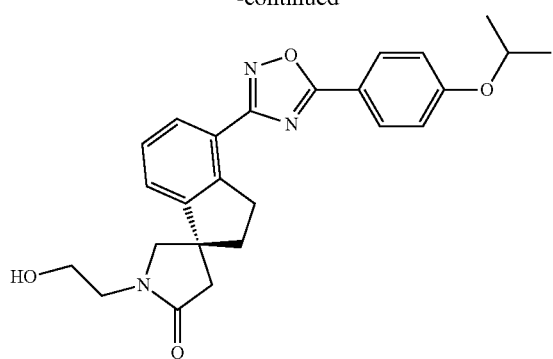
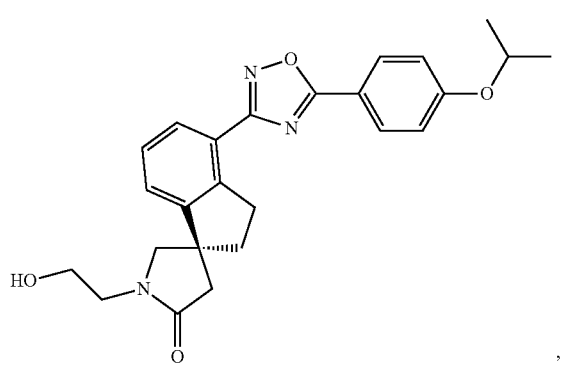
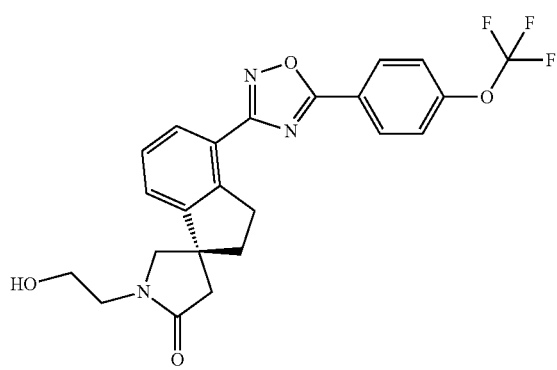
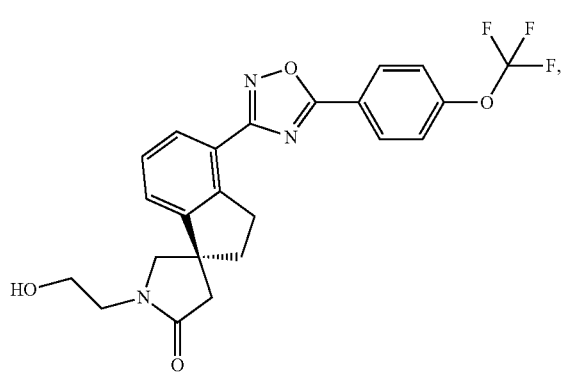
224
-continued
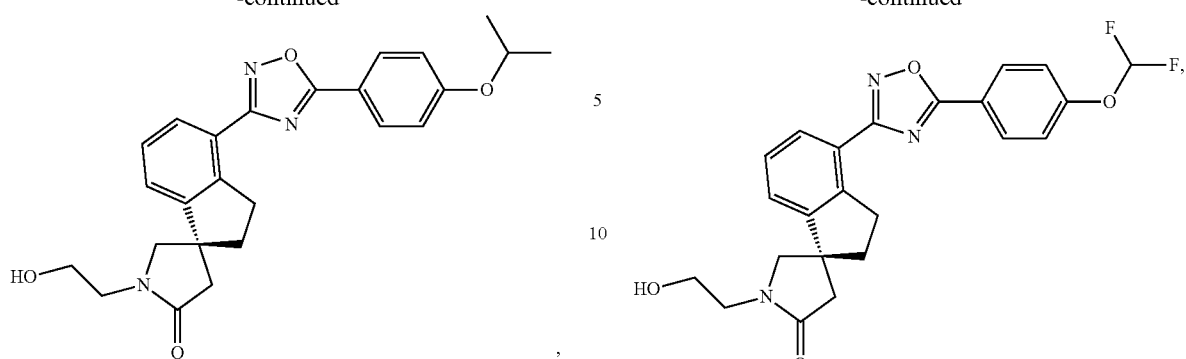
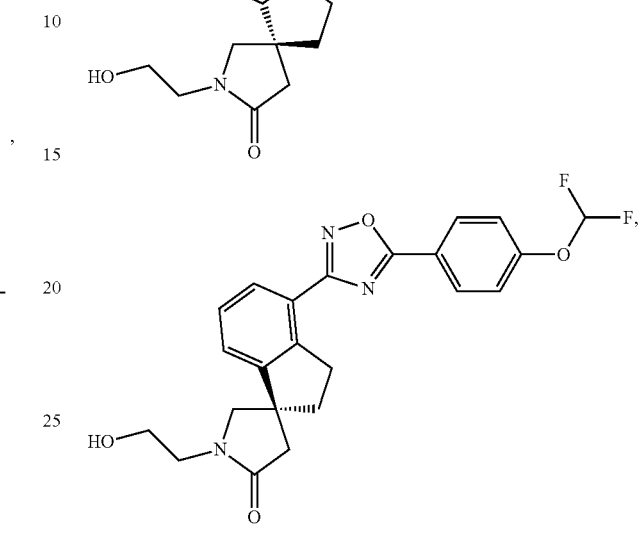
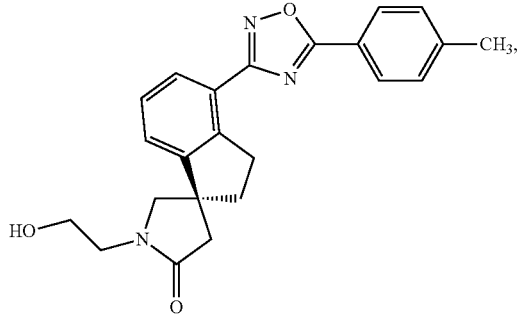
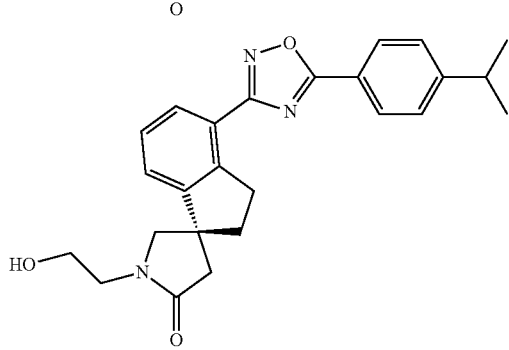

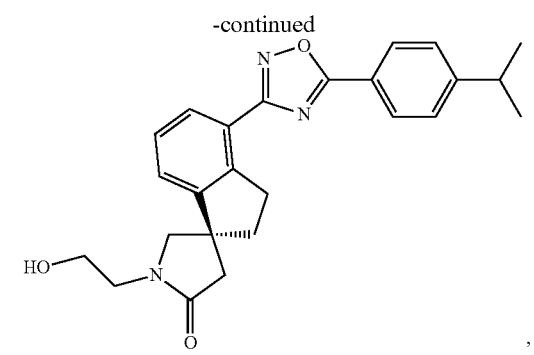,
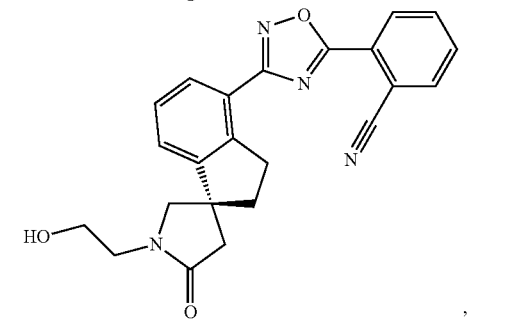,
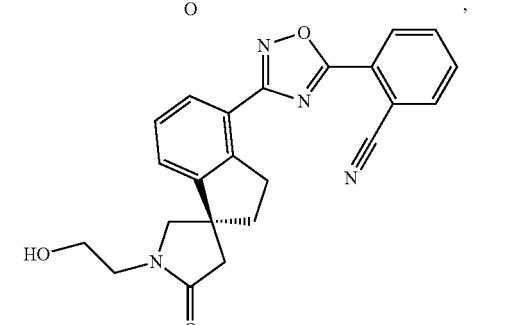,
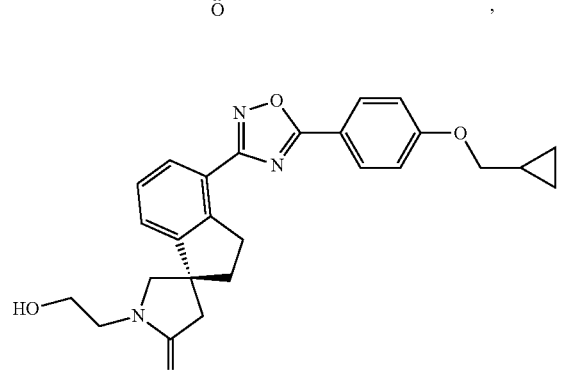,
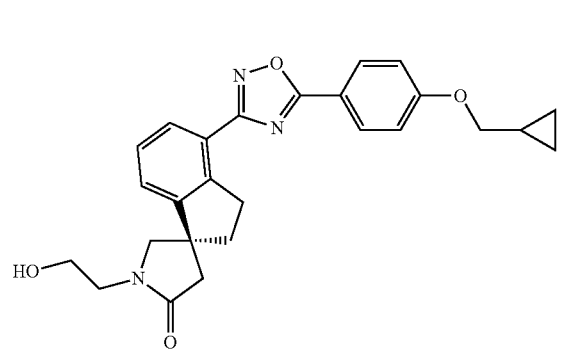,
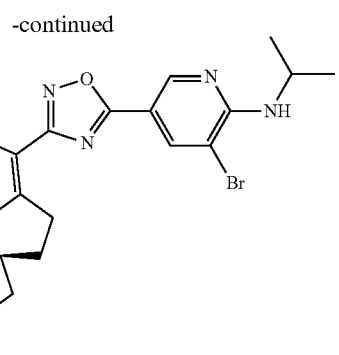,
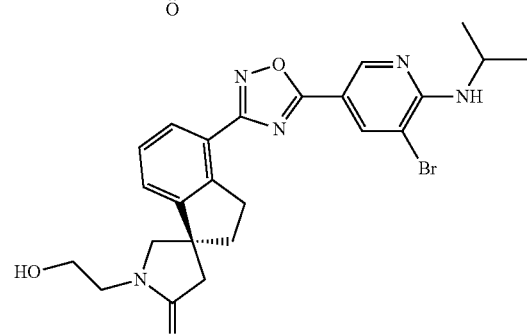,
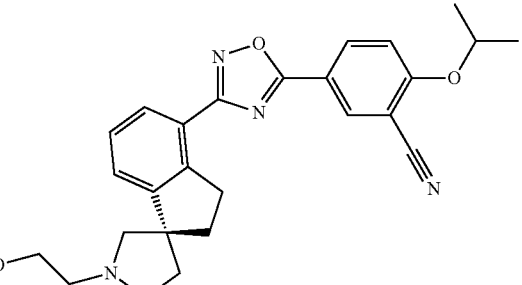,
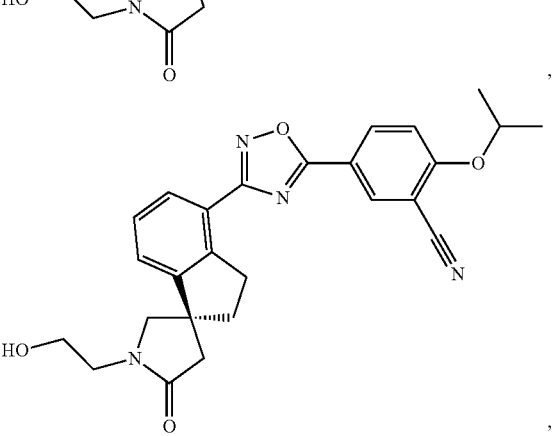,
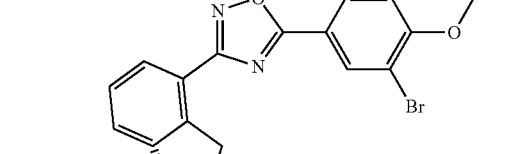,
, 227
-continued
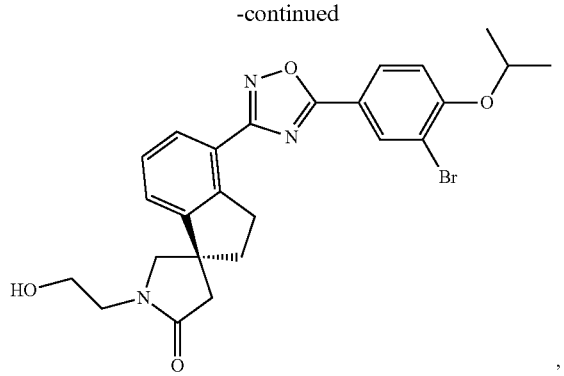
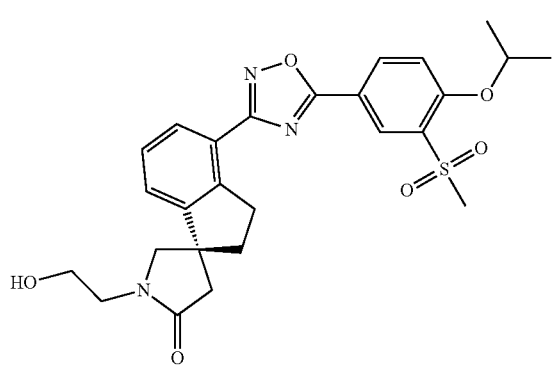
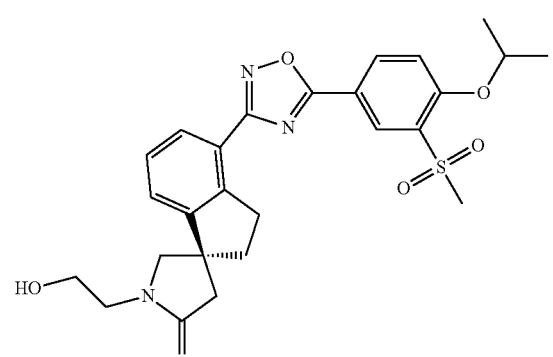
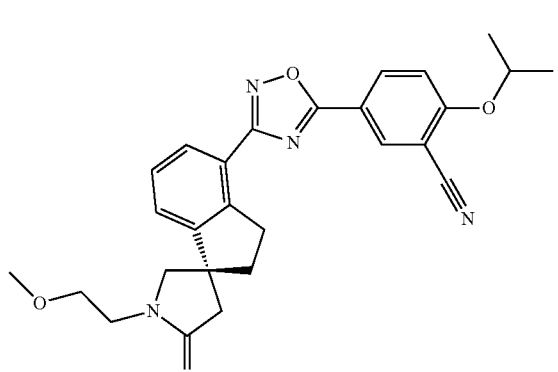
228
-continued
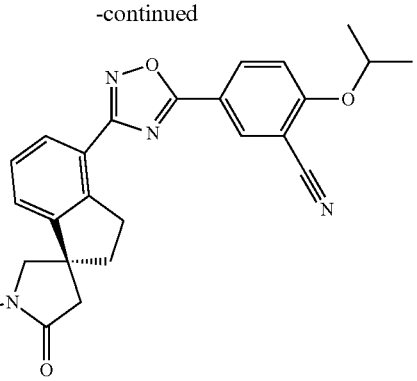
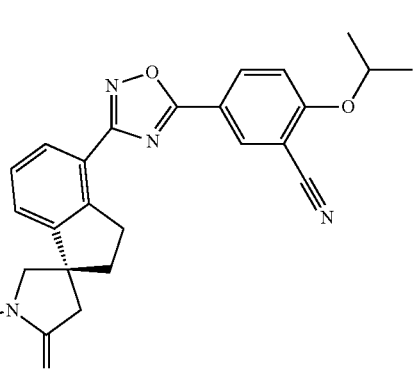

229
-continued
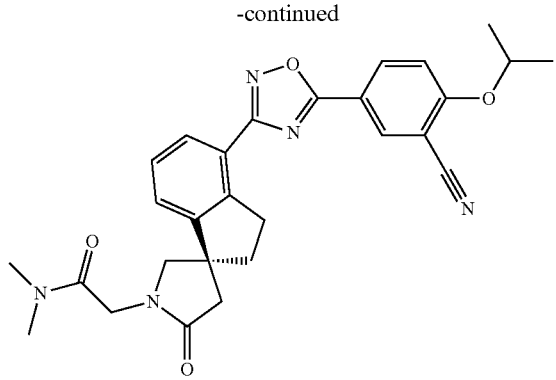
,
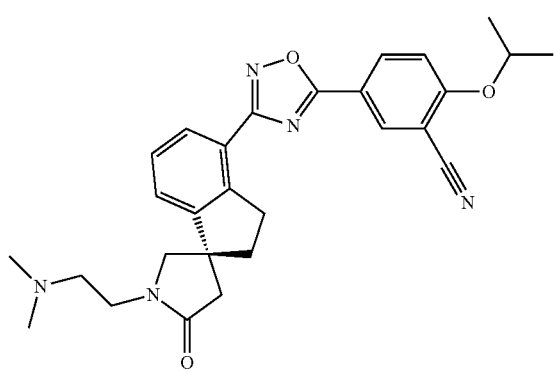
,
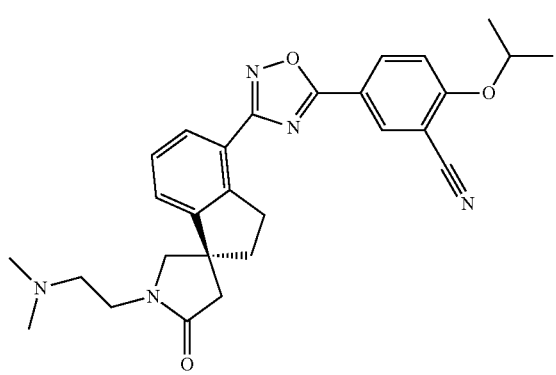
,
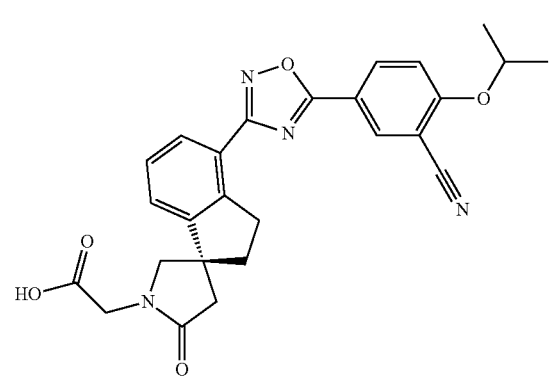
,
230
-continued
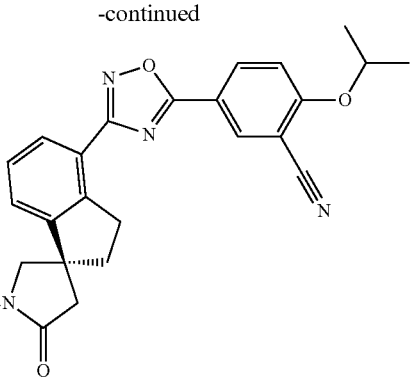
,
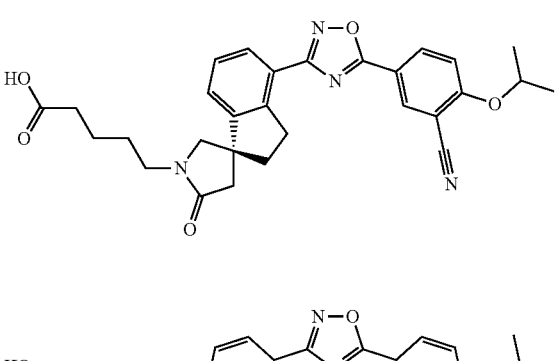
,
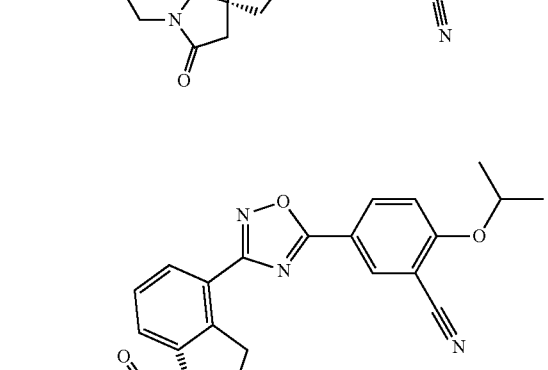
,
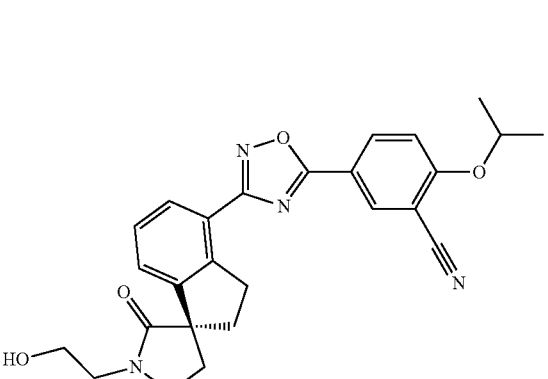
,

231
-continued
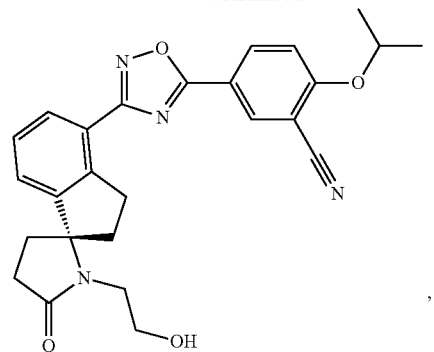
,
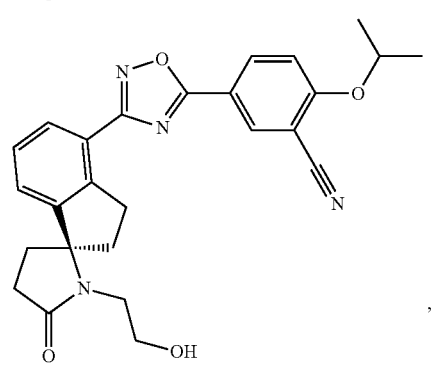
,
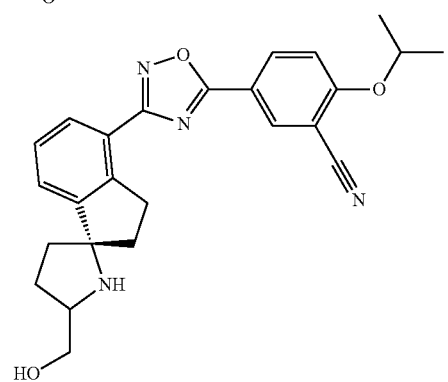
,
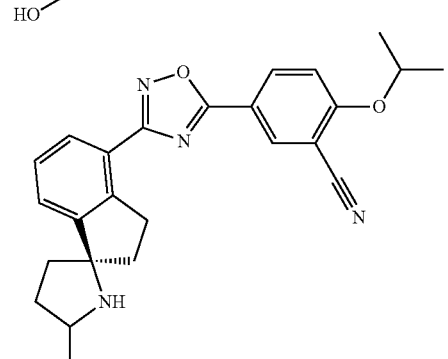
,
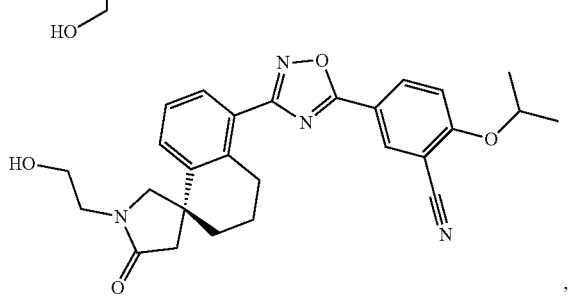
,
232
-continued
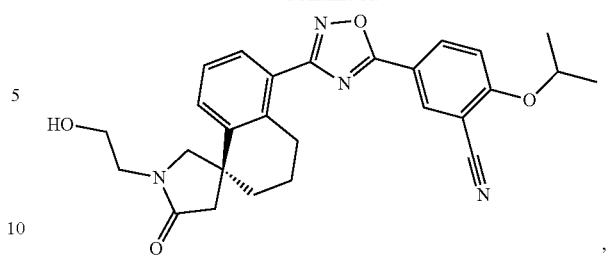
,
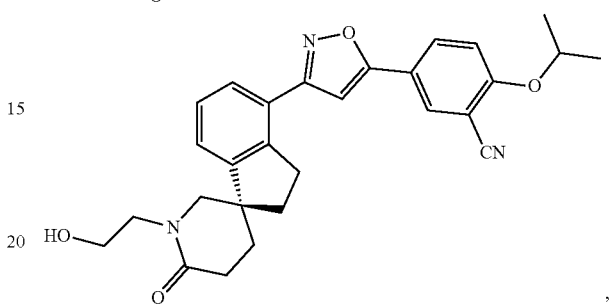
,
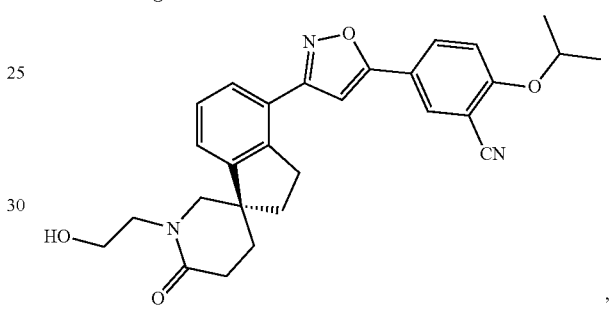
,
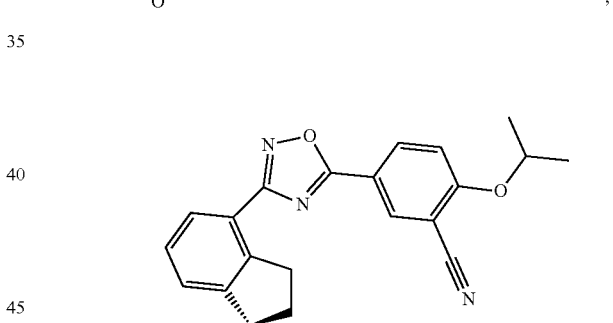
,
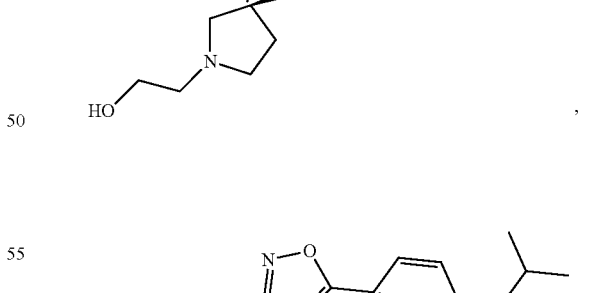
,
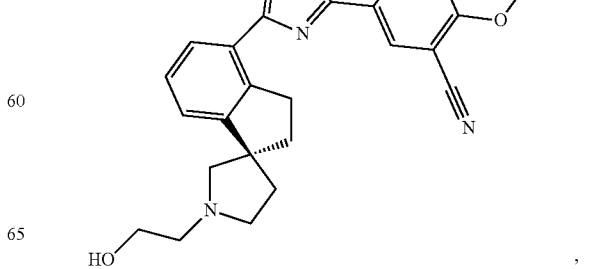
, 233
-continued
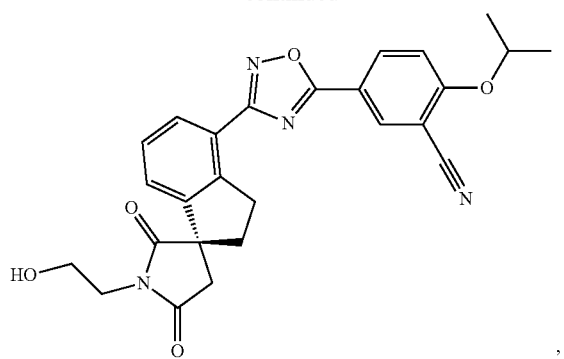
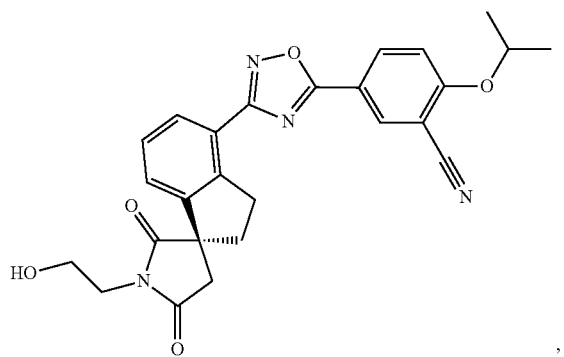
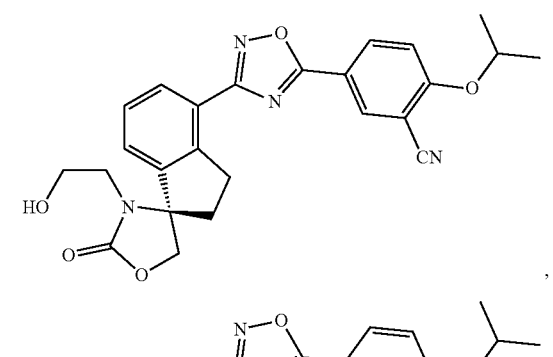
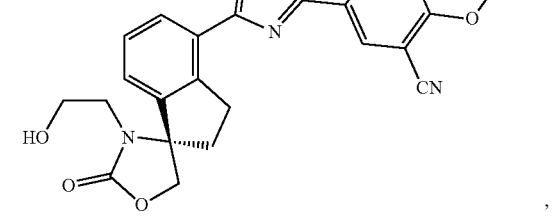
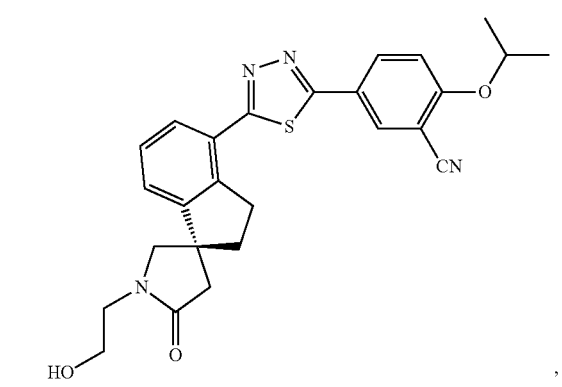
234
-continued
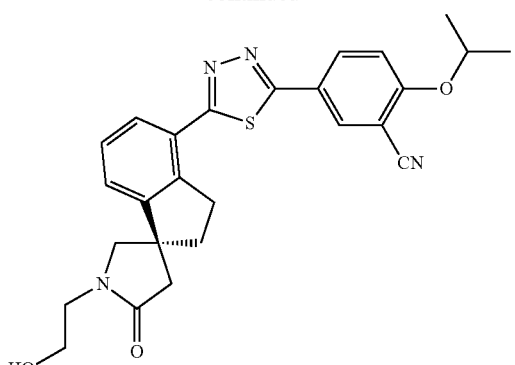
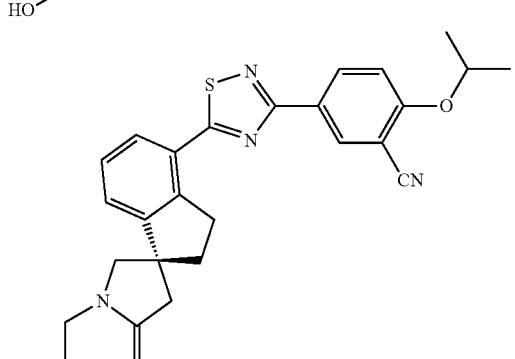
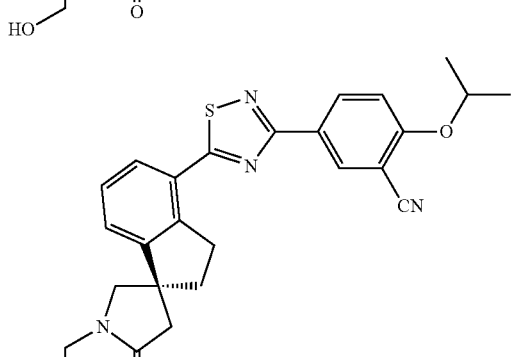
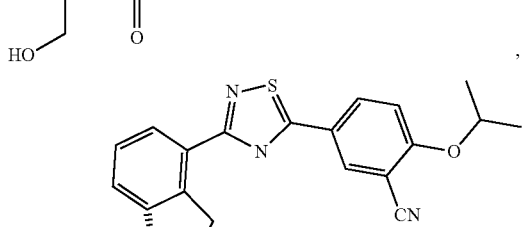
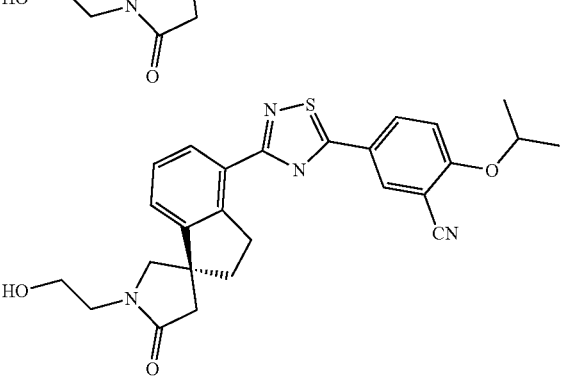

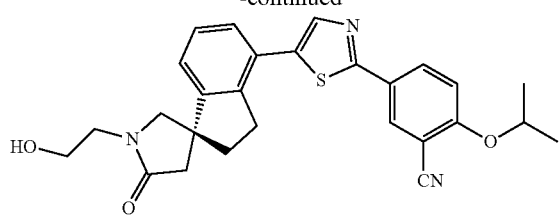
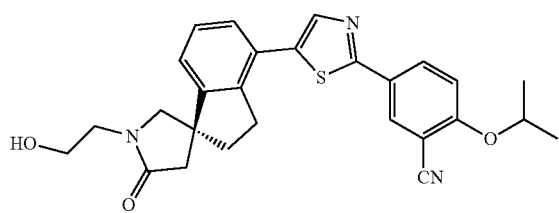
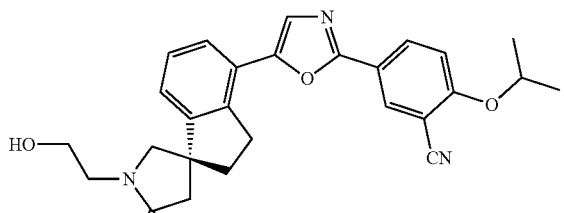
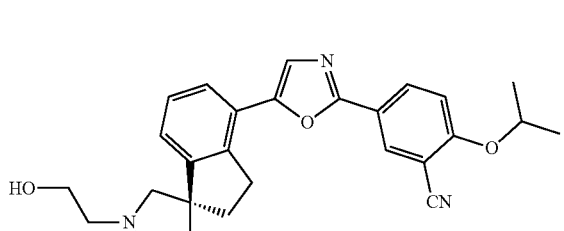
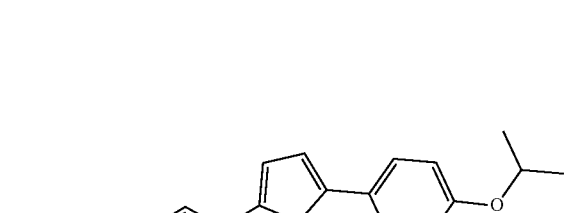
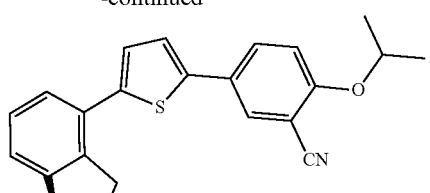
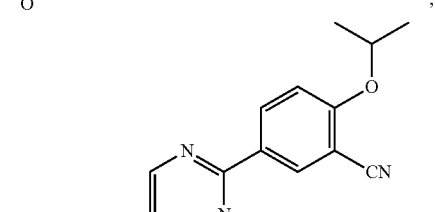
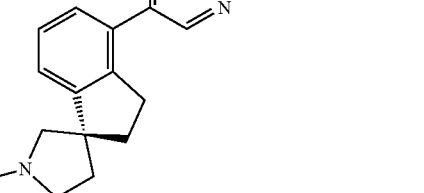
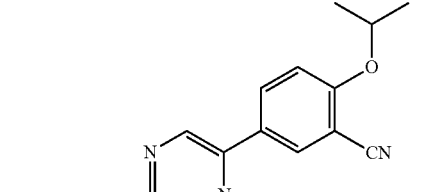
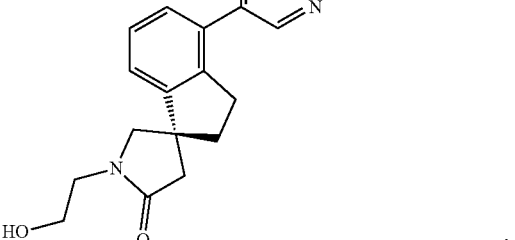

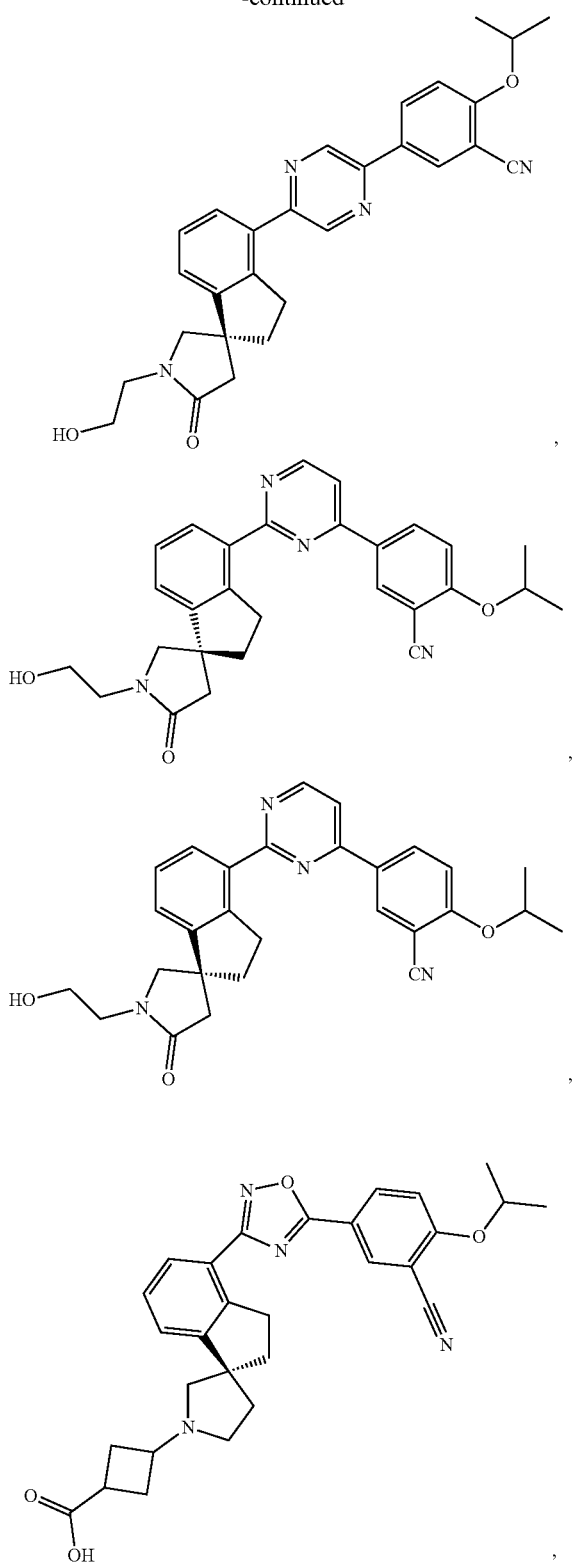

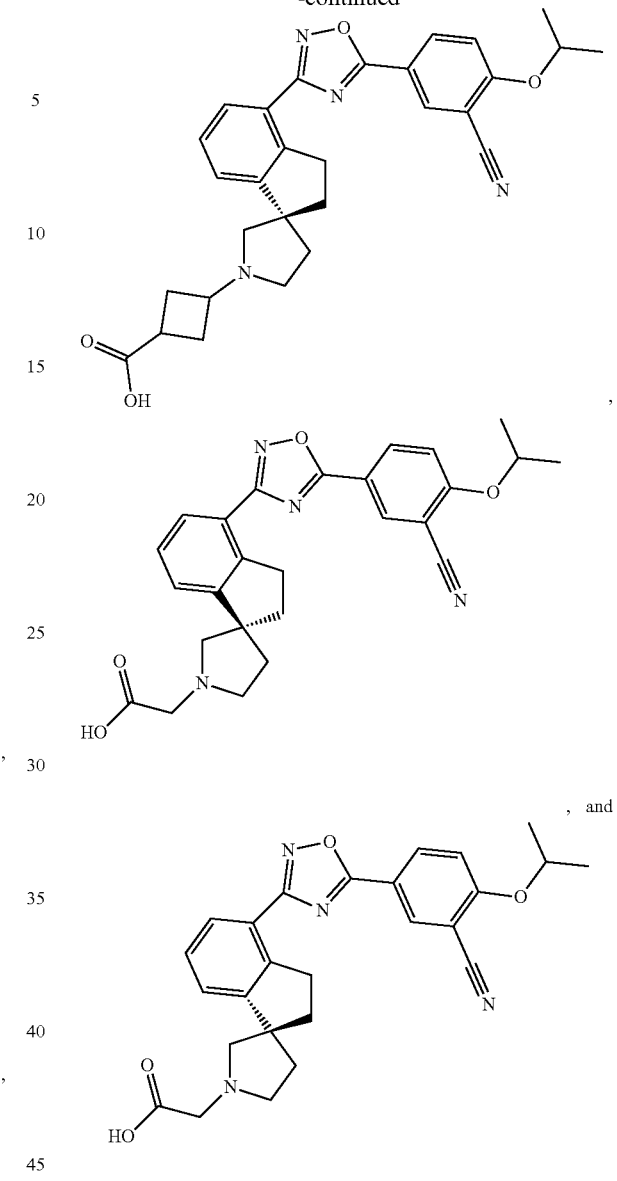

20. A pharmaceutical composition comprising a therapeutically effective amount of a compound, an optical isomer thereof or a pharmaceutically acceptable salt thereof according to claim 1 as an active ingredient, and pharmaceutically acceptable carriers.

21. A method of treating a disease associated with S1P1 receptor in a subject, comprising administering to the subject claim 1.

22. A method of treating a disease associated with S1P1 receptor in a subject, comprising administering to the subject a composition according to claim 20.

* * * * *

UNITED STATES PATENT AND TRADEMARK OFFICE
CERTIFICATE OF CORRECTION

PATENT NO. : 10,981,900 B2  Page 1 of 3
APPLICATION NO. : 16/489476
DATED : April 20, 2021
INVENTOR(S) : Peng Zhang et al.

It is certified that error appears in the above-identified patent and that said Letters Patent is hereby corrected as shown below:

In the Claims

In Column 197, at Lines 20-25: delete " " and replace with
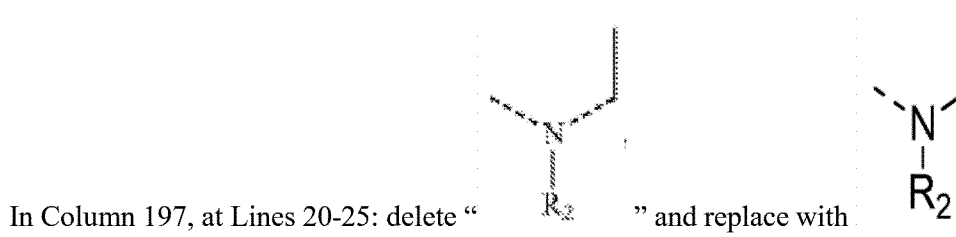

In Column 197, at Lines 20-25: delete " " and replace with
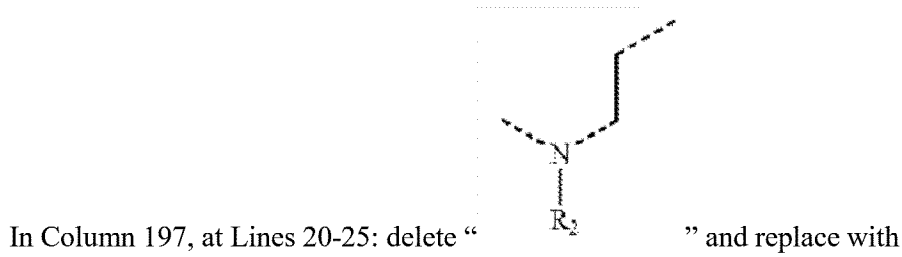

In Column 199, at Line 5: delete " " and replace with
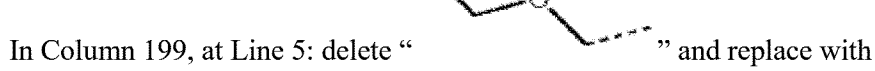

In Column 201, at Line 5: delete " " and replace with
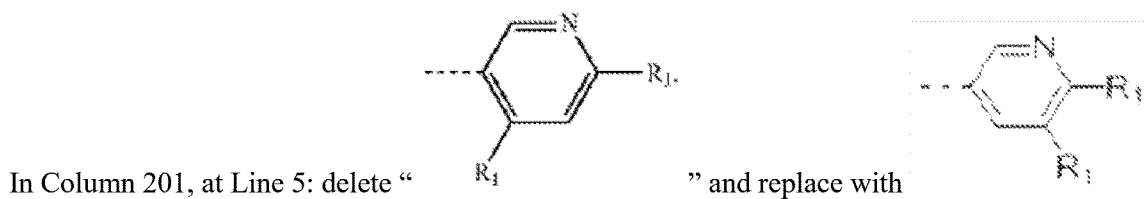

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,981,900 B2

In Column 214, at Lines 25-35: delete " 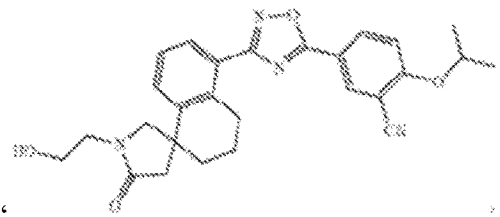 " and replace with

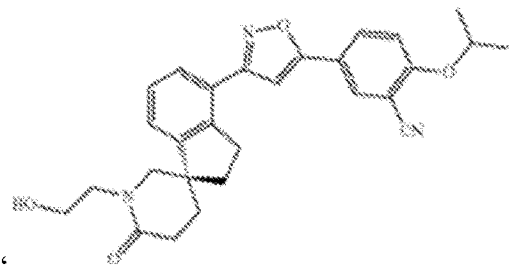

In Column 232, at Lines 15-25: delete "  " and replace with

In Column 232, Lines 25-35: delete " 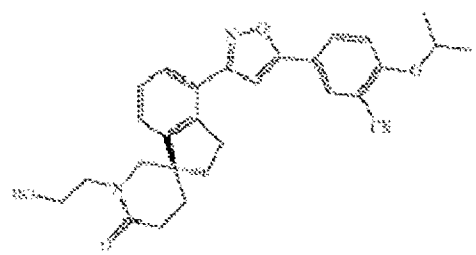 " and replace with

CERTIFICATE OF CORRECTION (continued)
U.S. Pat. No. 10,981,900 B2

In Column 235, Lines 55-65: delete " 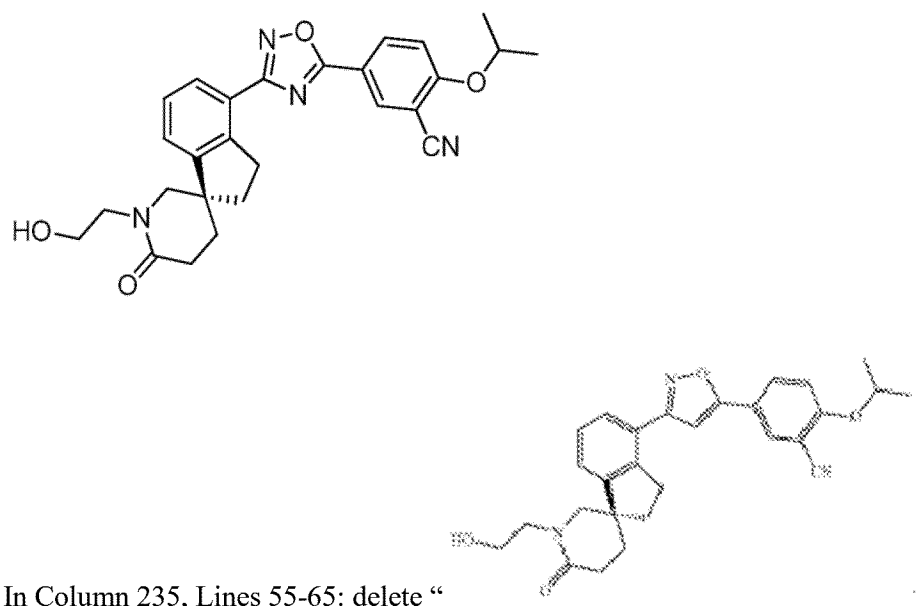 " and replace with